United States Patent [19]

Evans et al.

[11] Patent Number: 5,298,429
[45] Date of Patent: Mar. 29, 1994

[54] BIOASSAY FOR IDENTIFYING LIGANDS FOR STEROID HORMONE RECEPTORS

[75] Inventors: Ronald M. Evans, La Jolla, Calif.; Stanley M. Hollenberg, Seattle, Wash.; Vincent Giguere, Etobicoke, Canada

[73] Assignee: The Salk Institute for Biological Studies, La Jolla, Calif.

[21] Appl. No.: 807,135

[22] Filed: Dec. 10, 1991

Related U.S. Application Data

[60] Division of Ser. No. 108,471, Oct. 20, 1987, Pat. No. 5,071,773, which is a continuation-in-part of Ser. No. 922,585, Oct. 24, 1986, abandoned.

[51] Int. Cl.$^5$ ............... C12N 15/12; G01N 30/00
[52] U.S. Cl. ................... 436/501; 435/69.1; 435/172.3; 435/252.3; 435/320.1
[58] Field of Search ............. 436/501; 435/172.3

[56] References Cited

PUBLICATIONS

Nature 305: 551–554, 6 Oct. 1983, Dean et al. A 5'–Flanking Sequence Essential for Progesterone Regulation of an Ovalbumin Fusion Gene.
J. Biol. Chem. 258: 12693–12701, 25 Oct. 1983, Lai et al., Regulated Expression of the Chicken Ovalbumin Gene in a Human Estrogen–responsive Cell Line.
Nature 312: 779–781, 27 Dec. 1984, Miesfeld et al., Characterization of a Steroid Hormone Receptor Gene and mRNA in Wild-Type and Mutant Cells.
P.N.A.S. 82: 7889–7893, Dec. 1985, Walter et al., Cloning of the Human Estrogen Receptor cDNA.
Mol. & Cell. Biol. 2: 1044–1051, Sep. 1982, Gorman et al., Recombinant Genomes Which Express Chloramphenicol Acetyltransferase in Mammalian Cells.
Nature 308: 513–519, 5 Apr. 1984, Karin et al., Characterization of DNA Sequences Through Which Cadmium and Glucocorticoid Hormones Induce . . . .
Cell 46: 389–399, Aug. 1986, Miesfeld et al., Genetic Complementation of a Glucocorticoid Receptor Deficiency by Expression of Cloned Receptor cDNA.

*Primary Examiner*—Robert J. Hill, Jr.
*Assistant Examiner*—John D. Ulm
*Attorney, Agent, or Firm*—Pretty, Schroeder, Brueggemann & Clark

[57] ABSTRACT

Bioassays are disclosed which are useful for determining whether a compound is a hormone receptor agonist (i.e., is capable of promoting the transcription-activation activities of such receptors) or a hormone receptor antagonist (i.e., is capable of blocking the transcription-activation activities of such receptors). The invention bioassay is conducted by culturing test cells in the presence of at least one compound whose ability to function as a ligand for said receptor protein (or functional engineered or modified forms thereof) is sought to be determined. Alternatively, test cells are cultured in medium containing increasing concentrations of at least one compound whose ability to inhibit the transcription activation activity of hormone receptor agonists is sought to be determined, and a fixed concentration of at least one agonist for the receptor protein. Test cells employed in the practice of the present invention contain non-endogenous DNA which expresses hormone receptor (or functional modified forms thereof) and a DNA sequence encoding a hormone response element operatively linked to a reporter gene. The cultured cells are monitored for evidence of transcription of the reporter gene as a function of the concentration of test compound in the culture medium. The variation in transcription levels of the reporter gene as a function of concentration of test compound indicates the ability of test compound to promote or inhibit activation of transcription.

28 Claims, 79 Drawing Sheets

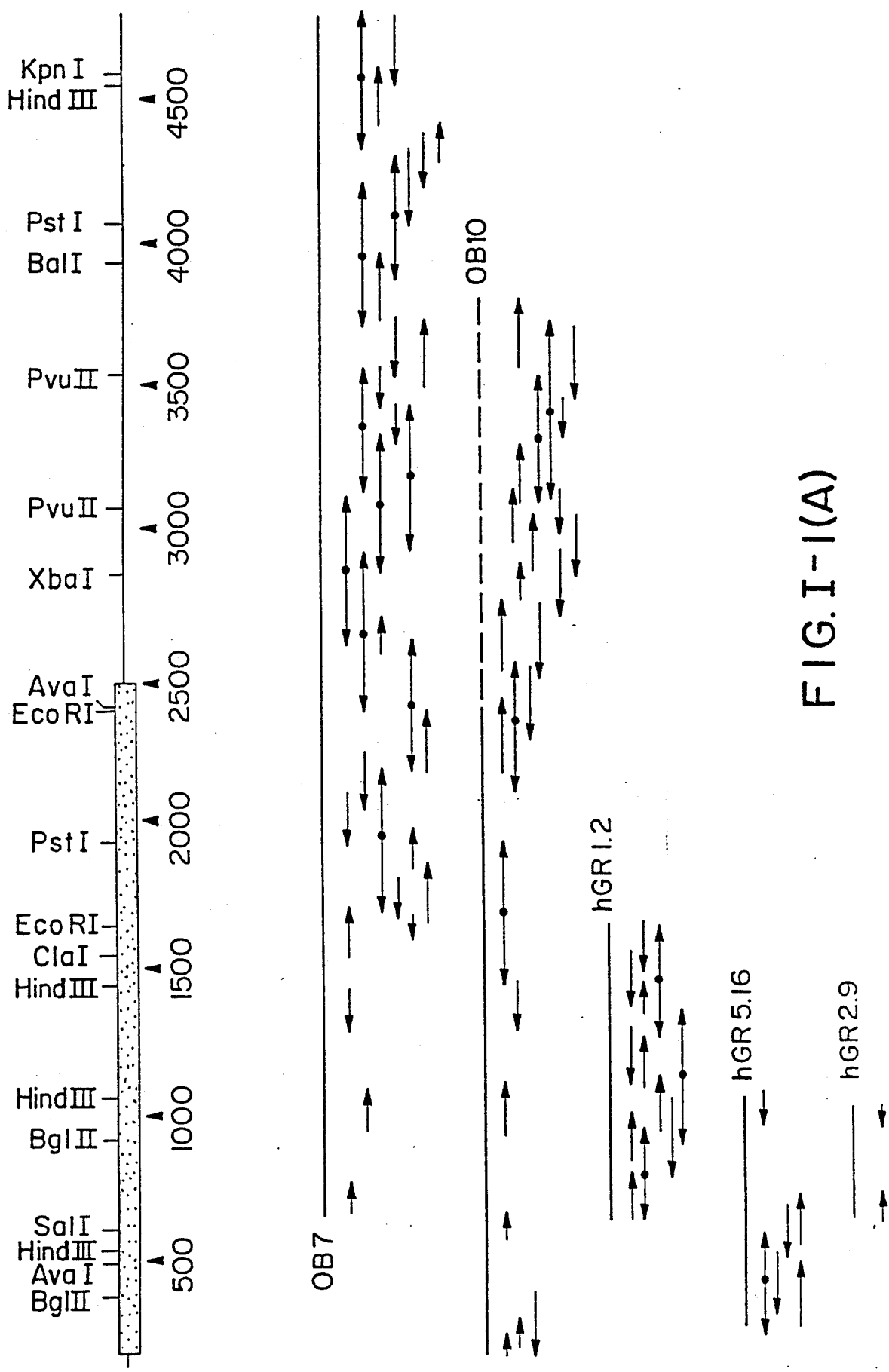
FIG. I-I(A)

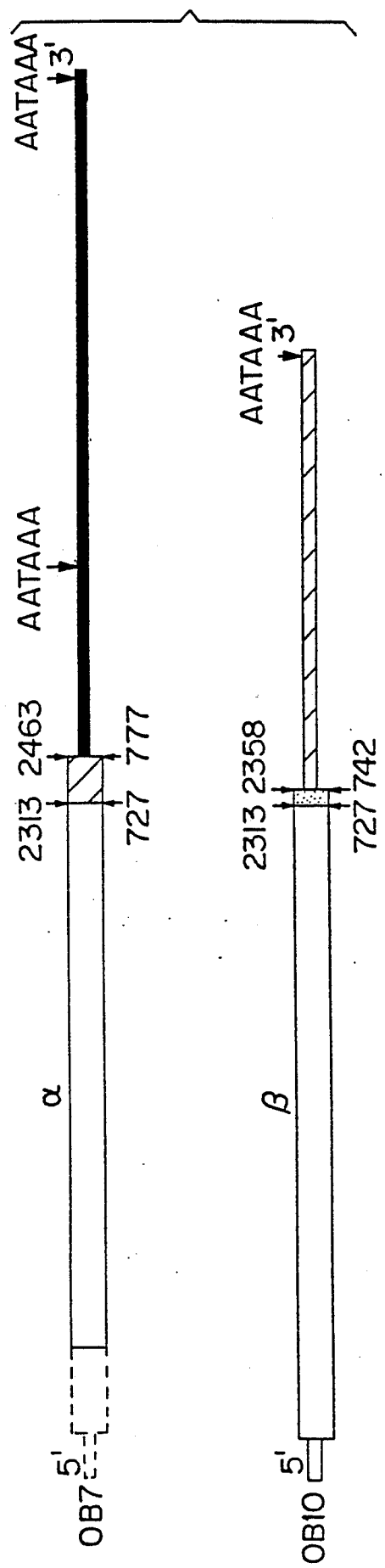
FIG. I-I(B)

```
TTTTTAGAAAAAAAAATATATTTCCCTCTGCTCCTTCTGCGTTCACAAGCTAAGTTGT
TTATCTCGGCTGCGCGGGAACTGCGCGGGTGCGGGGCGAGCGGCTCCTCTGCCAGAGT    120
        MetAspSerLysGluSerLeuThrProGlyArgGluGluArgGluAsnProSer
TGATATTCACTGATGGACTCCAAAGAATCATTAACTCCTGGTAGAGAAGAAAACCCCAGC
 20     SerValLeuAlaGlnGluArgGlyAspValMetAspPheTyrLysThrLeuArgGlyGly
        AGTGTGCTTGCTCAGGAGAGAGGGGAGATGTGATGGACTTCTATAAAACCCTAAGAGGAGGA    240
 40     AlaThrValLysSerAlaAlaSerProSerLeuAlaSerGlnSerAspSer
        GCTACTGTGAAGGTTTCTGCGTCTTCACCTCTGGCTTCTCAATCAGACTCC
 60     LysGlnArgLeuLeuValAspPheProLysGlyLeuLeuTyrMetGlyLeuGluThrLys
        AAGCAGCGAAGACTTTTGGTTGATTTCCAAAAGGCTAAGCAATGGGACTGTATATGGGAGAGACAGAAACAAAA    360
 80     AspLeuSerLysAlaValSerLeuSerMetGlyLeuTyrMetGlyLeuGluThrLys
        GATCTGTCCAAAGCAGTTTCACTCTCAATGGGACTGTATATGGGAGAGACAGAAACAAAA
100     ValMetGlyAsnAspLeuGlyPheProGlnGlyIleSerLeuSerSerGlyGlu
        GTGATGGGAAATGACCTGGGATTCCCACAGCAGGGCCAAATCAGCTTTCCTCGGGGGAA    480
120     ThrAspLeuLysLeuGluLeuGluSerIleAlaAsnLeuAsnArgSerThrSerValPro
        ACAGACTTAAAGCTTTTGGAAGAAAAGCATTGCAAACCTCAATAGGTCGACCAGTGTTCCA
140     GluAsnProLysSerSerAlaThrAlaValSerAlaAlaProThrGluLysGluPhe
        GAGAACCCCAAGAGTTCAGCATCCACTGCTGTGTCTGCCCCCACAGAGAAGGAGTTT    600
```

FIG. I-2a

```
                160
ProLysThrHisSerAspValSerSerGluGlnHisLeuLysGlyGlnThrGlyThr
CCAAAACTCACTCTGATGTATCTTCAGAACAGCAACATTTGAAGGGCCAGACTGGCACC
                        170
                190
AsnGlyGlyAsnValLysLeuTyrThrThrAspGlnSerThrPheAspIleLeuGlnAsp      720
AACGGTGGCAATGTGAAATTGTATACCACCAGACCAAAGCACCTTTGACATTTTGCAGGAT
                200
LeuGluPheSerSerGlySerProGlyLysGluThrAsnGluSerProTrpArgSerAsp
TTGGAGTTTTCTTCTGGGTCCCCAGGTAAAGAGACGAATGAGAGTCCTTGGAGATCAGAC
                        210
                230
LeuLeuIleAspGluAsnCysLeuSerProLeuAlaGlyGluAspAspSerPheLeu        840
CTGTTGATAGATGAAAACTGTTTGTCTCCCTCTGGGGAAGACGATTCATTCCTT
                240
LeuGluGlyAsnSerAsnGluAspCysLysProLeuIleLeuProAspThrLysProLys
TTGGAAGGAAACTCGAATGAGGACTGCAAGCCTCTCATTTTACCGGACACTAAACCCAAA
                        250
                270
IleLysAspAsnGlyAspLeuValLeuSerSerProSerAsnValThrLeuProGlnVal      960
ATTAAGGATAATGGAGATCTGGTTTTGTCAAGCCCCAGTAATGTAACACTGCCCCAAGTG
                280
LysThrGluLysAspPheIleGluLeuCysThrProGlyValIleLysGlnGluLys
AAAACAGAAAAAGAAGATTTCATCGAACTCTGCACCCCTGGGGTAATTAAGCAAGAAAA
                        290
```

```
         300
LeuGlyThrValTyrCysGlnAlaSerPheProGlyAlaAsnIleIleGlyAsnLysMet
CTGGGCACAGTTTACTGTCAGGCAAGCTTTCCTGGAGCAAATATAATTGGTAATAAAATG    1080
         320                        330
SerAlaIleSerValHisGlyValSerThrSerGlyValGlnMetTyrHisTyrAspMet
TCTGCCATTTCTGTTCATGGTGTGAGTACCTCTGGAGGACAGATGTACCACTATGACATG
         340                        350
AsnThrAlaSerLeuSerGlnGlnGlnAspGlnLysProIlePheAsnValIleProPro
AATACAGCATCCCTTTCTCAACAGCAGGATCAGAAGCCTATTTTTAATGTCATTCCACCA    1200
         360                        370
IleProValGlySerGluAsnTrpAsnArgCysGlnGlySerGlyAspAspAsnLeuThr
ATTCCCGTTGGTTCCGAAAATTGGAATAGGTGCCAAGGATCTGGAGATGACAACTTGACT
         380                        390
SerLeuGlyThrLeuAsnPheProGlyArgThrValPheSerAsnGlyTyrSerSerPro
TCTCTGGGAACTCTGAACTTCCCTGGTCGAACAGTTTTCTAATGGCTATTCAAGCCCC     1320
         400                        410
SerMetArgProAspValSerSerProSerSerThrAlaThrThrGlyProTyrTyrPro
AGCATGAGACCAGATGTAAGCTCTCCCTCCAGTCCACCGCAACAACAGGACCA
         420                        430
ProProLysLeuCysLeuValCysSerAspGluAlaSerGlyCysHisTyrGlyValLeu
CCTCCCAAACTCTGCCTGGTGTGCTCTGATGAAGCTTCAGGATGTCATTATGGAGTCTTA    1440
         440                        450
ThrCysGlySerCysLysValPhePheLysArgAlaValGluGlyGlnHisAsnTyrLeu
ACTTGTGGAAGCTGTAAAGTTTTCTTCAAAAGAGCAGTGGAAGGACAGCACAATTACCTA
         460                        470
CysAlaGlyArgAsnAspCysIleIleAspLysIleArgArgLysAsnCysProAlaCys
TGTGCTGGAAGGAATGATTGCATCATAGATAAAATTCGAAGAAAAAACTGCCCAGCATGC    1560
```

```
                480                                                 490
ArgTyrArgLysCysLeuGlnAlaGlyMetAsnLeuGluAlaArgLysThrLysLysLys
CGCTATCGAAAATGTCTTCAGGCTGGAATGAACCTGGAAGCTCGAAAAACAAAGAAAAAA 500                                                 510
IleLysGlyIleGlnGlnAlaIleThrThrGlyValSerGlnGluThrSerGluAsnProGly
ATAAAAGGAATTCAGCAGGCCACTACAACAGGAGTCTCACAAGAAACCTCTGAAAATCCTGGT  1680

520                                                 530
AsnLysThrIleValProAlaThrLeuProGlnLeuThrProThrLeuValSerLeuLeu
AACAAAACAATAGTTCCTGCAACGTTACCACAACTCACCCCTACCCTGGTGTCACTGTTG 540                                                 550
GluValIleGluProGluValLeuTyrAlaGlyTyrAspSerSerValProAspSerThr
GAGGTTATTGAACCTGAAGTGTTATATGCAGGATATGATAGCTCTGTTCCAGACTCAACT   1800

560                                                 570
TrpArgIleMetThrThrLeuAsnMetLeuGlyGlyArgGlnValIleAlaAlaValLys
TGGAGGATCATGACTACGCTCAACATGTTAGGAGGCGGCAAGTGATTGCAGCAGTGAAA 580                                                 590
TrpAlaLysAlaIleProGlyPheArgAsnLeuHisLeuAspAspGlnMetThrLeuLeu
TGGGCAAAGGCAATACCAGGTTTCAGGAACTTACACCTGGATGACCAAATGACCCTACTG  1920
```

FIG. I-2d

```
                    GlnTyrSerTrpMetAlaPheLeuMetAlaPheAlaLeuGlyTrpArgSerTyrArgGlnSer
600                 CAGTACTCCTGGATGTTTCTTATGGCATTTGCTCTGGGGTGGAGATCATATAGACAATCA

SerAlaAsnLeuLeuCysPheAlaProAspLeuIleIleAsnGluGlnArgMetThrLeu
620                 AGTGCAAACCTGCTGTGTTTTGCTCCTGATCTGATTATTAATGAGCAGAGAATGACTCTA    2040

ProCysMetTyrAspGlnCysLysHisMetLeuTyrValSerSerGluLeuHisArgLeu
640                 CCCTGCATGTACGACCAATGTAAACACATGCTGTATGTTTCCTCTGAGTTACACAGGCTT

GlnValSerTyrGluGluTyrLeuCysMetLysThrLeuLeuLeuSerSerValPro
660                 CAGGTATCTTATGAAGAGTATCTCTGTATGAAAACCTTACTGCTTCTCTCTTCAGTTCCT    2160

LysAspGlyLeuLysSerGlnGluLeuPheAspGluIleArgMetThrTyrIleLysGlu
680                 AAGGACGGTCTGAAGAGCCAAGAGCTATTTGATGAAATTAGAATGACCTACATCAAAGAG

LeuGlyLysAlaIleValLysArgGluGlyAsnSerSerGlnAsnTrpGlnArgPheTyr
700                 CTAGGAAAAGCCATTGTCAAGAGGGAAGGAAACTCCAGCCAGAACTGGCAGCGGTTTTAT    2280

GlnLeuThrLysLeuLeuAspSerMetHisGluValValGluAsnLeuLeuAsnTyrCys
720                 CAACTGACAAAACTCTTGGATTCTATGCATGAAGTGGTTGAAAATCTCCTTAACTATTGC

PheGlnThrPheLeuAspLysThrMetSerIleGluPheProGluMetLeuAlaGluIle
740                 TTCCAAACATTTTTGGATAAGACCATGAGTATTGAATTCCCCGAGATGTTAGCTGAAATC    2400

IleThrAsnGlnIleProLysTyrSerAsnGlyAsnIleLysLysLeuLeuPheHisGln
760                 ATCACCAATCAGATACCAAAATATTCAAATGGAAATATCAAAAACTTCTGTTTCATCAA
```

FIG. I-2e

LysSTOP
AAGTGACTGCCTTAATAAGAATGGTTGCCTTAAAGAAAGTCGAATTAATAGCTTTTATTG

TATAAACTATCAGTTGTCCTGAGAGGTTTTGTTGTTTATTTTTATTGTTTTCATCT 2520

GTTGTTTTGTTTAAATACGCACTACATGTGGTTTATAGAGGGCCAAGACTTGGCAACAG 2640

AAGCAGTTGAGTCGTCATCACTTTTCAGTGATGGGAGAGTAGATGGTGAAATTATTAGT

TAATATATCCCAGAAATTAGAAACCTTAATATGTGGACGTAATCTCCACAGTCAAAGAAG

GATGGCACCTAAACCACCAGTGCCCAAAGTCTGTGATGAACTTTCTCTTCATACTTTT

TTTCACAGTTGGGCTGGATGAAATTTTCTAGACTTTCTGTTGGTATCCCCCCCTGTAT 2880

AGTTAGGATAGCATTTTTGATTTATGCATGGAAACCTGAAAAAAAGTTTACAAGTGTATA

TCAGAAAGGGAAGTTGTGCCTTTTATAGCTATTACTGTCTGGTTTTAACAATTTCCTTT

ATATTTAGTGAACTACGCTTGCTCATTTTTTCTTACATAATTTTTATTCAAGTTATTGT

ACAGCTGTTTAAGATGGGCAGCTAGTTCGTAGCTTTCCCAATAAACTCTAAACATTAAT 3120

CAATCATCTGTGTGAAAATGGGTTGGTGCTTCTAACCTGATGGCACTTAGCTATCAGAAG

ACCACAAAAATTGACTCAAATCTCCAGTATTCTTGTCAAAAAAAAAAAAGCTCA

TATTTGTATATATCTGCTTCAGTGGAGAATTATATAGGTTGTGCAAATTAACAGTCCTA

FIG. I-2f

```
ACTGGTATAGAGCACCTAGTCCAGTGACCTGCTGGGTAAACTGTGGATGATGGTTGCAAA      3360
AGACTAATTTAAAAAATAACTACCAAGAGAGCCCTGTCTGTACCTAACGCCCTATTTTGC
AATGGCTATATGGCAAGAAAGCTGGTAAACTATTTGTCTTTCAGGACCTTTTGAAGTAGT
TTGTATAACTTCTTAAAAGTTGTGATTCCAGATAACCAGCTGTAACACAGCTGAGAGACT
TTAATCAGACAAAGTAATTCCTCTCACTAAACTTTACCCAAAAACTAAATCTCTAATAT      3600
GGCAAAAATGGCTAGACACACCCATTTTCACATTCCCATCTGTCACCATTGGTTAATCTTT
CCTGATGGTACAGGAAAGCTCAGCTACTGATTTTTGTGATTTAGAACTGTATGTCAGACA
TCCATGTTTGTAAAACTACACATCCCTAATGTGTGCCATAGAGTTAACACAAGTCCTGT
GAATTTCTCACTGTTGAAAATTATTTAAACAAATAGAAGCTGAGTAGCCCTTTCTG      3840
TGTGCACCTTACCAACTTTCTGTAAACTCAAAACTTAACATATTTACTAAGCCACAAGAA
ATTTGATTTCTATTCAAGGTGGCCAAATTATTTGTGTAATAGAAAAATCTAATA
TTAAAAATATGGAACTTCTAATATATTTTATATTTAGTTATATGTTTCAGATATATATCA
TATTGGTATTCACTAATCTGGGAAGGGAAGGGCTACTGCAGCTTTACATGCAATTTATTA      4080
```

FIG. I-2g

```
AAATGATTGTAAAATAGCTTGTATAGTGTAAAATAAGAATGATTTTAGATGAGATTGTT
TTATCATGACATGTTATATATTTTTGTAGGGTCAAAGAAATGCTGATGGATAACCTAT
ATGATTTATAGTTTGTACATGCATTCATACAGGCAGCGATGGTCTCAGAAACCAAACAGT
TTGCTCTAGGGGAAGAGGGGAGATGGAGACTGGTCCTGTGTGCAGTGAAGGTTGCTGAGGC        4320
TCTGACCCAGTGAGATTACAGAGGAAGTTATCCTCTGCCTCCCATTCTGACCACCCTTCT
CATTCCAACAGTGAGTCTGTCAGCGCAGGTTAGTTTACTCAATCTCCCCTTGCACTAAA
GTATGTAAAGTATGTAAACAGGAGACAGGAAGGTGGTGCTTACATCCTTAAAGGCACCAT        4560
CTAATAGCGGGTTACTTTCACATATACAGCCCCTCCCCCAGCAGTTGAATGACAACAGAAGCT
TCAGAAGTTTGGCAATAGTTTGCATAGAGGTACCAGCAATATGTAAATAGTGCAGAATCT
CATAGGTTGCCAATAATACACTAATTCCTTCTATCCTACAACAGAGTTTATTTCCAAA         4800
TAAAATGAGGACATGTTTTGTTTCTTTGAATGCTTTTTGAATGTTATTTGTTATTTC
AGTATTTTGGAGAAATTATTTAATAAAAACAATCATTGCTTTTGAAAAAAAAAAA
```

FIG.I-2h

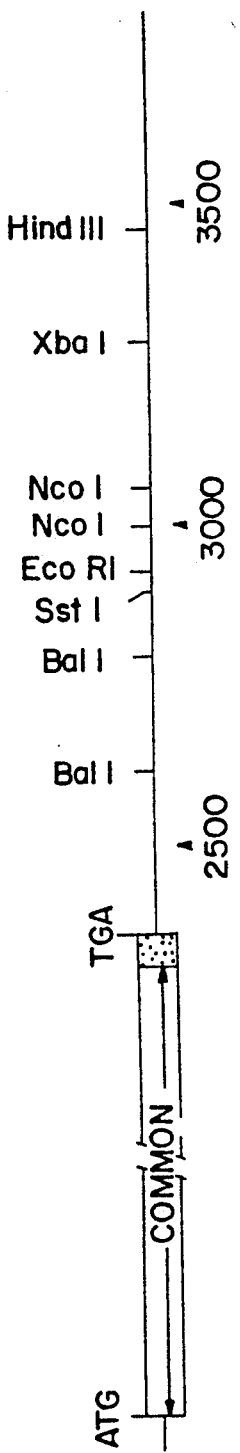
FIG. I-3(A)

FIG. I-3(B)

```
                                                       730
                                    ValValGluAsnLeuLeuAsnTyrCysPheLeuAspLysThrPheMetSerIle
                                    GTGGTTGAAAATCTCCTTAACTATTGCTTCCAAACATTTTGGATAAGACCATGAGTATT    2373
                                    740
                                    GluPheProGluMetLeuAlaGluIleIleThrAsnGlnIleProLysTyrSerAsnGly
                                    GAATTCCCCGAGATGTTAGCTGAAATCATCACCAATCAGATACCAAAATATTCAAATGGA    2433
                              α     760
                                    AsnIleLysLysLeuLeuPheHisGlnLysSTOP
                                    AATATCAAAAAACTTCTGTTTCATCAAAAGTGA.....
                                    770
---GlnLeuThrLysLeuLeuAspSerMetHisGlu
---GGTCTGACAAAACTCTTGGATTCTATGCATGAA                730
                              β     AsnValMetTrpLeuLysProGluSerThrSerHisThrLeuIleSTOP
                                    AATGTTATGTGGTTAAAACCAGAAAGCACACTCACACATTAATCTGATTTTCATCCCAA    2373

CAATCTTGGCGCTCAAAATAGAACTCAATGAGAAAAAGAGAAGATTATGTGCACTTCGTT    2433
AGTCATCTTAATTATGTGTGCTGTTAAAGAAGAGCTGTGGGCAGTTTAGGATACGTGGGGAAAAGAA
CCCAAACTGTTGAAGTTTCAGTGAGAGTTGGTTACTACCAACAAATTCCAAATGCTAAACTCTGTATTCTGTGGCATCCAA    2633
ATACAAGCAGAACTGAGGAGGCAGTTTGTGTCAGTTAGGACACTCTAGGAGTTGGTCTATATATCCAAATGAAGGAACCTTGGCCACCCAGAATTCAGGAA
AACTAACATGATTTGATGTAGTCCAGTTGTCCAGTTTCCTGTCAAACTTCCATGGTCTCATAATGGTAGAAACCACGCCTGGAATGCATAGCTTCGTAATATCAGAGG    2833
CAGGGAGCAATTCTGTCTGTGTCCAGTTTGTCTCTGGTTCACCAGGATAGTGTCAGGAACCAGGTTCAGAGCCTCACTCTGAGTTTCGTAATTTGTTATACAA    3033
TACATTGATCTGTGTGTGGACCTGGTCCACCCTCCTCAAATATCCCTCTAATATAAAAGGGTGCTTGTTCTCACAGTGTATCACAGTAGGTGAATGTTTTT    3233
CAAGCAACCTGAAAATACCTCTGTATGGCATTTTTCATCAAATATACACACTTTTATTTTTTATTTCTGATGAAAGG
CTGTATGAAGAAAAGTTGTAGTTGATTAGAATAACTTGCTTAAGAAGCTTTACATGCATTTTTTCATTTCAAATGCTAAATAAAATTAAAACCAGTGACTCCTG    3433
AATCTATATTATACTGTGTAGTTGTATGTTTAAACTTTTATCATTTTTATTTTTAAATAAAATAAATCTGCTTTTTCAAAAAAAAAAAAAAAA    3633
TTTAAAATAAAAAGTTGTGAAATGTTAAATGCCAAATATCATGAGAAACATCATAATAAAAGGGTGTGGGCAGTAAATGGGAGACAGGACTGTAAATGGGGACA
AACCTTGTGGAAAACGATTTAACTTGTCTTCATTTTTAAATTTCATTAATGCAGTGAACATTGTACCGAATTGGCAGTAAATGTTAG
CCATTTACACAGCAATGCCAAATGCCAAATCATAAAAAAATCATAAAAAAAAAAAAAAAAAAAAA    3820
```

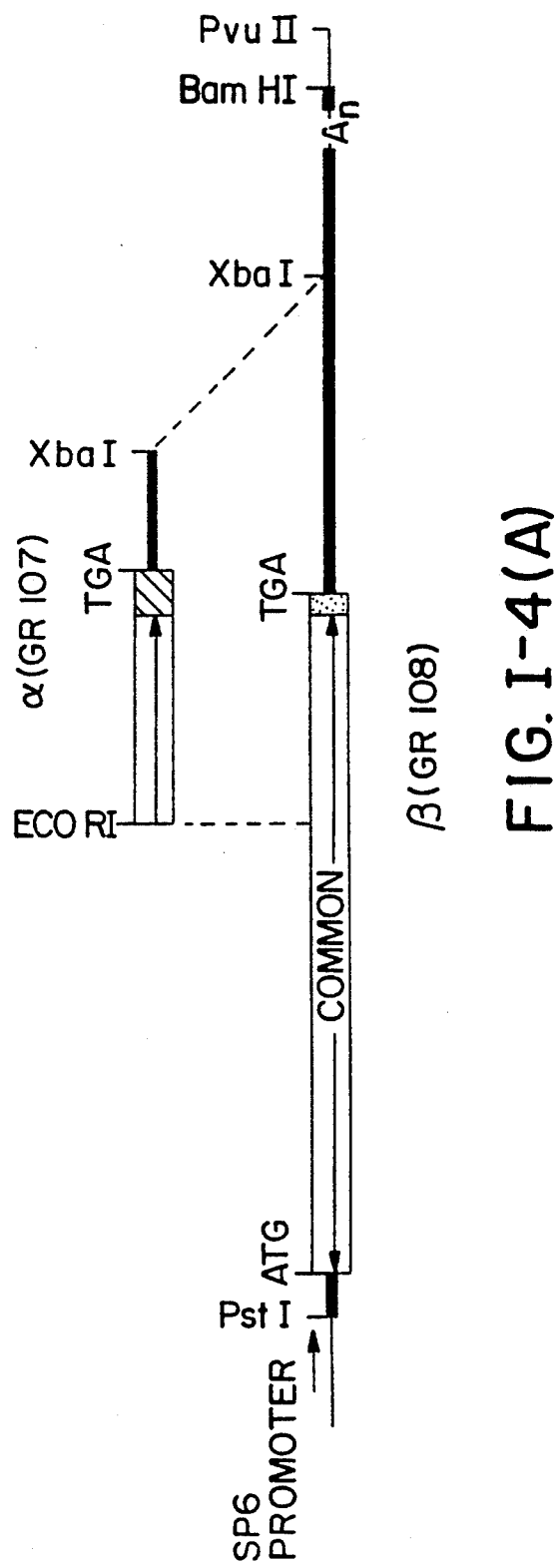
FIG. I-4(A)

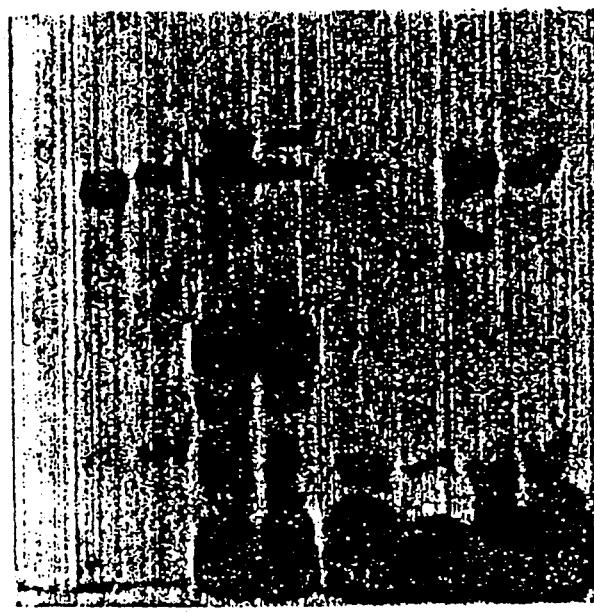
FIG. I-4 (B)

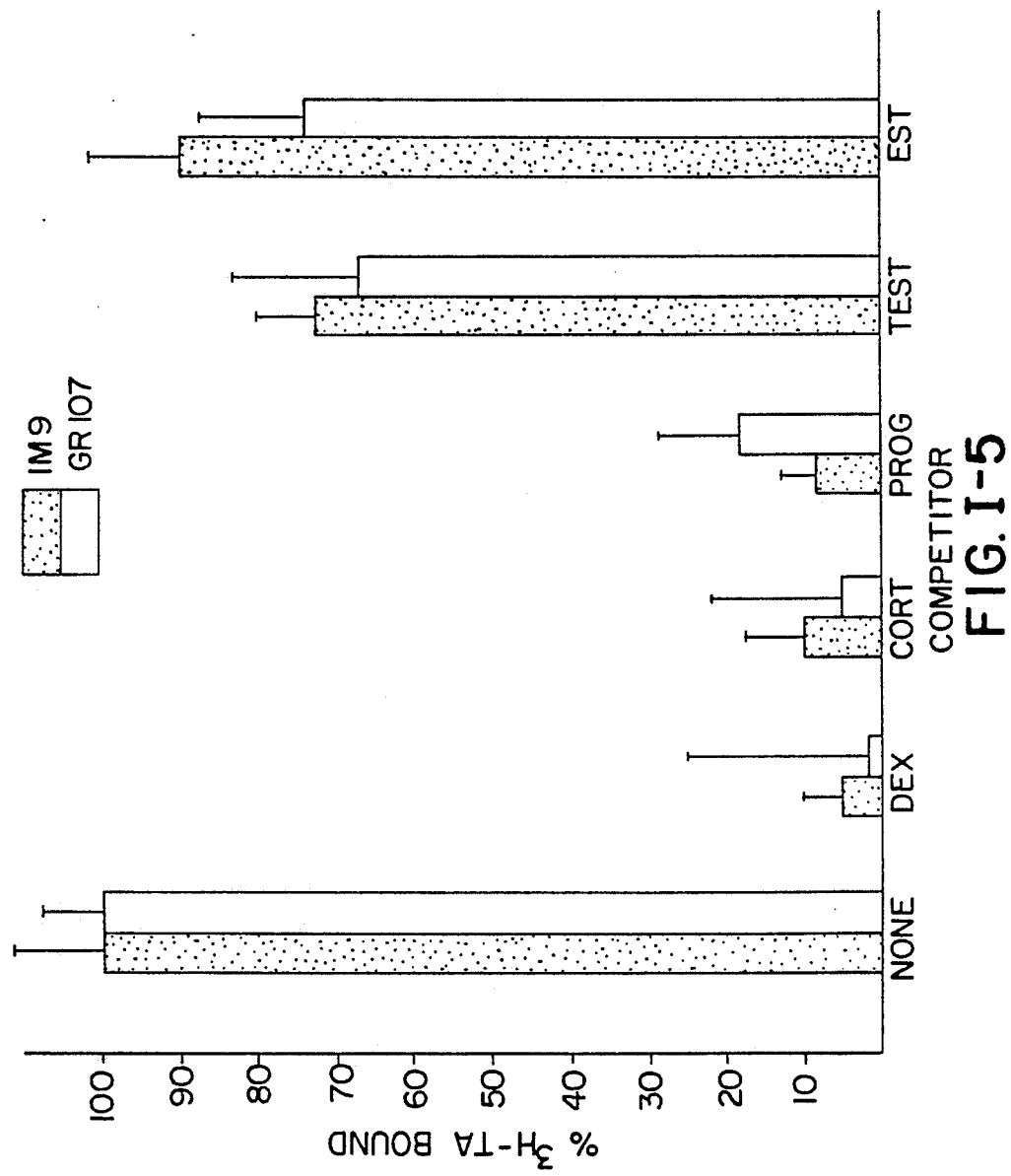

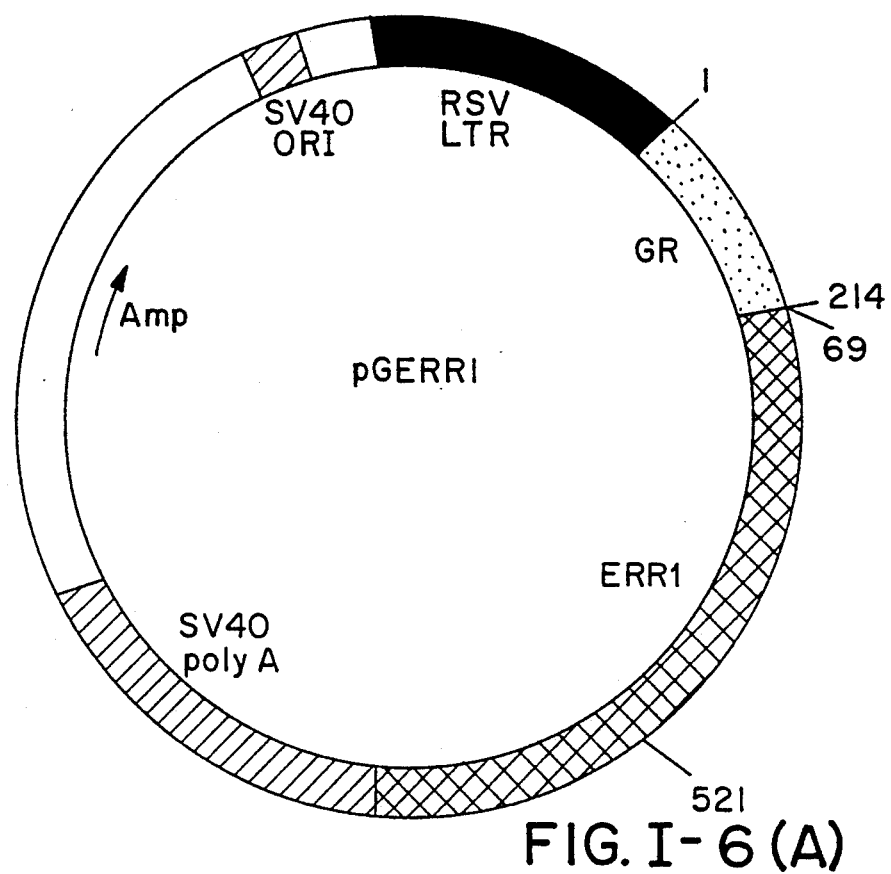
FIG. I-6 (A)
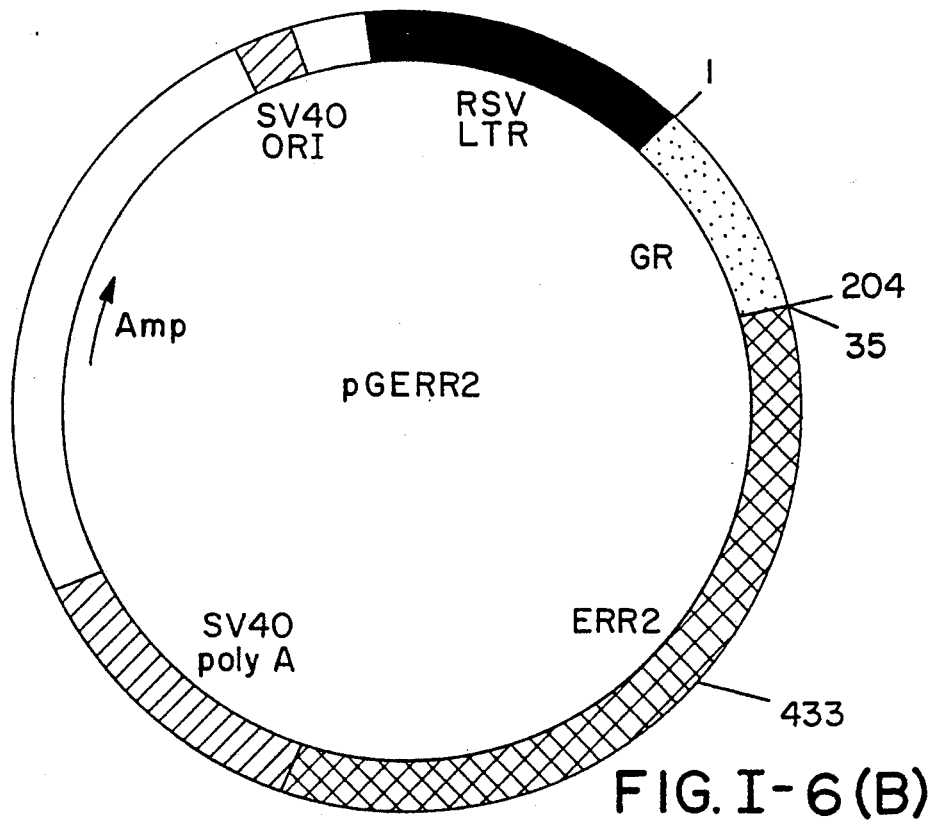
FIG. I-6 (B)

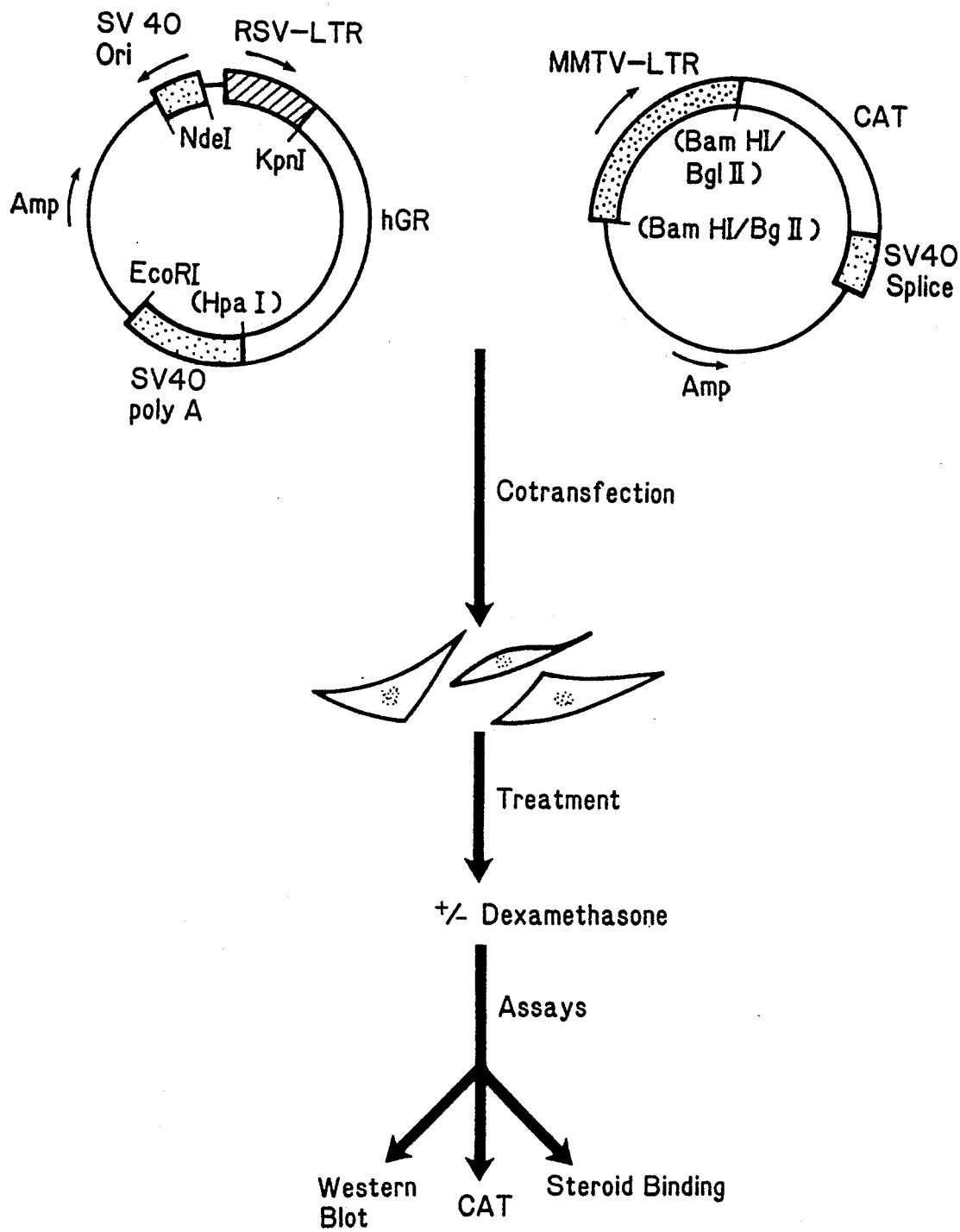
FIG. II-1

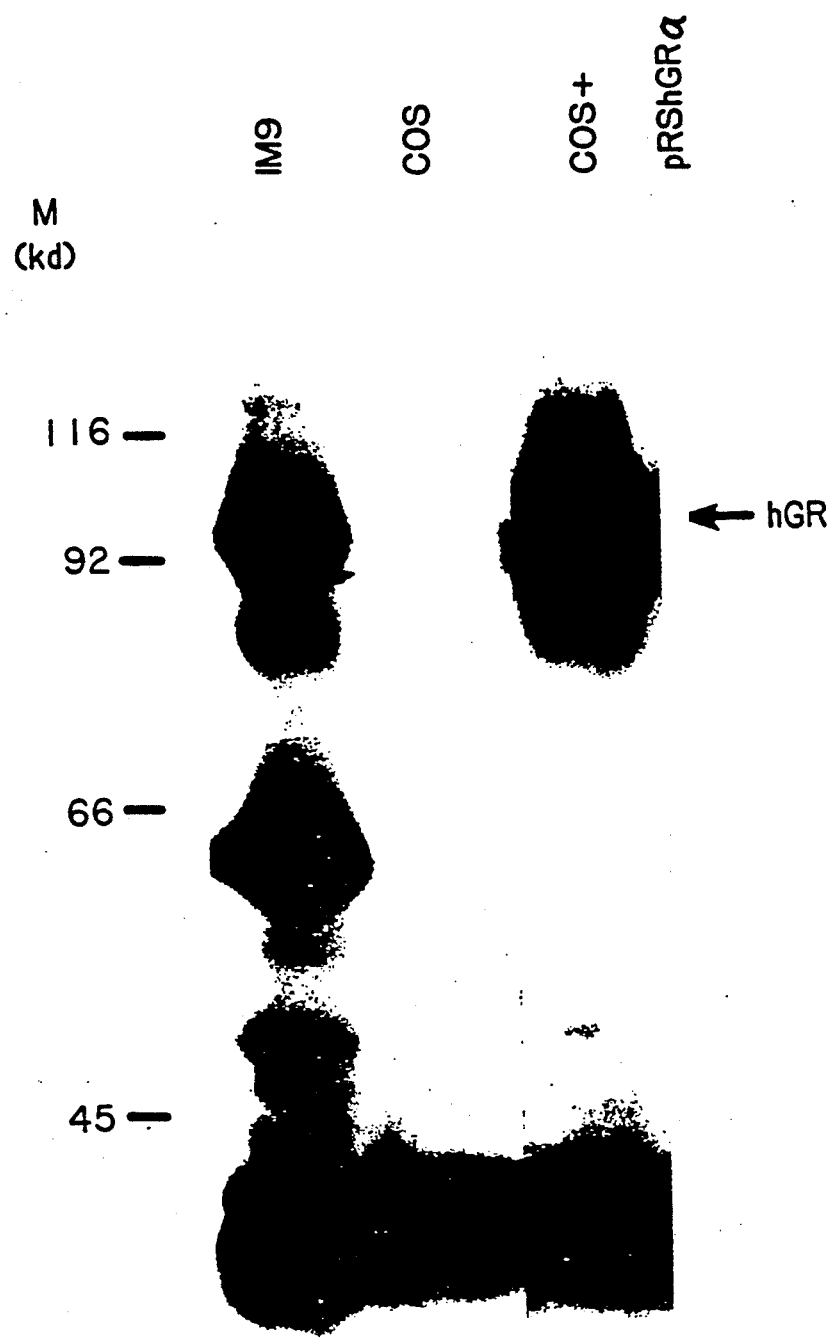
FIG. II-2

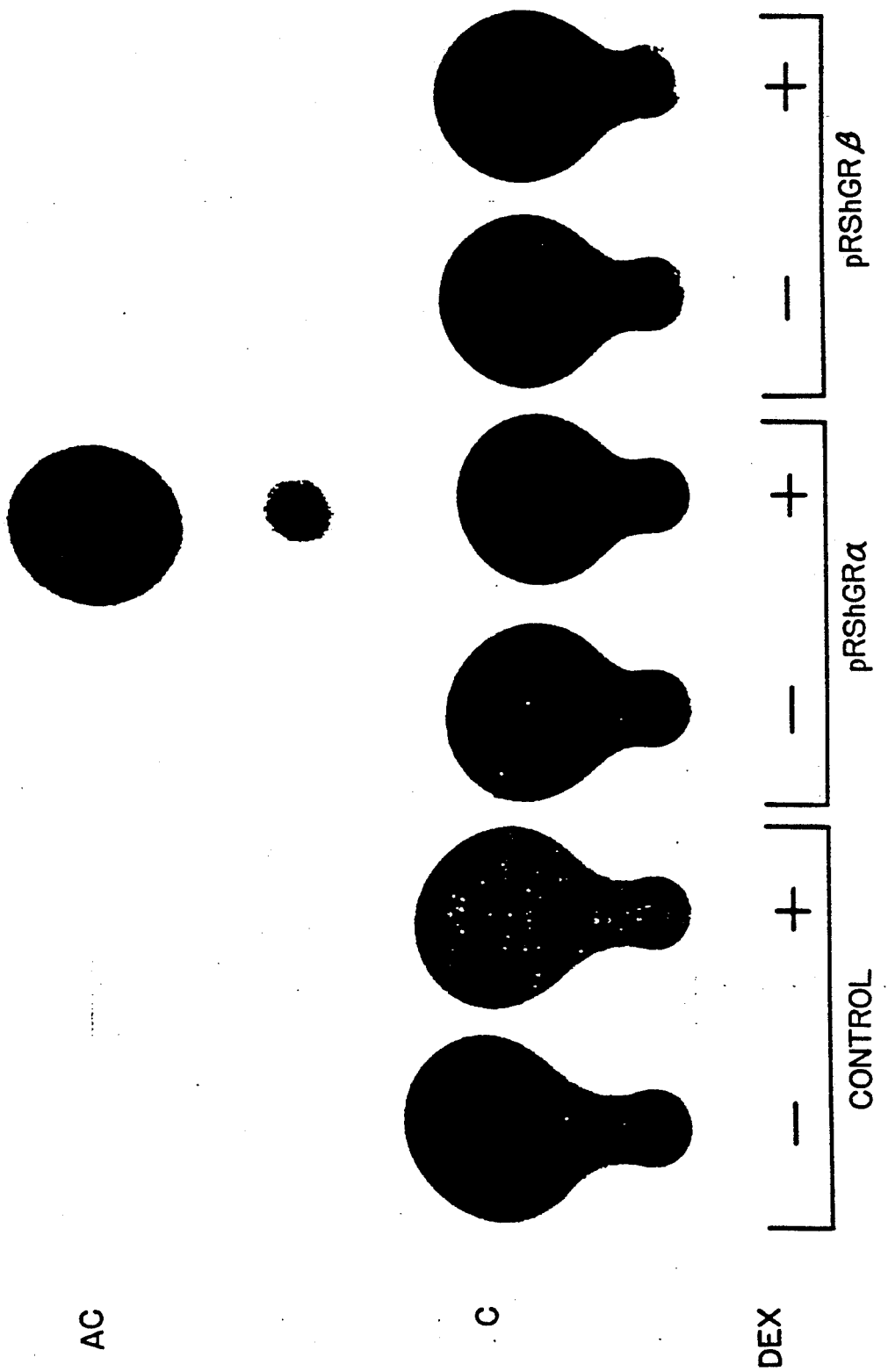

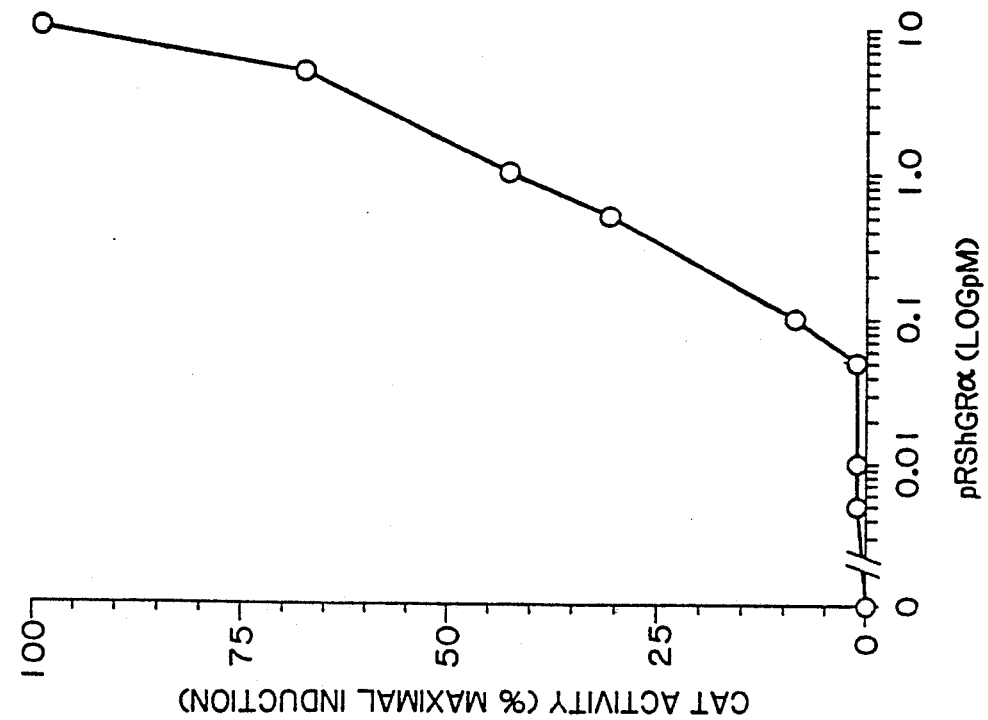
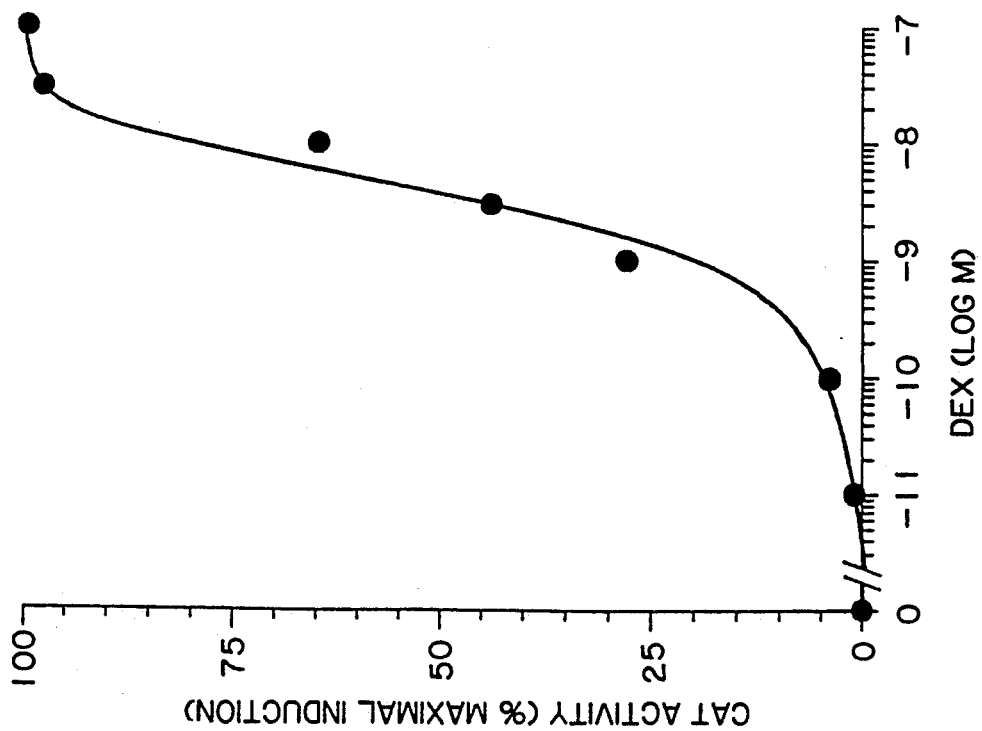
FIG. II-4 (A)
FIG. II-4 (B)

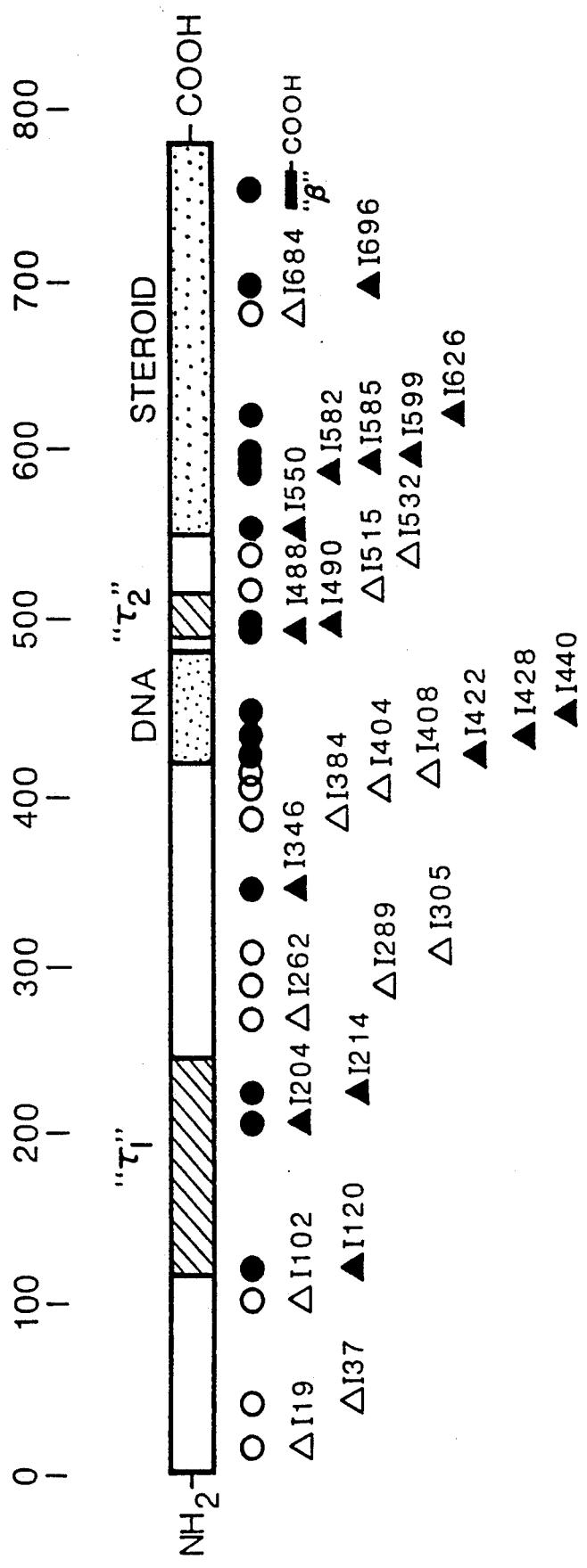
FIG. II-5

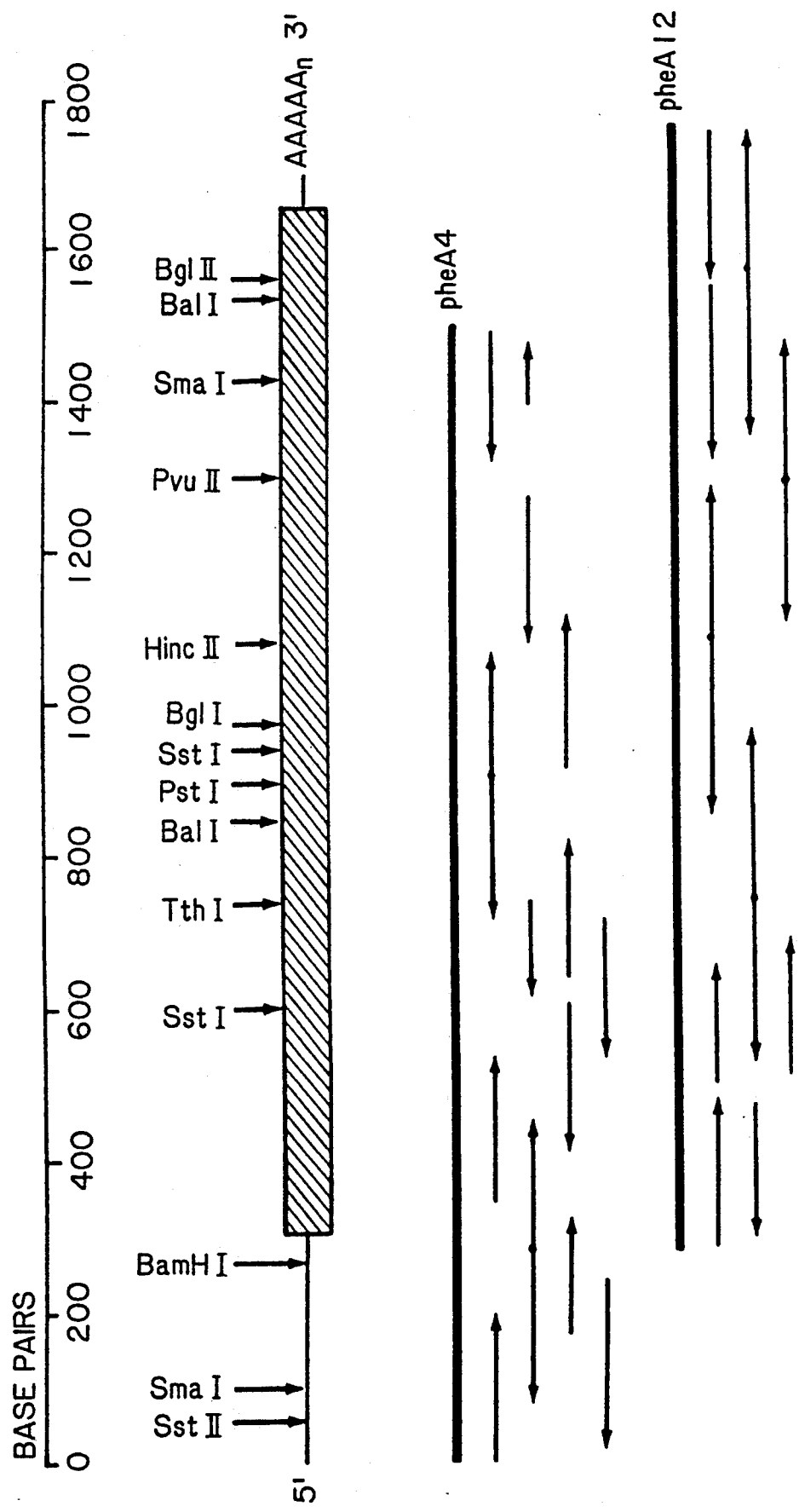
FIG. III-I (A)

```
                                                                                       90
CGGCGGGGATCAACTTTGCATGAATAATGTGAGTGCGCTTGGAAAAGAGACCTCCTGCTCCGCGGGCTCGGGGCAAGAGCCCGCAGGCTA
                                                                                       180
CCTTCCCGGGCAGGGGCGCTCAACCCAGGCACTGGTAATTTGGCTAGAGGACCGCGGGAGGCAGGGGATCTGCGAT
                                                                                       270
TTCCTTCTGGTGGCTGTGCTCCTGCGTGGGTGCCAAGTTCCACACATGATGATTAATGAATAAGAAGGAGATGTCAGTGAAAAAGGGATCCAG
                                                                                       20
            MetThrGluAsnGlyLeuThrAlaTrpLysAspLysHisCysProAspArgGluHis              360
AATGATTACTAACCTATAACCCCAACAGTATGACAGAAAATGGCCTTACAGCTTGGGACAAACCGAAGCACTGTCCAGACCGAGAACAC
            30                              40                        50
AspTrpLysLeuValGlyMetSerGluAlaCysLeuHisArgLysSerHisSerGluThrLeuLysAsnGluGlnSerSer        450
GACTGGAAGCTAGTAGGGATGTCTGAAGCTGCCTTACATAGGAAGAGCCATTCAGAGGAAGAGCACGTTGAAAAATGAACAGTCGTCG
           60                              70                        80
ProHisIleIleGlnThrThrTrpThrSerIlePheHisLeuAspHisAspAspAspValAsnAspGlnSerSerSerAlaGlnThr   540
CCACATCTCATCCAGACCACCTGGACTAGCATATTCCATCTGGACCATGATGATGATGTGAACGACCAGAGTGTCTCAAGTGCCAGACC
           90                              100                       110
PheGlnThrGluGluLysLysCysLysGlyTyrIleProSerTyrLeuAspLysAspLysAspGluLeuCysValValCysGlyAspLysAlaThr  630
TTCCAAACGGAGGAGAAGAAATGTAAAGGGTACATCCCCAGTTACTTAGACAAGGAGGAGCTCTGTGTAGTGTGTGGTGACAAAGCCACC
           120                             130                       140
GlyTyrHisTyrArgCysIleThrCysGluGlyCysLysGlyPhePheArgArgThrIleGlnLysAsnLeuHisProSerTyrSerCys    720
GGGTATCACTACCGCTGTATCACGTGTGAAGGCTGCAAGGGTTTCTTTAGAAGAACCATTCAGAAAAATCTCCATCCTATTCCTGT
           150                             160                       170
LysTyrGluGlyLysCysValIleAspLysValThrArgAsnGlnCysGlnGluCysArgPheLysLysCysIleTyrValGlyMetAla    810
AAATATGAAGGAAAGTGCATAGACAAAGTCACGCGAAATCAGTGCCAGGAATGTCGCTTTAAGAAATGCATCTATGTTGGCATGGCA
           180                             190                       200
ThrAspLeuValLeuAspAspSerLysArgLeuAlaLysArgLysLeuIleGluGluAsnArgGluLysArgArgArgGluLysLeuGln    900
ACAGATTTGGTGCTGGATGACAGCAAGAGACTGGCCAAGAGGAAGCTGATAGAGGAGAACCGGGAGAAAAGACGGCGGGAAGAGCTGCAG
```

FIG. III-1(B)-1

```
                                                                                        230
          210                      220                      LysSerIleGlyHisLysProGluProThrAspGluGluTrpGluLeuIleLysThrValThrGluAlaHisValAlaThrAsnAlaGln
AAGTCCATCGGGCACAAGCCAGAGCCCACAGACGAGGAATGGGAGCTCATCAAAACTGTCACCGAAGCCCATGTGGCGACCAACGCCCAA            990

260
          240                      250                      GlySerHisTrpLysGlnLysProLysPheLeuProGluAspIleGlyGlnAlaProIleGluValAsnAlaProGluGlyGlyLysValAsp
GGCAGCCACTGGAAGCAAAAACCGAAATTTCTGCCAGAAGACATTGGACAAGCACCAATAGTCGAAGTCAATGCCCCAGAAGGTGGAAAGGTTGAC      1080

290
          270                      280                      LeuAlaPheSerHisPheThrLysIleIleThrProAlaIleThrProAlaValValAspPheAlaLeuLysLeuProMetPheCysGlu
TTGGAAGCCTTCAGCCATTTTACAAAAATCATCACACCAGCAATTACCCCAGCAGTGGTGGATTTTGCCAAAAAGTTGCCTATGTTTTGTGAG         1170

320
          300                      310                      LeuProCysGluAspGlnIleIleLeuLeuLysGlyCysCysMetGluIleMetSerLeuArgAlaAlaValAlaArgTyrAspProGluSer
CTGCCATGTGAAGACCAGATCATCCTCCTCAAAGGCTGCTGTATGGAGATCATGTCCCTTCGCGCTGCTGTGGCGCTATGACCCGGAAAGT            1260

350
          330                      340                      GluThrLeuThrLeuAsnGlyGluMetAlaValIleArgGlyGlnLeuLysAsnGlyGlyValValSerAspAlaIlePheAsp
GAGACTTTAACCTTGAATGGGGAAATGGCAGTGATACGGGGTCAGCTGAAAAATGGGGGTGTTGGTGTCAGATGCGCCATCTTTGAC                1350

380
          360                      370                      LeuGlyMetSerLeuSerSerPheAsnLeuAspAspThrGluValAlaAlaLeuLeuGlnAlaLeuPheGluLeuAlaProGly
CTAGGCATGTCTCTGTCTTCTTTCAACCTTGATGACACTGAAGTAGCCGCTCTCCTTCAGGCCGTCCTTCCTGATGTCTTCAGATGCGCCGGGG        1440

410
          390                      400                      LeuAlaCysValGluArgIleGluLysTyrGlnAspSerPheLeuLeuAlaPheGluHisTyrIleAsnTyrArgLysHisHisValThr
CTTGCCTGTGTTGAGAGAATAGAAAAGTACCAAGATAGTTTCCTGCTTGCCTTTGAACACTATATCAATTACCGAAAACACCACGTGACA            1530

440
          420                      430                      HisPheTrpProLeuLeuMetLysValThrAspLeuArgMetIleGlyAlaCysHisSerAlaSerArgPheLeuHisMetLysValGlu
CACTTTTGGCCAAAACTCCTGATGAAGGTGACAGATCTGCGGATGATAGGAGCCTGCCATGCCAGCCGCTTCCTGCACATGAAGGTGGAA            1620

450                      CysProThrGluLeuProProLeuPheLeuGluValPheGluAspEnd
TGCCCCACAGAACTCCTCCCCCTTGTTCCTGAAGTGTTCGAGGATTAGACTGACTGGATTCCTTCCTATAATTCCAAAAAAAAAAAA                1710

FIG.Ⅲ-1(B)-2
```

```
      *  *    *  *  *  *  *  *  *  *  *  *  *  *  *  *  *  *  *  *  *  *  *  *  *  *  *  *  *  *  *
 36 Q  C  V  V  C  G  D  K  A  T  G  Y  H  Y  R  C  I  T  C  E  G  C  K  S  F  F  R  R  T  T  A  S  I    v-erbA
101 L  C  V  V  C  G  D  K  A  A  T  G  Y  H  Y  R  C  I  L  T  C  E  G  C  K  G  V  F  F  R  R  T  A  S  I  I    c-erbA
420 L  C  L  V  C  S  D  E  A  S  G  C  H  Y  G  V  L  T  C  G  S  C  K  V  A  F  F  K  K  R  A  V    hGR
184 Y  C  A  V  C  N  D  Y  A  S  G  Y  H  Y  G  V  W  S  C  E  G  C  K  A  F  F  K  R  S  I    hER
    +     +        +  +     +     +  +  +           +  +        +  +        +  +  +           +

*        *     *  *     *     *  *  *                 *  *                          *  *     *
 66 Q  K  N  L  H  P  T  Y  S  C  T  Y  D  G  C  C  V  I  D  K  I  T  R  N  Q  C  Q  L  C  R    v-erbA
131 Q  K  N  L  H  P  S  Y  S  C  K  Y  E  G  K  C  V  I  D  K  V  T  R  N  Q  C  Q  L  C  R    c-erbA
450 E  G  - -  Q  H  N  Y  L  C  A  G  R  N  D  C  I  I  D  K  I  R  R  K  N  C  P  A  C  R    hGR
214 Q  G  - -  H  N  D  Y  M  C  P  A  T  N  Q  C  T  I  D  K  N  R  R  K  S  C  Q  A  C  R    hER
    +        +     +  +     +           +  +        +  +     +  +  +        +  +     +  +

*        *  *        *  *  *        *                 *                    *  *  *     *
 96 F  K  K  C  I  S  V  G  M  A  M  D  L  V  L  D  D  S  K  R  V  A  K  R  K  L  I  E  E  N    v-erbA
161 F  K  K  C  I  Y  V  G  M  A  T  D  L  V  L  D  D  S  K  R  L  A  K  R  K  L  I  E  E  N    c-erbA
478 Y  R  K  C  L  Q  A  G  M  N  L  E  A  R  K  - - - - - - T  K  K  K  I  K  G  - -        hGR
242 L  R  K  C  Y  E  V  G  M  M  K  G  G  I  R  K  D  R  R  - -  G  G  R  M  L  K  H  - -    hER
       +  +        +  +                       +                          +  +           +

*           *  *        *     *                                *  *  *
126 R  Q  R  R  K  E  E  N  I  K  S  L  Q  H  R  P  S  P  S  A  E  E  W  E  L  I  H  V  V    v-erbA
191 R  E  K  R  R  E  E  L  Q  K  S  I  G  H  K  P  E  P  T  D  E  E  W  E  L  I  K  T  V    c-erbA
500 -  I  Q  Q  A  T  T  G  V  S  Q  E  T  S  E  N  P  G  N  K  T  I  V  P  A  T  L  P  Q  L    hGR
268 -  K  R  Q  R  D  D  G  E  G  R  G  E  V  G  S  A  G  D  M  R  A  A  N  L  W  P  S  P  L    hER
          +                          +                 +                                +

*  *  *  *              *  *  *  *  *              *  *  *     *
156 - - - - - - T  E  A  H  R  S  T  N  A  Q  G  S  H  W  K  Q  R  R  K  F  L  L  E  D  I    v-erbA
221 - - - - - - T  E  A  H  V  A  T  N  A  Q  G  S  H  W  K  Q  K  P  K  F  L  P  E  D  I    c-erbA
529 - - - - - - T  P  T  L  V  S  L  - - - - - - - - - - - - - - -  L  E  V    hGR
297 M  I  K  R  S  K  K  N  S  L  A  L  S  L  T  A  D  Q  M  V  S  A  - - - - - -  L  L  D    hER
                                                              +                          +

*  *     *                 *     *     *  *  *  *  *              *  *     *  *
181 G  Q  S  P  N  A  S  M  L  D  G  D  K  L  -  D  L  E  A  F  S  E  - -  F  T  K  I  I  T    v-erbA
246 G  Q  A  P  I  V  N  A  P  E  G  G  K  V  -  D  L  E  A  F  S  H  - -  F  T  K  I  I  T    c-erbA
539 I  E  P  E  V  L  Y  A  G  Y  D  S  S  V  P  D  S  T  W  R  I  M  T  T  L  N  M  L  G  G    hGR
322 A  E  P  P  I  L  Y  S  E  Y  D  P  T  R  P  F  S  E  A  S  M  M  G  L  L  T  N  L  A  D    hER
    +  +     +  +     +  +        +     +        +  +              +        +

*  *  *  *  *  *  *  *                 *  *        *  *  *  *  *              *  *  *
208 P  A  I  T  R  V  V  D  R  A  K  N  L  P  M  F  S  E  L  P  C  E  D  Q  I  I  L  L  K  G    v-erbA
273 P  A  I  T  R  V  V  D  F  A  K  K  L  P  M  F  C  E  L  P  C  E  D  Q  I  I  L  L  K  G    c-erbA
569 R  Q  V  I  A  A  V  K  W  A  K  A  I  P  G  F  R  N  L  H  L  D  D  Q  M  T  L  L  Q  Y    hGR
352 R  E  L  V  H  M  I  N  W  A  K  R  V  P  G  F  V  D  L  T  L  H  D  Q  V  H  L  L  E  C    hER
    +                 +  +        +     +  +  +        +                 +  +     +  +
```

FIG.III-2a

```
          *  * *  * *  *   *   *  * *  *  * * *    * * *   * * * *
238 C C M E I M S L R A A V R Y D P E S E T - - L T L S G E M A   v-erbA
303 C C M E I M S L R A A V R Y D P E S E T - - L T L N G E M A   c-erbA
599 S W M F L M A F A L G W R S Y R Q S S A N L L C F A P D L I   hGR
382 A W L E I L M I G L V W R S M E H P V K - - L L F A P N L L   hER
            +     -         +   + +        +   + + +       +

*     *   * * * * * * *        * * *              * *
266 V K R E Q L K N G G L G V V S D A - I F D - - - - - - L G K   v-erbA
331 V I R G Q L K N G G L G V V S D A - I F D - - - - - - L G M   c-erbA
629 I N E Q R M T L P C M Y D Q C K H M L Y V S S E L H R L Q V   hGR
410 L D R N Q G K - - C V E G M V E - - I F D - - - - - - M L L   hER
          +                               +

* * *                  * * * * * * * *   * * *
289 S L S A - - - - F N L D D T E V A L L Q A V L L M S S D - -   v-erbA
354 S L S S - - - - F N L D D T E V A L L Q A V L L M S S D - -   c-erbA
659 S Y - - - - - - - - - - E E Y L C M K T L L L L S S V P -     hGR
430 A T S S R F R M M N L Q G E E F V C L K S I I L L N S G V Y   hER
                           + +        + +    + +     +

*    * *   * * * *                     *    * * *
313 - - - R T G L I C V H K I E K C Q - - - - - - - E S Y L L A   v-erbA
378 - - - R P G L A C V E R I E K Y Q - - - - - - - D S F L L A   c-erbA
677 - - - K D G L K S Q E L F D E I R - - - - - - - M T Y I K E   hGR
460 T F L S S T L K S L E E K D H I H R V L D K I T D T L I H L   hER
              + + +    +   + +                              + +

* * * * * * * * *    * * *   *      * * * * * *  * * *
333 F E H Y I N Y R K H N I P H F W S K - - - L L M K V A D L R   v-erbA
398 F E H Y I N Y R K H H V T H F W P K - - - L L M K V T D L R   c-erbA
697 L G K A I V K R E G N S S Q N W Q R F Y Q L T K L L D S M H   hGR
490 M A K A G L T L Q - - - - Q Q H Q R L A Q L L L I L S H I R   hER
         + +                    +      + +  + +        +

* * * *         * * * * * * * * * * * *
360 M I G A Y A A S R F L H M K V E C P T E L ———————18 residues  v-erbA
425 M I G A C H A S R F L H M K V E C P T E L ———————11 residues  c-erbA
727 E V V ————————————————————————————————————————48 residues    hGR
516 H M S ————————————————————————————————————————77 residues    hER
```

FIG.III-2b

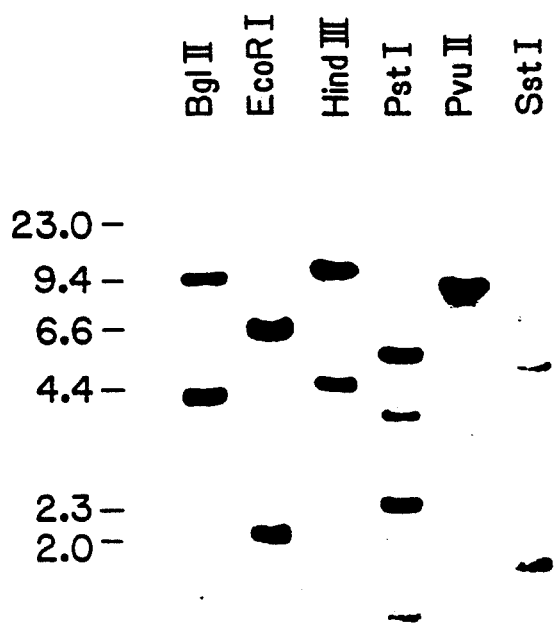
FIG. III - 3 (A)
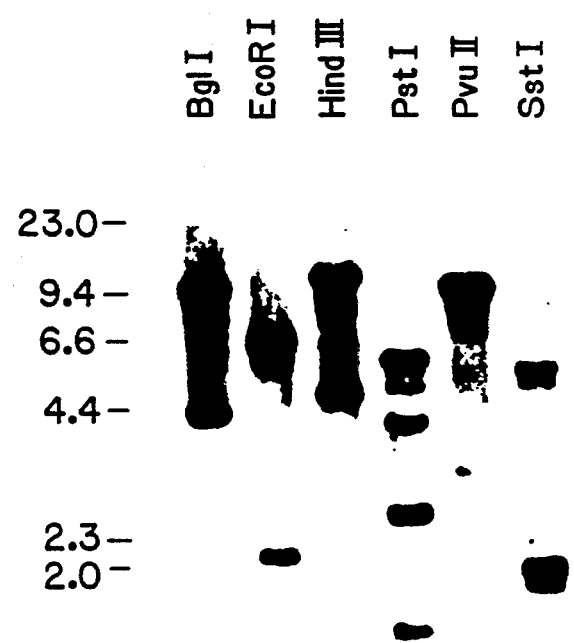
FIG. III - 3 (B)
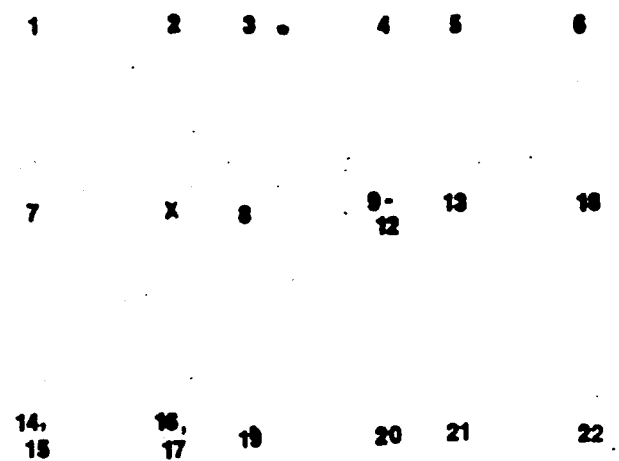
FIG. III - 3 (C)

FIG. III – 4 (A)

1 2 3 4 5

28S —

18S —

FIG. III-4 (B)
1 2 3 4
66kD —
45kD —
30kD —

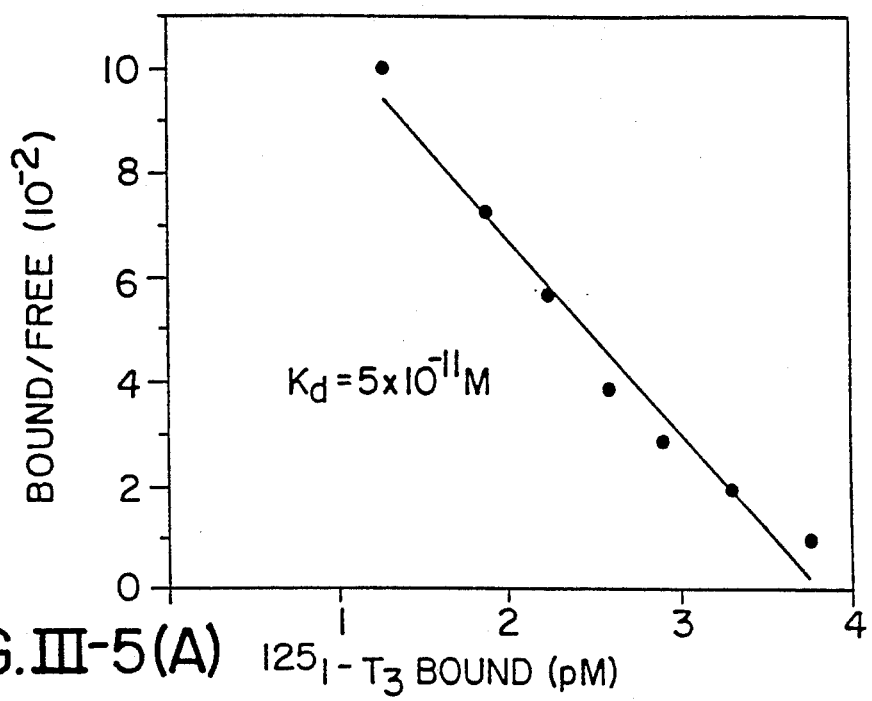
FIG.III-5(A)
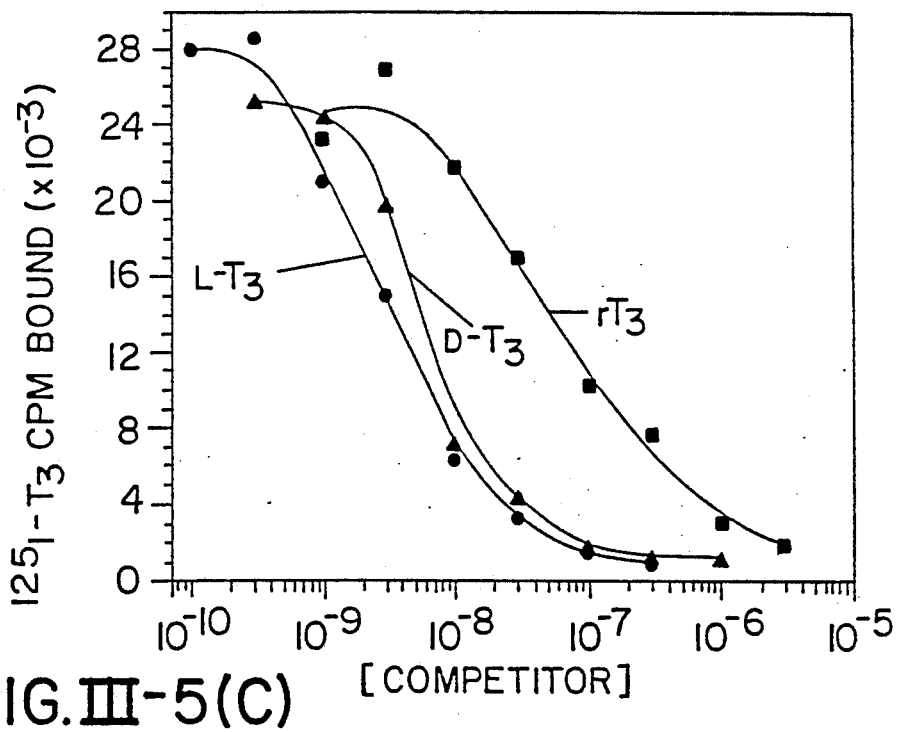
FIG.III-5(C)

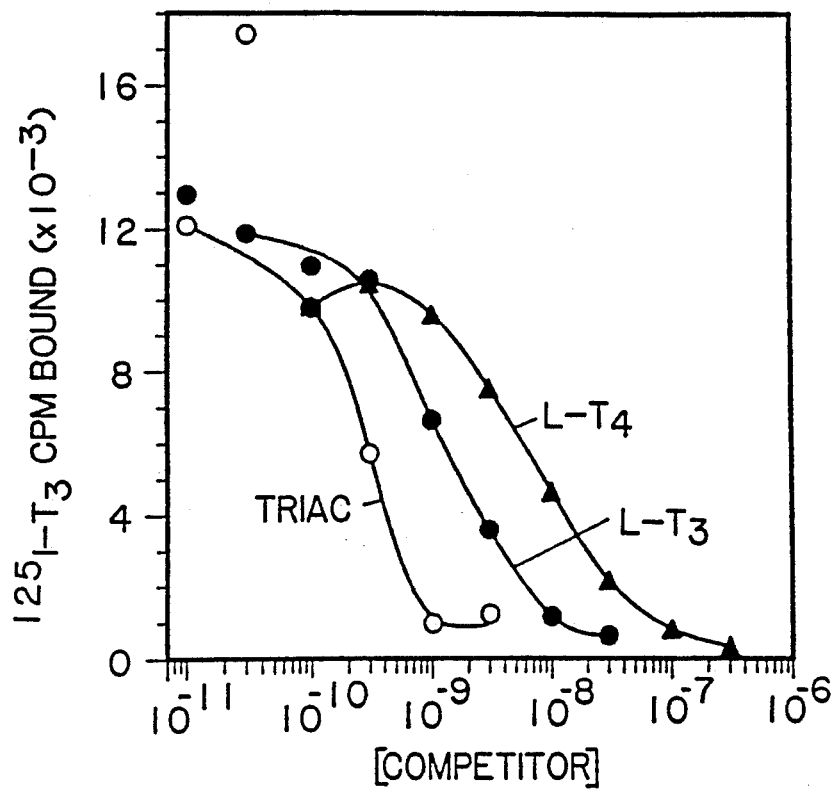
FIG. III - 5 (B)
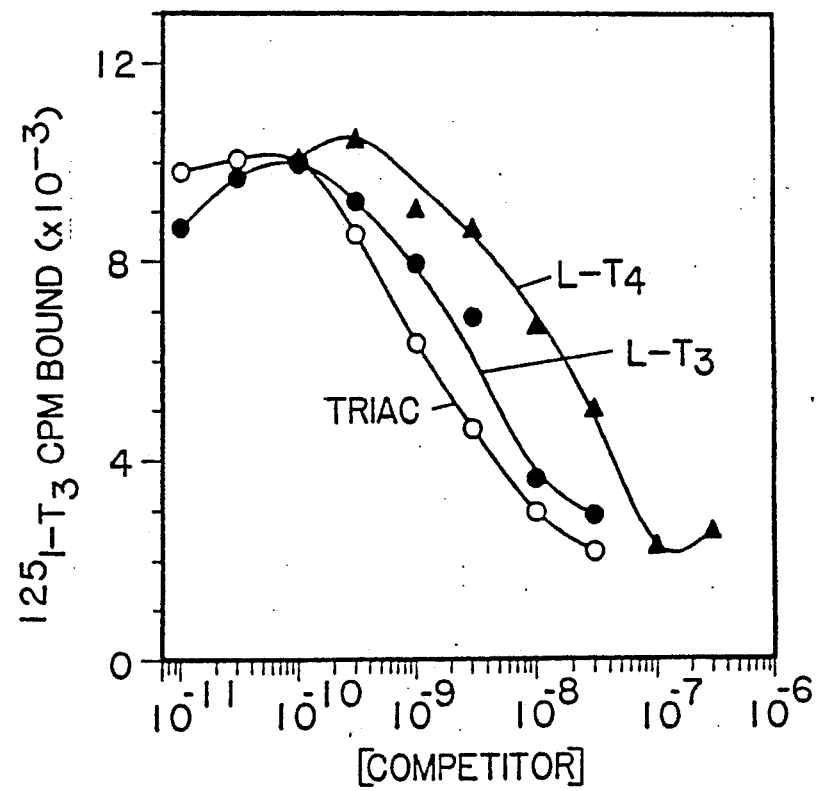
FIG. III - 5 (D)

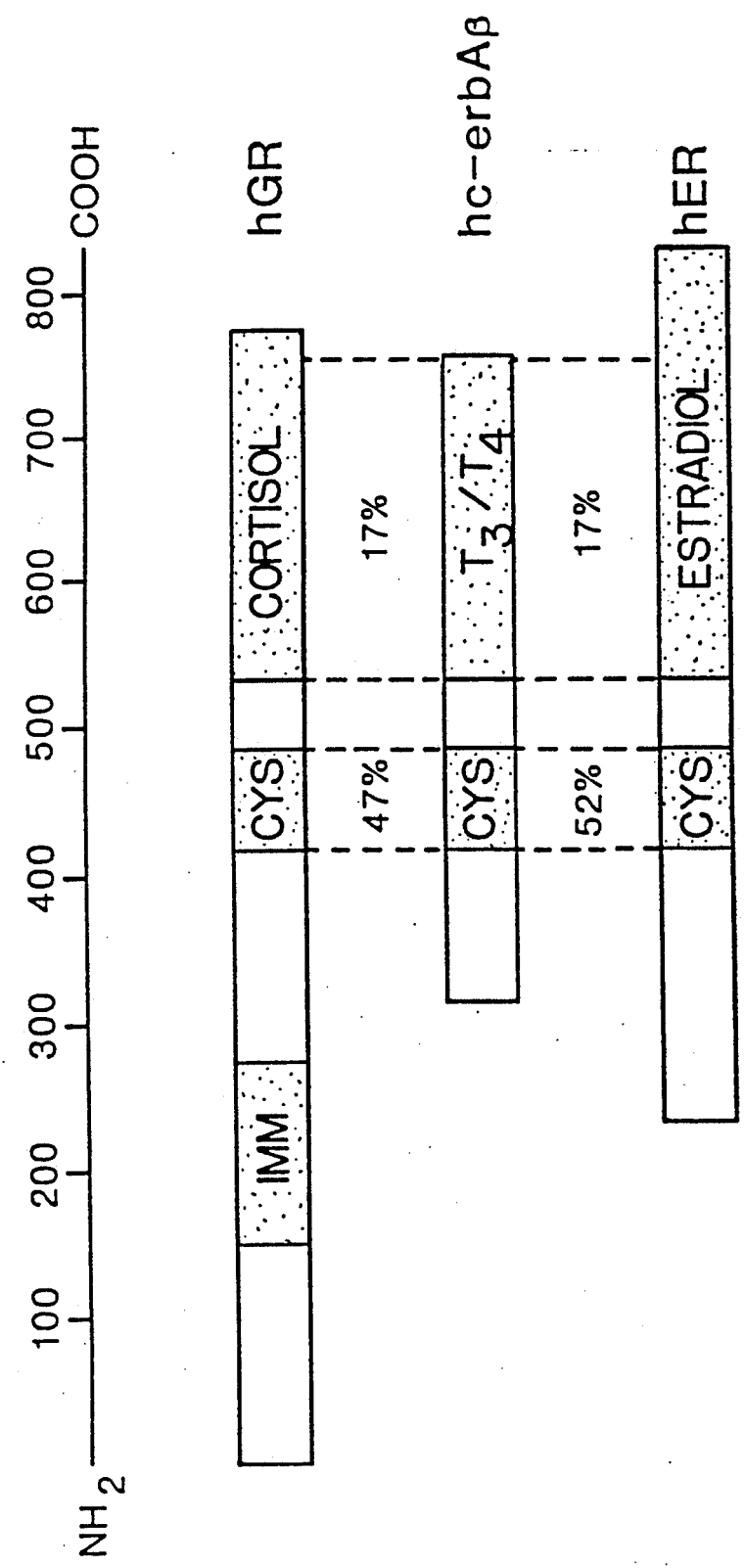
FIG. III – 6

```
                                                                                        90
GAATTGAAGTGAATGGAACAGAAGCAAGGTGGAGTGTGGGTCAGAGTGCAGGTCACCAGATGGAAAGCGA
              MetGluGlnLysProSerLysValGluCysGlySerAspProGluGluAsnSerAlaArgSerProAspGlyLysArg
                      10                        20
                                                                                        180
AAAGAAAAGACGGCCAATGTTCCCTGAAACCATGTCAGGGTATATCCCTAGTTACCTGGACAAAGAGAGCAGTGTGTCGTGT
LysArgLysAsnGlyGlnCysGlyAsnMetSerGlyTyrIleProSerTyrLeuAspLysAspGluGlnCysValValCys
        30                        40                        50
                                                                                        270
GGGACAAGGCAACTGGTTATCACTACCGCTGTATCACTTGTGAGGGCTGCAAGGGCTGCGCCACAATCCAGAAGAACCTCCAT
GlyAspLysAlaThrGlyTyrHisTyrArgCysIleThrCysGluGlyCysLysGlyCysAlaThrIleGlnLysAsnLeuHis
        60                        70                        80
                                                                                        360
CCCACCTATTCCTGCAAATATGACAGCTGCTGTGTCATTGACAAGATCACCCGCAATCAGTGCCAGTGCCGCTTCAAGAAGTGCATC
ProThrTyrSerCysLysTyrAspSerCysCysValIleAspLysIleThrArgAsnGlnCysGlnCysArgPheLysLysCysIle
        90                      100                      110
                                                                                        450
GCCGTGGGACATGCCATGACTTGGTTCTAGATGACTCGAAGCGGTGGCCAAGCGTAAGCTGAAGCAGAACCGGAAGGCGGGCGG
AlaValGlyMetAlaMetAspLeuValLeuAspAspSerLysArgValAlaLysLeuArgGluAsnArgGluArgArgArg
            120                      130                      140
                                                                                        540
AAGGAGGAGATGATCGATCACTGCAGCCTGATCGCAGCAGCCCAGAGCCCACTCCTGAAGAGTGGGATCGATCCACAGAGGCCCATCGC
LysGluGluMetIleArgSerLeuGlnGlnArgProGluProThrProGluLeuTrpAspLeuIleHisIleAlaThrGluAlaHisArg
            150                      160                      170                      180
                                                                                        630
AGCACCAATGCCAGGCCAGCCATTGGAAACAGAGGGGAAATTCCTGCCGATGACATTGGCCAGTCACCCATTGTCTCCATGCCGGAC
SerThrAsnAlaArgGlnAlaAsnGlyLysGlnArgGlyGluIleProAlaAspAspIleGlyGlnSerProIleValSerMetProAsp
                190                      200                      210                      220
                                                                                        720
GGAGACAAGGTGACCTGGAAGCTTCAGCAGCCGGAGTTACCAAGATCATCACCCGGCCATCACCCGTGTGGTGGACTTTGCCAAAAACTG
GlyAspLysValAspLeuGluGluAlaPheSerGluPheThrLysIleIleThrProAlaIleThrArgValValAspPheAlaLysLysLeu
                                220                      230
```

FIG. III – 7a

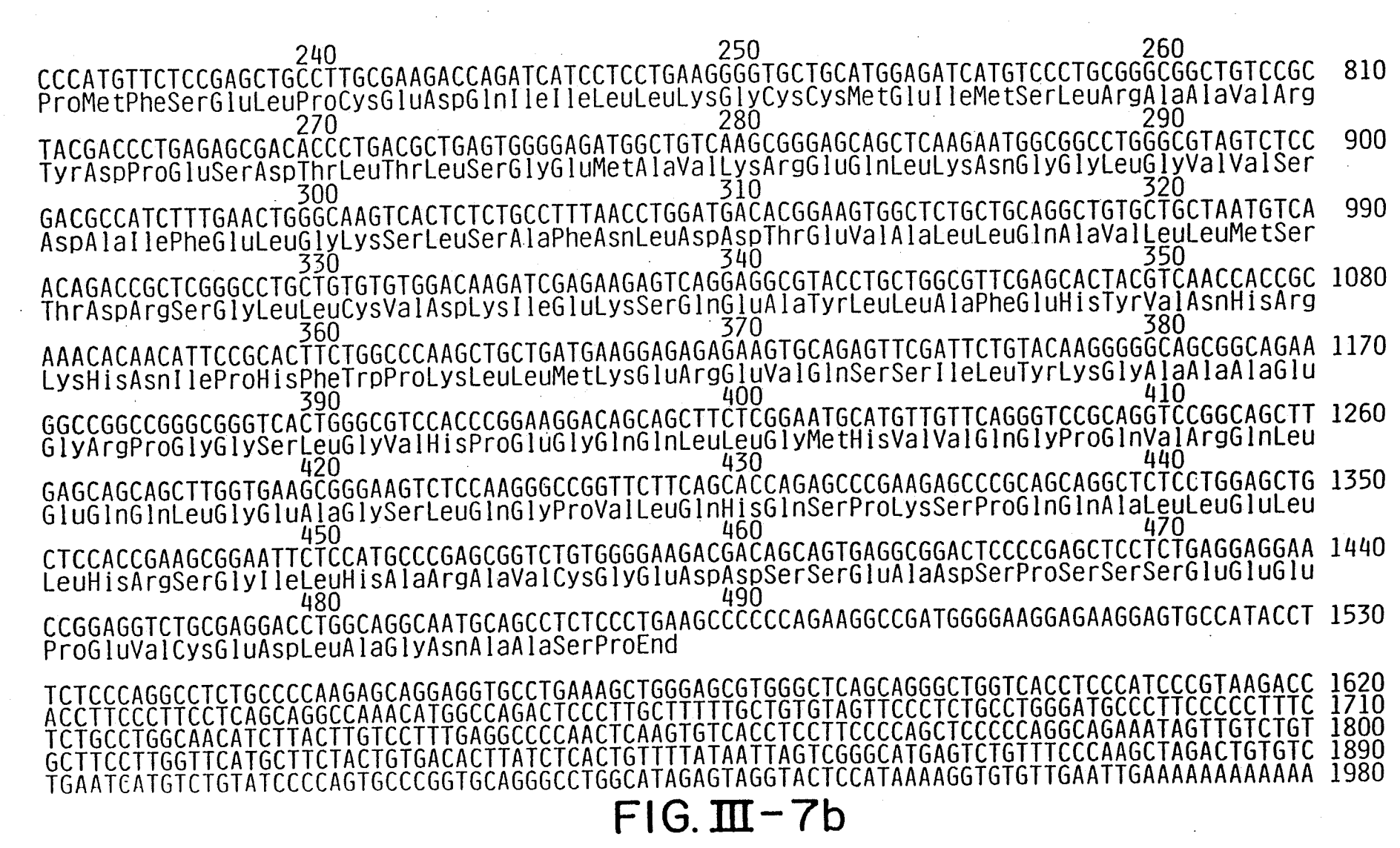

FIG. III-7b

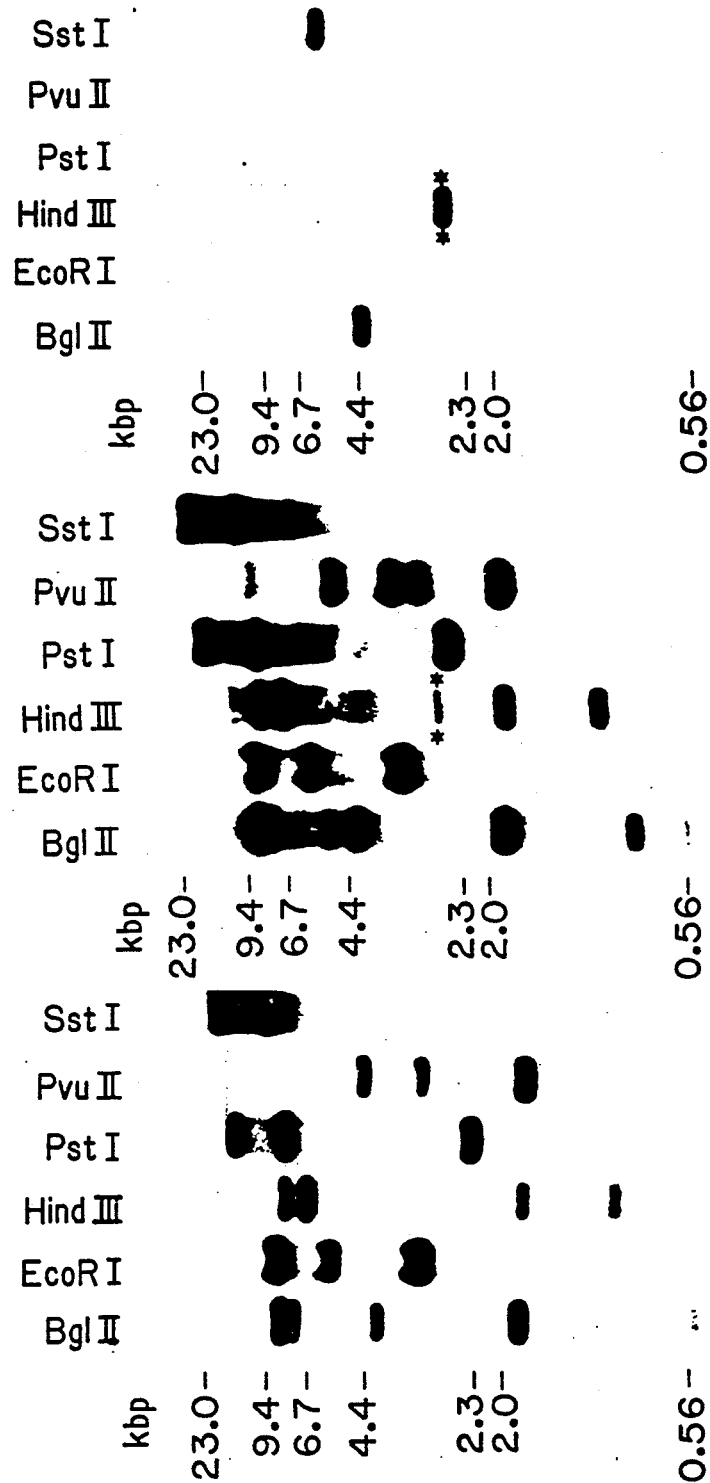

```
                                           SerThrLeuArgSerValSerThrGlySerSerArgProSerLysIleCysLeuValCysGlyAsp
λHGH    93   CAATTTCTTTCCCAG              CTCTACTTTACGAAGTGTTCTTACTGGATCTTCAAGACCTTCAAAAATATGTTTGGTGTGTGGGGAT
                  ― ― ―                      ‖‖‖‖    ‖‖‖    ‖   ‖ ‖ ‖ ‖  ‖‖‖  ‖  ‖‖‖‖‖‖‖‖‖     ‖‖‖‖‖‖ ‖‖‖
hGR   1328   GACCAGATGTAAGCTC    TCCTCCATCCAGTCCTCCAACAGCAACAGGACCACCTCCCAAACTCTGCCTGGTGTGCTCTGAT

GluAlaSerGlyCysHisTyrGlyValValThrCysGlySerCysLysLysValPhePheLysArgAlaValGlu
             GAGGCTTCAGGATGCCATTATGGGGTAGTCACCTGTGGCAGTTGCAAGAAGGTTTTCTTCAAAGAGCAGTGGAAG     GTAAATGTTC    258  λHGH
             ‖‖  ‖‖‖‖‖‖‖‖‖‖ ‖‖‖‖‖‖‖‖‖‖‖ ‖‖   ‖ ‖‖  ‖‖‖‖‖‖‖  ‖‖‖‖ ‖‖  ‖‖‖‖‖‖‖‖‖‖‖‖‖‖        ― ―
             GAAGCTTCAGGATGTCATTATGGAGTCTAACTTGTGGAAGCTGTAAGTTTTCTTCAAAAGAGCAGTGGAAG         GACAGCACAA   1493  hGR

FIG. Ⅳ – I (D)
```

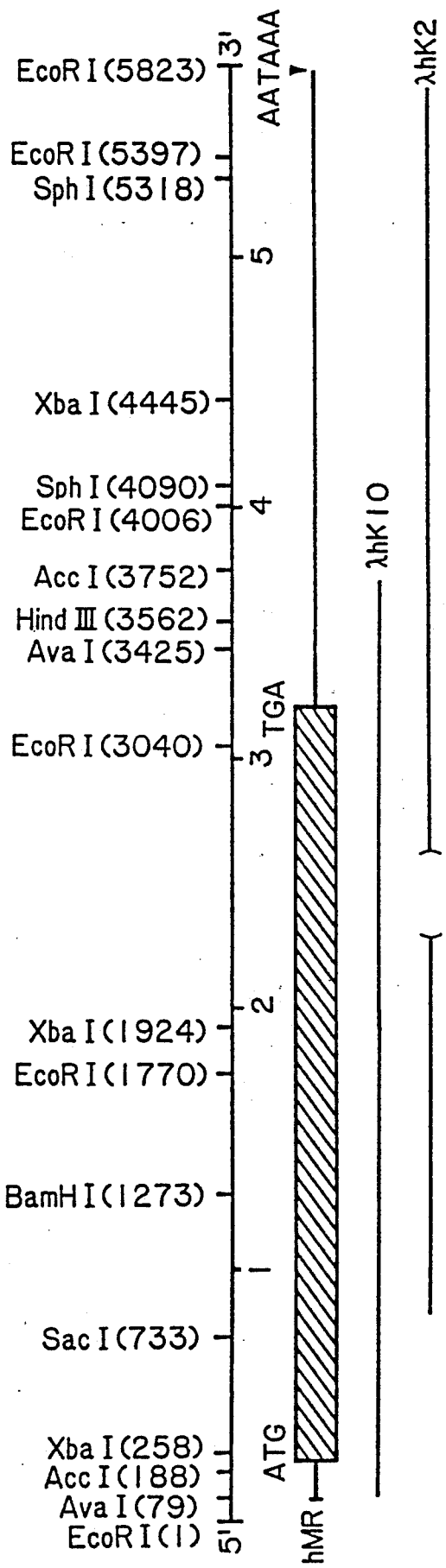
FIG. IV-2 (A)

FIG. IV-2(B)a

```
                                                                              Met
  1 GAATTCCGCGGAGCCAACTTCAGGCTGCTCAGAGGAAGCCCGTGCAGTCAGTCACCTGGGTGCAAGAGCGTTGC
    TGCCTCGGGCTCTCGCTGCAGGGAGCGGCACTCGCTGCCTGGATGTGGTTGGATTTAGGGGGGTCTCCGCA
                                                                              Met
                                                                              GluThrLysGlyTyrHisSerLeuProGlyLeuAspMetGluArgArgTrpGlyLeuValSerGlnValAlaVal
151 GCAGGGTTTCGTGGCGGTGGCAAGCGCTGCAACAGGTAGACGGGAGAGACGGACCCCGGCCGAGGCAGGATG
                     10                      20                      30                      40                      50
    GluThrLysGlyTyrHisSerLeuProGlyLeuAspMetGluArgArgTrpGlyLeuValSerGlnValAlaVal
    GAGACCAAAGGCTACCACAGTCTCCCTGGACTTGAGATATGGAAAGACGGTGGGTCAAGTTTCTCAGGCTGTG
                     10                      20                      30                      40                      50
    GluArgSerLeuGlyProThrGluArgThrAspGluAsnTyrMetGluIleValAsnValSerCysVal
301 GAGCGGTTCTTCCCTGGGACCTACAGAGAGGACCGATGAGAATAACTACATGGAGATTGTCAACGTAAGCTGTGTT
                     60                      70
    SerGlyAlaIleProAsnAsnSerThrGlnSerLysSerLysGlnLeuLeuProCysLeuGlnGln
    TCCGGTGCTATTCCAAACAACAGTACTCAAGGAAGCAAGAGCAAAACAACTCCCTTGCCTTCAGCAA
                     80                      90                     100
    AspAsnAsnArgProGlyIleIleThrSerAspIleLysLysThrGluLeuGluSerLysGluLeuSerAlaThrVal
451 GACAATAATCGGCCTGGGATTTATATCAGTGATATTAAAACTGAGCTGGAATCTAAGGAACTTTCAGCAACTGTA
                    110                     120
    AlaGluMetGlyLeuTyrMetAspSerValArgAspAlaAspSerTyrLeuValLysPheTyrLysGlyHisArgPro
    GCTGAGATGGGTTTATATGGACAGTGTAAGAGATGCTGACAGCTATCTTGTAAAGTTTTACAAAGGACATCGTCCT
                    130                     140                     150
    SerMetSerProAlaLysIleTyrGlnAsnValGlnLeuAsnValCysSerAspSerPheMetSerAspSerPheMetSerAspSerGlySerValAsnGlyValGlyVal
601 AGCATGAGTCCAGCTAAGATTTATCAGAATGTGAACAGTGTTGAACATTTACAAAGGAGTCCGGGAGCTCTGACTCTGATGTCCGTGAATGGTGGCGTC
                    160                     170                     180                     190                     200
    SerThrLeuSerCysValAsnThrProLeuArgSerPheMetSerAspHisCysHisGluLysSerProValCysSerProLeuAsnMetThr
    TCCACTCTAAGTTGTGTGAACACGCCCTTGAGATCATTATGTCTGACTCTGGGAGCTCTGTTGCAGCCCTCTGAACATGACA
                    210                     220                     230                     240
    MetArgAlaIleValLysSerProIleMetCysHisGluLysSerThrThrAlaSerPheGlySerPheProValHis
751 ATGCGCGCCATTGTTAAAAGCCCTATCATGTGTCATGAGAAAAGCACCACAGCTTTGGCAGTTTTCCAGTGCAC
                    210                     220                     230                     240                     250
    SerSerValCysSerProAlaGlyIleAsnSerValSerSerThrThrAlaSerPheGlySerPheProValHis
    TCTTCGGTTTGCAGCCCTGCTGGAATCAACTCTGTCCTCCACCACAGCTTTGGCAGTTTTCCAGTGCAC
                    230                     240                     250
    SerProIleThrGlnGlyThrProLeuThrCysSerProAsnAlaGluAsnArgGlySerArgSerHisSerPro
901 AGCCAATCACCCAGGGAACTCTCGACTGCTGAAAATGCTGAAAATGCTGAAAATGCTGAGGCTCCAGGTCGCACAGCCCT
                    260                     270
```

```
     AlaHisAlaSerAsnValGlySerProLeuSerSerProLeuSerSerProLeuSerSerMetLysSerSerIleSerSerProPro
     GCACATGCTAGCAATGTGGGCTCTCCTCTCAAGTCCGTTAAGTAGCATGAAATCCTCAATTCCAGCCCTCCA
                     280                    290                    300
     SerHisCysSerValLysSerProValSerSerProAsnAsnValThrLeuArgSerSerValSerSerProAla
1051 AGTCACTGCAGTGTAAAATCTCCAGTCTCCAGTCCAATAATGTCACTCTGAGATCCTCTGTGTCTAGCCCTGCA
                     310                    320
     AsnIleAsnAsnSerArgCysSerSerProValAlaAsnAsnAlaPheSerTyrThrAlaSerGlyThrSerProAla
     AATATTAACAACAACTCAAGGTGCCATCTCCAGTCCTGTAAACAATGCCTTCAGCTACACTGCTTCCGGTCCGGCA
                     330                    340                    350
     AlaSerThrValGlySerIleCysSerProValProSerTyrThrAlaSerGlyThrSerAlaGly
1201 GCCAGTACTGTGGGATCTATCTGTAGCCCTGTTCCTAGCTACACTGCTTCTGGCACCTCTGCTGGA
                     360                    370
     SerSerThrLeuArgAspValValGluSerAlaIleSerAsnGlyValThrGlyGlyGlyGlnLeuAsnIleValGlnTyrIleValGlnLeuAsnIleValGlnTyrIleValGlnLeuAsnIleProSerAspSerPheSerValPro
     TCCAGTACACTGCGGATGTGGTTCCCAGTGCCAGACACGCAGGAGAAAGGTGCTCAAGAGGTCCCTTTCCTAAG
                     380                    390                    400
     ThrGluGluValGluSerAlaIleSerAsnGlyValThrGlyGlyGlyGlnLeuAsnIleValGlnTyrIleValGlnLeuAsnIleProSerAspSerPheSerValPro
1351 ACTGAGGAAGTAGAGAGTGCCATCTCAAATGGTGTGACTGGCCAGCTTAATATTGTCCAGTACATAAAACCAGAA
                     410                    420
     ProAspGlyAlaPheSerSerCysLeuGlyLysAsnSerLysIleAsnSerAspSerPheLysGlyAsnProThrValAsnProPhePro
     CCAGATGGAGCTTTTAGCAGCTGCATGTTCAGGGAAGAATAGCAAAATAAATCGGATTCTTCATTCTCAGTACCA
                     430                    440
     IleLysGlnGluSerThrLysHisSerCysSerGlyThrSerPheLysGlyAsnProThrValAsnProPhePro
1501 ATAAAGCAAGAATCAACCAAGCATTCATGTTCAGGCACCTCTTTTAAAGGGAATCCAACAGTAAACCCGTTTCCA
                     450                    460                    470
     PheMetAspGlySerTyrPheSerPheMetAspAspLysAspTyrTyrSerLeuSerGlyIleLeuGlyIleProPro
     TTTATGGATGGCTCGTATTTTTCCTTTATGGATGATAAAGACTATTATTCCCTATCAGGAATTTTAGGACCACCT
```

FIG. IV-2(B)b

```
                                    490                                    500
        ValProGlyPheAspGlyAsnCysGluGlySerGlyPheProValGlyIleLysGluProAspAspGlySer
1651    GTGCCCGGCTTTGATGGTAACTGTGAAGGCAGCGGGATTCCCAGTGGGTATTAAACAAGAACCAGATGACGGGAGC
                                    510                                    520
        TyrTyrProGluAlaSerIleProSerSerAlaIleValGlyValAlaAsnSerGlyGlyGlnSerPheHisTyrArg
        TATTACCCAGAGGCCAGCATCCCTCCTCTGCTATTGTTGGGGTGAATTCAGGTGGACAGTCCTTCCACTACAGG
                                    530                                    540                                  550
        IleGlyAlaGlnGlyThrIleSerLeuSerArgSerAlaArgAspGlnSerPheGlnHisLeuSerSerPhePro
1801    ATTGGTGCTCAAGGTACAATACTTTATCACGATCGGCTAGAGAGACCAATCTTTCCAACACCTGAGTTCCTTCCT
                                    560                                    570
        ProValAsnThrLeuValGluSerTrpLysSerHisGlyAspLeuSerSerArgArgSerAspGlyTyrProVal
        CCTGTCAATACTTTAGTGGAGTCATGGAAATCACACGGCGACCTGTCGTCTAGAAGAAGTGATGGGTATCCGGTC
                                    580                                    590                                  600
        LeuGluTyrIleProGluAsnValSerSerThrLeuArgSerValSerArgValValThrCysGlySerValPhe
1951    TTAGAATACATTCCAGAAAATGTATCAAGCTCTACTTTACGAAGTGTTTCTACTTGTGGATCTGTCAAAGTTTTC
                                    610                                    620
        IleCysLeuValCysGlyAspGluAlaSerGlyCysHisTyrGlyValAlaGlyAlaArgAsnCysIleIleArg
        ATATGTTTGGTGTGTGGGGATGAGGCTTCAGGATGCCATTATGGGGTAGTACGGGCAGCTAGGAATTGCATCATTAGAGATTCGA
                                    630                                    640                                  650
        PheLysArgAlaValGlyGluGlnHisAsnTyrLeuCysAlaGlyAlaArgAsnLeuGlyMetAsnLeuAlaGlyAlaArgLysSerLys
2101    TTCAAAAGAGCAGTGGAAGGGCAACACAACTATTTATGTGCTGGAGCAAATGATTGCATTAGGAGCAGAAAGTCAAAG
                                    660                                    670
        ArgLysAsnCysProAlaCysArgLeuGlnLysCysLeuAlaValGlyMetAlaArgAspAspGlnIleProProPro
        CGAAAGAATTGTCCTGCTTGCAGACTTCAGAAATGTCTTCAAGCTGGAATGAATTAGGAGCACGAAAGTCAAAG
                                    680                                    690                                  700
        LysLeuGlyLeuLysLysGlyIleHisGluGluGluAlaLeuLysGluGlnValAlaProSerValAsnThrAlaLeuValProGln
2251    AAGTTGGGAAAGTTAAAAAGGGATTCACGAGGAGGAGCACAGCAGCCCACACCGCCGGTCAACACAGCACTGGTTCCTCAG
                                    710                                    720
        GlnSerProGluGlyThrThrTyrIleAlaProAlaLysGluProProProPro
        CAAAGCCCAGAGGAAGGGACAACGTACATCGCTCCTGCAAAGGAACCCCCG
                                    730                                    740                                  750
        LeuSerThrIleSerArgAlaLeuThrProSerProValMetValLeuGluAsnIleGluProIleValTyr
2401    CTCTCCACAATCTCACGAGCGCTCACACCTTCCCCCGTTATGGTCCTTGAAACATTGAACCTGAAATTGTATAT
                                                        760                                    770
```

```
      AlaGlyTyrAspSerSerLysProAspThrAlaGluAsnLeuLeuSerThrLeuAsnArgLeuAlaGlyLysGln
      GCAGGCTATGACAGCTCAAAACCAGATACAGCCGAAAATCTGCTCTCCACGCTCAACCGCTTAGCAGGCAAACAG
                     780                              790                              800
      MetIleGlnValValLysTrpAlaLysValLeuProGlyPheLysAsnLeuProGlyLeuGluAspGlnIleThrLeu
2551  ATGATCCAAGTCGTGAAGTGGGCAAAGGTACTTCCAGGATTTAAAAACTTGCCTCTTGAGGACCAAATTACCCTA
                                         810                              820

IleGlnTyrSerTrpMetCysLeuSerSerPheAlaLeuSerTrpArgSerTyrLysHisThrAsnSerGlnPhe
      ATCCAGTATTCTTGGATGTGTCTATCATCATTTGCCTTGAGCTGGAGATCGTACAAACATACGAACAGCCAATTT
                          830                              840                      850
      LeuTyrPheAlaProAspLeuValPheAsnGluGluLysMetHisGlnSerAlaMetTyrGluLeuCysGlnGly
2701  CTCTATTTTGCACCAGACCTAGTCTTTAATGAAGAGAAGATGCATCAGTCTGCCATGTATGAACTGTGCCAGGGG
                                         860                              870

MetHisGlnIleSerLeuGlnPheValArgLeuLeuGlnLeuThrPheGluGluTyrThrIleMetLysValLeuLeu
      ATGCACCAAATCAGCCTTCAGTTCGTTCGACTGCAGCTCACCTTTGAAGAATACACCATGAAAGTTTTGCTG
                             880                              890                900
      LeuLeuSerThrIleProLysAspGlyLeuLysSerGlnAlaAlaPheGluGluMetArgThrAsnTyrIleLys
2851  CTACTAAGCACAATTCCCAAAGGATGGCCTCAAAAGCCAGGCTGCATTTGAAGAAATGAGGACAAATTACATCAAA
                                         910

GluLeuArgLysMetValThrLysCysProAsnAsnSerGlyGlnSerTrpGlnArgPheTyrGlnLeuThrLys
      GAACTGAGGAAGATGGTAACTAAGTGTCCCAACAATTCTGGGCAGAGCTGGCAGAGGTTCTACCAACTGACCAAG
                            930                              940                      950
      LeuLeuAspSerMetHisAspLeuValSerAspLeuLeuGluPheCysPheTyrThrPheArgGluSerHisAla
3001  CTGCTGGACTCCATGCATGACCTGGTGAGCGACCTGCTGGAATTCTGCTTCTACACCTTCCGAGAGTCCATGCG
                                         940                              970

LeuLysValGluProPheProAlaMetLeuValGluIleIleSerAspGlnLeuProLysValGluSerGlyAsnAla
      CTGAAGGTAGAGTTCCCGCAATGCTGGTGGAGATCATCAGCGACCAGCTGCCCAAGGTGGAGTGGGGGAACGCC
                            980                  984
      LysProLeuTyrPheHisArgLysEnd
3151  AAGCCGCTCTACTTCCACCGGAAGTGACTGCCCGTGCCCAGAGAACTTTGCCTTAAGTTTCCCTGTGTTGTTC
      CACACCCAGAAGGACCCAAGAAAAACCTGTTTTAACATGTGATGGTTGATTCACACTTGTTCAACAGTTTCTCAA
```

```
3301  GTTTAAAGTCATGTCAGAGGTTTGGAGCCGGGAAAGCTGTTTTCCGTGGATTTGGCGAGACCAGAGCAGTCTGA
3451  AGGATTCCCCACCTCCAATCCCCAGCTTAGAACATGTCCTGTTCCTCGGCTTAGAAGCCATATCTAGTC
3601  AATAACTCTGATTTTGATATTTCACAGATGGAAGACGTTTAAGACTATTCTTAACTATGCCGTGTAGTTTCTGGTATCGTTCGCT
3751  TGTTTTAAAGGGTCAAGGACTACTTCTTTGTTATTAAAGACGTTTAAAGCTTTAAACAAAAATTAAAAAACTCGCCTCGTCCGCATCTGT
3901  ATGGGCATTAACAGAACTCGTGGGCCAGCAGCTGCCTTAGAACTGCTTAATTTTTGCAGCAGTCCTTCTGCATCACTG
4051  GTATAACACACTCGTTAGCGTCCAGCTTCCATTCTTACAAATAAGGATATTTTGAAAGAATATTTTGAAGATACAAAAAATCTTTAATGGTT
4201  TCTAGTATCTATTGTGTTGGCTTTACAAATAAGGTATAAGGATATTTTGAAGAATGTCCTGCATAATCTAATTTTTGCAGACACATACTATTTAAGTACACTGAA
4351  AATTATGAAGGACCTGAAATAAGTATTTTTGAAAGAATGTCCTGCATAATCTAATTTTTACTTTTGTTCTTGTAAATAACCACTGAA
4501  AATAGGATGAATTTTTTTGTAAGCTTCATAATCTTACTTTGTGTTTTCGTCATCGGGAATGACAACTCGTTGTTCGCTTGCGGTGTCTG
4651  ACAAGGTAATTTTAGCTTGAAACCTTTTTTGTAAGCTGCCTTCCATCGGGGAGTGCTGGGAACTTGATGGCTCAGAGCC
4801  AAAGCTGTGCCTTTGTCTCAGCACACGTTCATTTGGCTTCATTTCTGACCACACACAGATCAGATGGAACTTCCATGCACTCTCTCCTGT
4951  ACCTCTTCGGTTCTGCTAGGATCAGATCAGATTGGGAAAGGATTTTTATCTGATCGGAGAGTGAGATTACGAGATCAGATTGGGAAAGGATTTCAACATAAAAA
5101  TTTGTGGGACTCCTGGAAGTCTCTGGGGAAGCTGCACAATGGAAAGGAGACAACTGCACAATGGAACCGGTGGAGAATGGCAATGGATGCTGATGTTTGGCACTGAATGACATGGCTTTG
5251  CAGCTCCTGTGTTTCCCATTTTCCCTGGGGAAAAGGATGGCAAGCTGCCCCATCTGTTGGGAAATAAGGTTTCATTAATGCAGAGGAAACCTGTGA
5401  TGCCTCGGTTCTGCTGGAAAGACTAGGAAGGAAACCAATAACATATAAAATGCCAGGAGCAATTTCAGAGGTCAATTATAAATACAGCAGATCTTTA
5551  GCATCTCTTCCCCATTTCCCTGGGACGCGCCTTAAAATGCAGGAAGTCTTCAGATGATGAAAGCATGACAGCATGAAAATGAGAAT
5701  TAAAGATCCAGGATATATGCGCTAAAGTTTCGGGAAATCATCGAGGCATGATGCACTACCTTTATTATTTTATT
5851  GTTTAGATTTTTGCCCAAATGGTAGGTAGGTAGGTCACTAAACTTTTGCTGTCCAGCAAGGATGGCAACAATATAATAAACTATTTTCT
6001  TATCAGAGGCAAGATGGCCAAATCTTTTAAAAATGGATGTAGCTCAGGCAACATTGTCATAAATTGCAAGAGGAAACCTGTGA
6151  CCAGGGTTCACCTCAGGGAGTCTTTTACAGTTGCAATTGCACAGCTTTGAAGCAATTTATATGGCAGATCTTTA
6301  AAGCTGCACTGCAACTTACGGTGCACAGGAACAAATGGCTTAGTTCAGAATTGTAGATATCTAAAAATCTGTGA
6451  AATACAGTTGCTAGCAAAACAAACAGGTTTGGGCTTATATGTAGAGAACACTAATTAAGAATTCCTAAATGTTTTATAAAGTTACTGCCCTTT
6601  GGAGTTGCTACTTAACCTAGAAACAAATGGTTTGATTAATTTTTGATTAAAGAAAACACTACCTAATAAGTTGCTTGTACATCTTTATGCAAGA
6751  TCTGTGACTTACTTCTCTGTCTATAATTAAGAAAACACTAATTAAAGTTTAAAATGGAGCAATTTATATGGCAGATCTTTA
6901  GTCCAAATTGTCTTCATATAATTTGCAGGTAACTAATTAAGTTGTACCATATCCTTCTTAAAAATCCTTAAAAAAAAAAAAAAAC
7051  ATATGTCTGTCTTTGCAAAGGACTGTAAGACTGATTACAAGCAGATTACAATAAACCTTTACTTTTACTTTTACTTTTACTTTTGGTTACTTTTAAAAAAAAAAAAAAAA
```

FIG. IV-2(B)e

```
hMR  548  SSFPPVNTLVESWKSHGDLSSRRSDGYPVLEYIPENVSSSTLRSVSTGSS
              ||||   ||  | |        |       |
hGR  374  NLTSLGTLNFPGRTVFSNGYSSPS.......MRPDVSSPPSSSSTATTG
                              ┌── DNA ──┐
                              ↑
hMR  598  RPSKICLVCGDEASGCHYGVVTCGSCKVFFKRAVEGQHNYLCAGRNDCII
          |||| |||||||||||||||| ||||||||||||||||||||||||||
hGR  416  PPPKLCLVCSDEASGCHYGVLTCGSCKVFFKRAVEGQHNYLCAGRNDCII
                         └── DNA ──┘
                              ↓
hMR  648  DKIRRKNCPACRLQKCLQAGMNLGARKSKKLGKLKGIHEEQPQQQQPPPP
          |||||||||||| ||||||||||   |||| |||  
hGR  466  DKIRRKNCPACRYRKCLQAGMNLEARKTKKKIKGIQQATTGVSQ......
                                        ┌── STEROID
                                        ↑
hMR  698  PPPPQSPEEGTTYIAPAKEPSVNTALVPQLSTISRALTPSPVMVLENIEP
                                       ||| ||    |||| |||
hGR  510  .......ETSENPGNKTIVPATLPQLTPTLVSLLEVIEP
```

FIG. IV - 3a

```
hMR  748  EIVYAGYDSSKPDTAENLLSTLNRLAGKQMIQVVKWAKVLPGFKNLPLED
           ||||:|||||:|||:|||||||||||||:||||||:|||||||||||:|
hGR  542  EVLYAGYDSSVPDSTWRIMTTLNMLGGRQVIAAVKWAKAIPGFRNLHLDD hMR  798  QITLIQYSWMCLSSFALSWRSYKHTNSQFLYFAPDLVFNEEKMHQSAMYE
           |:||:||||| ||||| ||||||:|||:|||||||||  | :|| |  |
hGR  592  QMTLLQYSWMFLMAFALGWRSYRQSSANLLCFAPDLIINEQRMTLPCMYD hMR  844  LCQGMHQISLQFVRLQLTFEEYTIMKVLLLLSTIPKDGLKSQAAFEEMRT
           || ||:| || |||||||:||| :| |||||::|||||||||| ||: |
hGR  642  QCKHMLYVSSELHRLQVSYEEYLCMKTLLLLSSVPKDGLKSQELFDEIRM hMR  898  NYIKELRKMVTKCPNNSGQSWQRFYQLTKLLDSMHDLVSDLLEFCFYTFR
           ||||||| :|::||:||:|||||||||:|||||||:||::||:|| ||
hGR  692  TYIKELGKAIVKREGNSSQNWQRFYQLTKLLDSMHEVVENLLNYCFQTF hMR  948  ESHALKVEFPAMLVEIISDQLPKVESGNAKPLYFHRK      984
           :| || :|||:||:||: :|||:|  |  |:|||:|
hGR  741  LDKTMSIEFPEMLAEIITNQIPKYSNGNIKKLLFHQK      777
```

FIG. IV — 3b

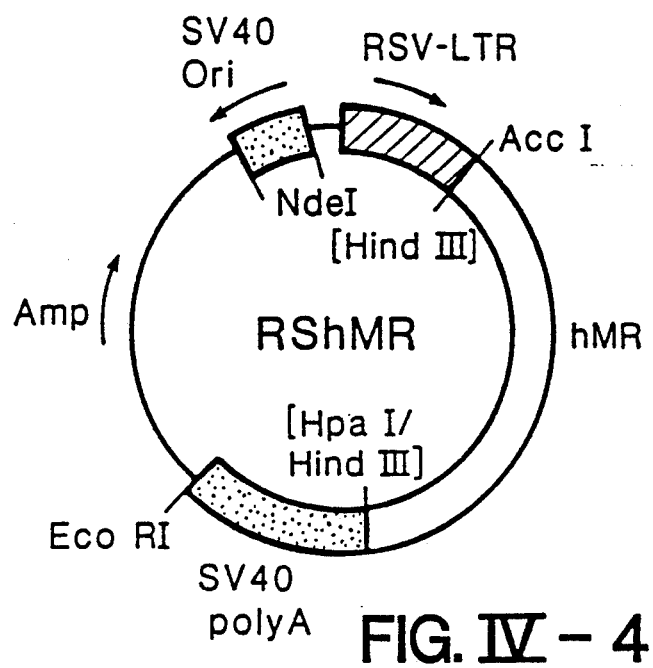
FIG. IV – 4 (A)
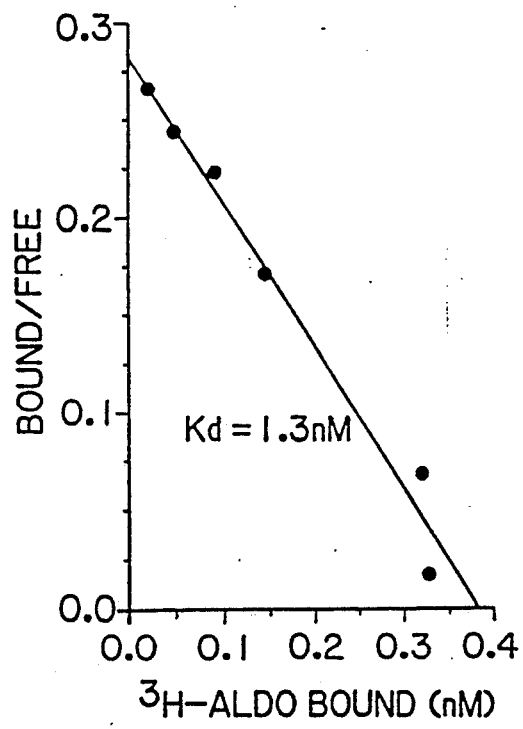
FIG. IV – 4 (B)

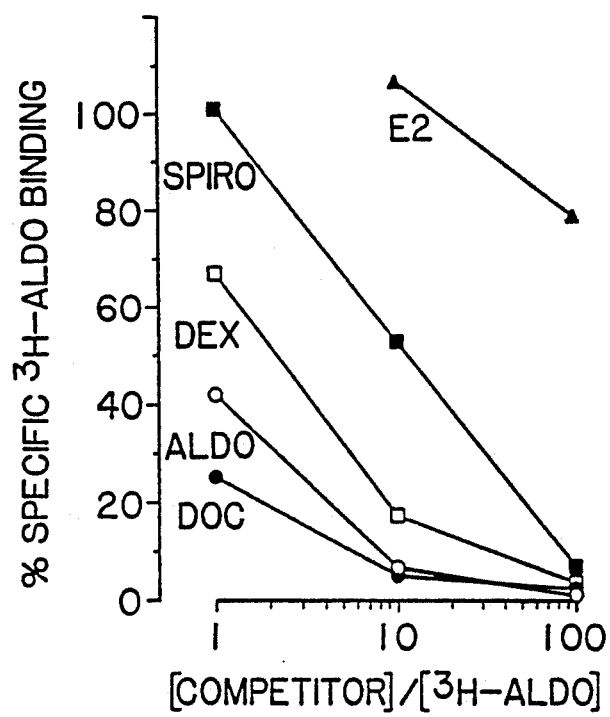
FIG. IV - 4 (C)
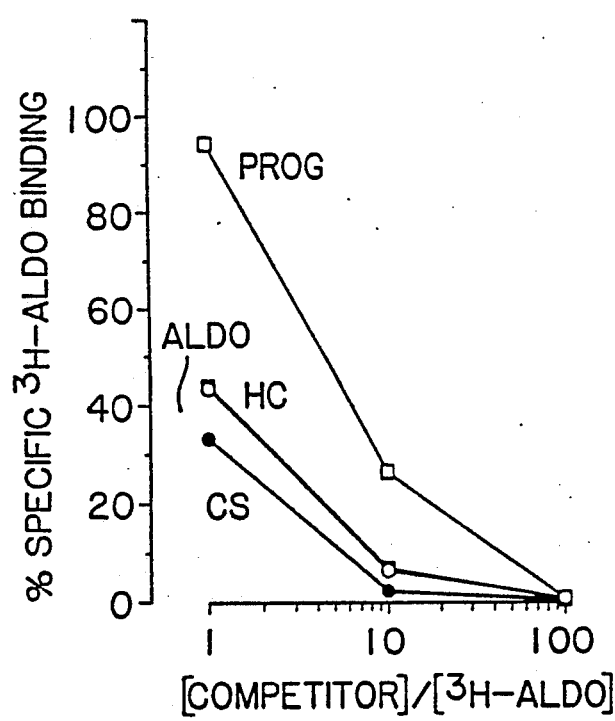
FIG. IV - 4 (D)

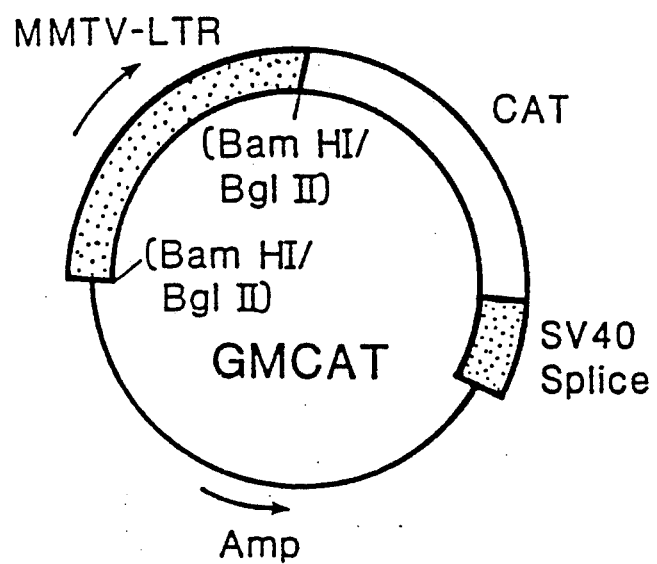
FIG. IV-5(A)

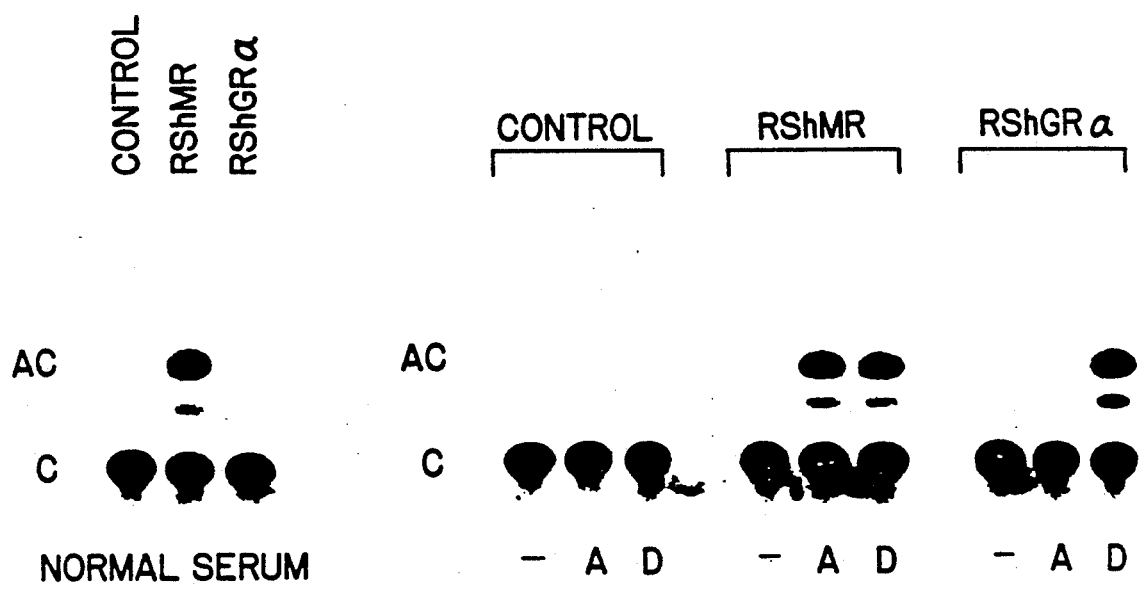
FIG. IV-5(B)
FIG. IV-5(C)

FIG. IV - 6

MUSCLE
SPLEEN
LIVER
HEART
PITUITARY
HIPPOCAMPUS
BRAIN
GUT
KIDNEY

28S --

18S --

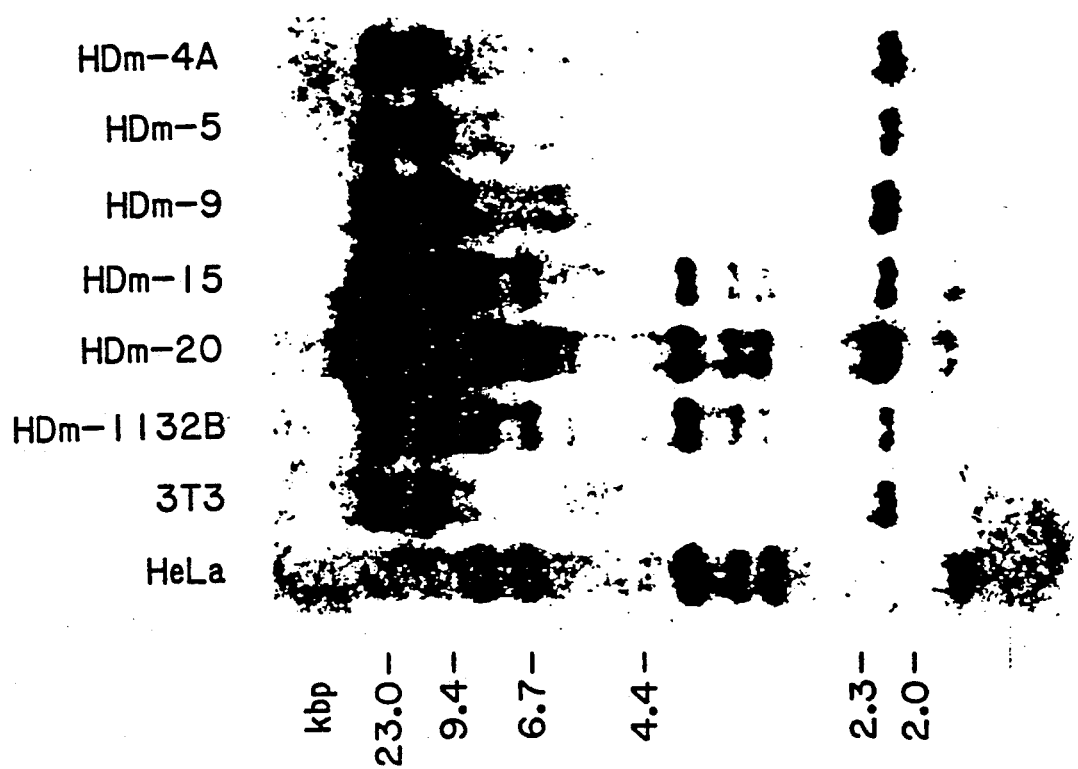
FIG. IV - 7

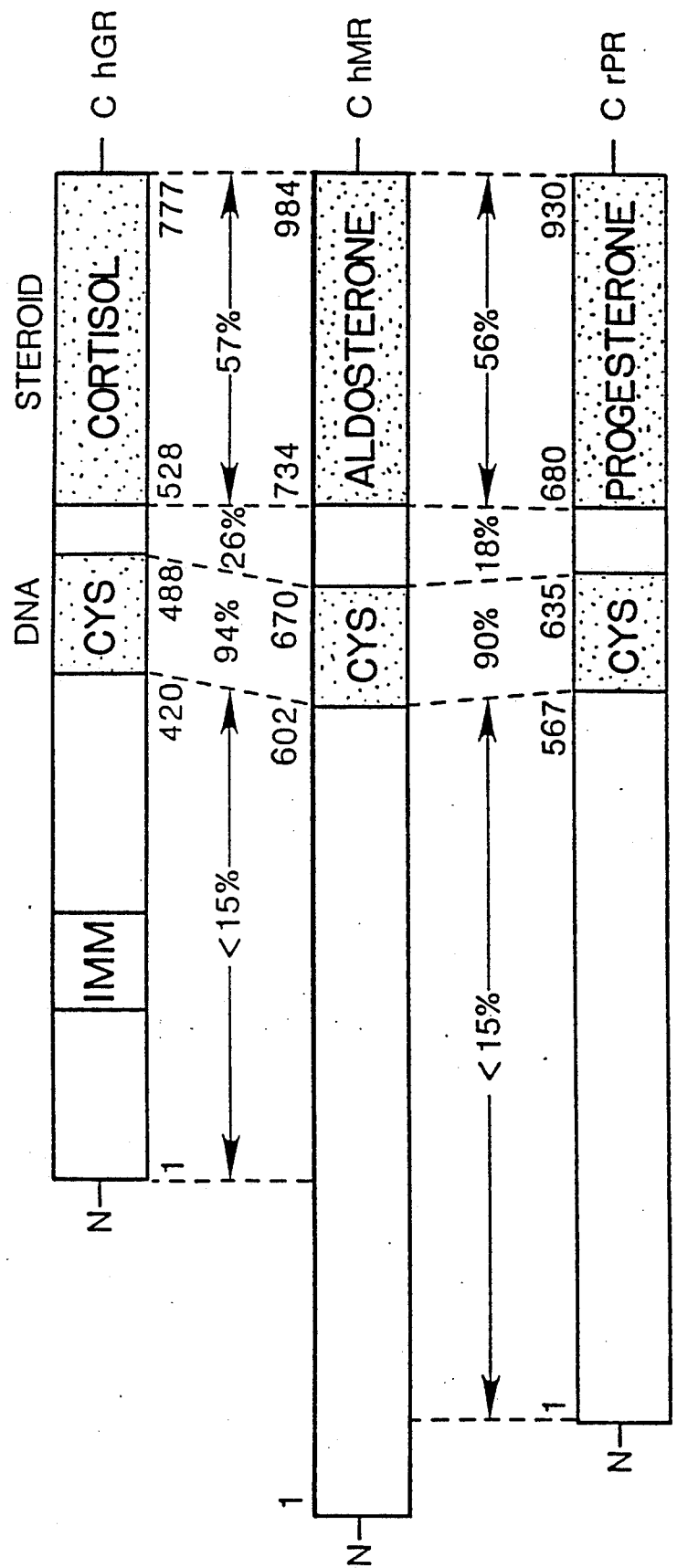
FIG. IV-8

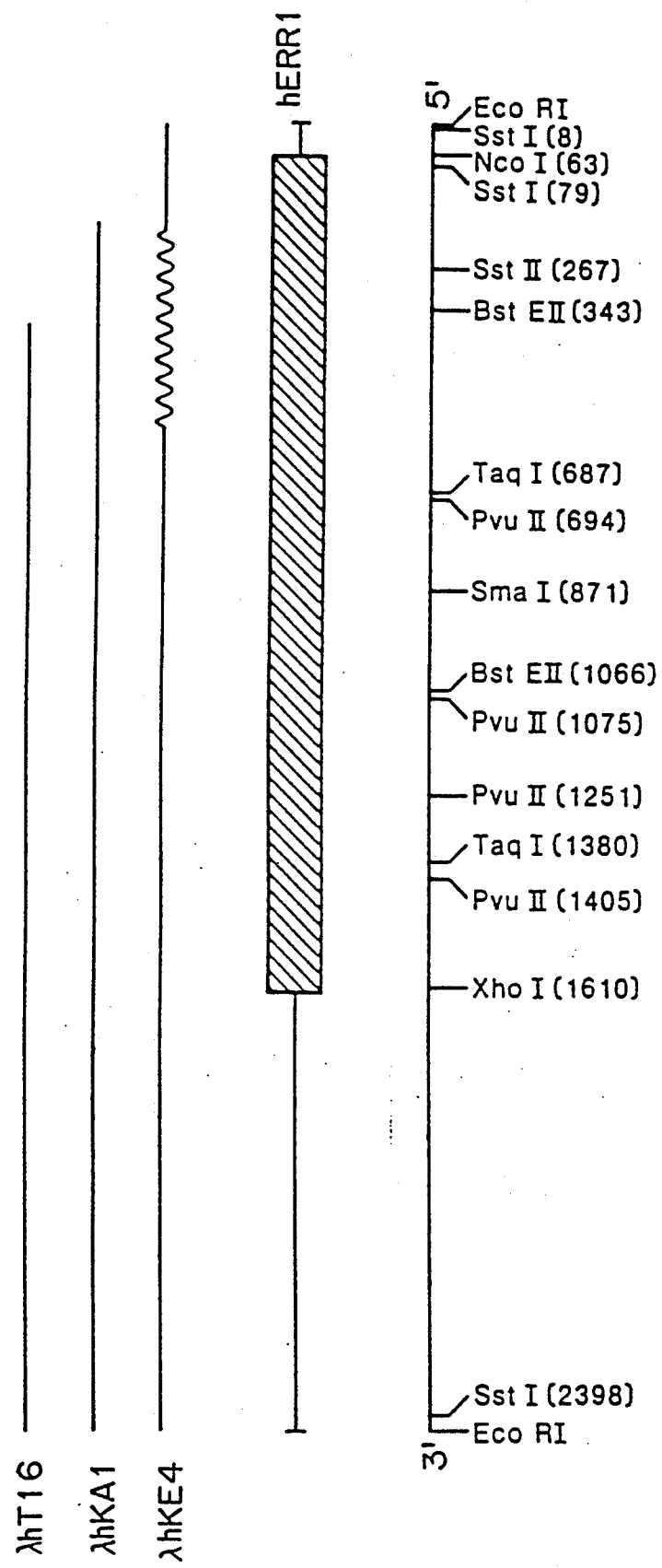
FIG. Ⅴ-1 (A)

```
                                                                        1
                                                                        MetGlyLeuGluMetSerSerLysAsp
  1  AGCTCACAGCAAGTCCAGGCTAGAGGTAGAAACGTGAGAGCCCCACGGCTGGGGAAGATTGCCATGGGAGATGAGCTCCAAGGAC 11                          21
        SerProGlySerLeuAspGlyArgAlaTrpGluAspAlaGlnLysProGlnSerAlaTrpCysGlyGlyArgLysThrArgValTyrAla
  91    AGCCCTGGCAGTCTGGATGGAAGAGCTTGGGAAGATGCTCAGAAACCACAGAAACCAGAGTGTATGCT 41                          51                          61
        ThrSerArgArgAlaProSerGluGlyGlyThrArgArgGlyAlaAlaAlaArgProGluGlyAlaAlaAlaArgProGluGlyProAla
 181    ACAAGCAGCCGGGCGGGGGCCGAGTGAGGGGACGCGGTGAGGGAGCGGCGGCCCGAGGGCGCGGAGGGCCCGAGGGCCCCGCG 71                          81                          91
        AlaProGlySerLeuArgHisSerGlyProLeuGlyProHisAlaCysProThrAlaLeuProGlnProGlnValThrSerAlaMetSer
 271    GCCCCCGGGTCACTCCGGCACTCCGGGCCTCCGGGCCCCCATGCGCTGCCGGACCGCGCTGCCGCAGCCCCAGGTGACCAGCGCCATGTCC 101                         111                         121
        SerGlnValValGlyIleGluProLeuTyrIleLysAlaGluProAlaSerProAspSerProLysGlySerGluThrSerGluThrGlu
 361    AGCCAGGTGGTGGGCATTGAGCCTCTACATCAAGGCAGAGCCGGCCAGTCCAGACTCCCTGAAGGGTTCCTGGAGACAGAGACCGGAG 131                         141                         151
        ProProValAlaLeuAlaProGlyProAlaLeuProAlaProThrArgCysLeuProGlyHisLysGluGluAspGlyGluAlaGlyProGly
 451    CCTCCTGTGGCCCTGGCCCCTGGTCCAGCTCCCGCTCCCACTCGCTGCCTCCCAGGCCACAAGGAAGAGGATGGGGAGGGGCCTGGC
```

```
     161
     GluGlnGlyGlyLysLeuValLeuSerSerLeuProLysArgLeuCysLeuValCysLeuValAspValAlaSerGlyTyrHisTyrGly
541  GAGCAGGGCGGGTGGGAAGCTGGTCAGTCTTCCCTGCCAAGCGCCTCTGCCTGGTCTGTGTGGGACGTGGCCTCCGGCTACCACTATGGT 191                                          211
     ValAlaSerCysGluAlaCysLysAlaPhePheLysArgThrIleGlnGlySerIleGluTyrSerCysProAlaSerAsnGluCysGlu
631  GTGGCATCCTGTGAGGCCTGCAAAGCCTTCTTCAAGAGGACCATCCAGGGCAGTATCGAGTACAGCTGTCCGGCTGTCCAACGAGTGTGAG 221                                          241
     IleThrLysArgArgGlyArgLysAlaCysGlnAlaCysArgPheThrLysCysLeuArgValGlyMetLeuLysGluGlyValArgLeuAsp
721  ATCACCAAGCGGAGACGGGAAGGCCAAGGCCTGCCAGGCCTGCCGCTTCACCAAGTGCCTGCGGGTGGGCATGCTCAAGGAGGGAGTGCGGCTGGAC 251                                          271
     ArgValArgGlyGlyArgGlnLysTyrLysArgArgProGluValAspProLeuProGlyProPheProProLeuProProAlaGlyProLeuAla
811  CGGGTCCGGGGCGGCAGAAGTACAAGCGGCGGCCCGAGGTGGACCCACTGCCCGGGCCCTTCCCTGCTGGGCCCCTGGCA 281                                          301
     ValAlaGlyGlyProArgLysThrAlaAlaProValAsnAlaAlaLeuValSerHisLeuLeuValValGluProGluLysLeuTyrAlaMet
901  GTCGCTGGAGGCCCCCGGAAGACAGCAGCCCCAGTGAATGCACTGGTGTCTCATCTGCTGGTGGTTGAGCCTGAGAAGCTCTATGCCATG
```

```
                461                             471                             481
       TyrGluAlaGlyArgArgAlaGlyProGlyGlyGlyAlaGluArgArgArgAlaGlyArgLeuLeuThrLeuLeuProLeuLeuArgGlnThr
1441   TATGAAGCCGGGCCGGGCTGGCCCCGGAGGGGTGCTGAGCGGCGGGCAGGCTGCTCACGCTACCGCTCCTCCCGCCAGACA
                501                             511
       AlaGlyLysValLeuAlaAlaHisPheTyrGlyValLysLeuGluGlyValLysLeuPheLeuMetLeuGluMetLeuGluAlaMet
1531   GCGGGCAAAGTGCTGGCCGCCATTTCTATGGGGTGAAGCTGGAGGGCAAGGTGTTCTTGGAGATGCTCGAGGCCATG
                521
       MetAspSTOP
1621   ATGGACTGAGGGCAAGGGGCAGCCCCAAGGGGTCAGCCCCTAGCATGGGGCTGGGGCTGGGGAGCCTGGGGG
1711   TCTGGGCAGTGCACAGCTGGAACGTGCTGGCTAATGCCCTGGGCCAGGCCATAACGGTGCCCTCTCCCCTAGG
1801   GGGTGTCAGAGAAGCCTTTGTCCAGGAACGTCTGCTGTTGCACAGTGCAAGCCATAACGGTGCCCAGAGTAGGGGCC
1891   TTGCGGAAGCATAGGGGGCTGCTGCTACCTATCTCAGGGAAGGAAGCAAACCAGAGCAATAACTCAGAGTCTCCCAGT
1981   GGGTGATGCTTTTGCTGCATTGCCCAACGGGACTTGGGACTCAGAAGCAATAACTGCCTCTATGCCCATGCCTCTC
2071   CTCTCCCCATCAGCTCCCAACGGCGCAGGACATGGGGCCAGGGGCAAGCCCAGAGCCCCTGTACAGAGACTCTATTTATTTTG
2161   CTTTCCCCAGGAGGGCAGCAGGACATGGGGCCAGGGGCAAGCCCAGAGCCCCTGTACAGAGACTCTATTAATGTATATTTGCTG
2251   GGTTTGGCAGGAGGGCAGGACCAGGGCAAGCCCAGAGCCTCTATTTAATGAGAAAAAAATATATAAGGTAGAAAAAA
2341   CAAAGAGAAACCGCTTTTGGTTTTAAACCTTTAACCTTTAAGCTCAAAAAAAAAAAAAAAAAAAAAA
```

FIG. Ⅴ-I(B)d

```
              311
      ProAspProAlaGlyProAspGlyHisLeuProAlaValAlaThrLeuCysAspLeuPheAspArgGluIleValThrIleSerTrp
                                           321                              331
 991  CCTGACCCCGCAGGCCCTGATGGGCACCTCCCAGCCGTGGCCACCCTCTGTGACCTGTTTGACCGAGAGATTGTGGTCACCATCAGCTGG 341                              351                              361
      AlaLysSerIleProGlyPheSerSerLeuSerAspGlnMetSerValLeuGlnSerValTrpMetGluValLeuValLeuValLeuGly
1081  GCCAAGAGCATCCCAGGCTTCTCATCGCTGTCTGACCAGATGTCAGTACTGCAGAGCGTGTGGATGGAGGTGCTGGTGCTGGTGCTGGGT 371                              381                              391
      ValAlaGlnArgSerLeuProLeuGlnAspLeuAlaLeuAlaPheAlaGluAspLeuValLeuValLeuAspGluGlyAlaArgAlaAlaGlyLeu
1171  GTGGCCCAGCGCTCACTGCCACTGCAGGATCTGGCCCTTGCGTTCGCTGAGGACTTAGTCCTGGTGCTGGATGAAGAGGGGGCACGGGCAGCTGGCCTG 401                              411                              421
      GlyGluLeuGlyAlaAlaAlaLeuLeuGlnLeuValArgArgLeuGlnAlaLeuGluArgLeuGluGlyGluArgGluTyrValLeuLeuLysAlaLeu
1261  GGGGAACTGGGGGCTGCCGCTCTGCTGCAACTAGTGCGGAGACTGCAGGCCCTGGAGCGCCTGGAGGGAGAGAGTATGTTCTACTAAAGGCCTTG 431                              441                              451
      AlaLeuAlaAsnSerAspSerValHisIleGluProArgLeuTrpSerSerCysGluLeuLysLeuLeuHisGluAlaLeuLeuGlu
1351  GCCCTTGCCAATTCAGACTCTGTGCACATCGAAGATGAGCCGAGGCTGTGGAGCAGCTGCGAGAAGCTCCTGCACGAGGCCCTGCTGGAG
```

FIG. V-I(B)c

```
                461
       TyrAlaGlyArgAlaGlyProGlyGlyGlyAlaGluArgArgArgAlaGlyArgLeuLeuThrLeuProLeuLeuArgGlnThr
1441   TATGAAGCCGGGGCTGGGCCTGGCCCCGGGAGGGGGGGCTGAGCGGCGGCGGGCCAGGCTGCTCACGCTACCGCTCCTCCGCCAGACA

481
       TyrAlaGlyArgAlaGlyProGlyGlyGlyAlaGluArgArgArgAlaGlyArgLeuLeuThrLeuProLeuLeuArgGlnThr 501                              511
       AlaGlyValLeuAlaHisPheTyrGlyValLysLeuGluGlyLysValProMetHisLysLeuPheLeuMetLeuGluAlaMet
1531   GCGGGCAAAGTGCTGGCCCATTTCTATGGGGTGAAGCTGGAAGGCAAGGTGCCCATGCACAAGCTGTTCTTGGAGATGCTCGAGGCCATG

521
       MetAspSTOP
1621   ATGGACTGAGGGCAAGGGTGGGACTGGTCGGCAGGACCTGCCTGGGGGCTCAGCCCCCAAGGGGCTCAGCCCTCCTCCCCAGCATGGGGG
1711   TCTGGCAGTGCAGTGCACAGCTGCAGGCCTGCACGTGCTGGGCTAATGCCTCAGCCCTCAGCCCCCATAACGGTGCCCCCAGAGTCCAGT
1801   GGGTGTCAGAAGCTCAGGGAACGTGCTGCACGTGCTGCTTCAGAGAACCAGCAGATAACTCAAAGCAATAACACTGCCCTGGACCCAGAGAGC
1891   TTGCGGATGTCCATAGGGGCCATAGGGGCGCTTTTGCTCTGTGCTGCTTAATCCCTAATCAGTGTCCCTCACCCCTATCCTAGAGTCCTC
1981   GGGTGATGCTTCATTGCATTGGGCATTCCCAACGAGCTCCTCAGGGGTAGGAGCCACCATGCTGCAGAGAGACTCTATTTATTTTTGCTG
2071   CTTCTCCCCATCAGTCCAGGGAGGGCAGGGACATGGGACCAGGGACAAGCTCATGCCCTGTACAGAGAGACTCTATTTATTTTTGCTG
2161   CTTCCCCATCAGTCCAGGGAGGCAGGGACATGGGACCAGGGACAAGCTCTGTACAGAGAGACTGTACTTGGCTGTATAATGTATTTGCTG
2251   GGTTTGGGCCAGGGAGGGCAGGGGACATGGGTTTTAAACCTTTAATGAGAAAAAATATATAATAATACCGAGCTCAAAAAAAAAAAAAAAA
2341   CAAAGAGAACCGCTTTGGTTTAAACCTTTAATGAGAAAAAATATATAATAATACCGAGCTCAAAAAAAAAAAAAAAAA
```

FIG.Ⅴ-I(B)d

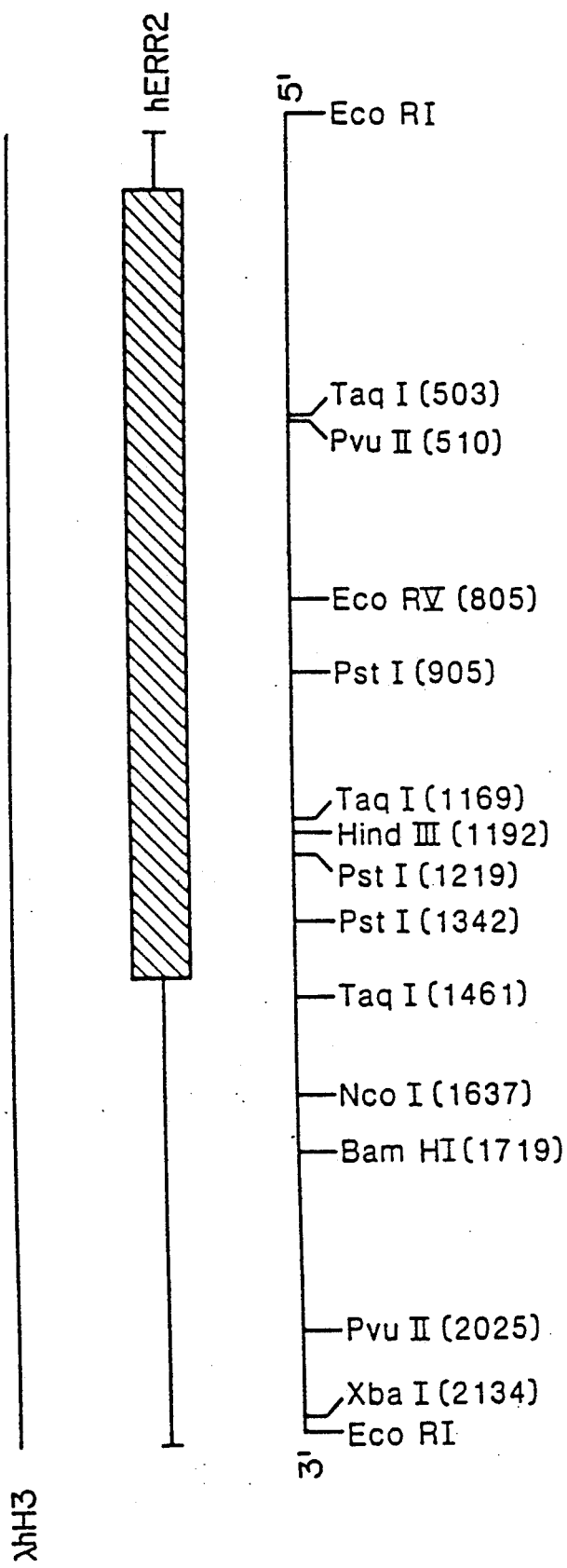
FIG. V-2 (A)

```
  1 CTCCTCCAACTGGGAATGCTAAAACGGGACTGATGGACGTGTCCGAACTCTGCATCCCGGACCCCCTCGGCTACCACAACCAGTAGGTTG
                   1                                          21
                   MetSerSerGluAspArgHisLeuGlySerSerCysGlySerPheIleLysThrGluProSerSerProSerSerGlyIle
 91 CTGAACCGAATGTCCGAAGACAGGCACCTGGGCTCTAGCTGCGGGCTCCTTCATCAAGACGGAGCCATCTAGCCTCCTCGGGCATT
      31                                         51
      AspAlaLeuSerHisHisSerProSerGlySerSerAspAlaSerGlyGlyPheGlyMetAlaLeuGlyThrHisAlaAsnGlyLeuAsp
181 GATGCCCTCAGCCACCACAGCCCAAGCGGCTCGGACGCGAGCGGCGGCTTTGGCATGGCCCTGGGCACCCACGCCAACGGTCTGGAC
        61                                         81
        SerProProMetPheAlaGlyAlaGlyLeuGlyAsnGlyLysGlyProCysArgLysSerTyrGluAspCysThrSerGlyIleMetGluAspSer
271 TCTCCGCCTATGTTCGCAGGTGCGGGGCTTGGGAACGGCAAACCCGTGTCGCAAGAGCTACGAGGACTGTACTAGGGTATCATGGAGGACTCG
          91                                        111
          AlaIleLysCysGluTyrMetLeuAsnAlaAlaIleProLysArgLeuCysLeuValCysGlyAspIleAlaSerGlyTyrHisTyrGlyVal
361 GCCATCAAGTGCGAGTACATGCTTAACGCTGCCATCCCCAAGCGCCTCTGTGTCGGGGACATTGCTTCTGGCTACCACTATGGAGTG
            121                                        141
            AlaSerCysGluAlaCysLysLysAlaPhePheLysArgThrIleGlnGlyAsnIleGluTyrSerCysProAlaThrAsnGluCysGluIle
451 GCCTCCTGCGAGGCTTGCAAGAAAGCGTTCTTCAAGAGAACCATTCAAGGAAACATCGAATACAGCTGCCCTGCCACCAACGAGTGTGAGATC
```

FIG. V-2(B)a

```
              151                         161                         171
     ThrLysArgArgLysSerCysGlnAlaCysArgPheMetLysCysLeuLysValGlyMetLeuLysValGlyGluGlyValArgLeuAspArg
541  ACCAAACGGAGGCGCAAGTCCTGTCAGGCCTGCCGGTTCATGAAATGCCTCAAAGTGGGGATGCTGAAGGTGAAGGAAGGCGTGCGCCTTGACCGG 181                         191                         201
     ValArgGlyGlyGlyArgGlnLysTyrLysArgGlnLeuAspSerGluAsnSerProTyrLeuAspInIleSerProProAlaLysLys
631  GTGCGAGGAGGAGGCCGCCAGAAGTACAAGAGACGGCTGGATTCGGAGAACAGCCCCTACCTAGAGCTTACAGATTTCCCCGCCTAAAAAG 211                         221                         231
     ProLeuThrLysIleValSerTyrTyrLeuLeuValAlaGluProAspLysLeuTyrAlaMetProAspValProGlyAspIle
721  CCATTGACTAAGATTGTCTCGTATCTACTGGTGGCCGAGCCGGACAAGCTGTACGCTATGCCTGACGTGCCTGAAGGGGATATC 241                         251                         261
     LysAlaLeuThrThrLeuCysAspLeuAlaAlaAspArgGluLeuValPheLeuIleSerTrpAlaAlaLysHisIleProGlyPheSerAsnLeu
811  AAGGCCCTGACCACTCTCTGTGACTTGGCAGAGATCGGGAGGTTGTTCCTCATTAGCTGGGCAGCAAGCACATCCCCAGGTTTCTCCAACCTG 271                         281                         291
     ThrLeuGlyAspGlnMetSerLeuGlnSerAlaTrpMetGluIleLeuLeuGlyIleValTyrArgSerLeuProTyrAspAsp
901  ACACTCGGGGACCAGATGAGCCTGCAGAGTGCCTGGATGGAGATCCTCCTGGGCATCGTGTACCGTCGCTTCCCCTATGATGAC
```

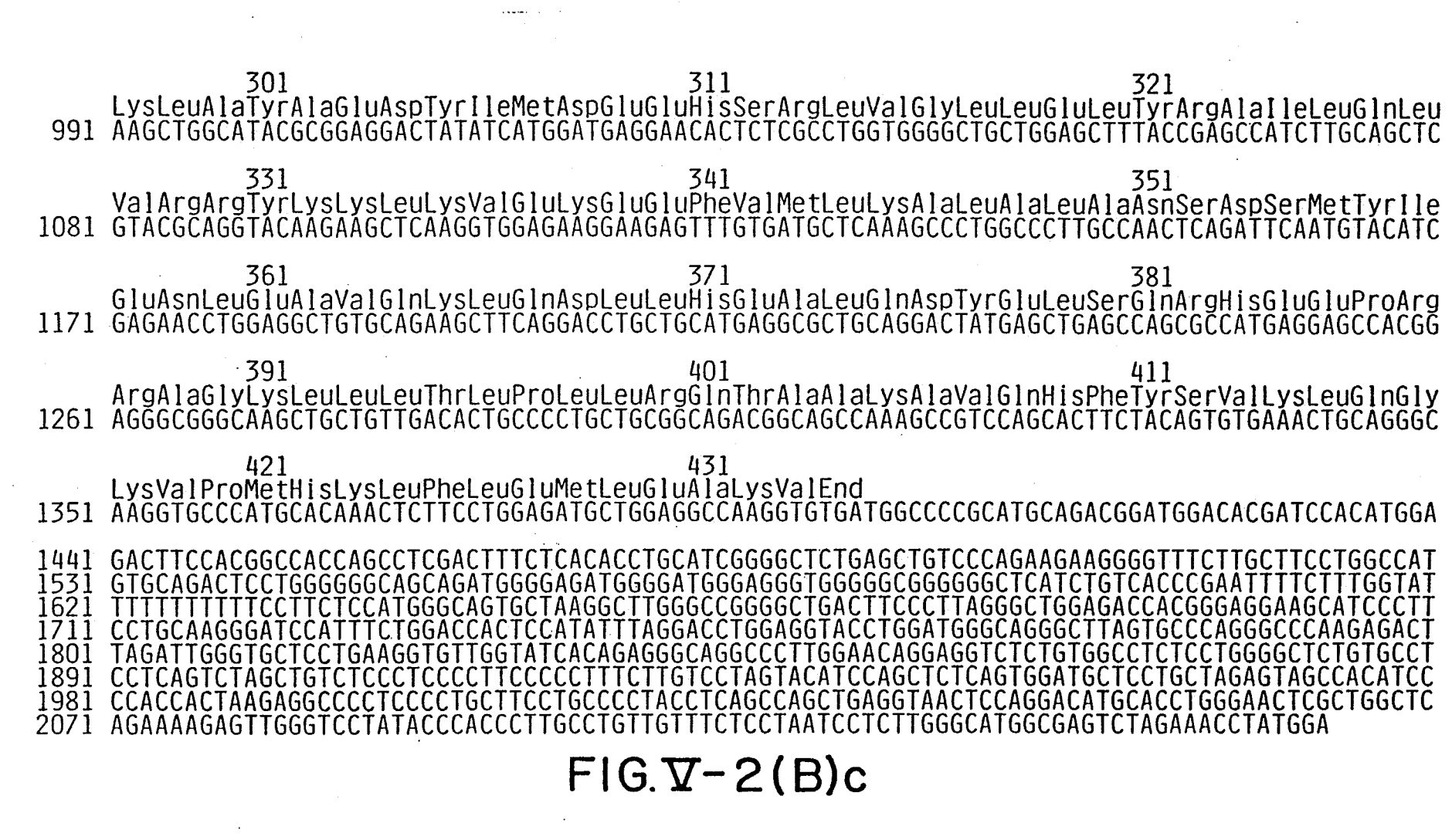

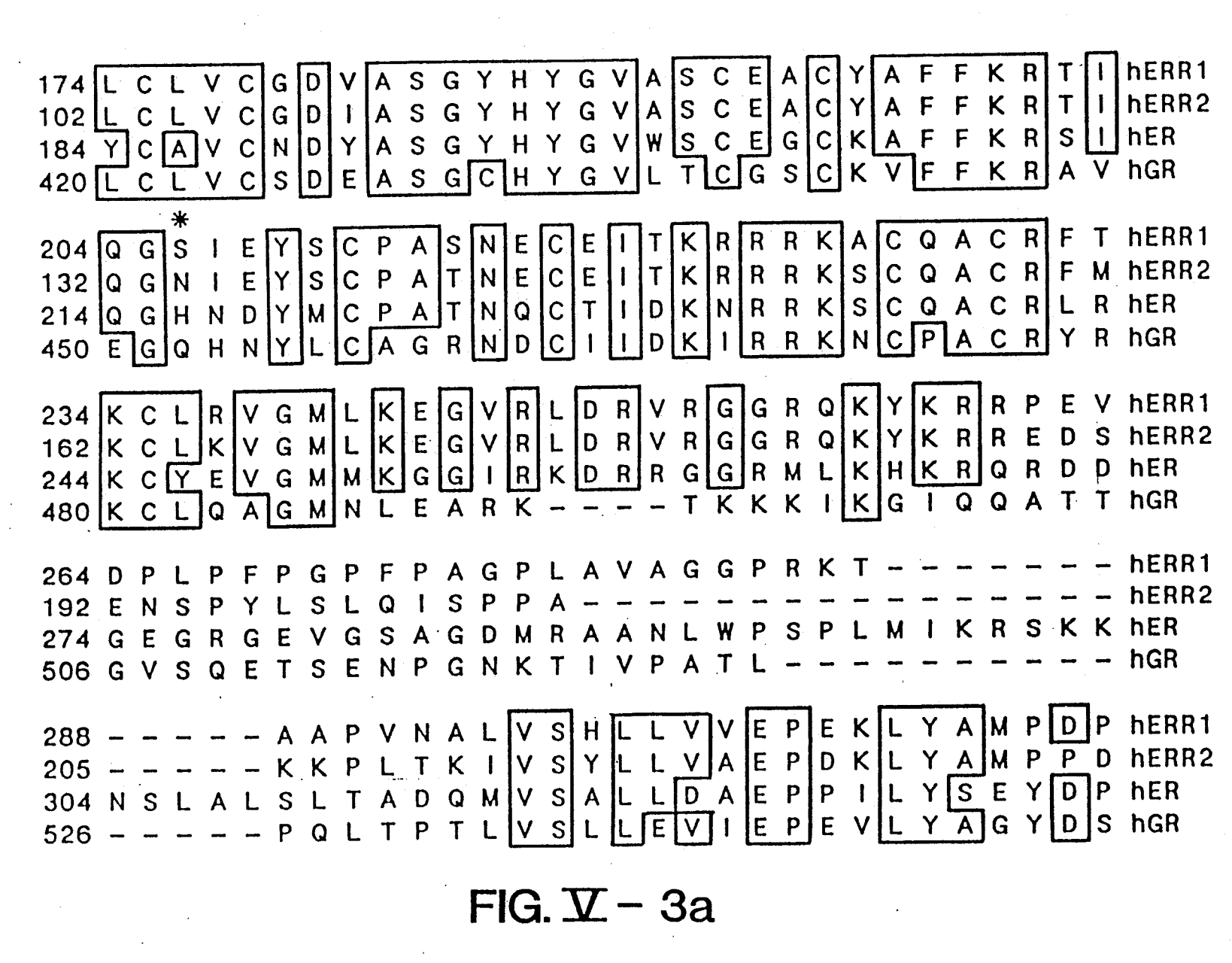

```
313  A G P D G H L P A V A T L C D L F D R E L   - V T   S W A K S  hERR1
231  D V P E G F - D   - K A L T L L C D L A D R E L V F L   - S W A K H  hERR2
334  T R P F S E A S M M G L L T N L A D R E L V H M   I N W A K R  hER
551  S V P D S T W R I M T T L N M L G G R Q V I A A V K - A  hGR

343  P G F   - S S L T L L S D Q M S V L Q S   - L L   - V L V E   - I L   V G G   V A Q  hERR1
261  - P G F   - S N L D L N D Q V T L L Q Y   - L L L E W L T   E - L - L Y - V -  hERR2
364  V P G F - V D L T L H D Q V H L L E C A W L E I L M I G L - W - L W - Y  hER
581  I P G F - R N L H L D D Q M T L L Q Y S W M F L M A F - A L G W  hGR

373  R S L - - P Y D D K   L - I - - V L Q - - D E - V L D E H S R T  hERR1
291  R S L - P Y D D - V K - - L - L M   - D - - - Y - - L D N R G K -  hERR2
394  R S M E H P V R L A N L L M A T S S - R F R M M N L Q G E E Y L C  hER
611  R S Y R Q S S A N L L C F A P D L L L L  hGR

398  G L L G L   G A A L - L L Q L V R R L - - Q A L R L K V - E K E L K   hERR1
316  G L L - Y R A - - L L - - Q V R R Y K K L R - M N L Q G E L M   hERR2
420  G M V F - D M L L A T S S R F R M M N L Q G E Y L K   hER
641  D Q C K - H   - L L - H M Y V S S E L H R L Q V S Y M K  hGR
```

FIG. V-3b

```
428 A L A L N S D S V H I E D E P R L W S C E K L L H E A L   hERR1
346 A L A L A N S D S M Y E N L E A V - Q K L L H E A L   hERR2
450 S - I L L L N S G V Y T F S L - - K S L Q D H - H R   hER
668 T L L S S V P K D G L - - K S Q E L F D E I R M      hGR

458 L E Y E - - - - A G R A G P G G A E R R A G R L      hERR1
375 Q D Y E - - - - L S Q R H E E P Q Q H Q R L A Q L    hERR2
479 V L D K I T D T L - H L M A K A G L T L Q Q Q Q R F Y Q L   hER
692 T Y I K - - - E L G K A I V K R E G N S S Q N W Q R    hGR

480 L T P L L R Q T A G K V L A H F Y G V K L E G K V P M H   hERR1
393 L T P L L R Q T A A K M V Q H F Y S V K L Q G K V P M H   hERR2
509 L L L S H I R H M S N K G M E H L Y S M K C K N V V P L Y   hER
719 T K L L D S M H E V V E Q L L N Y C F Q T F L D - K T M S   hGR

510 K L F L E M L E A M M D * *                              hERR1
423 K L F L E M L E A A K V L                                hERR2
539 D L L E M L D A H R L                     46 residues   hER
749 I E F P E M L A E I I T                   19 residues   hGR
```

FIG. V-3c

FIG. V-4 (A)

|  | RAT | HUMAN |
|---|---|---|
| | ADRENAL / CEREBELLUM / GUT / HEART / HIPPOCAMPUS / HYPOTHALAMUS / KIDNEY / LIVER / LUNG / MUSCLE / PROSTATE / SEMINAL VESICLE / SPLEEN / TESTIS | PLACENTA / PROSTATE |

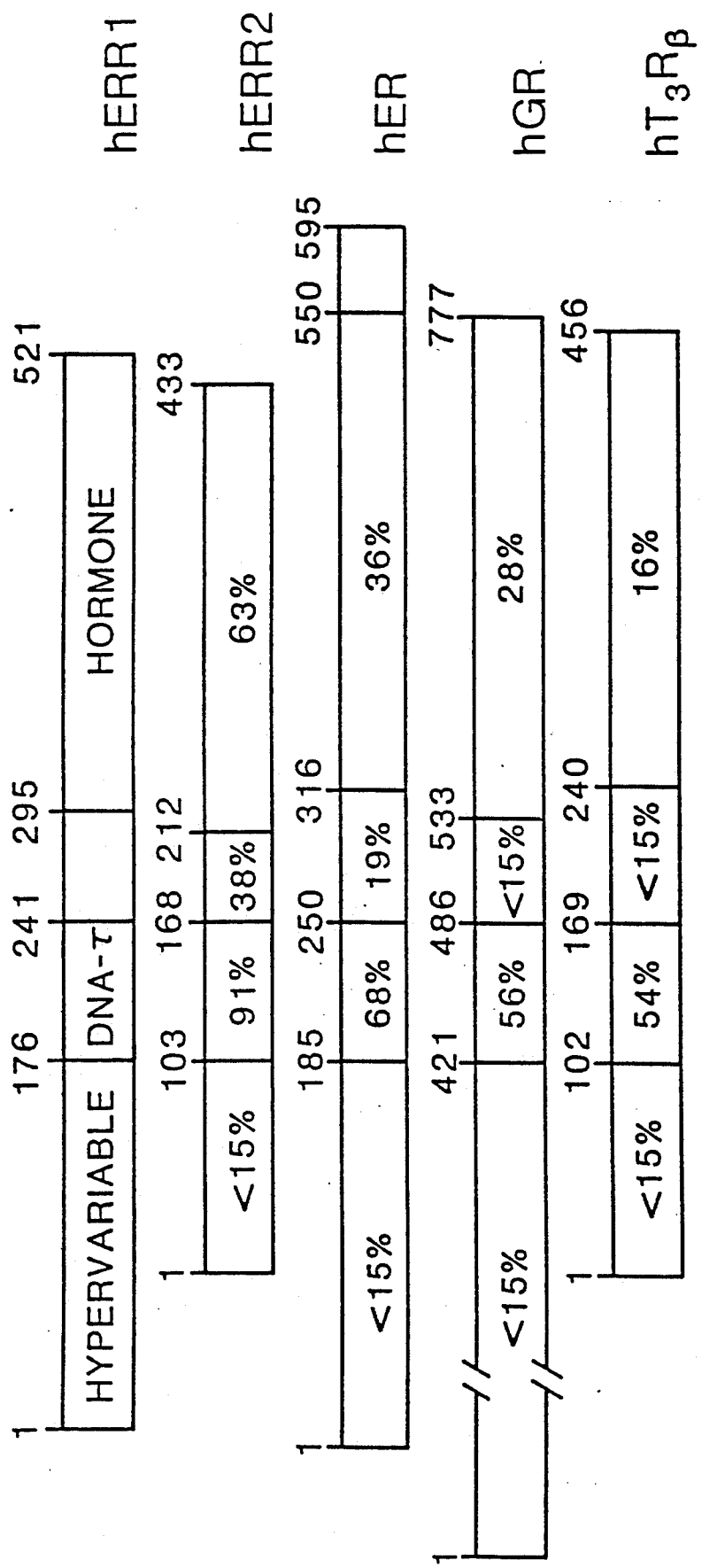
FIG. V-5

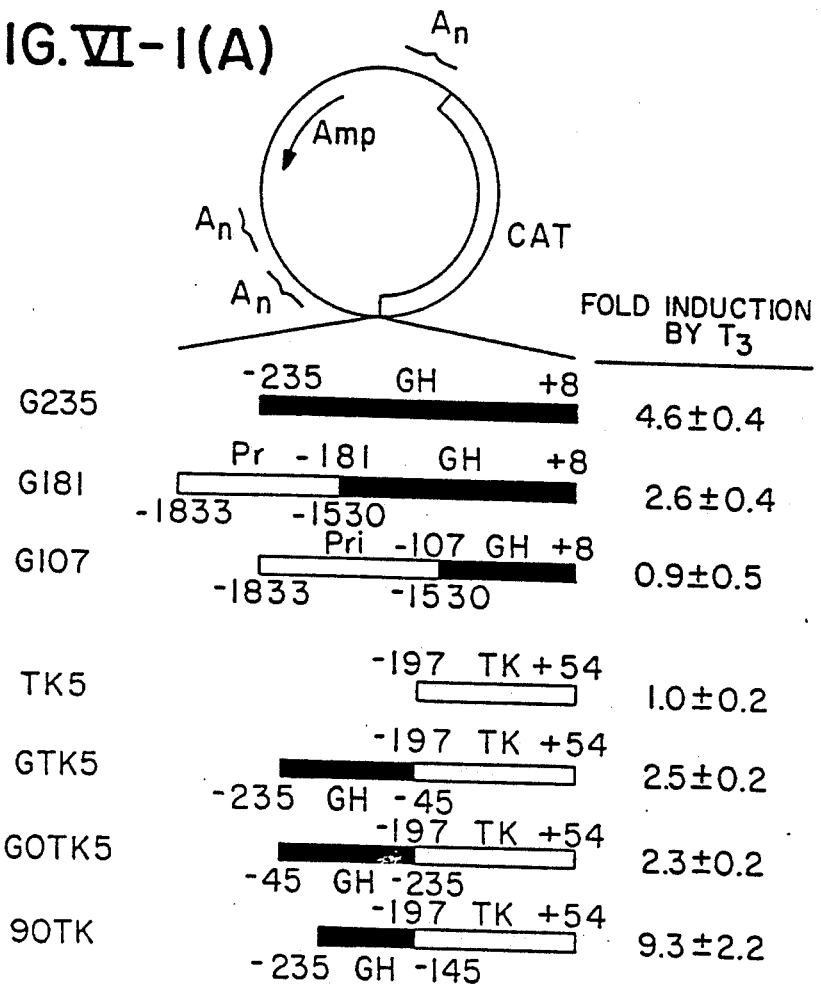
FIG. VI-1(A)
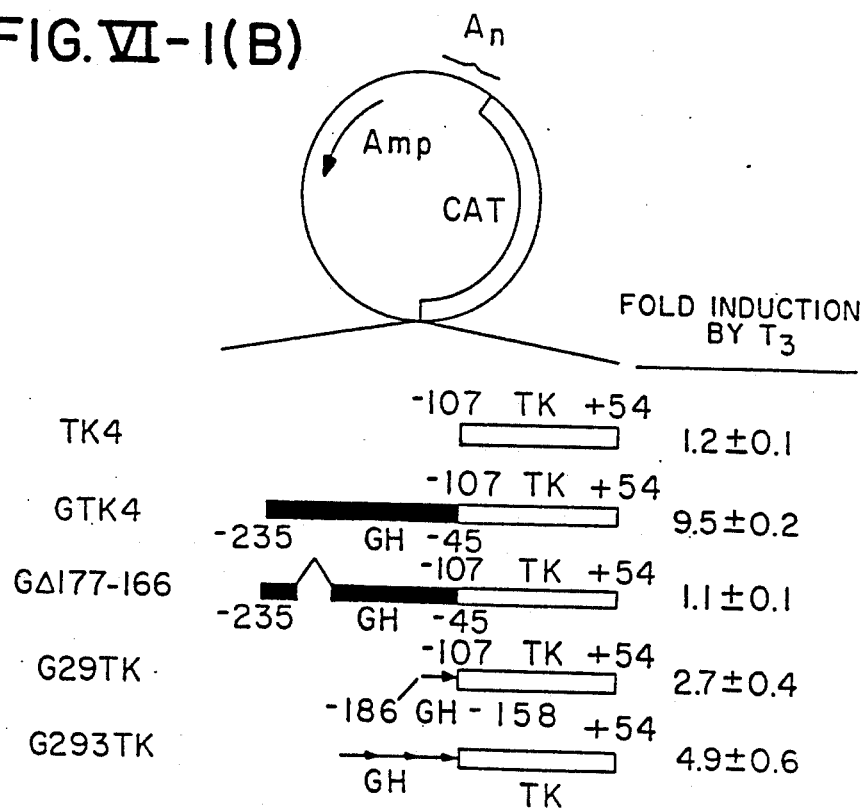
FIG. VI-1(B)

FIG. VI-I(C)
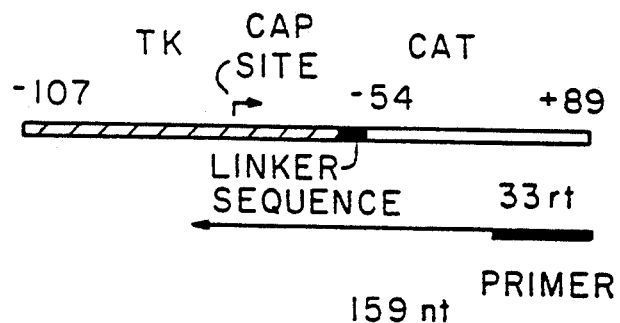
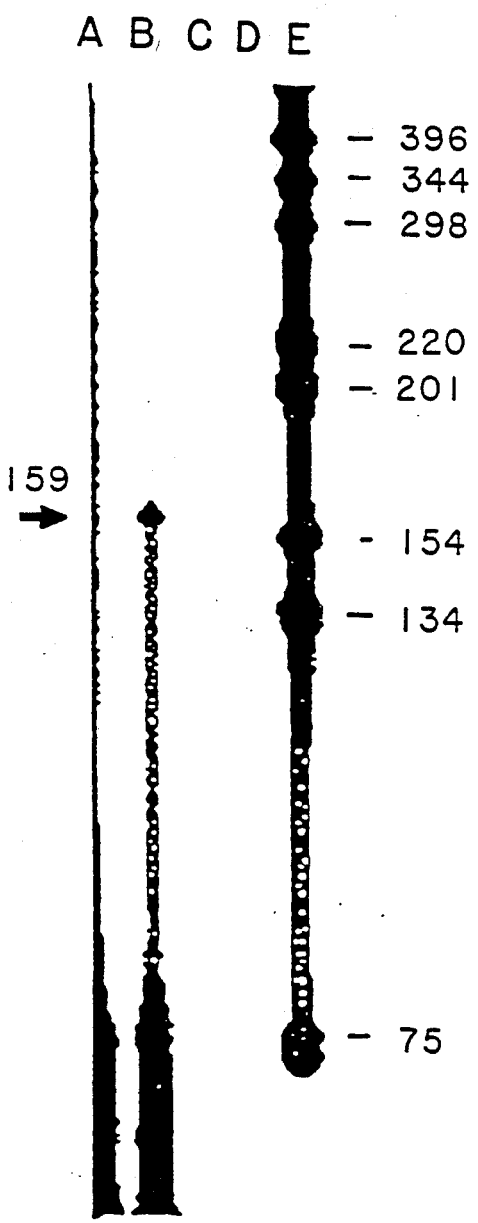

FIG. VI-2(A)
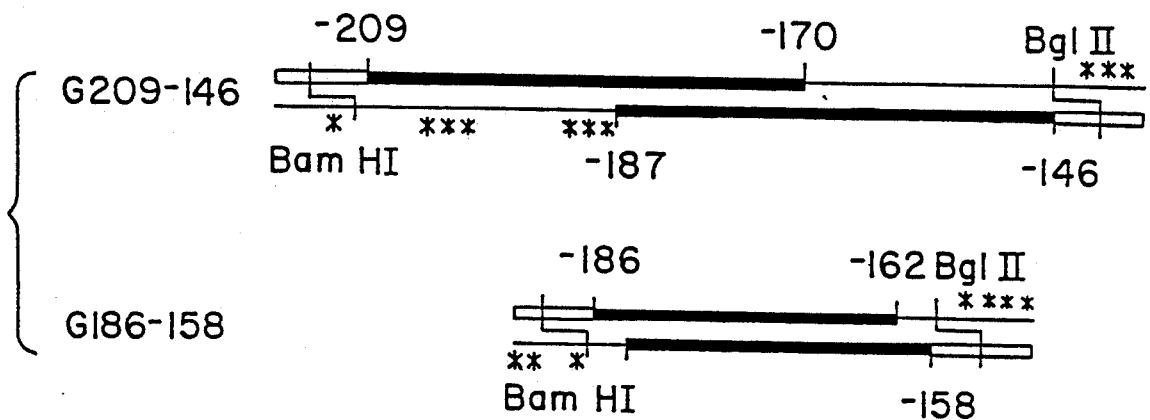
FIG. VI-2(B)
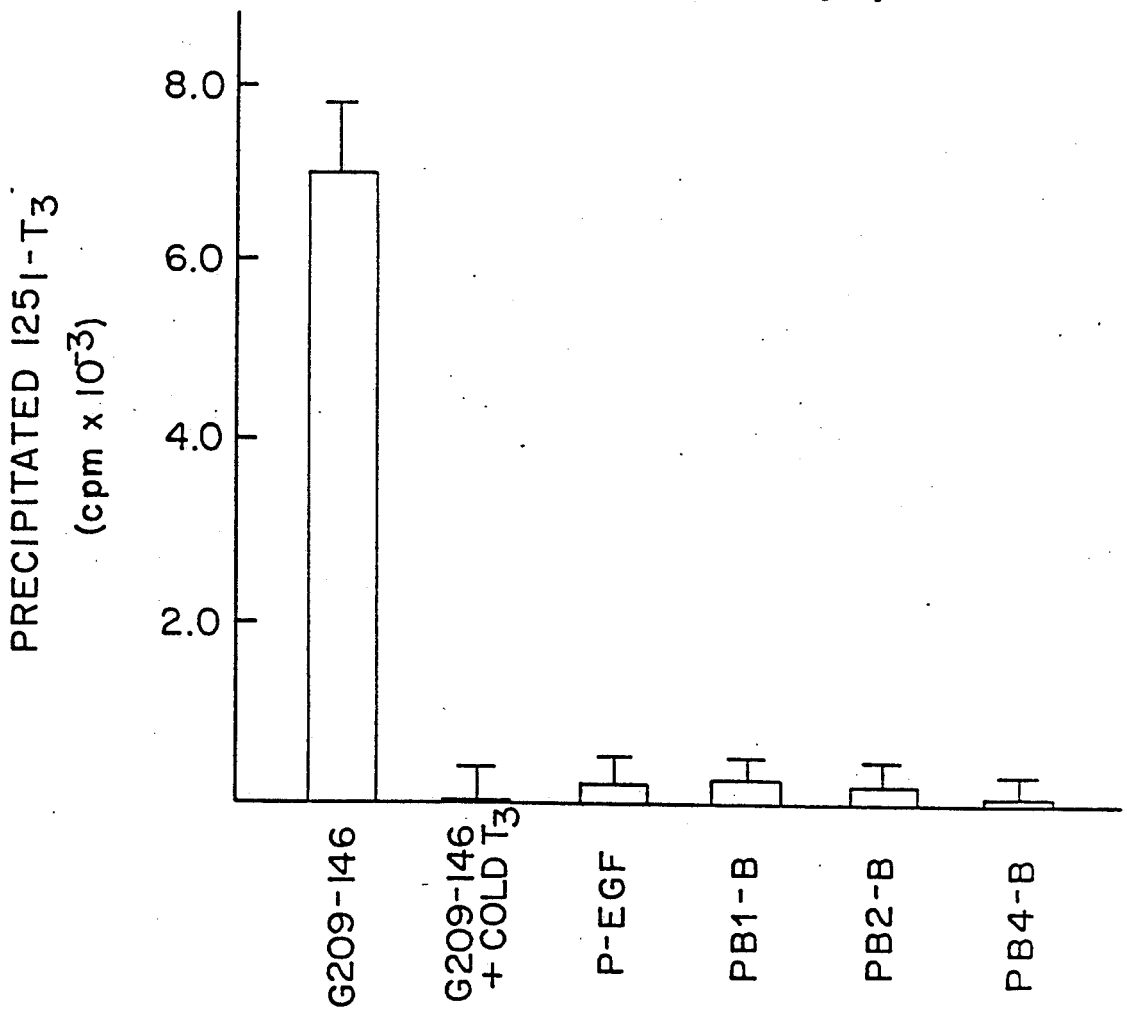

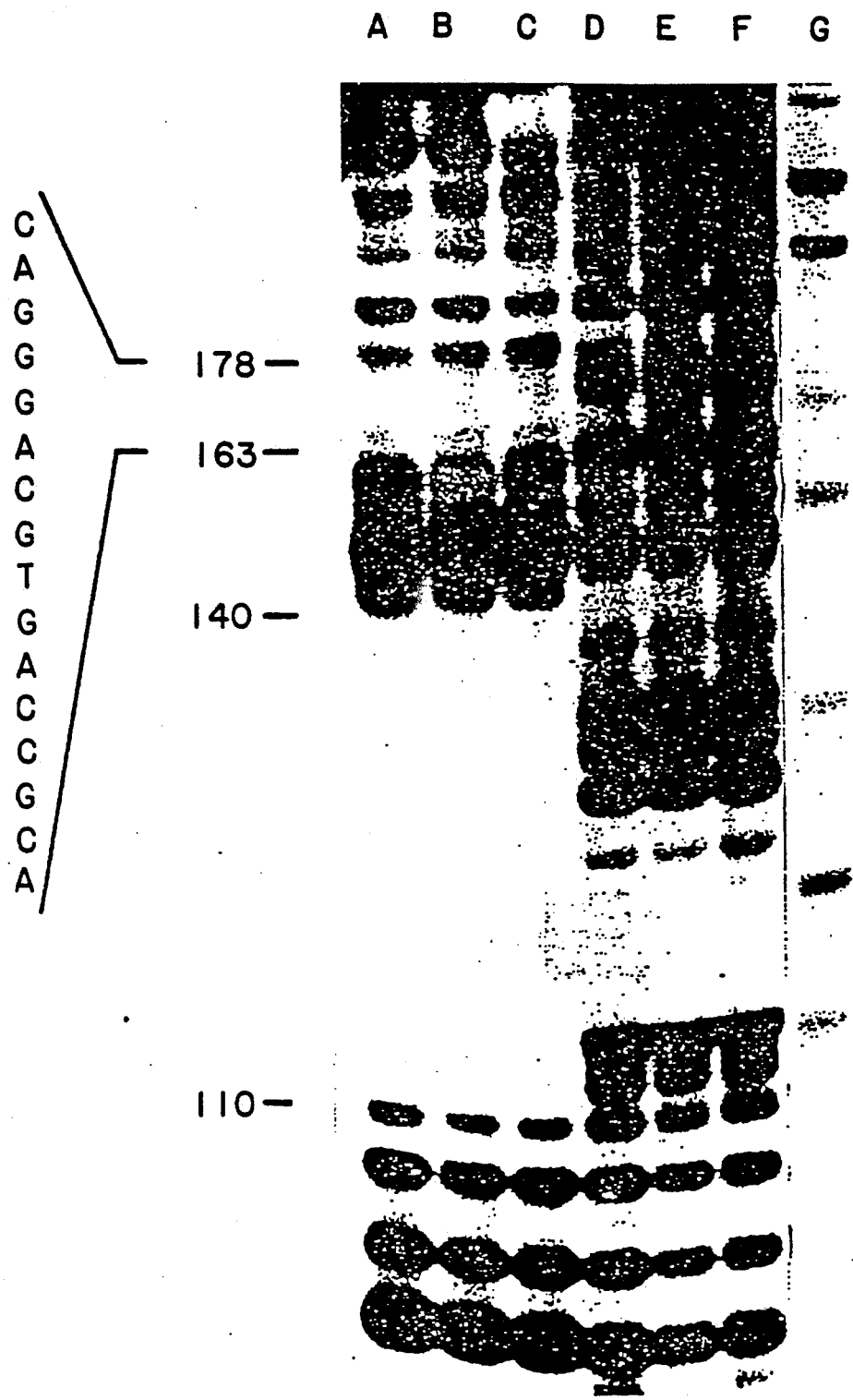
FIG. VI - 3

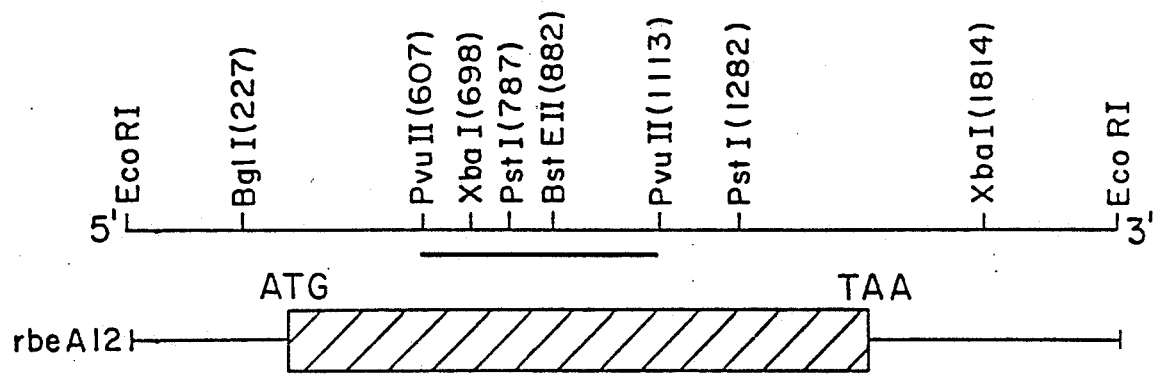
FIG.VII-1(A)

```
  1 CCAGGCGGCCAAGCCGAGGTATCTCCAGACAGGACAAGTCTCCAGACTTCCAGCCCCTAACCCAGTACCATT
 76 TACCAAGCCAGCTTGCCCCTAGCTCTCCACTCTGCCACTCCCAGCCCTCTAACCGGCCCTCCCGTT
151 TTTTGGGGCACAGGGCATGGTGTGAAAGGCTGAGTACTGAGGGGATACTGTGGGTGCTGTCCCCTAGGCCTG
226 GGTGGCGGGGGGTGGGTGGCCTGTGGGGGGCAGTGTGCCACCCAGTCTCTTGGCGTGCTGGAGG
                       MetGluGlnLysProSerLysValGluCysGlySerAspProGluGlnAsn
301 GCATCCCGGATGGAATTGAAGTGAACAGAGAAGCCAAGGTGGAGTGTGGGTCAGACCCAGAGGAGAAC
                        20                          30                  40
     SerAlaArgSerProAspGlyLysArgLysAsnGlyGlnCysProLeuLysSerSerMetSerGlyTyr
376 AGTGCCAGGTCACCAGATGGAAAGCGAAAAGGAAGAACGGCCAATGTCCCCTGAAAGCAGTGTCAGGGTAT
                  50                          60
     IleProSerTyrLeuAspLysAspGluGlnCysValValCysGlyAspLysAlaThrGlyTyrHisTyrArgCys
451 ATCCCTAGTTACCTGGACAAAGACGAGCAGTGTGTCGTGTGGGACAAGGCCACCGGTTATCACTACCGCTGT
              70                          80                          90
     IleThrCysGluGlyCysLysGlyPhePheArgArgThrIleGlnLysAsnLeuHisProThrTyrSerCysLys
526 ATCACTTGTGAGGGCTGCAAGGGCTTCTTTCGCCGTACAATCCAGAAGAACCTCCATCCCACCTATTCCTGCAAA
                          100                         110
     TyrAspSerCysValIleAspLysIleThrArgAsnGlnCysGlnLeuCysArgPheLysLysCysIleAla
601 TATGACAGCTGCGTCATCGACAAGATCACTCGGAATCAGTGCCAGTTGTGCCGGTTCAAGAAGTGCATCGCT
                  120                         130                         140
     ValGlyMetAlaMetAspLeuValLeuAspAspSerLysArgValAlaAlaArgLysLeuIleGluGlnAsnArg
676 GTGGGCATGGCCATGGACCTGGTTCTAGACGATTCAAAGCGGGTGGCCAAACGCAAGCTGATTGAGCAGAACCGG
                          150                         160
     GluArgArgLysGlyGluGlnIleArgSerLeuGlnIleArgProThrProGluGluTrpAspLeu
751 GAGAGGAGGAAGGGCGAAAGGAGGAGAGAATCGCTCGCTGCAGCAACAGCCACTCCTGAAGAGTGGGATCTG
                  170                         180                         190
     IleHisValAlaAlaThrGluAlaAlaHisArgSerThrAsnAlaGlnGlySerHisTrpLysGlnArgArgLysPheLeu
826 ATCCACGTTGCTACAGAGGCTGCACAGAGGCCATGCCCAGGGCAGCACCATTGCCAAACAGAGGCGAAAATTCCTG
                          200                         210
     ProAspAspIleGlyGlnSerProIleValSerMetProAspGlyAspLysValAspLeuGluAlaPheSerGlu
901 CCGGATGACATTGGCCAGTCACCTATTGTCTCCATGCCGGAACGGAGACAAGGTGGACTTAGAGGCCTTCAGCGAG
                          220                         230                         240
     PheThrLysIleIleThrProAlaIleThrArgValValAspPheAlaLysLysLeuProMetPheSerGluLeu
976 TTTACCAAGATCATCACCCGGCCATCACCCGCGTGGTGGACTTTGCCAAAAACTGCCATGTTCTCCGAGCTG
```

FIG. VII-1(B)a

```
                     250                                        260
         ProCysGluAspGlnIleIleLeuLeuLysGlyCysCysMetGluIleMetSerLeuArgAlaAlaValArgTyr
    1051 CCTTGTGAAGACCAGATCATCCTCCTGAAGGGCTGCTGCATGGAGATCATGTCCCTGCGGGCAGCTGTCCGCTAT
                        270                                        280                     290
         AspProGluSerAspThrLeuThrLeuSerGlyGluMetThrValLysArgLysGlnLeuLysAsnGlyGlyLeu
    1126 GACCCTGAGAGCGACACCCTGACCCTGAGTGGGGAGATGACGGTTAAGCGAAGCAGCTCAAGAATGGTGGCTTG
                        300                                        310
         GlyValValSerAspAlaIlePheGluLeuGlyLysSerLeuAspAspThrGluValAla
    1201 GGTGTAGTCTCCGACGCCATCTTTGAACTGGGCAAGTCACTCTCTGCCTTTAACCTGGATGATACGGAAGTGGCT
                        320                                        330                     340
         LeuLeuGlnAlaValLeuMetSerThrAspArgSerGlyLeuLeuCysValAspLysIleLeuLysSerGln
    1276 CTGCTGCAGGCTGTGCTTATGTCAACAGACCGCTCTGGCCTGCTGTGTGTGGACAAGATCCTGAAGAGTCAG
                        350                                        360
         GluAlaTyrLeuLeuAlaPheGluHisTyrValAsnHisArgLysHisAsnIleProHisPheTrpProLysLeu
    1351 GAGGCCTACCTGCTGGCGTTTGAGCACTACGTCAACCATCGCAAACACAATATTCCGCACTTCTGGCCCAAGCTG
                        370                                        380                     390
         LeuMetLysValThrAspLeuArgMetIleGlyAlaCysHisAlaSerArgPheLeuHisMetLysValGluCys
    1426 CTGATGAAGGTGACTGACCTCCGCATGATCGGGGCCTGCCACGCCAGCCGCTTCCTCCACATGAAAGTCGAGTGC
                                                400                                         410
         ProThrGluLeuPheProProLeuPheLeuGluValPheGluAspGlnGluValEnd
    1501 CCCACCGAACTCTTCCCCCCACTCTTCCTCGAGGTCTTTGAGGATCAGGAAGTCTAAGCCTCAGGCGGGCCAGAGG
    1576 GTGTGCGAGTGCTGGTGTCCCGTTGGGGAGGAGCTTGGAGAGACAAAGCTGAGGGGCTGAGGGAGAACCCCATCTTTC
    1651 TCTCCTTGGACAGCTGTTCCTCTCCGGGACAAATGAACTTGCTATAGATGAACTTGCTATGAAAGGCCGTGTGGGAGCCGCGCCAGACCGTGGAACCTCCAG
    1726 CCCTTGGACAGCCCAACCTCTAGAGGGAGGGAAGGGAAGAAGACTCACACACACAGGACTGAGAGGACAAGCGAGAGCCCATCTTGACTGTGAGTTCTG
    1801 GGACCCCAACCTCTAGAGGGAGGGAAGGGAAGAAGACTCACACACACAGGACTGAGAGGACAAGCGAGAGCCCATCTTGACTGTGAGTTCTG
    1876 AGGAATGAGGATAGGGCAGGTGCCCTTACTCACCCCGCCACAGTCTCCACAGGTGCCTGGCCACAGGAGCCCGCCAAGTTCCTTGGCCT
    1951 AGATTTCCCTTCAGGAGGCTAAAACGTAGTCATCCTAACTGCACTTTGCAAAGGACAGCTTGGCTTGG
    2026 CTTAGCTCCCTCCCTGGAGGCTAAAACGTAGTCATCCTAACTGCACTTTGCC   2079
```

FIG. Ⅶ-I(B)b

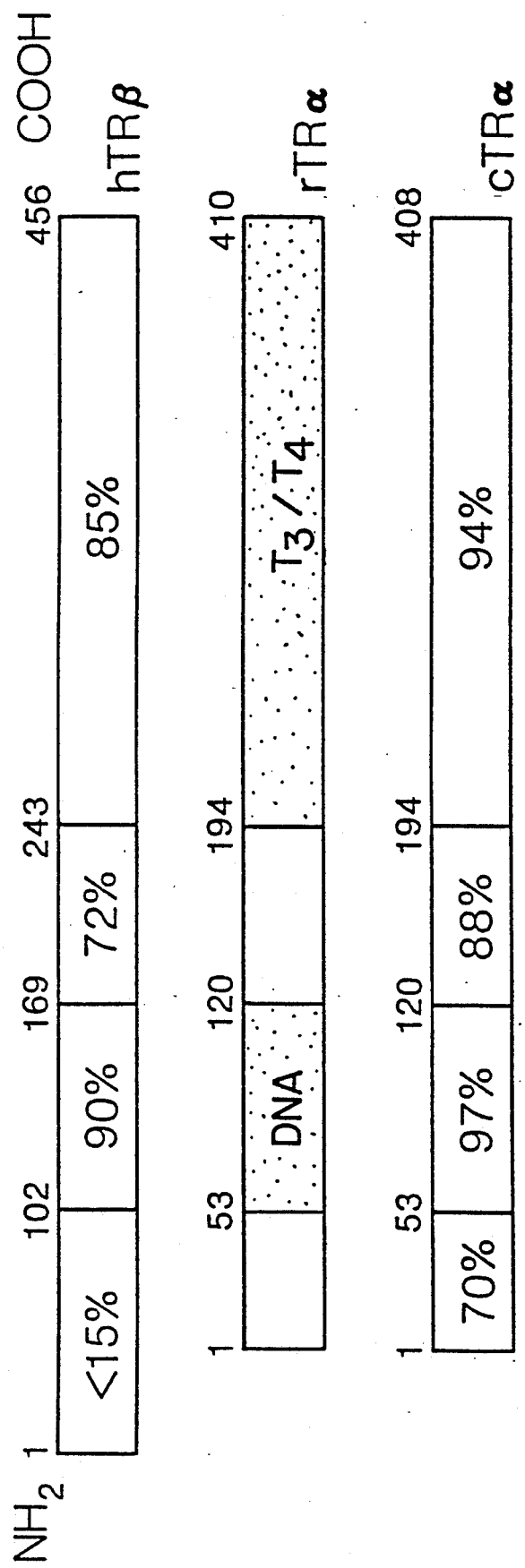
FIG. VII-2

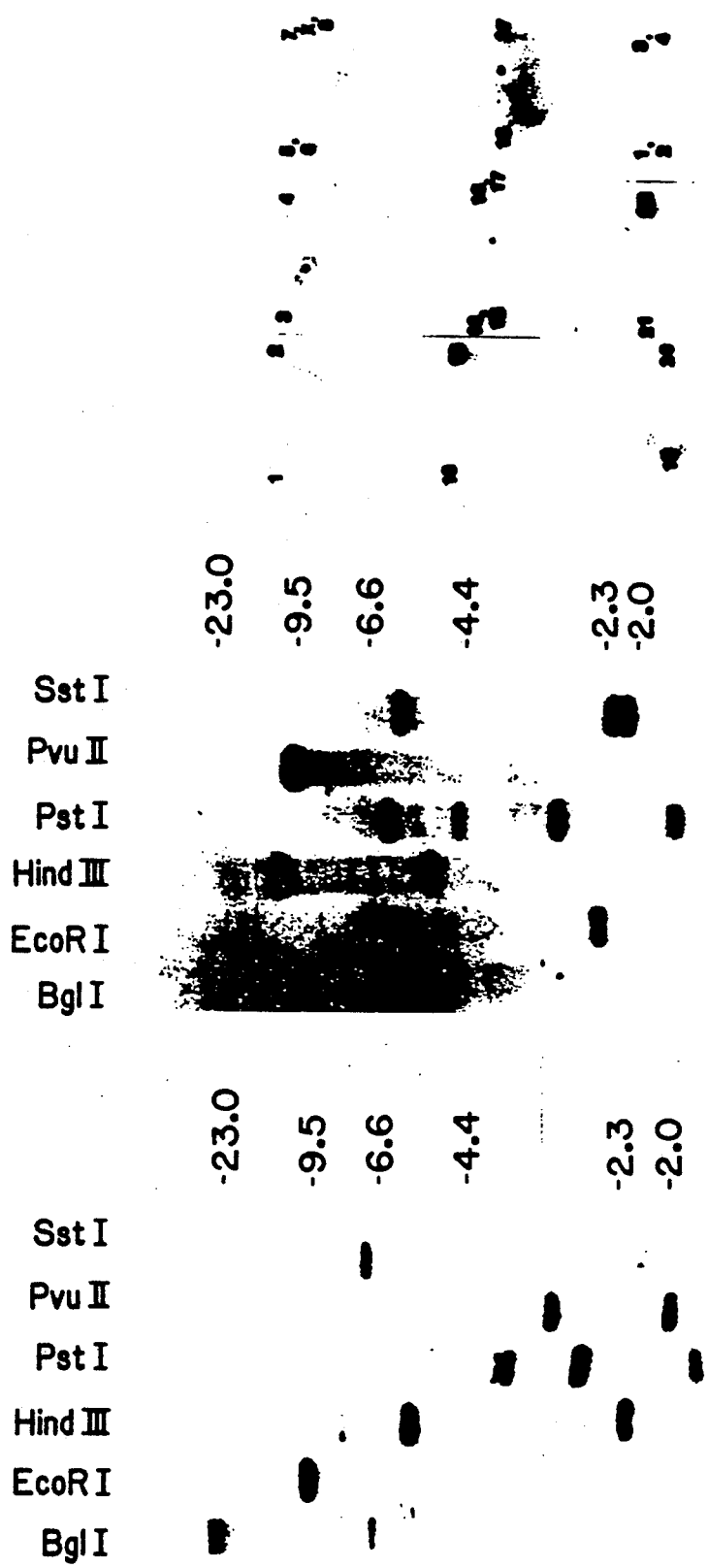

1  2  3

66K—

45K—

31K—

FIG. VII - 4(A)

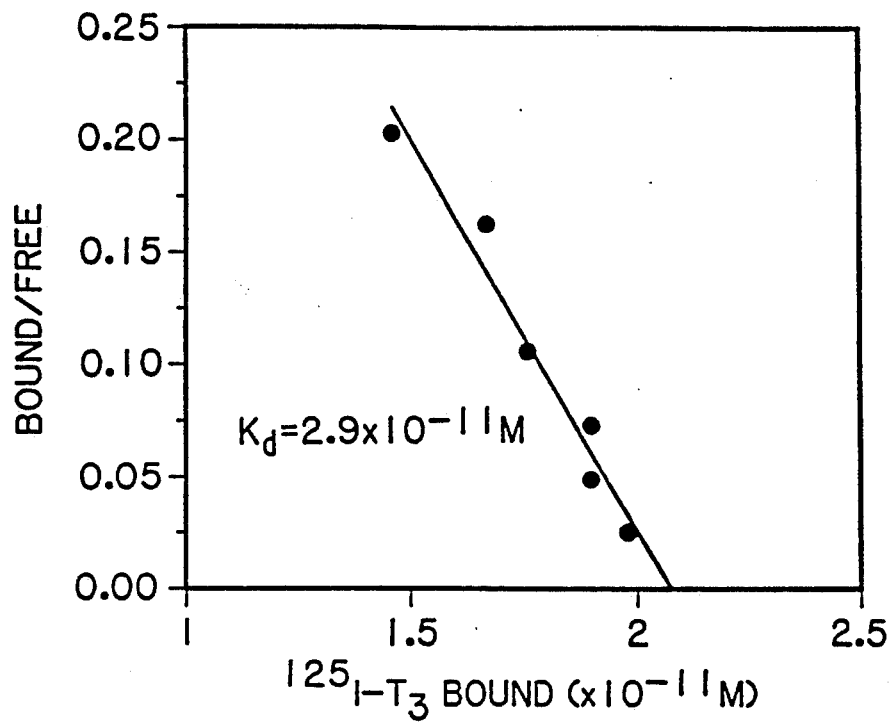
FIG. VII – 4(B)
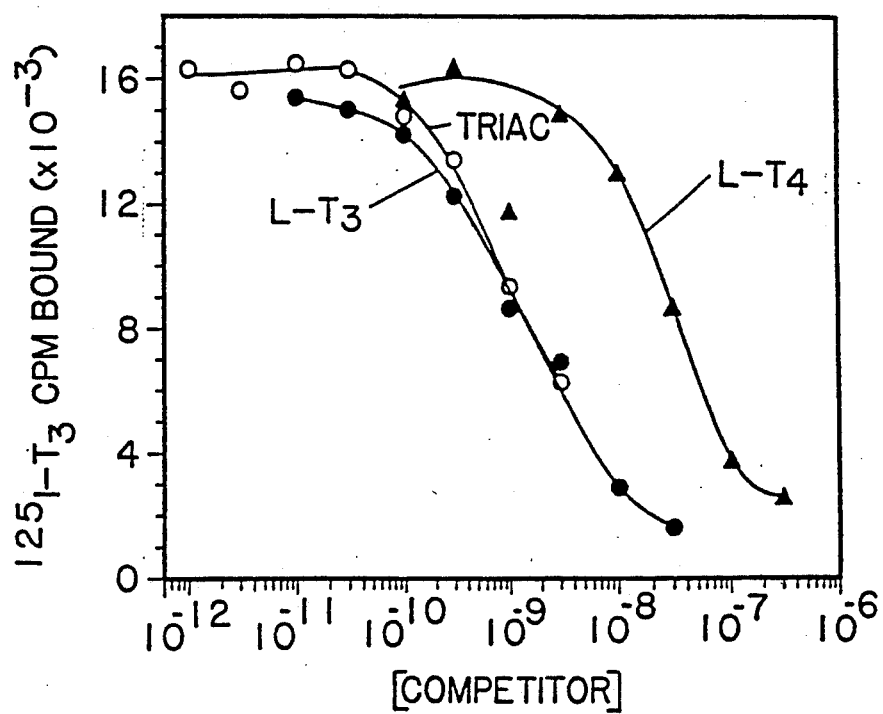
FIG. VII – 4(C)

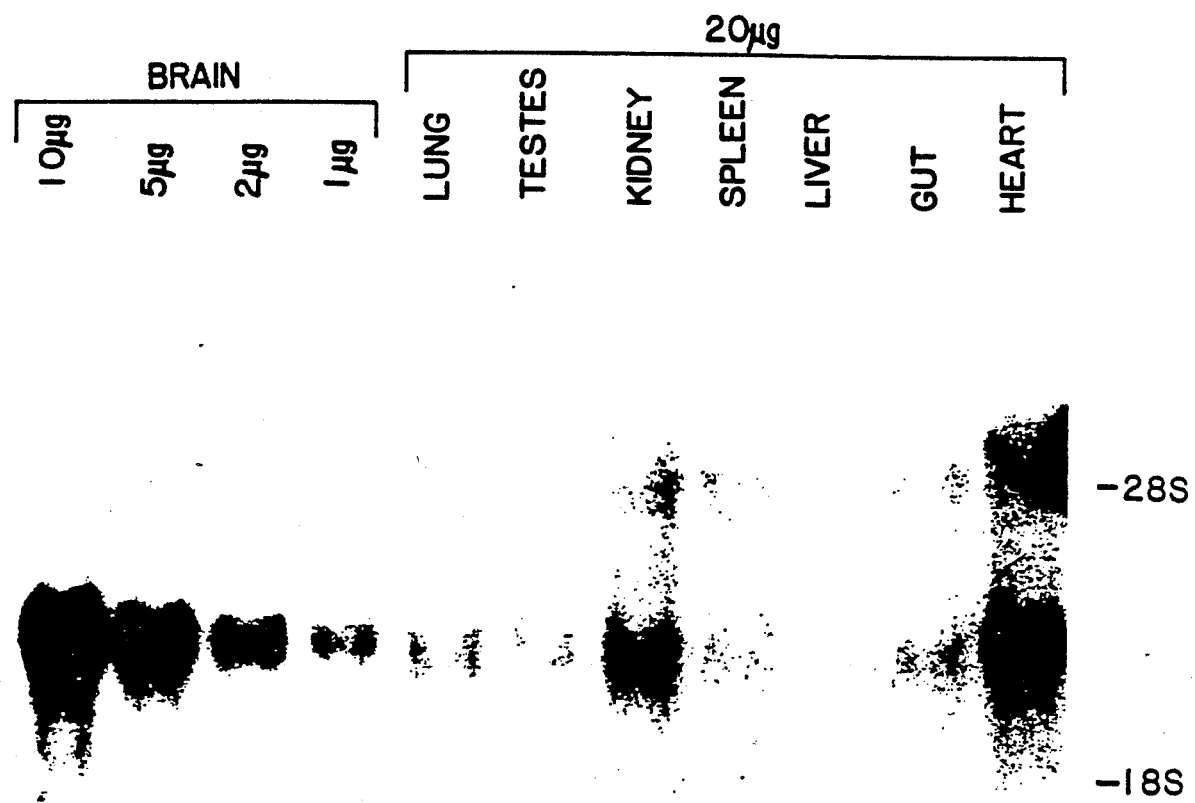
FIG. VII - 5

BIOASSAY FOR IDENTIFYING LIGANDS FOR STEROID HORMONE RECEPTORS

ACKNOWLEDGMENT

This invention was made with government support under a grant from the National Institutes of Health (Grant No. GM 26444).

RELATED APPLICATION

This is a divisional application of U.S. Ser. No. 07/108,471, filed Oct. 20, 1987, now U.S. Pat. No. 5,071,773 which is, in turn, a continuation-in-part of U.S. Ser. No. 06/922,585, filed Oct. 24, 1986, now abandoned.

FIELD OF THE INVENTION

The present invention relates to hormone receptor proteins and genes encoding them, modification of such receptors and genes by recombinant DNA and other genetic engineering techniques, plus uses of such receptors and genes, both unmodified and modified. More particularly, the invention concerns steroid and thyroid hormone receptors and associated genes. Most particularly, it concerns human glucocorticoid, mineralocorticoid and thyroid hormone receptors and genes for them. In addition the invention relates to a novel bioassay system for determining the functionality of hormone receptor proteins coded for by receptor DNA clones, plus novel methods for inducing and controlling expression of genes whose transcription is activated by hormones complexed with receptor proteins.

BACKGROUND OF THE INVENTION

Transcriptional regulation of development and homeostasis in complex eukaryotes, including humans and other mammals, birds, and fish, is controlled by a wide variety of regulatory substances, including steroid and thyroid hormones. These hormones exert potent effects on development and differentiation in phylogenetically diverse organisms and their actions are mediated as a consequence of their interactions with specific, high affinity binding proteins referred to as receptors. See generally, Jensen, et al., (1972); Gorski, et al., (1976); Yamamoto, et al., (1976); O'Malley, et al., (1969) Hayward, et al., (1982); and Asburner, et al., (1978).

Receptor proteins, each especially specific for one of the several classes of cognate steroid hormones (i.e., estrogens (estrogen receptor), progestogens (progesterone receptor), glucocorticoids (glucocorticoid receptor), androgens (androgen receptor), aldosterones (mineralocorticoid receptor) or for cognate thyroid hormones (thyroid hormone receptor), are known and distributed in a tissue specific fashion. See Horwitz, et al., (1978) and Pamiter, et al., (1976).

Turning now to the interaction of hormones and receptors, it is known that a steroid or thyroid hormone enters cells by facilitated diffusion and binds to its specific receptor protein, initiating an alosteric alteration of the protein. As a result of this alteration, the hormone/receptor complex is capable of binding to certain specific sites on chromatin with high affinity. See Yamamoto, et al., (1972) and Jensen, et al., (1968).

It is also known that many of the primary effects of steroid and thyroid hormones involve increased transcription of a subset of genes in specific cell types. See Peterkofsky, et al., (1968) and McKnight, et al., (1968). Moreover, there is evidence that activation of transcription (and, consequently, increased expression) of genes which are responsive to steroid and thyroid hormones (through interaction of chromatin with hormone receptor/hormone complex) is effected through binding of the complex to enhancers associated with the genes. (See Khoury, et al., 1983.)

In any case, a number of steroid hormone and thyroid hormone responsive transcriptional control units, some of which have been shown to include enhancers, have been identified. These include the mouse mammary tumor virus 5'-long terminal repeat (MTV LTR), responsive to glucocorticoid, aldosterone and androgen hormones; the transcriptional control units for mammalian growth hormone genes, responsive to glucocorticoids, estrogens, and thyroid hormones; the transcriptional control units for mammalian prolactin genes and progesterone receptor genes, responsive to estrogens; the transcriptional control units for avian ovalbumin genes, responsive to progesterones; mammalian metallothionein gene transcriptional control units, responsive to glucocorticoids; and mammalian hepatic alpha$_{2u}$-globulin gene transcriptional control units, responsive to androgens, estrogens, thyroid hormones and glucocorticoids. (See the Introduction portion of Experimental Section I of this Specification for references.)

A major obstacle to further understanding and more practical use of the steroid and thyroid hormone receptors has been the lack of availability of the receptor proteins, in sufficient quantity and sufficiently pure form, to allow them to be adequately characterized. The same is true for the DNA gene segments which encode them. Lack of availability of these DNA segments has prevented in vitro manipulation and in vivo expression of the receptor-coding genes, and consequently the knowledge such manipulation and expression will yield.

The present invention is directed to overcoming these problems of short supply of adequately pure receptor material and lack of DNA segments which encode the receptors.

REFERENCE LIST

The background section of the specification refers to the following publications.

PUBLICATIONS

1. Asburner, M., and Berendes, H. D. in *The Genetics and Biology of Drosophila*, Eds. Ashburner, M., and Wright, T. R. F., Vol. 2, pp. 315–395, Academic, London (1978).
2. Gorski, J., and Gannon, F., *A. Rev. Physiol.*, 38: 425–450 (1976)
3. Hayward, M. A., Brock, M. L. and Shapirof D. J., *Nucleic Acids Res.*, 10:8273–8284 (1982).
4. Horwitzy K. B., and McGuire, W. L., *J. Biol. Chem.*, 253: 2223–2228 (1978).
5. Jensen, E. V., and DeSombre, E. R., *A. Rev. Biochem.*, 41:203–230 (1972).
6. Jensen, E. V., et al., *Proc. Natl. Acad. Sci. U.S.A.*, 59:632–638 (1968).
7. Khoury, G., and Gruss, P., *Cell*, 33:313–314 (1983).
8. McKnight, G. S., and Palmiter, R. D., *J. Biol. Chem.*, 254:9050–9058 (1968).
9. O'Nalley, B. W., McGuire, W. L., Kohler, P. O., and Kornman, S. G.; *Recent Prog. Horm. Res.*, 25:105–160 (1969).

10. Parniter, R. D., Moore, P. B., Mulvihill, E. R. and Emtage, S., *Cell*, 8:557-572 (1976).
11. Peterkofsky, B., and Tomkins, G., *Proc. Natl. Acad. Sci. U.S.A.*, 60:222-228 (1968).
12. Yanamoto, K. R., and Alberts, B. M., *A. Rev. Biochem.*, 45:721-746 (1976).
13. Yamamoto, K. R., and Alberts, B. M., *Proc. Natl. Acad. Sci. U.S.A.*, 69:2105-2109 (1972).

OTHER PUBLICATIONS

Some of the information disclosed in this specification has been published:

The study disclosed in Experimental Section I has been published as: Hollenberg, S. M., Weinberger, C., Ong, E. S., Cerelli, G., Oro, A., Lebo, R., Thompson, E. B., Rosenfeld, M. G., and Evans, R. M., "Primary Structure and Expression of a Functional Human Glucocorticoid Receptor cDNA", *Nature* (London), 318:635-641 (December, 1985).

The study disclosed in Experimental Section II has been published as: Giguere, V., Hollenberg, S. M., Rosenfield, M. G., and Evans, R. M., "Functional Domains of the Human Glucocorticoid Receptor", (*Cell*, 46:645-652 (August, 1986)

The study disclosed in Experimental Section III has been published as: Weinberger, C., Thompson, C. C., Ong, E. S., Lebo, R., Gruol, D. J., and Evans, R. M., "The c-erb-A Gene Encodes a Thyroid Hormone Receptor", *Nature* (London), 324:641-646 (December, 1986).

The study disclosed in Experimental Section IV has been published as: Arriza, J. L., Weinberger, C., Cerelli, G., Glaser, T. M., Handelin, B. L., Houseman, D. E., and Evans, R. M., "Cloning of Human Mineralocorticoid Receptor Complementary DNA: Structural and Functional Kinship with the Glucocorticoid Receptor", *Science*, 237:268-275 (July, 1987).

The study disclosed in Experimental Section V is in press as: Giguere, V., Yang, N., Segui, P., and Evans, R. M., "Identification of a New Class of Steroid Hormone Receptors".

The study disclosed in Experimental Section VI is in press as: Glass, C. K., Franco, R., Weinberger, C., Albert, V. R., Evans, R. M., and Rosenfeld, M. G., "A c-erb-A Binding Site in the Rat Growth Hormone Gene Mediates Transactions by Thyroid Hormone".

The study disclosed in Experimental Section VII has been published as: Thompson, Catherine C., Weinberger, Cary, Lebo, Roger, and Evans, Ronald M., "Identification of a Novel Thyroid Hormone Receptor Expressed in the Mammalian Central Nervous System", *Science*, 237:1610-1614 (September, 1987).

BRIEF DESCRIPTION OF THE DRAWINGS

The following is a brief description of the drawings. More detailed descriptions are found in the Experimental Sections of this sepcification. To avoid confusion, drawings which are referred to in Experimental Section I are labeled with the prefix "I"; those referred to in Experimental Section II are labeled with the prefix "II", and so on.

The drawings comprise 40 figures, of which:

EXPERIMENTAL SECTION I

FIG. I-1 (*a* and *b*) is a drawing which shows the human glucocorticoid receptor cDNA sequencing strategy (FIG. I-1*a*), plus a schematic representation of cDNA clones (FIG. I-1*b*).

FIGS. I-2 (1 and 2) are drawings which show the cDNA and predicted primary protein sequence of human glucocorticoid receptor (hGR).

FIG. I-3 (*a* and *b*) is a drawing which shows the restriction map (FIG. I-3*a*) and nucleotide sequence (FIG. I-3*b*) of the 3' end of the human glucocorticoid receptor beta cDNA (beta-hGR).

FIG. I-4 (*a* and *b*) relates to an immunoblot comparison of hGR translated in vitro with in vivo hGR from cell extracts. FIG. I-4*a* is a drawing showing the vectors constructed for ia vitro transcription of the hGR cDNA sequence. FIG. I-4*b* is a photograph showing a Western blot analysis of in vitro translation products and cell extracts.

FIG. I-5 is a graph showing steroid-binding of alpha-hGR (GR107) translated in vitro.

FIGS. I-6 (*a* and *b*) are schematic drawings of expression plasmids pGERR1 and pGERR2. Plasmid pGERR1 was used to express estrogen related receptor hERR1; pGERR2 was used to express hERR2.

EXPERIMENTAL SECTION II

FIG. II-1 is a drawing showing a schematic representation of the hGR functional assay.

FIG. II-2 is a photograph showing a Western blot analysis which illustrates expression of hGR protein.

FIG. II-3 is a photograph of a blot which illustrates induction of CAT activity by hGR.

PIG. II-4 (A and B) is a graph. FIG. II-4A shows the doze-response to DEX of pRShGR alpha; FIG. II-4B shows the titration of pRShGRa.

FIG. II-5 in a schematic drawing showing the location of functional domains in hGR.

EXPERIMENTAL SECTION III

FIG. III-1 (*a*, *b*(1) and *b*(2)) are drawings which show (a) the restriction map and sequencing strategy, plus (b) the nucleotide and predicted amino acid sequence of human placenta c-erb-A cDNA.

FIG. III-2 is a drawing showing an amino acid sequence comparison between the carboxy-terminal portions of the v-erb-A oncogene product, the human placental c-erb-A polypeptide and the human glucocorticoid and oestrogen receptors.

FIG. III-3 (*a*, *b* and *c*) is a photograph of a blot showing Southern analysis and chromosome mapping of human placental DNA with c-erb-A DNA probes. FIG. III-3*a* shows human term placental DNA digested with endonucleases and separated on an agarose gel. FIG. III-3*b* shows an analysis of a placental DNA using c-erb-A as a probe. FIG. III-c shows chromosome mapping of the human c-erb-A genes.

FIG. III-4 (*a* and *b*) is a photograph showing human c-erb-A expression. FIG. III-4*a* is a blot showing a Northern analysis of RNA's from human cell lines and human placenta. FIG. III-4*b* illustrates synthesis of erb-A polypeptide in vitro.

FIG. III-5 (*a*, *b*, *c* and *d*) shows four graphs which relate to thyroid hormone binding to erb-A polypeptides synthesized in vitro. FIG. III-5*a* is a Scatchard analysis of $^{125}I$-$T_3$ binding to the erb-A polypeptides made in vitro. FIG. III-5*b* shows competition of thyroid hormone analogues in vitro. FIG. III-5*c* shows competition of triiodothyronine isomers from $^{125}I$-$T_3$ binding to polypeptides synthesized in vitro. FIG. III-5*d* shows competition of thyroid hormone analogues for $^{125}I$-$T_3$ binding to 0.4 KCl HeLa cell nuclear extracts.

FIG. III-6 is a schematic drawing which compares the steroid and thyroid hormone receptors.

FIG. III-7 is a drawing which shows the cDNA nucleotide sequence and the predicted primary protein sequence of human thyroid receptor hERBA 8.7. (The sequence of thyroid receptor hFA 8 is related to hERBA 8.7. See the Description of the Invention section which follows.)

EXPERIMENTAL SECTION IV

FIG. IV-1 (At B, C and D) is comprised of three photographs and one schematic drawing, all of which concern to isolation of a genomic sequence related to the hGR gene. FIG. IV-1A is a photograph showing high-stringency Southern analysis of human placenta DNA digested with the indicated nucleases. FIG. IV-4B is similar except that it shows low-stringency Southern analysis. FIG. IV-4C is also a photograph of a Southern blot; it demonstrates isolation of the genomic sequence in a clone designated lambda HGH. FIG. IV-4D is a schematic drawing which shows the intron-exon structure of lambda HGH genomic fragment and its homology with hGR.

FIGS. IV-2 (A, B-1 and B-2) are drawings which show the cDNA nucleotide sequence and the predicted primary protein sequence of human mineralocorticoid receptor. FIG. IV-2A shows the composite structure of hMR aligned with a line diagram of some restriction endonuclease cleavage sites. FIG. IV-2B 1 and 2 show the complete nucleotide sequence of hMR and its primary predicted amino acid sequence.

FIG. IV-3 is a drawing which shows the amino acid homology between mineralocorticoid receptor and glucocorticoid receptor.

FIG. IV-4 (A, B, C and D) is a drawing and three graphs which relate to the steroid-binding properties of expressed hMR. FIG. IV-4A shows the structure of expression plasmid pRShMr, the plasmid used to express hMR. FIG. IV-4B is a graph showing Scatchard analysis of tritiated aldosterone binding in extracts prepared from pRShMR-transfected COS cells. FIGS. IV-4C and D are graphs showing competition of unlabeled steroids for binding with [$^3$H]aldosterone in transfected COS cells.

FIG. IV-5 (A, B and C) is a drawing and two photographs which show transcriptional activation of MMTV LTR by hMR and hGR expression plasmids in transfected CV-1 cells. FIG. IV-5A is a schematic drawing of plasmid GMCAT. FIG. IV-5B is a photograph of a blot which shows differential CAT enzyme activity found after hMR or hGR transfection with normal serum. FIG. IV-5C is a photograph of a blot which shows differential induction of CAT activity by aldosterone or dexamethasone in cells transfected with hMR or hGR.

FIG. IV-6 is a photograph of a blot showing Northern analysis of mineralocorticoid receptor mRNA's in rat tissues.

FIG. IV-7 is a photograph showing chromosomal localization of hMR gene by Southern analysis of microcell hybrids.

FIG. IV-8 is a schematic drawing showing amino acid comparisons of the hGR, hMR, and hPR structures.

EXPERIMENTAL SECTION V

FIG. V-1 (A, B-1 and B-2) are drawings which show the cDNA nucleotide sequence and the predicted primary protein sequence of hERR1. FIG. V-1A shows the composite structure of hERR1 aligned with a line diagram of some restriction endonuclease cleavage sites. FIG. V-1B-1 and B-2 show the complete nucleotide sequence of hERR1 and its primary predicted amino acid sequence.

FIG. V-2 (A, B-1 and B-2) are drawings which show the cDNA nucleotide sequence and he predicted primary protein sequence of hERR2. FIG. V-2A shows the composite structure of hERR2 aligned with a line diagram of some restriction endonuclease cleavage sites. FIG. V-2B-1 and B2 show the complete nucleotide sequence of hERR2 and its primary predicted amino acid sequence.

FIG. V-3 is a drawing showing an amino acid sequence comparison between the carboxy-terminal regions of hERR1, hERR2, the human oestrogen and glucocorticoid receptors.

FIGS. V-4 (A and B) are photographs showing Northern blot hybridization of hERR1 (FIG. V-4A) and mRNA's in rat and human tissues (FIG. V-4B).

FIG. V-5 is a schematic drawing showing amino acid comparison between hERR1 and hERR2, hER and human thyroid hormone receptor (hT$_3$R beta).

EXPERIMENTAL SECTION VI

FIG. VI-1 (a, b and c) is comprised of two drawings, plus a drawing and a photography all of which relate to thyroid hormone responsiveness of various gene fusions containing-rat GE 5'-flanking sequences. FIG. VI-1a is a drawing which illustrates responsiveness of 5' and 3' deletions of the rat GH gene. FIG. VI-1b is a drawing which shows functional analysis of the putative T$_3$ receptor binding site. FIG. VI-1c is a drawing/photograph combination which illustrates an mRNA transcription initiation site analysis.

FIG. VI-2 (a and b) is a drawing which relates to binding of T$_3$ receptors to oligonucleotide probes containing biotin-11-dUTP. FIG. VI-1a is a schematic representation of two oligonucleotide probes used to assay T$_3$ receptor binding to GH 5'-flanking sequences. FIG. IV-1b is a graph showing precipitation of $^{125}$I-T$_3$ labeled T$_3$ receptors from GC2 nuclear extracts by various oligonucleotide probes.

FIG. VI-3 is a photograph showing a DNase I footprinting of the rat GH enhancer element by GC2 nuclear extracts.

FIG. VI-4 is a graph illustrating binding to oligonucleotides containing 64 and 29 base pairs of 5'-flanking GH sequence of rat pituitary cell T$_3$ receptors and an hc-erb-A in vitro translation product.

EXPERIMENTAL SECTION VII

FIG. VII-1 (A and B) is a schematic drawing which shows the restriction map (A), plus the nucleotide and predicted amino acid sequence (B), of thyroid hormone receptor cDNA from rat brain clone rbeA12.

FIG. VII-2 is a schematic drawing which compares the rat thyroid hormone receptor (rTR alpha) protein with the human thyroid hormone receptor (hTR beta) and chicken thyroid hromone receptor (cTR alpha) proteins.

FIG. VII-3 (A, B and C) is a photograph showing Southern blot analysis and human chromosomal localization of the rTR alpha gene. FIG. VII-3A is a blot showing human placenta DNA hybridized to a 500-bp PvuII fragment from rbeA12; FIG. VII-3B shows the placenta DNA hybridized to a 450-bp SstI fragment from hTR beta. FIG. VII-C shows chromosome mapping of the rTR alpha gene.

FIG. VII-4 (A, B and C) shows a photograph and two graphs which relate to in vitro translation and thyroid hormone binding of rTR alpha. FIG. VII-4A is a photograph of a SDS-polyacrylamide gel showing the in vitro translation products of rTR alpha. FIG. VII-4B is a graph showing a Scatchard analysis of $^{125}$I-T$_3$ binding to in vitro translated rTR alpha. FIG. VII-4C is a graph showing competition of thyroid hormone analogs for $^{125}$I-T$_3$ binding to in vitro translated rTR alpha.

FIG. VII-5 is a photograph of a gel which illustrates tissue distribution of rTR alpha mRNA.

DEFINITIONS

In the present specification and claims, reference will be made to phrases and terms of art which are expressly defined for use herein as follows:

As used herein, GR means glucocorticoid receptor. Disclosed DNA hGR codes for glucocorticoid receptor GR.

As used herein, MR means mineralocorticoid receptor. Disclosed DNA hMR codes for mineralocorticoid receptor MR.

An used herein, TR means thyroid receptor. Disclosed human DNA's c-erb-A, hERBA 8.7 and hFA8, and rat rbeA12, all code for thyroid receptor.

As used herein, hERR1 and hERR2 designate DNA's which code for estrogen-related receptor proteins.

As used herein, glucocorticoid hormones include cortisol, hydrocortisone (HC), and corticosterone (CS), and analogs thereof include dexamethasone (Dex), deoxycorticosterone (Doc), and triamcinolone acetonide.

As used herein, mineralocorticoids include aldosterone (Aldo), as well as corticosterone (CS), and deoxycorticosterone (Doc).

As used herein, thyroid hormones include thyroxine (T4) and triiodothyronine (T3).

As used herein, estrogens (or oestrogens) include estradiol-17 beta, and analogs thereof include diethylstilbestrol.

As used herein, progestogens include progesterone (Prog), and analogs thereof include promegestone.

As used herein, androgens include dihydroxytestosterone, and analogs thereof include methyltrienolone.

As used herein, MTV means mammary tumor virus; MMTV means mouse mammary tumor virus.

As used herein, RSV means Rous sarcoma virus; SV means Simian virus.

As used herein, CAT means chloramphenicol acetyltransferase.

As used herein, COS means monkey kidney cells which express T antigen (Tag). See Gluzman, Cell, 23:175 (1981). COS cells are useful in the bioassay system of the present invention.

As used herein, CV-1 means mouse kidney cells from the cell line referred to as "CV-1". CV-1 is the parental line of COS. Unlike COS cells, which have been transformed to express SV40 T antigen (Tag), CV-1 cells do not express T antigen. Like COS cells, CV-1 cells are useful in the bioassay system and methods of the present invention.

As used herein, when it is said that a protein has "hormone-binding properties characteristic of a hormone receptor", it means that, if, in any standard assay for binding-affinity between a hormone from a species, or a synthetic analog thereof, and its cognate receptor(s) from that species, the affinity of the protein for the hormone or synthetic analog is at least about 10% of the affinity of the hormone or analog and the cognate receptor(s) from that species.

As used herein, when it is said that the transcription-activating property of a protein (X) is "characteristic" of that of a hormone receptor (R), it means that, if, when tested in an assay such as the "cis-trans" receptor functionality bioassay system of the invention, (see Description of the Invention; also see Experimental Section II, especially FIG. II-1, plus the subsections labeled "Results" and "Experimental Procedures" which relate to use of the bioassay to show functional expression of hGR), the rate of expression from a gene (G) (whose transcription is activated by binding of: a receptor complexed with hormone or hormone analog) is, when protein (X) is employed in place of receptor (R), at least about 10% that shown when receptor (R) itself is used, as long as, in both the case of the "receptor" (R) and "protein (X)", the involved cells are bathed in the same concentration of hormone or analog thereof.

As used herein, when it is said that a protein has "hormone-binding or -transcription-activating properties characteristic of a hormone receptor", it is intended that the hormone receptor itself be encompassed within this definition.

As used herein, when it is said that the transcription of a gene (G) is "substantially activated by hormone (H), or hormone analog (aH)", it means that the transcription of gene (G) is induced by binding of: a hormone/receptor [(H) or (aH)/(R) or (r)] complex to chromatin near where gene (G) is located. Under this definition (R) is meant to designate "wild-type" or unaltered hormone receptors. The lower case (r) notation is meant to designate functional "engineered" or "modified" receptor proteins, or proteins encoded by mRNA variants of "wild-type" receptor genes.

As used herein, GRE's mean glucocorticoid response elements and TRE's mean thyroid receptor enhancer-like DNA sequences. GRE's are enhancer-like DNA sequences that confer glucocorticoid responsiveness via interaction with the GR. See Payvar, et al., Cell, 35:381 (1983) and Schiedereit, et al., Nature, 304:749 (1983). TRE's are similar to GRE's except that they confer thyroid hormone responsiveness via interaction with TR.

As used herein, the terms "transcriptional control unit", "transcriptional control element", "hormone responsive promoter/enhancer element" and "DNA sequences which mediate transcriptional stimulation" mean the same thing, and are used interchangeably.

As used herein, in the phrase "operative hormone responsive promoter/enhancer element functionally linked to an operative reporter gene", the word "operative" means that the respective DNA sequences (represented by the terms "hormone responsive promoter/enhancer element" and "reporter gene") are operational, i.e., work for their intended purposes; the word "functionally" means that after the two segments are linked, upon appropriate activation by a hormone-receptor complex, the reporter gene will be expressed as the result of the fact that the "hormone responsive promoter" was "turned on" or otherwise activated.

As used herein, the term "receptor-negative" means that no receptor is detectable in the cell, or if it is, only a de minimus amount (i.e., a barely detectable amount) of receptor is present.

As used herein, a "mutant" of a DNA of the invention means a DNA of the invention which has been genetically engineered to be different from the "wild-type" or unmodified sequence. Such genetic engineering can include the insertion of new nucleotides into the wild-type sequences, deletion of nucleotides from the wild-type sequences, or a substitution of nucleotides in the wild-type sequences.

Use of the term "substantial sequence homology" in the present specification and claims means it is intended that DNA or RNA sequences which have de minimus sequence variations from the actual sequences disclosed and claimed herein are within the scope of the appended claims.

The amino acids which comprise the various amino acid sequences appearing herein may be identified according to the following three-letter or one-letter abbreviations:

| Amino Acid | Three-Letter Abbreviation | One-Letter Abbreviation |
| --- | --- | --- |
| L - Alanine | Ala | A |
| L - Arginine | Arg | R |
| L - Asparagine | Asn | N |
| L - Aspartic Acid | Asp | D |
| L - Cysteine | Cys | C |
| L - Glutamine | Gln | Q |
| L - Glutamic Acid | Glu | E |
| L - Histidine | His | H |
| L - Isoleucine | Ile | I |
| L - Leucine | Leu | L |
| L - Lysine | Lys | K |
| L - Methionine | Met | M |
| L - Phenylalanine | Phe | F |
| L - Proline | Pro | P |
| L - Serine | Ser | S |
| L - Threonine | Thr | T |
| L - Tryptophan | Trp | W |
| L - Tyrosine | Tyr | Y |
| L - Valine | Val | V |

The nucleotides which comprise the various nucleotide sequences appearing herein have their usual single-letter designations (A, G, T, C or U) used routinely in the art.

In the textual portion of the present specification and claims, references to Greek letters are written as alpha, beta, etc. In the Figures the corresponding Greek letter symbols are somtimes used.

Expression plasmid pGEM3 is commercially available from Promega Biotec, 2800 South Fish Hatchery Roads Madison, Wis. 53711.

DEPOSITS

Plasmids pRShGR-alpha, pRShMR, peA101, rbeA12 and GMCAT, all of which are in *E. coli* HB101, plasmids pE4 and pHKA, both of which are in *E. coli* DH5, plus plasmids phH3t phERBA 8.7 and phFA 8, have been deposited at the American Type Culture Collection, Rockville, Md., U.S.A. (ATCC) under the terms of the Budapest Treaty on the International Recognition of Deposits of Microorganisms for Purposes of Patent Procedure and the Regulations promulgated under this Treaty. Samples of the plasmids are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this applications is filed or in which any patent granted on any such application is granted.

The ATCC Deposit Numbers for the ten deposits are as follows:

| | |
| --- | --- |
| pRShGR-alpha | 67200 |
| pRShMR | 67201 |
| peA101 | 67244 |
| rbeA12 | 67281 |
| GMCAT | 67282 |
| pE4 | 67309 |
| pHKA | 67310 |
| phERBA 8.7 | 40374 |
| phFA 8 | 40372 |
| phH 3 | 40373 |

SUMMARY OF THE INVENTION

In one aspect, the present invention comprises a double-stranded DNA segment wherein the plus or sense strand of the segment contains a sequence of triplets coding for the primary sequence of a protein which has hormone-binding ana/or transcription-activating properties characteristic of a hormone receptor protein selected from the group consisting of: a glucocorticoid receptor, a mineralocorticoid receptor and a thyroid hormone receptor. According to this aspect of the invention, the double-stranded DNA segment is one which is capable of being expressed into the receptor protein.

In another aspect, the invention comprises a single-stranded DNA, which is the sense strand of a double-stranded DNA according to the invention, and an RNA made by transcription of a double-stranded DNA of the invention.

In another aspect, the invention comprises plasmids which contain DNA illustrative of the DNA of the present invention. These plasmids have been deposited with the American Type Culture Collection for patent purposes. The plasmids of the invention include plasmids selected from the group consisting of: pRShGR-alpha (ATCC #67200), pRShMR (ATCC #67201) peA101 (ATCC #67244); rbeA12 (ATCC #67281), GMCAT (ATCC #67282), pE4 (ATCC #67309), PHKA (ATCC #67310), phERBA 8.7 (ATCC #40374), phFA8 (ATCC #40372). and phH3 (ATCC #40373).

In still another aspect, the invention comprises a cell, preferably a mammalian cell, transformed with a DNA of the invention. According to this aspect of the invention, the transforming DNA is capable of being expressed in the cell, thereby increasing the amount of receptor, encoded by this DNA, in the cell.

Further the invention comprises cells, including yeast cells and bacterial cells such as those of *E. coli* and *B. subtilis*, transformed with DNA's of the invention.

Still further the invention comprises novel receptors made by expression of a DNA of the invention, or translation of an mRNA of the invention. According to this aspect of the invention, the receptors will be protein products of "unmodified" DNA's and mRNA's of the invention, or will be modified or genetically engineered protein products which, as a result of engineered mutations in the receptor DNA sequences, will have one or more differences in amino acid sequence from the corresponding naturally occurring "wild-type" or cognate receptor (i.e., the naturally occurring receptor of known sequence with the greatest amino acid sequence homology to the novel receptor). Preferably these receptors, whether "unmodified" or "engineered", will have at least about 10% of the hormone binding activity and/or at least about 10% of the transcription-activating activity of the corresponding naturally occurring cognate receptor.

The invention also comprises a novel method for determining the functionality of hormone receptor proteins produced from the DNA's (or mRNA's) of the invention. The new method, which is referred to herein as the "cis-trans" bioassay system, utilizes two plasmids: an "expression" plasmid and a "reporter" plasmid. According to the invention, the expression plasmid can be any plasmid which contains and is capable of expressing a receptor DNA of the invention, or an engineered mutant thereof, in a suitable receptor-negative host cell. Also according to the invention, the reporter plasmid can be any plasmid which contains an operative hormone responsive promoter/enhancer element functionally linked to an operative reporter gene.

In practicing the "cis-trans" bioassay of the invention, the expression plasmid (containing a "receptor" DNA of the invention) and the reporter plasmid are cotransfected into suitable receptor-negative host cells. The transfected host cells are then cultured in the presence and absence of a hormone, or analog thereof, which is able to activate the hormone responsive promoter/enhancer element of the reporter plasmid. Next the transfected and cultured host cells are monitored for induction (i.e., the presence) of the product of the reporter gene sequence. Finally, according to the invention, the expression and steroid binding-capacity of the receptor protein (coded for by the receptor DNA sequence on the expression plasmid and produced in the transfected and cultured host cells), is measured. (See FIG. II-2 for a schematic drawing of this "cis-trans" bioassay system.)

The "cis-trans" bioassay system is especially useful for determining whether a receptor DNA of the invention has been expressed in a transformed host cell; it is also useful in determining whether a receptor of the invention has at least about 10% of the binding activity of the corresponding naturally occurring cognate receptor, as well as whether such a receptor has at least about 10% of the transcription-activating activity of the corresponding naturally occurring cognate receptor.

Finally, it has been discovered, with the use of the DNA's of the invention, that a necessary and sufficient condition, for activation of transcription of a gene (G) whose transcription is activated by hormones complexed with receptors is the presence of the hormone and its receptor in the same cell as (G). This discovery has enabled us to provide improved compositions and methods for producing desired proteins in genetically engineered cells.

Two of these methods are methods of the present invention. The first is a method for inducing transcription of a gene whose transcription is activated by hormones complexed the receptors. The second is a method for genetically engineering a cell and then increasing and controlling production of a protein coded for by a gene whose transcription is activated by hormones complexed with receptor proteins.

In discussing these two methods, a gene whose transcription is activated by hormones complexed with receptor proteins will be referred to as gene (G). The hormone which activates gene (G) will be referred to as (H), and any of its analogs as (aH). Receptor protein will be referred to as (R), and functional modifications thereof as (r). Finally, the cell where gene (G) is located will be referred to as (C), and the protein coded for by gene (G) will be referred to as (P).

According to the gene induction method of the invention, cell (C), which contains gene (G), is transformed by a DNA of the invention, which is capable of being expressed in cell (C) and which codes for receptor (R) or a modified functional form (r) thereof; and the concentration of hormone (H), or analog (aH), in cell (C) is increased to a level at least sufficient to assure induction of expression of gene (G).

According to the method for engineering a cell and then producing protein (P): gene (G), which codes for protein (P), is placed in cell (C) so that it is under the control of a transcriptional control element to which hormone (H), when complexed with receptor (R), can bind, thereby inducing transcription of gene (G). Also according to this protein production method, both hormone (H) and receptor (R) are present in cell (C). The presence of receptor (R) is assured by transforming cell (C) with a DNA of the invention which codes for receptor (R), or a functional modified form (r) thereof. The presence of hormone (H), or its synthetic analog (aH) is assured by bathing transformed cell (C) in a bathing solution which contains hormone (H) or analog (aH). Then, according to the method, the transcription of gene (G) is controlled by controlling the concentration of (H) or (aH) in the bathing solution used to bath transformed cell (C). By so controlling the transcription of gene (G), it is possible to control the production of protein (P) in cell (C).

As those skilled in the art will appreciate, based on this teaching, it will now be possible to engineer cells so that production of a protein (P), encoded by a gene (G) whose transcription is activated by a hormone/receptor complex, in controlled by simply assuring the presence of hormone (H) and its receptor in cell (C) where gene (G) in located, and then controlling the concentration of hormone (H) or its analog that is present in cell (C).

DESCRIPTION OF THE INVENTION

The present invention relates, in part, to DNA segments which code for proteins having the hormone-binding and/or transcription-activating properties characteristic of glucocorticoid, mineralocorticoid and thyroid hormone receptors. According to this aspect of the invention, these DNA segments are ones capable of being expressed, in suitable host cells, thereby producing glucocorticoid, mineralocorticoid and thyroid hormone receptors or receptor-like proteins. The invention also relates to mRNA's produced as the result of transcription of the sense stands of the DNA's of the invention.

The DNA's of the invention are exemplified by DNA's referred to herein as: human glucocorticoid receptor DNA (hGR); human thyroid hormone receptor DNA's (hTR: hTR alpha and hTR beta; hTR alpha is exemplified by hERBA 8.7 and hFA 8; hTR beta is exemplified by cellular or "c-erb-A"); rat thyroid hormone receptor (rbeA12), which is the rat homolog of human thyroid receptor alpha; human mineralocorticoid receptor (hMR); and new human steroid hormone receptors (hERR1 and hERR2). The sense strand cDNA nucleotide sequences, and the predicted primary protein sequences coded for thereby, are shown in FIG. I-2-1 and 2-2 for hGR; in FIG. III-1 B-1 and B-2 for human c-erb-A, and in FIG. III-7 for hERBA 8.7 and hFA 8; in FIG. IV-2 B-1 and B-2 for hMR; in FIGS. V-1 B-1 and B2 and V-2 B-1 and B2 for hERR1 and hERR2, respectively; and in FIG. VII-1B for rat thyroid receptor rbeA12.

DNA's hGR, human c-erb-A, hERBA 8.7, hFA8, hMR, hERR1, and hERR2 are preferred DNA's of the invention. Also preferred are the plasmids which carry these and other DNA's of the invention. Preferred plasmids include: pRShGR-alpha, pRShMR, peA101, rbeA12, GMCAT, pE4, PHKA, phERBA 8.7, phFA 8, and phH3.

In addition to pRShGR-alpha, preferred DNA's include modifications of pRShGR-alpha which are designated herein as I9, I37, I102, I120, I204, I214, I262, I289, I305, I346, I384, I403, I408, I422, I428, I440, I448, I490, I515, I532, I550, and I684, where "I" stands for "Insert", and the number following the "I" represents the DNA modification designation. Most preferred of the modified pRShGR DNA's are those which encode proteins having at least about 10% of the transcription-activating properties characteristic of human glucocorticoid receptor; those DNA's include I9, I37, I102, I120, I204, I214, I262, I289, I305, I346, I384, I403, I408, I422, I428, I440, I448, I490, I515, I532, I5 50, and I684.

Construction of pRShGR-alpha is detailed in the part of the specification labeled "Experimental Section II". (See especially subsection II. F. (b), "Recombinant Plasmids".) Experimental Section II also details construction and properties of the pRShGR-alpha modifications referred to in the preceding paragraph.

With regard to the cDNA sequence for hGR shown in FIG. II-2, the two C's at the 5'-end of the indicated sequence are part of the KpnI site joining the indicated segment to the 3' end of the segment which includes the RSV-LTR, and the T at the 3'-end of the indicated sequence is a few bases 5' of the point where the indicated segment is joined to the segment which includes the SV40 polyadenylation signal.

pRShMR was constructed in essentially the same manner as pRShGR-alpha and is essentially the same as pRShGR-alpha. Stated another way, with the exception of minor modifications at the insertion sites, the hMR segment shown in FIG. IV-2 B1 and B2 replaces hGR, the sequence of which is shown in FIG. I-2 (1 and 2). Like pRShGR-alpha, pRShMV contains the receptor protein DNA coding sequence under the control of the promoter from Rous Sarcoma virus, plus the SV40 origin of replication. See Footnote 41 in the Reference portion of Experimental Section IV; also see FIG. IV-4A; compare with FIG. II-1.

With regard to the hMR sequence shown in FIG. IV-2 B1 and B2, the AG at the 5'-end of the segment is a few base pairs downstream of a HindIII site, whereby the hMR segment is joined to the RSV-LTR-containing segment. The AA at the 3'-end of the segment shown in FIG. IV-2 B1 and B2 is a few bases upstream of the 5'-end of the segment which includes the SV40 polyadenylation signal.

Plasmid peA101 carries the entire coding region of human thyroid receptor c-erb-A. (The gene for c-erb-A been localized to human chromosome 3; the protein product encoded by this receptor gene is now referred to as hTR beta. See Experimental Section III; compare with Experimental Section VII.)

Plasmid peA101 was constructed by inserting the EcoRI fragment from pheA12 (spa FIG. III-1 B-1 and B2) into the EcoRI site of expression vector pGEM3 (Promega Biotec), in the correct orientation. For further detail on this construction see Experimental Section III, subsection III. I., under the heading labeled: FIG. III-4 (a and b) Methods.

In addition to the hTR receptor which has been localized to human chromosome 3, we have discovered a second thyroid hormone receptor that is distinct from the protein sequence predicted by plasmid peA101. We have now isolated and characterized this new and unexpected thyroid receptor from both the rat than the human. In the rat this new thyroid hormone receptor is encoded by the DNA of plasmid rbeA12. (The DNA and predicted primary protein sequence for rbeA12 is shown in FIG. VII-1A and B) In the human, the new thyroid hormone receptor is encoded by plasmid clone hERBA 8.7, and its related clone hFA 8. (See FIG. III-7 for the sequences of hERBA 8.7) hERBA 8.7 and hFA8 are cDNA products from the same gene. The DNA sequence of clone hFA 8 is identical with the DNA sequence for hERBA 8.7 (shown in FIG. III-7) with the following exceptions. The hFA 8 sequence is shorter than the sequence shown in FIG. III-7. More specifically, nucleotides 1 a (G), through 514 an (A), of the ERBA 8.7 sequence are missing in the hFA 8 sequence. In addition the hFA 8 sequence has a deletion which extends from the guanine (G) at base pair position 1138 through the guanine (G) at base pair 1244. This deletion eliminates amino acids 368, a (Glu), through 406, a (Gln) from the polypeptide encoded by the hFA 8 clone. As stated above, our initial thyroid receptor has been localized to chromosome 3. As we show in Experimental Section VII, the human gene for the new thyroid hormone receptor has been localized to human chromosome 17. Rat thyroid receptor rbeA12 represents the rat homolog of the human gene product from chromosome 17.

Because they are encoded by distinct genetic loci, the chromosome 17 gene products are now classified as hTR alpha and the chromosome 3 gene product is classified as hTR beta. Although highly related, the alpha and beta gene products contain specific changes in their primary amino acid sequence. Also, alpha and beta products display characteristically distinct patterns of expression.

The actions of thyroid hormones are widespread and dependent upon these receptors. Prior to our cloning of thyroid hormone receptor, this receptor had not been purified or biochemically characterized. Also, the scientific literature was entirely devoid of any evidence suggesting the-existence of multiple thyroid hormone receptor gene products. The existence of multiple receptors will be useful as the basis for developing thyroid hormone analogs that selectively activate only one class of these receptors. This could have widespread clinical impact and thus represents an exciting and important discovery.

The initial thyroid hormone receptor we characterized was peA12, the receptor now referred to as human thyroid receptor beta. We used this beta clone to screen, by molecular hybridization, a rat brain cDNA library for related sequences. This led to the identification of plasmid rbeA12 and its subsequent identification as a novel thyroid hormone receptor of the alpha class. Rat rbeA12 in turn was used as a molecular hybridization probe to clone the human homolog to the rbeA12 gene product. The human product is encoded by clones hERBA 8.7 and hFA 8.

Additional thyroid receptor cDNA's (rat thyroid receptor rbeA12, and human thyroid receptors hERBA 8.7 and hFA8 can be expressed by inserting their cDNA's, in the correct orientation, into expression vector pGEM3, as was done for c-erb-A.

Turning now to plasmid GMCAT, it is a reporter plasmid that contains the MTV LTR linked to the bacterial gene for chloramphenicol acetyltransferase (CAT). As a result of this linkage, use of pGMCAT provides an enzymatic assay for assessing transcriptional activity of the MTV promoter. Since the MTV promoter contains several glucocorticoid response elements (GRE's), reporter plasmid pGMCAT can be cotransfected with expression plasmids carrying glucocorticoid or mineralocorticoid receptor DNA's, now known or later discovered, into suitable host cells. (Such cotransfection is part of the receptor "cis-trans" functionality bioassay system of the present invention. This aspect of the invention is discussed more fully below.) Detection of CAT activity in the co-transfected host cells shows that the polypeptides produced by the receptor expression plasmids are functional, i.e., have transcription activating properties characteristic of receptor proteins. Plasmid pGMCAT has been deposited with the ATCC for patent purposes; it has been accorded ATCC #67282. (See FIG. IV-5A for a schematic drawing of pGMCAT.)

Plasmid GHCAT is an example of another reporter plasmid which is useful in the present invention. pGHCAT contains a portion of the growth hormone promoter functionally linked to the bacterial gene for chloramphenicol acetyltransferase (CAT). Because of this linkage, use of pGHCAT provides an enzymatic assay for assessing transcriptional activity of the growth hormone (GH) promoter. Since the GH promoter contains a thyroid hormone response element (TRE), reporter plasmid pGHCAT can be cotransfected with expression plasmids carrying thyroid hormone receptor DNA's, now known or later discovered, into suitable host cells. (Such cotransfection is also part of the "cis-trans" receptor functional bioassay system of the present invention. This aspect of the invention is discussed more fully below.) When pGHCAT is used with a TR expression plasmid (which for example could carry hTR alpha or hTR beta DNA) to cotransfect suitable host cells, detection of CAT activity in the co-transfected host cells can be used to show that the polypeptides produced by the thyroid receptor (TR) expression plasmids are functional, i.e., have transcription activating properties characteristic of thyroid receptor proteins.

Plasmids pE4 and pHKA relate to cDNA's which encode an estrogen related receptor referred to herein as hERR1. (See Experimental Section V, especially FIG. V-1A, B1 and B2.) Plasmid pE4 carries the cDNA segment referred to in FIG. V-1A, B1 and B2 as lambda hKE4; pHKA carries the segment referred to in that same figure as lambda hKA1. Both pE4 and phKA1 have been deposited with the ATCC for patent purposes. The two plasmids can be joined as follows to produce a single plasmid (pGMERR1) which contains the entire coding sequence for estrogen related receptor hERR1.

The preferred procedure for joining the two cDNA clones pE4 and PHKA makes use of a synthetic linker which is complementary at each end for a specific restriction enzyme site present in each cDNA. More specifically, the inserts from lamba hKA1 and lambda hKE4 are cloned as EcoRI fragments into the plasmid vector pGM3 (Promega Biotec); we named them pGMKA and pGMKE, respectively. Next, pGMKA is cut by NarI and HindIII and the fragment encoding hERR1 is purified from agarose gel (fragment 1). pGMKE is cut by DraIII and HindIII and the fragment encoding the 5' end region of HERR1 and the vector sequences is purified from agarose gel (fragment 2). Thirdly, two synthetic oligonucleotides complementary to each other are synthesized. The oligonucleotides are as follows:

Oligo I:  GTGCCTGGTGCGGTGGGAG-GAAAACCAGAGTGTATGCTACAAG-CAGCCGGCGGG;

Oligo II: CGCCCGCCGGCTGCTTGTAG-CATACACTCTGGTTTTCCTCCCACCGCAC-CAGGCACTTT.

Finally, Fragment 1 and 2 and Oligo I and II are ligated to each others according to standard methods known well to those skilled in the art, and then transformed into the bacterial stain DH5. The resulting colonies are screened for the DNA construct referred to herein an pGMERR1. Plasmid pGMERR1 can be used to express hERR1. See FIG. I-6 (a and b) for a schematic drawing of pGMERR1.

Plasmid phB3 relates to clone lambda hH3 which was isolated from a human heart lambda gt11 cDNA library using a nick-translated 700-bp EcoRI-SmaI fragment representing the 5' portion of lambda hKA1. (Clones lambda hKE4 and lambda hKA1 were isolated from a human kidney lambda gt10 cDNA library; see Experimental Section V., H., especially, the subsections labeled as FIG. V-1 (A, B, C and D) and FIG. V-2 (A, B, C and D) Methods.) Clone lambda hH3 carries cDNA which codes for an estrogen related receptor referred to herein as hERR2. The cDNA from phH3 can be inserted into pGM3 to create pGMERR2, a drawing of which is also shown in FIG. I-6 (a and b). The functional and structural characteristics of receptor-like polypeptides hERR1 and hERR2 are disclosed and discussed in Experimental Section V.

One of the added discoveries we have made employing the DNA's of the invention is the remarkable sequence homology among the various hormone receptors, within one species, and, for any particular receptor, among species. (,w for example, FIG. III-2 which compares the carboxy-terminal portions of the v-erb-A oncogene product, the human placental c-erb-A polypeptide, and the human glucocorticoid and estrogen receptors; FIG. III-6 which compares the steroid and thyroid hormone receptors; FIG. IV-3 which compares the amino acid homology between mineralocorticoid receptor and glucocorticoid receptor; FIG. IV-8 which shows the amino acid comparisons between hGR, hMR, and hPR structures; FIG. V-3 which compares the carboxy-terminal regions of hERR1, hERR2, the human estrogen and human glucocorticoid receptors; and FIG. V-5 which shows the amino acid comparison between hERR1, hERR2, hER and human thyroid hormone receptor, hT$_3$R beta.) As a result of this homology the DNA's and RNA's of the invention can be used to probe for and isolate a gene from virtually any species coding for a hormone receptor which activates transcription by binding to chromatin DNA after complexing with hormone. By so using the DNA's and RNA's of the invention, especially the preferred DNA's that have been deposited with the ATCC for patent purposes, those skilled in the art, without undue experimentation, can screen genomic libraries to find other glucocorticoid, mineralocorticoid and thyroid hormone receptors which fall within the scope of the present invention. This aspect of the invention is illustrated by our discovery of estrogen-related receptors hERR1 and hERR2 (see Experimental Section V, especially subsection A., Introduction, and subsection B., cDNA Clones for Receptor hERR1), and rat thyroid receptor and human thyroid receptors TR alpha (see Experimental Section VII, especially subsection C., Isolation of a Second Thyroid Receptor DNA, and FIG. VII-1A and B.)

DNA's and sense strand RNA's of the invention can be employed, in conjunction with the induction and protein production methods of the invention for example, to make large quantities of substantially pure receptor proteins. In addition, the substantially pure receptor proteins thus produced can be employed, using well known techniques, in diagnostic assays to determine the presence of specific hormones in various body fluids and tissue samples.

Further, the receptor proteins of the invention can be employed in screening for receptor-agonists and receptor-antagonists by using binding assays such as the one discussed in Experimental Section III for binding $T_3$ to the receptor encoded by peA101, or in the "cis-trans" receptor functionality bioassay of the invention, which will be discussed below.

Finally, because the receptor proteins of the invention can be produced in substantially pure form they can be crystallized, and their structure can be determined by x-ray diffraction techniques. As will be apparent to those skilled in the art, such determinations are very useful when engineering "synthetic" or modified receptor protein analogs.

In addition to DNA's and RNA's, and the novel receptor proteins produced thereby, the present invention discloses three general methods: one relates to a bioassay for determining the functionality of receptor proteins; the other two relate methods for inducing and controlling expression of genes whose transcription is activated by a hormone-receptor complex bound to chromatin DNA. Each of the three general methods will be discussed separately.

The new bioassay system for testing receptor functionality, which we refer to as the "cis-trans" bioassay system, utilizes two plasmids: an "expression" plasmid and a "reporter" plasmid. According to the invention, the expression plasmid can be any plasmid capable of expressing a receptor DNA of the invention, or a mutant thereof, in a suitable receptor-negative host cell. Also according to the invention, the reporter plasmid can be any plasmid which contains an operative hormone responsive promoter/enhancer element, functionally linked to an operative reporter gene. (See the definitions section of this specification for an explanation of the terms used herein.) The plasmids pGMCAT and pGHCAT are examples of reporter plasmids which contain an operative hormone responsive promoter/enhancer element functionally linked to an operative reporter gene, and can therefore be used in the receptor functionality bioassay of the invention. In pGMCAT, the operative hormone responsive promoter/enhancer element is the MTV LTR; in pGHCAT it is functional portion of the growth hormone receptor. In both pGMCAT and GHCAT the operative reporter gene is the bacterial gene for chloramphenicol acetyltransferase (CAT).

In practicing the "cis-trans" receptor functionality bioassay of the invention, the expression plasmid and the reporter plasmid are cotransfected into suitable receptor-negative host cells. The transfected host cells are then cultured in the presence and absence of a hormone, or analog thereof, able to activate the hormone responsive promoter/enhancer element of the reporter plasmid. Next the transfected and cultured host cells are monitored for induction (i.e., the presence) of the product of the reporter gene sequence. Finally, according to the invention, the expression and/or steroid binding-capacity of the hormone receptor protein, or mutant thereof (coded for by the receptor DNA sequence on the expression plasmid and produced in the transfected and cultured host cells), is measured. (See FIG. II-2 for a schematic drawing of this "cis-trans" bioassay system.)

When using the "cis-trans" receptor functionality bioassay system of the invention to determine the functionality of glucocorticoid or mineralocorticoid receptors, in preferred forms, plasmids will carry a selectable marker such as the amp gene. In addition, in preferred forms the reporter plasmids will have the MTV LTR or a functional portion of the growth hormone promoter as the hormone responsive promoter/enhancer element. MTV LTV is preferred because it is known that glucocorticoid hormones stimulate the rate of transcription of MTV DNA by increasing the efficiency of transcription initiation at a unique site within the MTV LTR. Moreover, glucocorticoid receptors bind specifically to DNA sequences mapped within the MTV LTR, and thus can confer glucocorticoid responsiveness to a heterologous promoter. (Am Experimental Section II, especially subsection C. (a), Assay System and Experimental Design.) It is also known that mineralocorticoid receptor shows functional kinship with the glucocorticoid receptor, and that the DNA binding domain of hMR recognizes the MTV LTR. (See Experimental Section IV, especially subsection E.: Expression and Hormone Binding, and subsection F.: Transcriptional Activation). Growth hormone promoter is preferred because its activation is responsive to binding by thyroid hormone-receptor complex.

Preferred host cells for use with the "cis-trans" bioassay system of the invention are COS cells and CV-1 cells. (See Experimental Section II, subsection C. (a) Assay System and Experimental Design, for use of the preferred host cells in the bioassay system of the present invention.) COS-1 (referred to as COS) cells are mouse kidney cells that express SV40 T antigen (Tag); CV-1 do not express SV40 Tag. CV-1 cell are convenient because they lack any endogenous glucocorticoid or mineralocorticoid or other known steroid or thyroid hormone receptors. Thus, via gene transfer with appropriate expression vectors, it is possible to convert these host cells from receptor negative to receptor positive. The presence of Tag in the COS-1 derivative lines allows the introduced expression plasmid to replicate and provides a relative increase in the amount of receptor produced during the assay period.

Expression plasmids containing the SV40 origin of replication (ori) can propagate to high copy number in any host cell which expresses SV40 Tag. Thus our expression plasmids carrying the SV40 "ori" can replicate in COS cells, but not in CV-1 cells. Although the increased expression afforded by high copy number is desired, it is not critical to the disclosed bioassay system. The use of any particular cell line as a "host" is also not critical. The expression vectors are so efficient that, in our hands, the assay has worked in all the hosts we have examined. CV-1 cells are preferred only because they are particularly convenient for gene transfer studies and provide a sensitive and well-described host cell system.

The "cis-trans" bioassay system is especially useful for determining whether a receptor DNA of the invention has been expressed in a transformed host cell; it is also useful in determining whether a receptor of the invention has at least about 10% of the binding activity of the corresponding naturally occurring cognate receptor, plus whether such a receptor has at least about 10% of the transcription-activating activity of the corresponding naturally occurring cognate receptor.

FIG. II-2 schematically illustrates use of the "cis-trans" receptor functionality bioassay system of the invention when used to determine the functionality of receptor polypeptides coded for by hGR cDNA. Details of the bioassay, and its effectiveness as a quantifiable bioassay system to test receptor functionality, are disclosed and discussed in Experimental Section II. (See especially, subsection F., Experimental Procedures, and subsection C., (b), Expression of Functional hGR.) As that experimental section shows, in addition to the CAT enzymatic assay, which can be used to show activation of the hormone responsive promoter/enhancer element, Western blot analysis of the transfected host cells can be used to demonstrate synthesis of receptor polypeptides which are indistinguishable with respect to mobility from the cognate receptors used as controls. Moreover, by using the "cis-trans" bioassay system of the invention, activation of the receptors (produced in the transfected and cultured host cells) by specific hormones can also be examined, as can their hormone-binding capabilities and characteristics. As Experimental Section II demonstrates, when this was done for hER, it was shown that the hGR of the invention is functional and binds with glucocorticoid hormones with the same specificity and concentrations as does the cognate receptor.

Finally, as stated in the Summary sections by using the DNA's of the invention we have discovered that a necessary and sufficient condition for activation of transcription of a gene (G), whose transcription is activated by hormones complexed with receptors, is the presence of the hormone and its receptor in the cell (C) where (G) is located. (The method by which hormone (H) and receptor (R) effect gene G's transcription is not fully understood. However, it is believed that receptor (R), when complexed with hormone (H), binds to specific DNA sites, referred to in the art as "transcriptional control elements" or "DNA sequences which mediate transcriptional stimulation", which are located on the chromatin near where gene (G) is located. This binding by the hormone/receptor, or (H)/(R), complex seems to act in a way not yet understood, as a hormone dependent "switch" that "turns on", or in some other manner activates, the promoter for gene (G), and thus stimulates the transcription of the (G) gene.)

Our discovery has enabled us to provide improved compositions and methods for producing desired proteins in genetically engineered cells. Two of these methods are methods of the present invention. The first is a method for inducing transcription of a gene whose transcription is activated by hormones complexed the receptors. The second is a method for engineering a cell and then increasing and controlling production of a protein encoded by a gene whose transcription is activated by hormones complexed with receptor proteins.

Again, in discussing these two methods, a gene whose transcription is activated by hormones complexed with receptor proteins will be referred to as gene (G). The hormone which activates gene (G) will be referred to as (H), and any of its analogs as (aH). Receptor protein will be referred to as (R), and functional modifications thereof as (r). Finally, the cell where gene (G) is located will be referred to as (C), and the protein coded for by gene (G) will be referred to as (P).

According to the gene induction method of the invention, cell (C), which contains gene (G), is transformed by a DNA of the invention, which is capable of being expressed in cell (C) and which codes for receptor (R) or a modified functional form (r) thereof; and the concentration of hormone (H), or analog (aH), in cell (C) is increased to a level at least sufficient to assure induction of expression of gene (G).

As we show in Experimental Section II, when we used the induction method of the invention, to our great surprise, the presence of (H) and (R) in the cell (C) where gene (G) was located not only induced transcription of gene (G) but also increased production of protein (P) 500–1000 fold. This finding showed us that the induction method can be used to not only induce transcription, but to increase and control it as well. This finding also led us to develop our method for engineering a cell and then controlling production proteins (P) coded for by genes (G) whose transcription is activated by hormones complexed with receptors. This method will be discussed more fully below.

Our induction method can also be used to increase and control production of protein (P) by simply adjusting the concentration of hormone (H), or analog (aH), available to cell (C). (As those skilled in the art will understand, by transforming cell (C) with a DNA of the inventions an adequate supply of (R) or (r) can be assured in cell (C) so that lack of (R) or (r) will no longer be a limiting factor in the transcription of gene (G). This being the case, by simply increasing the amount of (H) or (aH) in the culture solution, it will be possible to increase transcription of gene (G) and consequently the amount of protein (P) that is produced in (C) cells.)

The induction method of our invention can be used to induce expression of any gene (G) that is under transcriptional control of a transcriptional control element activated by binding of a steroid or thyroid hormone receptor complexed with one of its hormones (H), or analogs (aH) thereof, as long as: (1), a DNA is available which codes for receptor (R), or a functional modified form (r) thereof which has the transcription-activating properties of (R); (2), cell (C) is a cell that can be cultured; and (3), cell (C) can be transformed to express the (R)- or (r)-coding DNA needed to complex with hormone (H) or analog (aH).

Without undue experimentation those skilled in the art can use any of the deposited DNA's of the invention as probes to search genomic libraries for (R)- or (r)-coding DNA's which are not now available. Once found, these DNA's, if expressible in the cell (C) where gene (G) is located, can be used to transform (C) cells. Methods for transforming cultured cells are well known and can be used by those skilled in the are without undue experimentation. Also without undue experimentations those skilled in the art can determine what the base level of (H) is in cell (C), if any is present, as well as what the concentration of (H) or (aH) must be in order to induce and control transcription of gene (G), and thus production of protein (P). The requisite concentrations of (H)

can be supplied to transformed (C) cells by adding (H) or (aH) to the culture solutions used to bath cultured (C) cells.

We have taught that a necessary and sufficient condition for transcription of gene (G) is the presence of (H) or (aH) and (R) or (r) in the cell (C) where gene (G) is located, and that transcription of gene (G), and therefore production of protein (P), can be induced and controlled by simply increasing the amount of (H) or (aH) in the culture solutions used to bath transformed (C) cells. As those skilled in the art will appreciate, based on these teachings, it will now be possible to engineer cells so that production of a protein (P), encoded by a gene (G) whose transcription is activated by a hormone/receptor complex, is controlled by simply assuring the presence of hormone (H) and its receptor in cell (C) where gene (G) is located, and then controlling the concentration of hormone (H) or its analog that is present in cell (C). This concept is the basis for the cell engineering and protein production method of our invention.

According to our engineered cell and protein production method: (1), cell (C) is engineered to contain gene (G) so that transcription of gene (G) is under the control of a transcriptional control element to which an appropriate hormone/receptor, (H)/(R), complex can bind, thereby activating transcription of gene (G); (2), cell (C), which now contains gene (G) under the control of a transcriptional control element, is transformed by a DNA of the invention, which is capable of being expressed in cell (C) and which codes for receptor (R) or a modified functional form (r) thereof; and (3), finally the concentration of hormone (H), or analog thereof, in cell (C) is adjusted so that the transcription of gene (G) is not only induced but effectively increased and controlled by increasing the amount of hormone (H) that is available to cell (C) from the culture solution used to bath transformed (C) cells. By so increasing and controlling gene (G)'s transcription, production of protein (P) is also increased and controlled.

As with the induction method, in our engineered cell and protein production method, both hormone (H) and receptor (R) are present in cell (C). Again, as with the induction method, the presence of receptor (R), or a functional modified form (r) thereof is assured by transforming cell (C) with a (R)- or (r)-coding DNA of the present invention. As stated above, methods for transforming cultured cells are well known and can be used by those skilled in the art without undue experimentation. The presence of (H), or its analog (aH), is assured, and the concentration of (H) or (aH) is controlled, by simply bathing transformed (C) cells in bathing solutions which contain appropriate concentrations of (H) or (aH). Appropriate concentration, i.e., concentrations of (H) or (aH) needed to for cell (C) to produce a given amount of protein (P) can be determined in a given situation by those skilled in the art, without undue experimentation.

Again, as those skilled in the art will understand, by transforming cell (C) with a DNA of the invention, an adequate supply of (R) or (r) can be assured in cell (C) so that lack of (R) or (r) will no longer be a limiting factor in the transcription of gene (G). This being the case, by simply increasing the amount of (H) or (aH) in the culture solution, it will be possible to increase the amount of protein (P) that is produced in (C) cells.

As was true with our induction method, the engineered cell and protein production method of our invention can be used to control expression of any gene (G) that can be inserted into cell (C) so that it is under transcriptional control of a transcriptional control element activated by binding of a steroid or thyroid hormone receptor (R) complexed with one of its hormones (H)), or analogs thereof, as long as: (1), a DNA is available which codes to receptor (R), or a functional modified form (r) thereof which has the transcription-activating properties of (R); (2), cell (C) is a cell that can be cultured; and (3), the (R)-or (r)-coding DNA is capable of being expressed in cell (C) where gene (G) is located.

Again, without undue experimentation, those skilled in the art can use any of the deposited DNA's of the invention as probes to search genomic libraries for (R) - or (r)-coding DNA sequences not now available. Once found, these DNA's, if expressible in cell (C) where gene (G) is located, can be used in the engineered protein production method of the present invention.

Also without undue experimentation, those skilled in the art can determine what the base level of (H) is in cell (C), if any is present, as well as what the concentration of (H) or (aH) must be in order to induce and control transcription of gene (G), and thus production of protein (P). The requisite concentration of (H) needed to assure the production of a desired amount of protein (P) can be supplied to transformed (C) cells by adding (H) or (aH) to the culture solutions used to bath cultured (C) cells.

Various aspects of the present invention are further explained and exemplified in the seven experimental sections which follow. Experimental Section I relates to human glucocorticoid receptor. More specifically, that section discloses the primary structure of hGR cDNA, as well its expression into a polypeptide which is functionally indistinguishable from previously disclosed hGR proteins. Experimental Section II relates to functional domains of hGR. As that section discloses, GR contains at least four functional domains, two of which were expected and correspond to the predicted DNA- and steroid-binding domains, and two of which were not expected, and have potent effects on transcription. Experimental Section III relates to thyroid hormone receptor c-erb-A. As that section discloses, c-erb-A encodes a thyroid hormone receptor we now refer to as hTR alpha. Taken in conjunction with our unexpected discovery of a second thyroid hormone receptor (see Experimental Section VII), the data disclosed about c-erb in Section III will be extremely useful in gaining further knowledge about thyroid receptor proteins. Experimental Section IV relates to human mineralocorticoid receptor, which we show has a structural and functional similarity to glucocorticoid receptor. Experimental Section V discloses a new and unexpected class of steroid hormone receptors we refer to as hERR1 and hERR2. These receptors provide the first evidence for the existence of a novel steroid hormone system. In conjunction with our disclosure of a new "cis-trans" bioassay systems the new estrogen-related hERR1 and hERR2 receptors will provide the basis for development of an assay system that will systematically lead to the identification of novel hormones. The identification of such novel systems is likely to have widespread physiologic and clinical significance. In Experimental Section VI we disclose some of our data relating to the sites in a rat thyroid receptor c-erb-A oligonucleotide which we found were necessary for $T_3$ regulation. Such knowledge, taken in conjunction with Experimental III and our disclosure in Experimental Section VII of a new and unexpected thyroid hormone receptor that is linked to human chromosome 17, will be useful in characterizing the thyroid receptor proteins.

Without further elaboration, it is believed that one of ordinary skill in the art, can, using the preceding description, and the following Experimental sections, utilize the present invention to its fullest extent. The material disclosed in the experimental sections, unless otherwise indicated, is disclosed for illustrative purposes and therefore should not be construed as being limitive in any way of the appended claims.

EXPERIMENTAL SECTION I

Primary Structure and Expression of a Functional Human Glucocorticoid Receptor cDNA

I. A. Summary

Here we report the complete amino-acid sequence of the human glucocorticoid receptor (hGR), deduced from human lymphoid and fibroblast cDNA clones. The sequence reveals various structural features of the receptor, including the major immunogenic domain and a cysteine/arginine/lysine-rich region which may constitute a portion of the DNA-binding domain. We describe the use of the SP6 transcription vector system to generate analytical amounts of full-length protein, and demonstrate that the cell-free translated protein is both immunoreactive and possesses steroid-binding properties characteristic of the native glucocorticoid receptor. Weinberger, et al., (1985b) describes the homology of the hGR sequence to that of the oncogene v-erb-A.

I. B. Introduction

The glucocorticoid receptor is widely distributed and expressed in many cultured cell lines, and the control of gene expression by glucocorticoids, therefore, has been widely studied as a model for transcriptional regulation. A number of glucocorticoid-responsive transcription units, including mouse mammary tumor virus (MMTV) (Ringold, et al., 1975; Parks, et al., 1974), mouse and human metallothionein (Hager, et al., 1981; Karin, et al., 1980), rat alpha$_{2M}$-globulin (Kurtz, et al., 1977) and rat and human growth hormone (Spindler, et al., 1982; Evans, et al., 1982; Robins, et al., 1982) genes have been identified. DNA sequences mediating transcriptional stimulation of several of these genes have been localized. For MMTV, these sequences are discrete genomic regions upstream of the transcriptional start site which appear to exert their actions independently of orientation and position (Chandler, et al., 1983; Ostrowski, et al., 1984). The steroid/receptor complex appears to bind to these regulatory sequences and purified receptor has been used to define the specific binding sites (Govinda, et al., 1982; Scheidereit, et al., 1983; Pfahl, 1982; Payvar, et al., 1983). Based on the footprinting analyses of several responsive genes, a consensus DNA binding sequence sharing the core sequence 5' TGT/CTCT 3' has been proposed (Karin, et al., 1984).

The ability of the glucocorticoid-responsive element (GRE) to alter its position and orientation yet still maintain promoter inducibility suggests that it resembles the class of cis-acting regulatory sequences termed enhancers (Chandler, et al., 1983). First discovered in viruses and subsequently in cellular genes, these sequences are necessary for efficient transcription in vivo (Laimonis, et al., 1982; Benoist, et al., 1981; Baerji, et al., 1983). It has been suggested that enhancers are recognized by trans-acting factors that mediate regulatory effects by tissue-specific transcriptional control. Although the enhancer factors have not been well characterized, the glucocorticoid receptor may serve as a paradigm for these putative gene activator proteins.

The availability of radiolabeled high-affinity glucocorticoid analogues such as dexamethasone and triamcinolone acetonide has led to the development of purification strategies resulting in the isolation of nearly pure rat and human receptors (Simons, et al., 1981; Gehring, et al., 1983). Although the receptor migrates as a dimer in sucrose gradients, analysis on denaturing SDS-polyacrylamide gels detects a single polypeptide of relative molecular mass $(M_t) \sim 94,000$ (94K) (Westpahl, et al., 1982; Wrange, et al., 1979). The native polypeptide contains intrinsic specificity for steroid binding and DNA sequence recognition. By using as probes monoclonal and polyclonal antibodies raised against the purified rat and human receptors (Okret, et al., 1981; Harmon, et al., 1984; Gametchu, et al., 1984), it has been possible to identify a major immunogenic region in the receptor residing on a portion of the molecule that is distinct from the steroid- and DNA-binding regions (Carlstedt-Duke, et al., 1982; Wrange, et al., 1984; Dellweg, et al., 1982). To gain further information about the structure of this molecule and to begin an analysis of the molecular mechanisms by which it regulates gene transcription, we set out to clone receptor cDNA sequences. By using receptor-specific antibodies as probes, we and others have isolated clones containing human or rat glucocorticoid receptor cDNA inserts (Weinberger, et al., 1985a; Miesfeld, et al., 1984).

I. C. Results (a) GLUCOCORTICOID RECEPTOR cDNA

A library of cDNA clones was constructed in the phage expression vector lambda gt11 using poly(A)+ RNA from the human lymphoid cell line IM-9 as template, as described previously (Weinberger, et al., 1985a). This library was initially screened with a rabbit polyclonal antiserum to the purified glucocorticoid receptor, resulting in the isolation of several immunopositive candidate clones from $\sim 2.5 \times 10^5$ plaques. The beta-galactosidase fusion proteins generated from these clones were used to affinity-purify receptor epitope-specific antibody, which was subsequently recovered and identified by binding to protein blots of cellular extracts. Three clones containing inserts expressing antigenic determinants of the human glucocorticoid receptor were isolated. The inserts of these clones, although of different sizes, cross-hybridized, indicating that they contained a common sequence which presumably delimits the major immunogenic domain of the receptor. Together, these clones spanned 1.4 kilobase pairs (kbp) but were clearly not long enough to code for the entire receptor, which was estimated to require $\sim 2,500$ nucleotides to encode a polypeptide of $M_t$ 94K.

To isolate additional cDNA clones we again screened the original library and also examined a second library (given by H. Okayama) prepared with poly(A)+ RNA from human fibroblasts in the vector described by Okayama and Berg (1983). Using one of the immunopositive cDNA inserts (hGR1.2) as probe, 12 clones were isolated that, together, covered more than 4.0 kbp. The nucleotide sequences of these clones were determined by the procedure of Maxam and Gilbert (1977) according to the strategy indicated in FIG. I-1a. RNA blot analysis indicated that a cDNA insert of 5-7 kilobases (kb) would be necessary to obtain a full-length clone and sequence analysis indicated that the overlapping clones OB7 and hGR5.16 spanned an open reading frame of 720 amino acids, not large enough to encode the complete receptor. Therefore, a second human fibroblast cDNA library of ~2×10$^6$ transformants was screened, yielding a clone (OB10) containing a large insert that extended 150 base pairs (bp) upstream of the putative translation initiation site (see FIG. I-1a and 1b. Sequence analysis predicts two protein forms, termed alpha and beta, which diverge at amino acid 727 and contain additional distinct open reading frames of 50 and 15 amino acids, respectively, at their carboxy termini (see FIG. I-1b). The alpha form, represented by clone OB7, is the predominant form of glucocorticoid receptor because eight cDNA clones isolated from various libraries contain this sequence.

(b) cDNA AND PROTEIN SEQUENCES

FIG. I-2-1 and 2-2 shows the 4,800-nucleotide sequence encoding the human alpha glucocorticoid receptor, determined using clones hGR1.2, hGR5.16, OB7 and OB10. The translation initiation site was assigned to the methionine codon corresponding to nucleotides 133-135 because this is the first ATG triplet that appears downstream from the in-frame terminator TGA (nucleotides 121-123). However, in the absence of amino-terminal peptide sequence information, unequivocal determination of the initiation site is not yet possible. The codon specifying the lysine at position 777 is followed by the translation termination codon TGA. The remainder of the coding sequence is covered by multiple overlapping clones, with OB7 containing a 4.3-kb insert that continues to the poly(A) addition site and OB10 containing the putative initiator methionine. The 3' regions of clones OB7 and OB10 diverge at nucleotide 2,314, as shown by both restriction endonuclease and DNA sequence analysis. At this junction, the alpha-receptor continues with a unique sequence encoding an additional 50 amino acids whereas the beta-receptor continues for only 15 additional amino acids (FIG. I-3a and b). The 3'-untranslated region of OB7 is 2,325 nucleotide: long, while that of OB10 is 1,433 nucleotides. There is no significant homology between these two regions, an indicated by direct sequence comparison (FIGS. I-2-1 and 2-2 and I-3a and b) or by hybridization analysis under stringent conditions (data not shown).

In additions we have isolated from a human primary fibroblast library another cDNA clone, OB12 (data not shown)r which contains sequences identical to OB7 but uses the polyadenylation signal at nucleotide 3,101 (FIGS. I-1b and I-2-1 and 2-2), giving rise to a shorter 3'-untranslated region. Use of probes specific for the 3'-untranslated region of OB7 to screen a human placenta cDNA library reveals that most clones terminate at the first poly(A) site in OB7. Thus, messenger RNA variation is the apparent consequence of both alternative polyadenylation and alternative RNA splicing (see below). The fact that the human fibroblast library contained both cDNA's suggests that both receptor forms may be present in the same cell.

(c) ANALYSIS OF ALPHA- AND BETA-RECEPTOR PROTEIN

Sequence analysis reveals that the alpha and beta forms of the human glucocorticoid receptor are 777 and 742 residues long, respectively; the two forms are identical up to residue 727, after which they diverge. To examine the receptor levels in vivo, cytoplasmic extracts from several human and mouse cell lines were probed by immunoblot analysis with a polyclonal antibody directed against the human glucocorticoid receptor (Harmon, 1984). Alpha- and beta-receptor cDNA's were inserted into the SP6 transcription vector to create synthetic mRNA for in vitro translation (FIG. I-4a). The RNA's were separately added to a rabbit reticulocyte lysate system and the unlabeled products analyzed by SDS-polyacrylamide gel electrophoresis (SDS-PAGE). The two RNA's program the synthesis of distinct translation products whose migration differences are consistent with the predicted polypeptide lengths of the two forms (FIG. I-4b, lanes 2, 3). Cytoplasmic extracts from untreated IM-9 cells and IM-9 cells treated with 1 microM triamcinolone acetonide serve as markers (FIG. I-4b, lanes 4,5) for the 94K receptor (the 79K form represents a putative receptor degradation product) (Wrange, et al., 1984). Note that after steroid treatment, the intensity of the 94K band is reduced, corresponding to tighter receptor/chromatin binding and, therefore, receptor translocation to the nucleus. The alpha form co-migrates with the 94K band of the negative receptor while the beta form migrates more rapidly (see FIG. I-4b, compare lanes 2,3 with lanes 4,5). A comparison of cytoplasmic extracts from various human and mouse cell lines reveals the presence of only the alpha-receptor (see FIG. I-4b, lanes 6-9). Interestingly, the mouse ADR6 lymphoma cell line (Danielsen, et al., 1984), selected for resistance to steroid-induced lysis, contains no steroid-binding activity and shows no immunoreactive receptor (see FIG. I-4b, lane 7). Therefore, based on characterization of multiple receptor cDNA clones and receptor protein by immunoblot analysis, we conclude that the predominant physiological form of the glucocorticoid receptor is the alpha (94K) species.

(A) EXPRESSION OF hGR IN VITRO

To provide additional evidence that the cloned receptor is functional, we investigated the possibility that the in vitro-translated products might be able to selectively bind corticosteroids. Accordingly, the rabbit reticulocyte lysate was incubated with the radiolabeled synthetic glucocorticoid analogue $^3$H-triamcinolone acetonide ($^3$H-TA) before or after addition of in vitro-synthesized alpha or beta hGR RNA. As shown in FIG. I-5, those lysates programmed with alpha-hGR RNA acquired selective steroid-binding capacity; unexpectedly, the beta-receptor synthesized in vitro failed to bind competable $^3$H-TA. The in vitro-synthesized alpha-hGR bound radiolabeled steroid which could be competed with by addition of excess unlabeled cortisol or dexamethasone; however, binding of $^3$H-TA was not effectively competed with by addition of excess unlabeled oestrogen or testosterone. In contrast, excess progesterone constituted an effective competitor, consistent with the previously reported anti-glucocorticoid activities of progesterone (Rousseau, et al., 1972). To confirm these results, the competition experiments were repeated with native glucocorticoid receptor prepared from extracts of human lymphoid cells. Both the in vitro-translated receptor and the natural in vivo receptor have nearly identical properties with regard to steroid binding and competition with excess unlabeled steroid analogue (see FIG. I-5).

(a) hGR SEQUENCES MAP TO AT LEAST TWO GENES

The human glucocorticoid receptor gene has been functionally mapped to chromosome 5. Analysis of somatic cell hybrids constructed by fusing receptor-deficient mouse T cells (EL4) with human receptor-containing T cells (CEM-C7) indicated that segregants expressing the wild-type CEM-C7 receptor maintained human chromosome 5 while dexamethasone-resistant segregants had lost this chromosome (Gehring, et al., 1985).

To confirm the authenticity of our cDNA clones, we mapped receptor cDNA sequences using Chinese hamster/human somatic cell hybrids containing only human chromosome 5 (HHW454). DNA's extracted from human placenta, HHW454 hybrid cells and Chinese hamster ovary (CHO) cells were digested with EcoRI or HindIII restriction endonucleases and separated on a 0.8% agarose gel. DNA fragments transferred to nitrocellulose were probed with a portion of the receptor-coding region derived from nucleotides 570–1,640 (See hGR1.2A in FIG. I-1a and b). In addition to CHO-specific EcoRI bands of 6.8 and 17 kbp, DNA from the hybrid cell line also contains human-specific bands of 3.0 and 5.0 kbp (see FIG. 6a, lanes 2, 3 of Hollenberg, et al., 1985). (The study disclosed herein as Experimental Section I was published as Hollenberg, et al., 1985. FIGS. 6 and 7 appear in the paper but not in the present specification.) Unexpectedly, a DNA fragment of 9.5 kbp is found in total human DNA but not in the hybrid line (see Hollenberg, et al., 1985, FIG. 6a, lane 1). Similarly, HindIII digestion revealed a 7.5 bkp band that is not present in the chromosome 5 hybrid cell DNA (see Hollenberg; et al., 1985, FIG. 6a, lane 4). These results indicate that the receptor cDNA maps to human chromosome 5, but that there are additional receptor-related sequences elsewhere in the genome. To map these sequences, we used a dual-laser fluorescence-activated cell sorter (FACS) to sort mitotic chromosome suspensions stained with DIPI/chromomycin in conjunction with Hoechst 33258 chromomycin; this technique allows separation of the 24 human chromosome types into 22 fractions (Lebo, et al., 1984). After the chromosomes were sorted directly onto nitrocellulose, the chromosomal DNA was denatured and hybridized to the hGR cDNA probe. In addition to confirming the chromosome 5 localization, additional sequences were found on chromosome 16 (see Hollenberg, et al., 1985, FIG. 6b). To confirm this localization, DNA's from mouse erythroleukaemia cells and a mouse erythroleukaemia cell line containing human chromosome 16 (see Bode, et al., 1981) were digested with HindIII and probed with hGR cDNA (see Hollenberg, et al., 1985, FIG. 6c); as predicted, the only DNA fragment found in the hybrid and not in the control was the 7.5-kbp DNA fragment, thus establishing the chromosome 16 assignment (see Hollenberg, et al. , FIG. 6c, lanes 1, 2).

Additional Southern blot analyses using the EcoRI-XbaI fragments from OB7 and OB10 3'-untranslated regions revealed hybridization only to chromosome 5 (data not shown). We conclude that both the alpha- and beta-receptor cDNA's are probably encoded by a single gene on chromosome 5 and suggest that the two cDNA forms are generated by alternative splicing. In addition, we conclude that another gene residing on human chromosome 16 contains homology to the glucocorticoid receptor gene, at least between nucleotides 570 and 1,640. It is not clear whether these sequences on chromosome 16 represent a related steroid receptor gene, a processed gene or pseudogene, or a gene that shares a common domain with the gene for the glucocorticoid receptor. Genomic cloning and DNA sequencing may provide the answer.

To determine the size of the mRNA encoding the glucocorticoid receptor, Northern blot hybridization (Bode, et al., 1981) experiments were performed using cytoplasmic mRNA isolated from a human fibroblast cell line, HT1080. Using the hGR1.2 coding sequence as probe, multiple mRNA's of 5.6, 6.1 and 7.1 kb were detected. Treatment of these cells with glucocorticoid for 24 h leads to a 2–3-fold reduction in receptor mRNA's, suggesting a potential negative feedback regulation.

I. D. Discussion

Structural analysis of the glucocorticoid receptor is a prerequisite for gaining insight into the mechanisms by which this regulatory molecule exerts its effects on gene transcription. Here, we have presented the primary sequence of the human glucocorticoid receptor deduced from nucleotide sequence analysis of cDNA clones.

Isolation of hGR cDNA's has revealed the existence of multiple mRNA's encoding at least two forms of the polypeptide. The predicted proteins differ at their carboxy termini by the substitution of 50 amino acids in the case of alpha-hGR and 15 amino acids in the case of beta-hGR. The alpha glucocorticoid receptor is the major form identified in several human cell lines and cDNA libraries. However, a recent report by Northrop; et al. (1985) characterizes two forms of the receptor in mouse lymphoid cells. The relationship of alpha- and beta-hGR to the mouse doublet species remains to be established. Also, the cellular distribution and potential function of beta-hGR are unclear, although it is possible that variant receptors are used for tissue-specific functions. We are now generating antisera to synthetic peptides specific for each human receptor form to elucidate their tissue-specific expression.

Among the cDNA's selected using the immunopositive phage DNA insert hGR1.2A as probe were those containing 3' ends similar to OB7, except that polyadenylation was signaled earlier by the use of an AATAAA at nucleotide 3,101. These clones have been isolated from both human fibroblast and placental libraries (data not shown). Alternative poly(A) site selection is a feature of many eukaryotic transcription units (Darnell, 1982). In some instances, selection of poly(A) sites specifies particular polypeptide products (Amara, et al., 1982; Rosenfeld, et al., 1983; Alt, et al., 1980; Schwarzbauer, et al., 1983) while in other cases, alternative poly(A) site selection produces no change in the primary structure of the polypeptide (Setzer, et al., 1982) while in other cases, alternative poly(A) site selection produces no change in the primary structure of the polypeptide (Setzer, et al., 1982). The selection of poly(A) sites during receptor transcription may (1) alter the stability of the mRNA in a particular tissue, (2) lead to splicing changes, or (3) be random, with no physiological consequence.

The in vitro translation studies described here provide direct evidence that the cloned molecule encodes the complete glucocorticoid receptor. First, the in vitro-translated product is identical in size to the native glucocorticoid receptor and is immunologically reactive with receptor-specific antiserum. Second, the in vitro-translated protein acts functionally as a glucocorticoid receptor in that it is capable of selectively binding the synthetic glucocorticoid triamcinolone acetonide. This binding is specifically competed with by glucocorticoids, glucocorticoid analogues and progesterone but is not competed with by the sex steroids testosterone and oestrogen. In this respects the in vitro-translated receptor behaves identically to the in vivo receptor from human lymphoid cells, providing the first evidence of a function for the cloned molecule. The acquisition of steroid-binding properties does not appear to require any specific modifications or, if it does, these modifications can occur in the in vitro translation mix.

The results presented here provide the information necessary for studying the molecular interactions of a eukaryotic transcriptional regulatory protein with its target genes. These structural studies provide a basis from which the glucocorticoid receptor, its gene, and its RNA products can be analyzed. Furthermore, the ability to express receptor in vitro provides a novel means by which the consequence of specific in vitro mutagenesis can be rapidly tested. Finally, the isolation of genes responsive to glucocorticoids and specific regulatory elements by both mutagenic and protein-binding studies suggests that this protein can serve as a very useful model for analysis of inducible eukaryotic gene regulation.

I. E. Detailed Description of Figures Referred to in Experimental Section V

FIG. I-1.

Human glucocorticoid receptor cDNA sequencing strategy and schematic representation of cDNA clones. a, the composite cDNA for the alpha glucocorticoid receptor is represented at the top, with noncoding (lines) and coding (stippled portion) sequences indicated. Common 6-nucleotide restriction enzyme sites are shown. Overlapping cDNA inserts used to determine the sequence are shown: arrows beneath the regions sequenced show the direction and extent of sequencing. The dashed line at the 3' end of OB10 indicates divergent sequence. Numbers refer to nucleotide positions in OB10 relative to the 5'-most transcribed sequence. b, cDNA's encoding the alpha and beta forms of the receptor (OB7 and OB10, respectively). The 5' end of OB7 (broken lines) is contributed by the OB10 clone. Protein-coding information is represented by wide bars; untranslated sequences are indicated by thin bars. Nucleotides and amino acids are numbered above and below the coding sequence, respectively. Common DNA sequences extend to nucleotide 2,313 (amino-acid residue 727), at which point the alpha- and beta-receptor forms diverge, with the alpha cDNA's (OB12, OB7) continuing in an open reading frame for 150 nucleotides (50 amino acids) and the beta cDNA (OB10) continuing for 45 nucleotides (15 amino acids; see FIG. I-3a and b). Hexanucleotide signals (AATAAA) just upstream of the poly(A) in the clones are indicated, with the first hexanucleotide in OB7 serving as poly(A) in OB12.

FIG. I-1 METHODS.

The inserts hGR1.2, hGR2.9 and hGR5.16 were isolated from a lambda gt11 IM-9 lymphoid cell cDNA library as described previously (Weinberger, et al., 1985). Two clones were isolated from cDNA libraries constructed by H. Okayama in pcD (Okayama, et al., 1983) using poly(A)+ mRNA from GM637 human fibroblasts (OB7) and primary human fibroblasts (OB10). Screening was performed with the hGR1.2-cDNA, radiolabeled by nick-translation with $^{32}$P-dCTP. Sequences were determined by the chemical cleavage method of Maxam and Gilbert (1977).

FIG. I-2-1 and 2-2 cDNA and predicted protein sequence of human glucocorticoid receptor. The complete alpha coding sequence and OB7 3'-untranslated region are shown, with the deduced amino acids given above the long open reading frame. An upstream in-frame stop codon at nucleotides 121–123 and putative additional polyadenylation signals in OB7 are underlined.

FIG. I-3a and b.

Restriction map and nucleotide sequence of the 3' end of the human glucocorticoid receptor beta cDNA. a, The common 6-nucleotide restriction enzyme sites are shown for the 3'-untranslated region of OB10. b, The cDNA sequence of the beta form (OB10) from nucleotide 2,281 to 3,820 compared with the protein-coding information found in the 3'-terminal coding portion of the alpha form (OB7). Amino acids encoded by each of the cDNA's are presented above the nucleotide sequences. Putative polyadenylation signals (AATAAA) in the 3'-untranslated sequence of OB10 are underlined.

FIG. I-4a and b.

Immunoblot comparison of hGR translated in vitro with in vivo hGR from cell extracts. a, The vectors constructed for in vitro transcription of the hGR cDNA sequence. The complete alpha (pGR107) and beta (pGR108) coding sequences were placed under the transcriptional control of the SP6 promoter in pGEM1. Vector sequences, noncoding cDNA sequences and coding sequences are indicated by thin lines, thick bars and boxed regions, respectively. The poly(A) tract of ~60 nucleotides is indicated by $A_{pi}$. Divergent coding sequences are indicated by striped and stippled regions. b, Western blot analysis of in vitro translation products and cell extracts. Unlabeled translation products synthesized in a rabbit reticulocyte lysate system with no added RNA (lane 1) or with RNA synthesized from pGR108 (beta, lane 2) or pGR107 (alpha, lane 3) were fractionated on a 7.5% SDS-polyacrylamide gel. Additional lanes are: cytoplasmic extracts from IM-9 (lane 4), IM-9 treated with 1 microM triamcinolone acetonide (lane 5), HeLa (lane 6), ADR6.M1890.AD1 mouse lymphoma (lane 7), S49 mouse lymphoma (lane 8) and EL4 lymphoma (lane 9). Proteins were transferred to nitrocellulose and probed with anti-hGR antibody, followed by $^{125}$I-labeled *Staphylococcus aureus* protein A as described previously (Weinberger, et al., 1985).

FIG. I-4a and b METHODS.

To construct an expression vector containing the entire alpha coding sequence shown in FIG. I-2, the 3' coding sequence of OB7 was fused to OB10 5' coding information. OB7 was partially digested with EcoRI, completely digested with XbaI, and the 1.20-kbp fragment was gel-purified and ligated with EcoRI/XbaI-digested OB10 to produce the intermediate pOB107. The entire pOB107 cDNA sequence including the 5' poly(G) tract (11 nucleotides, nt) and 3' poly(A) tract (~60 nt) was excised by partial PstI/complete BamHI digestion. The resultant 3.5-kb fragment was gel-purified and inserted between the PstI and BamHI sites of pGEM1 (Promega Biotec) to yield pGR107. Plasmid pGR108 was directly constructed from POB10 by partial PstI/complete BamHI digestion and insertion of the resulting cDNA insert into the corresponding sties of pGEM1. Capped SP6 transcripts were synthesized from PvuII-linearized pGR107 and pGR108, as described by Krieg and Melton (1984), with simultaneous capping effected by reduction of the GTP concentration from 400 to 100 microM and addition of m⁷GppG (Pharmacia) to 500 microM. Transcripts were purified by P60 chromatography and translated with micrococcal nuclease-treated rabbit reticulocyte lysate (Promega Biotec) in conditions suggested by the manufacturer. Preparation of IM-9 cytosol from steroid-treated cells was as described previously (Weinberger, et al., 1985). Size markers are phosphorylase B (97K), bovine serum albumin (66K) and ovalbumin (45K).

FIG. I-5.

Steroid-binding of alpha-hGR translated in vitro. Binding to IM-9 cytosol extract (stippled bars) and to reticulocyte lysate containing SP6-generated alpha-hGR RNA (GR107; open bars) are shown. Bars represent bound $^3$H-triamcinolone acetonide (TA) determined with a 100-fold excess of various steroid competitors; 100% competition was determined using unlabeled TA as competitor. The values represent the mean of triplicate determinations, with error bars showing $P<0.05$. Steroid competitors are dexamethasone (Dex), cortisol (Cort), progesterone (Prog), testosterone (Test), and oestradiol (Oest).

FIG. I-5 METHODS.

Binding assays were performed in 100 microliters containing 10 Mm Tris-HCl PB 7.4, 100 Mm NaCl, 1 Mm EDTA, 10 mM sodium molybdate, 10 dithiothreitol, 150 mM $^3$B-TA (20 Ci mmol$^{-1}$; Amersham) and 10 microliters translation mixture or 100 microgram fresh 1M-9 cytosol. Unlabeled steroid competitor (15 microM) was added as indicated. After 2 h at 0° C., samples were extracted twice for 5 min. each with 5 microliter of 50% dextran-coated charcoal to remove unbound steroid, and counted. Uncompeted and fully competed values for the alpha glucocorticoid receptor (GR107) were 490 and 290 c.p.m., respectively. Reticulocyte lysate translation mixtures without added transcript or programmed with beta-receptor SP6 RNA (GR108) contained no competable $^3$H-TA binding.

ADDITIONAL FIGURES.

The scientific study presented here as Experimental Section I was published in *Nature*, 318:635-641 (1985). The *Nature* publication contain two figures which are not included in this Experimental section. Those figures are: FIG. 6, Chromosome mapping analysis of hGR cDNA; FIG. 7, Northern blot analysis of hGR cDNA.

I. F. References Referred to in Experimental Section I

1. Alt, F. W. , et al., *Cell,* 20:293-301 (1983).
2. Amara, S. G., Jonas, V., Rosenfeld, M. G., Ong, E. S., and Evans, R. M., *Nature*, 298:240-244 (1982).
3. Baerji, J., Olson, L., and Schaffner, W., *Cell,* 33:729-740 (1983).
4. Benoist, C., and Chambon, P., *Nature,* 298:304-310 (1981).
5. Bode. U., Deisseroth, A., and Hendrike D., *Proc. Natl. Acad. Sci. U.S.A.,* 78:2815-2819 (1981).
6. Bourgeois, S., and Newby, R. F., *Cell,* 11:423-430 (1977).
7. Carlstedt-Duke, J., Okret; S., Wrange, O., and Gustafsson; J. -A., *Proc. Natl. Acad. Sci. U.S.A,* 79:4260-4264 (1982).
8. Chandler, V. L., Maler, B. A., and Yamamoto, K. R., *Cell,* 33:489-499 (1983).
9. Danielsen, M., and Stallcup, M. R., *Mole. Cell. Biol.,* 4:449-453 (1984).
10. Darnell, J. E., *Nature,* 297:365-371 (1982).
11. Dellweg, H. G., Hotz, A., Mugele, K., and Gehring, U., *EMRO J.,* 1:285-289 (1982).
12. Evans, R. M., Birnberg, N. C., and Rosenfeld, M. G., *Proc. Natl. Acad. Sci. U.S.A.,* 79:7659-7663 (1982).
13. Gametchu, B., and Harrison, R. W., *Endocrinology,* 114:274-279 (1984).
14. Gehring, U., and Hotz, A., *Biochemistry,* 22:4013-4018 (1983).
15. Gehring, U., Segnitz, B., Foellmer, B., and Francke, U., *Proc. Natl. Acad. Sci. U.S.A.,* 82:3751-3755 (1985).
16. Govinda, M. V., Spiess, E., and Majors, J., *Proc. Natl. Acad. Sci. U.S.A.,* 79:5157-5161 (1982).
17. Grosschedl, R., and Birnstiel, M. L., *Proc. Natl. Acad. Sci. U.S.A.,* 77:7102-7106 (1980).
18. Grove, J. R., Dieckmann, B. S., Schroer, T. A., and Ringold, G. M., *Cell,* 21:47-56 (1980).
19. Hager, L. J., and Palmiter, R. D., *Nature,* 291:340-342 (1981).
20. Harmon, J. M., et al., *Cancer Res.,* 44:4540-4547 (1984).
21. Karin, M., Anderson, R. D., Slater, E., Smith, K., and Herschman, H. R., *Nature,* 286:295-297 (1980).
22. Karin, M.,. et al., *Nature,* 308:513-519 (1984).
23. Krieg, P. A., and Melton, D. A., *Nucleic Acids Res.,* 12:7057-7070 (1984).
24. Kurtz, D. T., and Feigelson, P., *Proc. Natl. Acad. Sci. U.S.A.,* 74:4791-4795 (1977).
25. Laimonis, L. A., Khoury, G., Gorman, C., Howard, B., and Gruss, P., *Proc. Natl. Acad. Sci. U.S.A.,* 79:6453-6457 (1982).
26. Lebo, R. V., and Bastian, A. M., *Cytometry,* 3:213-219 (1982).
27. Lebo, R. V., et al., Science, 225:57-59 (1984).
28. Maxam, A., and Gilbert, W., *Proc. Natl. Acad. Sci. U.S.A.,* 74:560-564 (1977).
29. Miesfeld, R., et al., *Nature,* 312:779-781 (1984).
30. Northrop, J. P., Gametchu, B., Harrison, R. W., and Ringold, G. M., *J. Biol. Chem.,* 260:6398-6403 (1985).
31. Okayama, H., and Berg, P., *Molec. Cell Biol.,* 3:280-289 (1983).
32. Okret, S., Carlstedt-Duke, J., Wrange, O., Carlstrom, K., and Gustafsson, J. -A., Biochem, *Biophys. Acta,* 677:205-219 (1981).
33. Ostrowski. M. C., Huang, A. L., Kessel, M., Woolford, R. G., and Hager, G. L., *EMBO J.,* 3:1891-1899 (1984).
34. Parks, W. P., Scolnick, E. M., and Kozikowski, E. H., *Science,* 184:158-160 (1974).
35. Payvar, F., et al., *Cell,* 35:381-392 (1983).
36. Pfahl, M., *Cell,* 31:475-482 (1982).
37. Ringold, G. M., Yamamoto, K. R., Tomkins, G. M., Bishop, J. M., and Varmus, H. E., *Cell,* 6:299-305 (1975).
38. Robins, D. M., Pack, I., Seeburg, P. H., and Azel, R., *Cell* 29:623-631 (1982).
39. Rosenfeld, M. G., et al., *Nature,* 304:129-135 (1983).
40. Rousseau, G. G., Baxter, J. D., and Tomkins, G. M., *J. Molec. Biol.,* 67:99-115 (1972).
41. Scheidereit, C., Geisse, S., Westphal, H. M., and Beato, M., *Nature,* 384:749-752 (1983).
42. Schwarzbauer, J. E., Tamkun, J. W., Lemischka, I. R., and Hynes, R. O., *Cell,* 35:421-431 (1983).
43. Setzer, D. R., McGrogan, M., and Schimke, R. T., *J. Biol. Chem.,* 257:5143-5147 (1982).
44. Simons, S. S. , and Thompson, E. B. , *Proc. Natl. Acad. Sci. U.S.A.,* 78:3541-3545 (1981).
45. Spindler, S. R., Mellon, S. H., and Baxter, J. D., *J. Biol. Chem.,* 257:11627-11632 (1982).

46. Thomas, P. S., *Proc. Natl. Acad. Sci. U.S.A.*, 77:5201-5205 (1980).
47. Weinberger, C., Hollenberg, S. M., Rosenfeld, M. G., and Evans, R. M., *Nature*, 318:670-672 (1985b).
48. Weinberger, C., et al. *Science*, 228:740-742 (1985a).
49. Westphal, H. M., Moldenhauer, G., and Beato, M., *EMBO J.*, 1:1467-1471 (1982).
50. Wrange, O., Carlstedt-Duke, J.,. and Gustafsson, J. -A., *J. Biol. Chem.*, 254:9284-9290 (1979).
51. Wrange, O., Okret, S.,. Radojcic, M., Carlstedt-Duke, J., and Gustafsson, J. -A., *J. Biol. Chem.*, 259:4534-4541 (1984).
52. Yamamoto, K. R., Stampfer, M. R., and Tomkins, G. M., *Proc. Natl. Acad. Sci. U.S.A.*, 71:3901-3905 (1974).

EXPERIMENTAL SECTION II

Functional Domains of the Human Glucocorticoid Receptor

II. A. Summary

Human glucocorticoid receptor (hGR) produced in CV-1 cells via transfection of an hGR expression vector functions as a necessary and sufficient factor for the transcriptional activation of the MTV-CAT fusion gene. The magnitude of the induction (500-1000 fold) reveals that the hGR may act as a transcriptional "switch", converting a silent promoter containing a glucocorticoid response element to an activated state. Stimulation of transcription of the MTV-CAT gene fusion by hGR is not dependent on transcriptional factors that are limiting in CV-1 cells. Characterization of 27 insertional mutants of the hGR allowed the location of at least four functional domains, two of which correspond to the predicted DNA- and steroid-binding domains. The other two domains are referred to as tau for their potent effects on transcription. This raises the possibility that other regions in the receptor are necessary for full transcriptional activation but are not specifically involved in steroid or DNA binding.

II. B. Introduction

The primary structure of two classes of steroid hormone receptors have been elucidated by cloning and sequencing of their cDNA. An Experimental Section I discloses, identification of cDNA's encoding the human glucocorticoid receptor (hGR) revealed two forms of the protein, of 777 (alpha) and 742 (beta) amino acids, which differ at their carboxyl termini. (The Experimental Section I disclosure has been published as Hollenberg, et al., 1985.) The human estrogen receptor is a somewhat smaller protein of 595 amino acids (Greene, et al., 1986; Green, et al., 1986). Amino acid sequence comparisons revealed extensive regions of homology not only between the two classes of receptors but also with the v-erb-A oncogene product of avian erythroblastosis virus (Weinberger, et al., 1985; Greene, et al., 1986; Green, et al., 1986). This supports the suggestion that steroid receptor genes and the c-erb-A proto-oncogene are derived from a common primordial ancestral regulatory gene (Weinberger, et al., 1985).

On the basis of the amino acid sequence of hGR deduced from the cloned cDNA (see Experimental Section I), the locations of functionally and immunologically important regions of the protein have been proposed (Weinberger, et al., 1985). These include an immunological domain located in the amino-terminal half of the protein, a DNA-binding domain that shows structural similarities with other DNA-binding proteins, and the glucocorticoid-binding site localized near the carboxyl terminus of the molecule. However, the location of each domain is tentative, and no domain involved in the activation of transcription itself has been identified. In this study, we sought to confirm the proposed sites of the functional domains within the hGR and to find other regions of importance by introducing amino acid alterations in the hGR protein. We first developed a novel expression system in monkey kidney cells in which the synthesis of functional hGR is directed by the transcription of the cDNA under the control of the long terminal repeat (LTR) of the Rous sarcoma virus (RSV). The functions of the synthesized receptor were monitored by the induction of transcription of the mouse mammary tumor virus (MTV) LTR as measured by chloramphenicol acetyltransferase (CAT) assays (Gorman, et al., 1982a) and steroid hormone binding. This new expression system allowed us to investigate the effect of insertional mutagenesis on the various functions of the receptor, which led us to propose a more detailed model of the domain structure of the hGR. Our results, based on the analysis of 27 insertional mutations, confirm the notion that the glucocorticoid receptor is composed of discrete functional domains (Weinberger, et al., 1985). In addition, they identify additional sequences outside the proposed DNA- and steroid-binding domains, which, as stated above, we refer to as tau for their potent effects on transcription.

II. C. Results (a) ASSAY SYSTEM AND EXPERIMENTAL DESIGN

The assay system and strategy used to study the expression of functional hGR from the cloned cDNA (See Experimental Section I) is shown in FIG. II-1. In these experiments, a glucocorticoid-responsive promoter/enhancer element linked to a reporter gene was introduced into a receptor-negative cell. Thus, in principle, this construction should be transcriptionally inactive. For our assay, we chose to use the MTV LTR fused to the sequence coding for chloramphenicol acetyltransferase (CAT) (EC2.3.1.28). It has been demonstrated previously that glucocorticoid hormones stimulate the rate of transcription of MTV DNA (Ringold, et al., 1977) by increasing the efficiency of transcription initiation at a unique site within the MTV LTR (Ucker, et al., 1983). Moreovers, glucocorticoid receptors bind specifically to DNA sequences mapped within the MTV LTR (Payvar, et al., 1983), which can confer glucocorticoid responsiveness to a heterologous promoter (Chandler, et al., 1983). Cotransfection of pMTVCAT (or pGMCAT) with a receptor expression plasmid provides functional receptors that allow induction of CAT activity upon treatment of the transfected cells with glucocorticoid hormone. In addition, biochemical studies such as steroid binding activity and Western blot analysis of the expressed receptors can be performed simultaneously.

The expression vector linking the RSV LTR to full length hGR cDNA (pRShGR alpha) was designed to obtain high levels of expression in a wide range of host cell types. The vector pRShGR alpha is a derivative of pRSVCAT (Gorman, et al., 1982b) in which the coding sequence of the CAT gene was replaced by the hGR cDNA. The origin of replication of SV40 was introduced into the vector to allow the recombinant plasmid to propagate to high copy numbers in COS-1 (referred to as COS) monkey kidney cells that express T antigen (Tag) (Gluzman, 1981). COS cells and parental cell line CV-1 offer the additional advantage of having undetectable levels of glucocorticoid receptors (unpublished observation and FIGS. II-2 and II-3).

(h) EXPRESSION OF FUNCTIONAL hGR

The above assay was designed to overcome some of the major difficulties encountered in studying the mechanisms of action of steroid hormone receptors. These difficulties include low intracellular levels of receptor, possible heterogeneity of receptors, and lack of a quantifiable bioassay system to test receptor functions. Accordingly, we first looked at the relative amount of hGR that could be made by COS cells transfected with pRShGR alpha. FIG. II-2 (right lane), a Western blot analysis of transfected COS cells, demonstrates that COS cells synthesized an hGR polypeptide of 94 kd that is indistinguishable with respect to mobility from the hGR present in the IM9 cell line (left lane). Moreover, the amount of hGR present in transiently transfected COS cells is greater than the level found in IM9 cells, which contain between 100,000–200,000 receptors per cell (Harmon, et al., 1984). This expression system not only provides us with cells carrying high intracellular levels of hGR, but eliminates the possibility of receptor microheterogeneity, which could interfere in the functional study of hGR.

To test the functional capability of the expressed hGR as a positive transcriptional factor, we performed CAT assays with cell extracts obtained after cotransfection with pMTVCAT and pRShGR alpha. Transfection into both COS and the parental CV-1 cells was examined. As expected (Alwine, 1985), the presence of SV40 Tag in COS cells increased basal activity of the MTV LTR (data not shown) Thus, CV-1 cells, which do not express the SV40 Tag, were used to achieve maximal induction. As shown in FIG. II-3, cotransfection of pMTVCAT with a control plasmid does not generate CAT activity in CV-1 cells. Similarly, cotransfection of pMTVCAT and pRShGR alpha does not produce any CAT activity. However, treatment of the same cotransfected CV-1 cells with dexamethasone (DEX) turns on the transcription of the MTV-CAT fusion gene. The induction factor is very large (approximately 500–1000 fold) since basal levels of CAT activity produced by pMTVCAT are barely detectable (often zero) in CV-1 cells. As a control experiment, we cotransfected the beta form of the hGR (see Experimental Section I), which was shown to be unable to bind steroids (see Table II-1). FIG. II-3 demonstrates that hGR beta is not functional in our expression assay. The activation of transcription by hGR is also restricted to promoters containing a glucocorticoid-responsive element. When pMTVCAT was substituted for pMTVCAT, a plasmid containing the regulatory region of the human metallothionein Ia gene, which is responsive to heavy metals but not to glucocorticoids, no induction of CAT activity was observed after hormonal treatment of the transfected CV-1 (data not shown). These results demonstrate that in cells the hGR acts as a necessary and sufficient factor that functions as a steroid-dependent transcriptional switch.

Based on this assay, the activation of the receptor by steroids could be examined. As shown in FIG. II-4A, DEX exhibits an $ED_{50}$ value of 3 nM on hGR-induced CAT activity, which is in agreement with $ED_{50}$ values observed for DEX (5 nM) in a variety of psychological actions. Specificity of hGR action was further tested by treating cotransfected CV-1 cells with 100 nM testosterone, oestradiol, and progesterone. These steroids failed to induce CAT activity with the exception of progesterone, which stimulated hGR function at a value of 1% of the maximal induction produced by DEX (data not shown). These results indicate that transfected CV-1 cells synthesize functional hGR that interacts with pharmacological ligands with the specificity and concentrations of the natural receptor.

Studies on specific interaction between enhancer-containing molecules and cellular components have shown that CV-1 cells contain limiting amounts of cellular factors required for the function of certain viral enhancers (Scholer and Gruss; 1984). In those cells, CAT activity generated by transfected pSV2CAT (Gorman, et al., 1982a) reaches a plateau at 0.3 pmol of plasmid per dish. Similarly, if the hGR interacts with limiting factors, we should be able to saturate the CAT activity induced by transfection of increasing amounts of pRShGR alpha with a constant quantity of pMTVCAT. In this experiment, 2 pmol (5 micrograms) of pMTVCAT DNA was used and increasing amounts of pRShGR alpha DNA were added, together with nonspecific carrier DNA, to yield a total of 30 micrograms per dish. FIG. II-4B demonstrates that CAT activity could be detected when as little as 0.03 pmol (100 ng) of pRShGR alpha per dish was transfected and that no plateau in CAT activity was reached. These data suggest that stimulation of transcription of the MTV-CAT fusion gene by hGR is not dependent on transcriptional factors that are limiting in CV-1 cells.

(c) MAPPING OF FUNCTIONAL DOMAINS IN hGR

Understanding the mechanisms by which hGR regulates gene transcription first required the characterization of its functional domains. Based on limited proteolysis studies of the glucocorticoid receptor (Carlsdedt-Duker 1982; Dellweg, et al., 1982; Wrange, et al., 1984; Reichman, et al., 1984) and on the analysis of the primary structure of the hGR (see Experimental Section I), a model for the structure of the receptor has been proposed (Weinberger, et al., 1985). This model identifies three major domains—an immunological domain spanning from amino acid 145 to 280, a DNA-binding domain extending from amino acids 421 to 481, and a steroid-binding domain located near the carboxyl terminus of the protein. To test this model, we generated 27 site-specific insertional mutations in the glucocorticoid receptor coding sequence via a linker-scanning approach. These genetically engineered mutants were then assayed for their ability to stimulate gene transcription and to bind steroid hormone.

To generate linker-insertion mutants of the hGR, the plasmid pRShGR alpha was first linearized by partial cleavage using a restriction enzyme that cleaves DNA molecules with high frequency. The linear form of the plasmid was isolated and a BamHI linker was added to restore the open reading frame encoding the hGR. The resulting mutants carry three or four additional amino acids, which disrupt the wild-type sequence of the protein. Using this technique, we have generated a random series of hGR mutants (FIG. II-5). The ability of these mutants to express full-length hGR was estimated by Western blot analysis. The amounts of hGR produced were shown not to vary by more than 30%, and thus none of the mutants appear to destabilize the expressed protein.

The functional properties of each mutant are compared with that of the wild-type hGR in Table II-1. CAT activity induced by 12 out of 27 hGR mutants was comparable with wild-type level. Analysis of the 15 hGR mutants having a diminished or a complete loss of function, as assayed by induction of CAT activity, shows that they belong to four separate groups. A cluster of these mutants located between amino acids 120 and 215 in the so-called immunogenic domain forms the first group. Although no specific function has been assigned to this region of the receptor molecule, three mutants (I120, I204, and I214) show decreased capacity to induce CAT activity. Those mutants retained their full ability to bind steroids.

Perhaps not surprisingly, the second group of defective mutants is found in the putaive DNA-binding domain of the receptor. This domain is cysteine-rich and consists of two repeat units of about 25 amino acids each, which could fold into a loop structure coordinated by a $Zn^{2+}$ ligand (Miller, et al., 1985). In mutant I422, the sequence motif CYS-$X_2$-Cys is changed to Cys-$X_5$-Cys. The presence of the additional amino acids completely abolishes receptor function. Mutant I440 bears a similar insertion of four amino acids between the two other cysteines involved in the formation of the first loop and also fails to induce any detectable level of CAT activity. On the other hand, mutant I428 extends the length of the loop itself, from 13 to 17 amino acids. Although severely diminished, induction of CAT activity by I428 is still measurable. Steroid-binding capacity of all three mutants located in the DNA-binding domain was shown to be in the range of wild-type level. The third region affected by the mutations is located next to the DNA-binding domain. Mutants I488 and I490 show low levels of CAT activity but bind steroid efficiently. The fourth group covers the last 200 amino acids of the receptor protein. Five mutants (I582, I589, I599, I626, and I696) show undetectable levels of CAT activity. This lack of functional activity is o correlated with their total incapacity to bind dexamethasone. These results show that the steroid-binding region encompasses a large portion of the protein, all clustered near the C terminus. In contrast to the amino terminus of the molecule, this region is extremely sensitive to changes in the primary structure of the receptor.

(d)

TABLE II-I

| | Functional Properties of hGR Mutants | | |
|---|---|---|---|
| hGR | Inserted Amino Acids | CAT Activity (%) | DEX Binding (%) |
| alpha | — | 100 | 100 |
| I9 | RIR | 117 | NT |
| I37 | RIRA | 95 | NT |
| I102 | GSV | 130 | NT |
| I120 | RGSA | 2 | 76 |
| I204 | RIR | 3 | 125 |
| I214 | RGSA | 2 | 79 |
| I262 | ADPR | 97 | NT |
| I289 | RIR | 125 | NT |
| I305 | ADPR | 86 | NT |
| I346 | ADPR | 19 | 107 |
| I384 | RIR | 101 | NT |
| I403 | ADPR | 114 | NT |
| I408 | ADPR | 55 | NT |
| I422 | GSV | 0 | 105 |
| I428 | RIRA | 2 | 92 |
| I440 | ADPR | 0 | 69 |
| I488 | GSV | 15 | 96 |
| I490 | RIRA | 10 | 115 |
| I515 | RIR | 109 | NT |
| I532 | GSV | 115 | NT |

TABLE II-I-continued

| | Functional Properties of hGR Mutants | | |
|---|---|---|---|
| hGR | Inserted Amino Acids | CAT Activity (%) | DEX Binding (%) |
| I550 | ADPR | 5 | 19 |
| I582 | RIR | 0 | 0 |
| I589 | GSV | 0 | 0 |
| I599 | SDP | 0 | 0 |
| I626 | ADPR | 0 | 0 |
| I684 | RGSA | 79 | 81 |
| I696 | RGSA | 0 | 0 |
| beta | C-terminal deletion | 0 | 0 |

CV-1 or COS cells were transfected with pRShGR alpha, pRShGR beta, or a mutated hGR alpha and assayed for CAT activity and steroid-binding capacity. After transfection, CV-1 cells were cultured for 2 days in the presence of 10 nM DEX before cell lysis and CAT assay; COS cells were maintained in normal media. The two parameters are quantified as percentage (%) of wild-type hGR activity. Amino acids inserted in hGR alpha are given in the one-letter code. NT means not tested. Differences in amino acid composition between hGR alpha and hGR beta are represented in FIG. II-5 and in Experimental Section I.

II. D. Discussion

We have shown that hGR produced in CV-1 cells via transfection of an hGR expression vector functions as a necessary and sufficient factor for the transcriptional activation of the MTR-CAT fusion gene. The magnitude of the induction reveals the hGR may act as a transcriptional "switch", which can convert a silent promoter containing a glucocorticoid response element to an activated state. Unlike other transcriptional factors that are constitutively active, stimulation of transcription by hGR is totally dependent upon the presence of glucocorticoid hormones (FIGS. II-3 and II-4A). The production of an excessive quantity of the protein within a cell is not sufficient to induce transcription of a regulated gene. The mechanism by which hGR is activated by the hormone is poorly understood butt in analogy with the cyclic AMP-binding protein, is likely to involve allosteric transitions within the protein (McKay and Steitz, 1981; Gages and Adhya, 1985).

We have observed that activation of transcription by hGR is not restricted by factors present in limiting quantity in CV-1 cells (FIG. II-4B). These results suggest that the binding of hGR-steroid complex to a glucocorticoid-responsive enhancer is sufficient to increase the activity of general transcriptional factors at nearby promoters. Similar properties for several other transcriptional factors have been reported. For examples Adf1, a transcription factor that activates the proximal promoter of the alcohol dehydrogenase (Adh) gene in D. melanogaster, binds the Adh template DNA in the absence of other protein factors and requires only endogenous RNA polymerase Ii and a fraction containing another general transcription factor to activate initiation of Adh RNA synthesis (Heberlein, et al., 1985). In a different type of experiment using the recombinant plasmid pSV2CAT, which contains SV40 enhancer/promoter elements; Scholer and Gruss (1984) have shown a requirement of a cellular molecule(s) for the function of enhancer-containing DNA. Their experiments indicated the presence of a limited amount of cellular factor(s) required for the activation of the CAT gene by the SV40 enhancer element. However, no exhaustion of general transcriptional factors was observed. These data suggest that the mechanism of action of specific positive transcriptional factors is likely to involve alterations in chromatin structure induced by the factor itself that would facilitate the activity of general transcription factors or the polymerase itself (Moreau, et al., 1981; Wasylyk, et al., 1983). It has been previously shown that glucocorticoid treatment causes both reversible and persistent changes in chromatin structure in DNA regions containing a segment of the MTV LTR (Zaret and Yamamoto, 1984). The mechanism by which bound receptors protentiate promoter activity remains to be completely elucidated. However, the availability of a system that overexpresses hGR will facilitate the future studies on the molecular basis of transcription activation by positive transcriptional factors.

The results of the characterization of the 27 insertional mutants supports and extends our previous suggestion that the human glucocorticoid receptor is composed of a series of functional domains. It is noteworthy that all mutants that affect steroid binding are clustered at the carboxyl terminus. In addition to suggesting that this region functions as a discrete domain encoding hormone specificity, the results imply the possibility that the other domains identified within the receptor may serve discrete functions. Accordingly, the ability of the receptor to recognize and to interact with specific DNA sequences appears to reside in the Cys-Lys-Arg-rich regions which is highly conserved with the estrogen receptor and the oncogene product v-erb-A. It seems logical that mutations in these regions would diminish the ability of the receptor molecule to activate transcription since activation depends on both the ability of the ligand to induce an allosteric transformation and the ability of the transformed molecule to recognize and interact with the DNA. Based on the initial model of steroid receptor structure (Weinberger, et al., 1985), these were expected outcomes of a mutagenic characterization. The unexpected outcome, however, is the identification of at least two other regions influencing transcriptional activity. This raises the intriguing possibility that other domains are present in the receptor that are necessary for transcriptional activation but are not specifically involved in either steroid or DNA binding. Mutants I120, I204, and I214 bind steroid with wild-type affinity but have diminished transcriptional activity. These mutants clearly demonstrate that this domain, which we refer to as $tau_1$, is functionally important and required to obtain complete activity of the hGR. Interestingly, nonfunctional truncated mutants (i.e., 40 kd) found in several lines of glucocorticoid-resistant cells are retained in nuclei more efficiently than the wild-type receptor, but fail to activate transcription (Yamamoto, et al., 1976; Andreasen and Gehring, 1981; Westphal, et al., 1984). The receptor fragment missing in these "increased nuclear transfer" ($nt^i$) mutants is evidently the amino terminus of the protein since they retain hormone-binding capacity. We note that $tau_1$, coincides with the major immunogenic domain of the hGR (Weinberger, et al., 1985), indicating that it is probably on the external surface of the molecule. Speculations on how this domain can fulfill its functions include self-interaction leading to receptor dimerization, possible interactions with general transcriptional factors such as RNA polymerase II, and/or modulation of DNA binding by exerting allosteric influence over the remainder of the activated receptor (Dellweg, et al., 1982). $Tau_1$ is englobed by the amino terminus of the receptor, a region which is not held in common with the smaller estrogen receptor. Perhaps the estrogen receptor gains the equivalent function of this domain by interacting with a second protein, or, alternatively, $tau_1$ may interact with other residues within the glucocorticoid receptor itself, as opposed to interacting with other regulatory molecules. The other tau region (which we refer to as $tau_2$) that affects transcriptional activation is a region that is present in the estrogen receptor and the v-erb-A oncogene. Its location also suggests that it may act as a "hinge" region linking the steroid- and DNA-binding domains. Thus, these mutants could block the allosteric transformation necessary for receptor activation.

A third region affected by amino acid insertions is located in the putative DNA-binding domain described by Weinberger, et al. (1985). This domain is composed of two repeated units containing a Cys-Lys-Arg-rich sequence and is the most intensively conserved when compared with the v-erb-A oncogene and the estrogen receptor (Weinberger, et al., 1985; Green, et al., 1986; Greene, et al., 1986). These repeated units were first observed in the factor TF-IIIa (Miller, et al., 1985) and have since been found by sequence homology searches in a number of other nucleic acid-binding proteins (Berg, 1986). Based on experimental and theoretical studies of the factor TFIIIa, Miller and colleagues (1985) proposed a novel mechanism by which proteins bind DNA molecules. In their model, each unit is folded into a "fingered" structure centered on a zinc ion. A finger could bind to a half-turn of DNA. Mutants I422 and I440 carry an amino acid insertion that disrupts the motif $Cys-X_2-Cys$ central to the finger model. These mutants are totally inactive with respect to transcriptional activation but retain their ability to bind glucocorticoid hormone. Preliminary experiments revealed that these mutants also fail to translocate to the nucleus after hormone treatment and to bind DNA in vitro (S. Hollenberg, unpublished observations). These mutated receptors demonstrate the functional importance of the finger motifs present in hGR. The third mutant located in this region, I428, has the finger extended by the addition of four amino acids. Transcriptional activity of I428 is greatly impaired (2% of wild-type level), but is still detectable. Thus, the loops are apparently more tolerant of change than the zinc-binding motif. The demonstration that finger-like domains are functionally important in hGR leads us to propose that steroid hormone receptors are metallo-proteins, which may have evolved from a primordial ancestral DNA-binding protein.

Together, these data suggest that the receptor is composed of a melange of regulatory domains, which may have been pirated over evolutionary time to condense into the primordial steroid hormone receptor, which in turn gave rise to the large family of hormone response genes present in the mammalian genome. The transcriptional activity of this molecule demonstrates its potential ability to act as a genetic switch, which is consistent with the role of steroid hormones in activating a variety of developmental lineages and homeostatic functions. The design of the mutations allows for the convenient generation of any desired set of small or large deletional mutants and the ability to switch domains between related molecules to study function. In conjunction with the rapid and quantitative functional assays described in this section, it is now possible to direct specific questions as to the functional nature of the tau, DNA-, and steroid-binding domains.

II. E. Detailed Description of Figures Referred to in Experimental Section II FIG. II-1.
SCHEMATIC REPRESENTATION OF THE hGR FUNCTIONAL ASSAY:
In this assay, an expression vector containing the hGR alpha cDNA or a mutant derived from it is co-transfected into CV-1 or COS cells with a plasmid carrying the CAT gene under the control of the MTV LTR. The cells are then cultured in the presence or absence of hormone. CV-1 cells were used to monitor induction of CAT activity, and COS cells were used to measure steroid-binding capacity and the expression of hGR protein.

FIG. II-2.
EXPRESSION OF hGR PROTEIN:
COS cells were mock-transfected (center lane) or transfected with plasmid pRShGR alpha (right lane) and analyzed 2 days later for the presence of hGR protein. Crude cytoplasmic extracts were resolved by SDS-PAGE and analyzed by Western blot. Cytoplasmic extract from IM9 cells was loaded on the same gel for comparison (left lane).

FIG. II-3.
INDUCTION OF CAT ACTIVITY BY hGR:
Subconfluent CV-1 cells were cotransfected with either pRSVgal (control), pRShGR alpha, or pRShGR beta and the reporter plasmid pMTVCAT and cultured for 2 days in the presence (+) or absence (−) of 16 nM dexamethasone. CAT assays were performed as indicated in Experimental Procedures (see Section II. F.). C, chloramphenicol; AC, 3-acetylchloramphenicol.

FIGS. II-4A and B.
DOSE-RESPONSE TO DEX AND TITRATION OF pRShGR ALPHA:
(A) CV-1 cells cotransfected with pRShGR alpha and pMTVCAT (10 micrograms each plasmid) were cultured in the presence of increasing concentrations of dexamethasone. The apparent ED50 value for DEX was 3 nM. The levels of CAT activity were plotted as percentages of the maximal response observed in a particular experiment. No CAT activity was detected in the absence of DEX.

(B) Titration. Increasing amounts of pRShGR alpha were cotransfected into subconfluent CV-1 cells with a constant amount of pMTVCAT (5 micrograms). The plasmid pBR322 was used as carrier DNA to yield a total of 30 micrograms DNA per plate. Cells were cultured for 2 days in the presence of 10 nM DEX and CAT activity was measured and plotted as in (A).

FIG. II-5.
LOCATION OF FUNCTIONAL DOMAINS IN hGR:
The hGR is schematically represented with putative domains involved in transcription activation, $tau_1$, and $tau_2$, indicated by hatched areas. The DNA-binding domain is represented by a stippled box; the steroid-binding domains by a dotted box. The positions of BamRI linker insertions are indicated by triangles and circles. The numbers refer to the amino acid position (see Experimental Section I) after which the insertion occurs. Open symbols represent mutants capable of inducing hormone-dependent transcriptional activity at wild-type levels, as measured by CAT activity, and closed symbols indicate greatly diminished or abolished function. The bar indicates the location of the divergent amino acids present in hGR beta, which is not functional.

II. F. Experimental Procedures (a) CULTURE CONDITIONS
CV-1 and COS-1 cells were grown at 37° C. in Dulbecco's modified Eagle's medium supplemented with 5% (v/v) fetal calf serum, 400 microg/ml ampicillin, and 100 microg/ml streptomycin. Cells were passed every 3 days and never allowed to reach confluency in order to obtain good transfection efficiency. All transfected cultures were maintained at 37° C. with 5% $CO_2$.

(b) RECOMBINANT PLASMIDS
Plasmid pRShGR alpha and pRShGR beta, which direct the synthesis of the two forms of hGR in CV-1 and COS cells, were constructed from three DNA fragments. The first fragment is derived from pRSVCAT (Germany et al., 1982b) and contains the RSV LTR, pBR322 sequences, and SV40 polyadenylation site. To obtain this fragment, pRSVCAT was cut with HindIII and the ends repaired by treatment with the Klenow fragment of DNA polymerase I. KpnI linkers were added to these ends by standard procedures (Maniatis, et al., 1982), and the plasmid was subsequently cut with HpaI, which removed the CAT coding sequence. The second fragment contains the coding sequence of either hGR alpha or hGR beta. Plasmids pOB113 and pOB117 (S. M. Hollenberg, unpublished results), which contain the entire coding sequences of the alpha and beta form of hGR, respectively, were cut with BamHI. The ends were repaired with Klenow, and the plasmids were cut with KpnI. Ligation of the first and second fragments created plasmid pRhGR alpha and pRhGR beta. The third fragment to be added consists of a PvuII-HindIII fragment containing the SV40 ORI obtained from the plasmid pSV2CAT (Gorman, et al., 1982a). The ends of this fragment were repaired by treatment with Klenow, and NdeI linkers were added to them. This DNA fragment, containing the SV40 ORI, was then introduced into the single NdeI site present in pRhGR alpha and pRhGR beta. Finally, the single BamHI site present in these plasmids was destroyed and replaced with a XhoI site by insertion of a synthetic adaptor. The resulting plasmids are pRShGR alpha and pRShGR beta. Plasmids pMTVCAT and pMTIaCAT were gifts from S. Gould.

(c) INSERTIONAL MUTAGENESIS
Insertion of amino acids disrupting the wild-type sequence of hGR alpha was performed by the following method. Full-length linear pRShGR alpha DNA was generated by partial digestion with restriction enzymes AluI, DpnI, and BstNI. In the case of DNA cut by BstNI, the ends were first repaired with Klenow. The DNA molecules were then fractionated by agarose gel electrophoresis, and the linear form of the plasmid was extracted. BamHI linkers of 8- or 12-mer were added to restore the original reading frame of the hGR amino acid sequence. Plasmids carrying a single BamHI linker in the coding region of hGR were sequenced (Maxam and Gilbert, 1980) to confirm the position of the linker and the integrity of the hGR mutants.

(d) CELL TRANSFECTION AND CAT ASSAY
The recombinant DNA constructs were introduced into CV-1 cells by calcium phosphate coprecipitation (Wigler, et al., 1979) or into COS cells by DEAE-dextran (Deans, et al., 1984). Each plasmid preparation used for transfection was purified using two consecutive CsCl-EtBr equilibrium gradients. After transfection with the CAT gene constructs, CV-1 cells were prepared for CAT assay as described by Gorman, et al. (1982a). The assays were performed with one third of the total cellular extract and an incubation time of 6 hr.

(e) WESTERN BLOT ANALYSIS

Crude extracts from COS cells were prepared by lysis with a buffer containing 10 mm Tris-CH1 (pH 7.5), 100 mM NaCl, 1 mM EDTA, 0.5% Triton X-100. Equal amounts of protein (100 micrograms) were resolved by 7.5% polyacrylamide, gel electrophoresis, transferred to a nitrocellulose filter, and probed with anti-hGR antibody GR884 (Harmon, et al., 1984), followed by $^{125}$I-labeled Staphylococcus aureus protein A. Filters were air dried and exposed to film. The amount of receptor was quantitated by scanning the autoradiographs.

(f) STEROID BINDING ASSAY

COS cells were lysed in hypotonic buffer containing 10 mm Tris-HCl (pH 7.5), 10 Mm NaCl, 1 Mm EDTA, 5 micrograms/ml antipain, 5 micrograms/ml leupeptin, and 0.5 mM PMSF by Dounce homogenization and centrifuged 10 min. at 15,000×g to yield the cytosolic fraction. Incubations were performed in hypotonic buffer adjusted to 100 mM NaCl and contained 100 micrograms of protein from the cytosolic fraction and $2\times10^{-8}$[$^3$H]DEX (Amersham, 95 Ci/mmol) in total volume of 200 microliters. Nonspecific binding was measured by the addition of $2\times10^{-6}$ unlabeled DEX. Reactions were carried out at 0° C. for 2 hr., followed by a 5 min. incubation with 20 microliters of 50% dextran-coated charcoal (10:1 activated charcoal:dextran) and centrifugation at 15,000×g for 2 min. at 4° C. Supernatants were counted by liquid scintillation methods in a Beckman LS-7800 liquid scintillation spectrophotometer. Each assay usually gave 2500-3000 cpm [$^3$H] labeled steroid; unlabeled DEX competed for 70% of this binding.

II. G. References Referred to in Experimental Section II

1. Alwine, J. C., *Mol. Cell. Biol.*, 5:1034-1043 (1985).
2. Andreasen, P. A., and Gehring, U., *Eur. J. Biochem.*, 120:443-449 (1981).
3. Bazett-Jones, D. P., Yeckel, M., and Gottesfeld, J. F., *Nature*, 317:824-828 (1985).
4. Berg, J., *Science*, 232:485-487 (1986).
5. Carlstedt-Duke, J., Okret, S., Wrange, O., and Gustafsson, J. -A., *Proc. Natl. Acad. Sci., USA*, 79:4260-4264 (1982).
6. Chandler, V. L., Maler, B. A., and Yamamoto, K. R., *Cell*, 33:489-499 (1983).
7. Deans, R. J., Denis, K. A., Taylor, A., and Wall, R., *Proc. Natl. Acad. Sci., USA*, 81:1292-1296 (1984).
8. Dellweg, H. -G., Hotz, A., Mugele, K., and Gehring, U., *EMBO J.*, 1:285-289 (1982).
9. Dynan, W. S., and Tjian, R., *Cell*, 32:669-680 (1983).
10. Garges, S., and Adhya, S., *Cell*, 41:745-751 (1985).
11. Gluzman, Y., *Cell*, 23:175-182 (1981).
12. Gorman, C. M., Moffat, L. F., and Howard, B. H., *Mol. Cell. Biol.*, 2:1044-1051 (1982a).
13. Gorman, C. M., Merlino, G. T., Willingham, M. C., Pastan, I., and Howard, B. H., *Proc. Natl. Acad. Sci., USA*, 79:6777-6781 (1982b).
14. Green, S., Walter, P., Kumar, V., Krust, A., Bornert, J. M., Argos, P., and Chambone P., *Nature*, 320:134-139 (1986).
15. Greene, G. L., Gilna, P., Waterfield, M., Baker, A., Bort, Y., and Shine, J., *Science*, 321:1150-1154 (1986).
16. Barmon, J. M., Risen, H. J., Brower, S. T., Simons, S. S., Langley, C. L., and Thompson, E. B., *Cancer Res.*, 44:4540-4547 (1984).
17. Heberlein, U., England, B., and Tjian, R., *Cell*, 41:965-977 (1985).
18. Hollenberg, S. M., Weinberger, C., Ong, E. S., Cerelli, G., Oro, A., Lebo, R., Thompson, E. B., Rosenfeld, M. G., and Evans, R. M., *Nature*, 318:635-641 (1985).
19. Khoury, G., and Gruss, P., *Molecular Cloning: A Laboratory Manual*, Cold Spring Harbor, N.Y. (1982).
20. Maxam, A. M., and Gilbert, W., *Proc. Natl. Acad. Sci., USA*, 74:560-564 (1977).
21. McKay, D. B., and Steitz, T. A., *Nature*, 290:744-749 (1981).
22. Miller, J., McLachlan, A. D., and Klug, A., *EMBO J.*, 4:1609-1614 (1985).
23. Moreau, P., Hen, R., Wasylyk, B., Everett, R., Gaub, M. P., and Chambon, P., *Nucl. Acids Res.*, 9:6047-6067 (1981).
24. Parker, C. S., and Topol, J., *Cell*, 37:273-283 (1984).
25. Payvar, F., DeFranco, D., Firestone, G. L., Edgar, B., Wrange, O., Okret, S., Gustafsson, J. -A., and Yamamoto, K. R., *Cell*, 35:381-392 (1983).
26. Reichman, M. E., Foster, C. M., Eisen, L. P., Eisen, H. J., Torain, B. F., and Simons, S. S., Jr., *Biochemistry*, 23:5376-5384 (1984).
27. Ringold, G. M., Yamamoto, K. R., Bishop, J. M., and Varmus, H. E., *Proc. Natl. Acad. Sci., USA*, 74:2879-2883 (1977).
28. Sawadogo, M., and Roeder, R. G., *Cell*, 43:165-175 (1985).
29. Scholer, H. R., and Gruss, P., *Cell*, 36:403-411 (1984).
30. Shyamala, G., *Biochem. Biophys. Res. Commun.*, 64:408-415 (1975).
31. Ucker, D. S., Firestone, G. L., and Yamamoto, K. R., *Mol. Cell. Biol.*, 3:551-561 (1983).
32. Wasylyk, B., Wasylyk, C., Augereau, P., and Chambon, P., *Cell*, 32:503-514 (1983).
33. Weinberger, C., Hellenberg, S. M., Rosenfeld, M. G., and Evans, R. M., *Nature*, 318:670-672 (1985).
34. Westphal, H. M., Mugele, K., Beator M., and Gehring, U., *EMBO J.*, 3:1493-1498 (1984).
35. Wigler, M., Sweet, R., Sim, G. K., Wold, B., Pellicer, A., Lacy, E., Maniatis, T., Silverstein, S., and Axel, R., *Cell*, 16:777-785 (1979).
36. Wrange, O., Okret, S., Radojcic, M., Carlstedt-Duker J., ana Gustafsson, J. -A., *J. Biol. Chem.*, 259:4534-4541 (1984).
37. Yamamoto, K. R., Gehring, U., Stampfer, M. R., and Sibley, C., *Rec. Prog. Hormone Res.*, 32:3-32 (1976).
38. Zaret, K. S., and Yamamoto, K. R., *Cell*, 38:29-38 (1984).

EXPERIMENTAL SECTION III

The C-erb-A Gene Encodes a Thyroid Hormone Receptor

III. A. Summary and Introduction

The human glucocorticoid receptor (hGR) complementary DNA has been sequenced (see Weinberger, et al., 1985b and Experimental Section I) and shown to be functionally active (see Experimental Section II). Interestingly, sequence analysis of the receptor showed it to be related to the product of the v-erb-A oncogene product of avian erythroblastosis virus (AEV) (see Weinberger, et al., 1985). This led to the proposal that the steroid receptors and the erb-A oncogene products share a common primordial archetype and that the erb-A proto-oncogene products may also be proteins that bind to DNA enhancer elements. Recent characterization of the human oestrogen (Green, et al., 1986 and Greene, et al., 1986), chicken progesterone (Jeltsch, et al., 1986 and Conneely, et al., 1986) and human aldosterone (J. Arriza, C. W. and R. M. E., unpublished data) receptors further support these conclusions.

Accordingly, we started characterizing the human c-erb-A proto-oncogene even though its functional identification could not be ensured. During the progress of these studies, advances were made in detailing the functional domains of the glucocorticoid receptor (See Experimental Section II) which indicated that the hGR hormone binding domain was unusually large, encompassing the carboxy-terminal 300 amino acids. This entire region has distant but significant similarity to the carboxy terminus of v-erb-A which therefore focused our attention on classes of molecules that might exert transcriptional regulatory effects similar to those of steroid hormones.

The molecular mechanism of thyroid hormone stimulation of gene expression seems to be similar to that outlined for steroids (see Eberhardt, et al., 1980). Thyroid hormone is present in all chordate species examined and exerts profound effects on development and differentiation, such as metamorphosis in amphibians (see Eberhardt, et al., 1980). Like steroids, thyroid hormones may enter cells by passive diffusion and bind to high affinity nuclear receptors which in turn mediate a rapid and selective activation of gene expression (Tata, et al., 1966 and Oppenheimer, et al., 1972). Evidence favoring this hypothesis has come largely from studies of the induction of growth hormone and its messenger RNA in the somatotroph of the rat anterior pituitary and in a number of related rat somatotrophic cell lines (Samuels, et al., 1973 and Tsai, et al., 1974). Thyroid hormones rapidly increase the transcription of the growth hormone gene in these cells (Martial, et al., 1977 and Evans, et al., 1982). The increase in transcription is accompanied by increased levels of nuclear thyroid hormone-receptor complexes, is time- and concentration-dependent, and is independent of protein synthesis (see Samuels, et al., 1976; Spindler, et al., 1982; and Yamer et al., 1984).

The similarity of steroid and thyroid hormone actions led us to examine the possibility that the erb-A protein may itself be the thyroid hormone receptor. We first isolated and characterized a cDNA for human c-erb-A. The sequence predicts a 456 amino acid polypeptide containing a cysteine/lysine/arginine-rich region similar to the putative DNA-binding domain of steroid hormone receptors and a carboxy-terminal region distantly related to the steroid binding domain. Using the functional assay developed for analyzing the hormone binding properties of cloned steroid receptors (see Experimental Section I), we demonstrated that the translation product from the human c-erb-A cDNA possesses intrinsic thyroid hormone binding activity, characteristic of the native thyroid hormone receptor molecule.

III. B. Characterization of c-erb-A cDNA's

To isolate a human c-erb-A cDNA, a 500-base pair (bp) PstI DNA fragment isolated from a region of the AEV genome containing only the v-erb-A gene (Vennstrom, et al., 1980) was used as a $^{32}$p-labeled probe to screen two human placenta cDNA libraries. Two overlapping lambda gt10 cDNA clones were obtained by screening two independent libraries of ~10$^6$ phage recombinants each. The restriction maps were deduced for each of the cDNA clone EcoRI inserts from pUC8 subclones, pheA4 and pheA12 (FIG. III-1a). Nucleotide sequence analysis of these overlapping 1.5 kilobase (kb) cDNA clones revealed that the composite sequence contains a long open reading frame of 456 amino acids with a presumptive initiator methionine codon at nucleotide number 301 and a terminator codon at 1,669 in the sequence (FIG. Ill-1b). Seven codons upstream of the ATG is an in-frame terminator TAA providing support for the initiator methionine, although another methionine found 26 codons downstream makes this assignment tentative. No consensus polyadenylation addition signal (AATAAA, see Proudfoot, et al., 1976) is discernible in the 27 nucleotides between the terminator and poly(A) tract in pheA12.

A predicted polypeptide of relative molecular mass 52,000 ($M_1$=52K)t encoded within the human c-erb-A cDNA translational open reading framer shares 82% amino acid identity with the region downstream from the viral gag sequences (Debuire, et al., 1984) in AEV. No gaps in the amino acid comparison were revealed. The human c-erb-A amino acid sequence is homologous with the viral protein beginning at viral amino acid residue 37 (FIG. III-2). The carboxy-terminus of c-erb-A differs from that of v-erb-A in the following manner: amino acid sequence similarity of the two polypeptides terminates at residue 445 of c-erb-A and residue 380 of v-erb-A (FIG. III-2).

Alignment of the human c-erb-A nucleic acid sequence with that of v-erb-A shows that ~74% of the human gene is identical to the viral gene in the region of amino acid homology (nucleotides 563–1636 in c-erb-A, data not shown). These comparisons, coupled with previous data describing other human erb-A genes mapping to chromosome 17 (Jansson, et al., 1983; Spurr, et al., 1984; and Dayton, et al., 1984), indicate that the human placenta c-erb-A gene we have isolated is distinct. One of the two chromosome 17 erb-A genes (both of which we propose to call hc-erb-A alpha) has 82% similarity with the v-erb-A gene by nucleotide sequence and 89% by amino acid identity (See Dayton, 1984). Therefore, the placenta c-erb-A cDNA, which we propose to call hc-erb-A beta, is more distantly related to the viral erb-A gene than the hc-erb-A alpha genes.

Amino acid sequence comparisons between the vital and cellular erb-A protein products and the glucocorticoid receptor indicate graded levels of homology with the carboxy-terminal half of the hGR (FIG. III-2). The highest degree of similarity is found in a cysteine-rich sequence of 65 amino acids beginning at c-erb-A amino acid residue 102 (see Weinberger, et al., 1985). There is 47% amino acid identity in the comparison with the hGR and 52% identity when c-erb-A is compared with the human oestrogen receptor (hER) amino acid sequence (FIG. III-2). We have proposed that this region of the hGR represents the DNA binding domain[4]. Mutagenesis and expression studies have provided direct evidence for its role in transcriptional activation (see Experimental Section II). Regions downstream from the cysteine-rich domain, which correspond to the hormone binding domain, contain reduced yet significant (17%) homology to the hGR and hER as found previously with the viral erb-A product (am Weinberger, et al., 1985; Green, et al., 1986; and Greene, et al. 1986).

III. C. Multiple erb-A Genes

Hybridization of restriction endonuclease-digested human placenta DNA with a labeled DNA fragment derived from the cysteine-rich region of the c-erb-A polypeptide (FIG. III-1a, b1 and b2), produced two bands in every digestion with the exception of PvuII (FIG. III-3a). The greater intensity of the 9.4 kb-band suggested that it contains two hybridizing DNA fragments. When the hybridization conditions were relaxed, additional bands were observed in the products of each enzyme digestion. For example, two faint bands of 5.1 and 3.6 kb were seen after PstI digestion (FIG. III-3b). The hybridization probe contains a single internal PstI site (FIG. III-1a) which probably explains the increased number of PstI bands detected with this probe.

Similar high-stringency hybridization experiments were performed using a 260 bp EcoRI-BamHI fragment from the 5′ untranslated region of pheA4 (FIG. III-1a and data not shown). Two hybridizing DNA fragments were detected with all restriction enzymes providing further support for the existence of two related c-erb-A genes. No additional DNA bands were seen when the hybridization was performed under relaxed conditions using this probe (data not shown). We conclude that there are two closely related hc-erb-A beta proto-oncogenes and a third, less similar one, in the human genome.

Laser-sorted chromosomes were prepared from human lymphoid cells (Lebo, et al., 1984), bound to nitrocellulose filters and hybridized under non-stringent hybridization and washing conditions using the 1.5-kb EcoRI insert from pheA4 (FIG. III-3c). This probe detected only human chromosome 3-specific DNA and suggests that the three c-erb-A beta-related genes are chromosomally linked, although we cannot strictly exclude the possibility that the non-stringently hybridizing erb-A gene maps in another chromosome. Interestingly, another steroid receptor/erb-A genomic fragment has recently been identified by characterizing the integration site for hepatitis B virus in a human hepatocellular carcinoma (Dejean, et al., 1986). This locus has also been mapped on human chromosome 3 suggesting that the erb-A genes may be closely linked.

III. D. Expression of c-erb-A Genes

Northern blots hybridizing cytoplasmic poly(A)-containing RNA's, isolated from various human cell lines or human term placenta, with a 650-bp BamHI-PstI fragment from the pheA4 (FIG. III-1a) revealed a single RNA species of 2,000 nucleotides that is most abundant in HeLa and MCF-7 cells (FIG. III-4a). The size of the mRNA indicates that we have isolated a nearly full-length c-erb-A cDNA. HT1080 cells contain a small amount of the 2-kb transcript while it is undetectable in IM-9 cells. Human placenta appears to contain multiple species of 5, 3 and 2.5 as well as 2.0 kb RNA. It is unclear whether the multiple placenta bands represent nuclear precursors, or mature mRNA's from a single gene, or the products of other erb-A genes.

The protein products of the human c-erb-A cDNA were characterized by in vitro translation. A cDNA containing the entire c-erb-A coding region was inserted into the EcoRI site of the expression vector pGEM3 in both orientations. Capped RNA transcripts synthesized by T7 polymerase f rom these templates were used to program protein synthesis in rabbit reticulocyte lysates and the $^{35}$S-methionine-labeled products were separated on SDS-polyacrylamide gels (Laemmli, 1970) Proteins with $M_r$ of 55, 52, and 35K were detected when peA101 DNA (erb-A sense transcripts) was used as template (FIG. III-4b, lanes 3 and 4) but not when peA102 DNA (erb-A antisense transcripts) was used (FIG. III-4b, lane 2). The 55 and 52K products may correspond to polypeptides initiating translation at methionines 1 and 27, respectively (FIG. III-1b1 and b2), while the 35K product may be a proteolytic breakdown product.

III. E. Thyroid Hormone Binding

Structural similarity of the steroid ligands as well as the partial amino acid sequence homology (40%) between the carboxy termini of the hGR and hER (which specify the hormone binding domains; see Krust, et al., 1986) support the hypothesis that the steroid receptors comprise a family of regulatory proteins. The more distant homology between the carboxy terminus of c-erb-A and the steroid receptors suggested that erb-A proto-oncogenes probably do not encode steroid receptors, but is consistent with the hypothesis that erb-A may respond to other molecules. We have shown that in vitro translation can be used an a means to characterize hormone binding activity of cloned steroid receptors (am Experimental Section I). Accordingly, this assay was employed to identify the putative c-erb-A ligand.

Steroid and thyroid hormones exert their effects through fundamentally similar mechanisms. To address the possibility that erb-A may be the thyroid hormone receptor, the in vitro translation products were mixed with $^{125}$I-3,5,3′-triiodo-L-thyronine ($^{125}$I-T$_3$) in a hormone binding reaction (see Samuels, et al., 1974). Non-specific hormone binding was determined by adding a 500-fold molar excess of cold T$_3$ to parallel samples. Remarkably, the mixture containing the 55 and 52K polypeptides (peA101) acquired $^{125}$I-T$_3$ binding whereas the anti-sense RNA-programmed lysates (peA102) had only background binding. Hormone binding was sensitive to proteases but not nucleases (data not shown). Affinity of T$_3$ for the cloned erb-A protein was determined by Scatachard analysis (FIG. III-5a). A $K_d$ value of $5 \times 10^{-11}$M was obtained, which is virtually identical to the T$_3$ binding ($6 \times 10^{-11}$M) in HeLa cell nuclear extracts (data not shown).

Specific analogues of thyroid hormones have characteristic competition patterns for T$_3$ binding to the native thyroid hormone receptor. We determined whether the erb-A product synthesized in vitro shared the same intrinsic hierarchy of affinities for a range of natural and synthetic thyroid hormones. Competition of $^{125}$I-T$_3$ binding was most effectively achieved with 3,5′; 3′-triiodothyroacetic acid (TRIAC) which inhibited 50% of $^{125}$I-T$_3$ binding at 300 pM (FIG. III-5b). In addition, L-thyroxine (FIG. III-5b), D-T$_3$ and reverse T$_3$ (3,3′,5′-triiodo-L-thyronine) competed more poorly than T$_3$ (FIG. III-5c), while 100 microM vitamin D$_3$, aldosterone, cortisol, testosterone, progesterone or oestradiol did not compete (data not shown), consistent with the biochemical properties of the rat thyroid hormone receptor (am Samuels, et al., 1974; Samuels, et al., 1979; and Latham; et al., 1976).

High salt (0.4M KCl) HeLa cell nuclear extracts contained thyroid hormone ($^{125}$I-T$_3$) binding activity, while none was found in cytoplasmic or low-salt (0.1M KCl) nuclear extracts (data not shown). Competition of thyroid hormone binding in the nuclear extracts was quantitatively similar to that of lysates containing c-erb-A made in vitro (compare FIG. III-5b and d). Furthermore, thyroid hormone binding using 0.4M KCl nuclear extracts from IM-9 cells, which contain undetectable levels of c-erb-A mRNA (FIG. III-4a, lane 4), is negligible when compared with similar HeLa extracts (data not shown). These results provide direct evidence that c-erb-A is the thyroid hormone receptor.

III. F. Conclusions

The data in this section provide three criteria that identify the c-erb-A product as the thyroid hormone receptor. First, the overall structural homology of c-erb-A is likely to be a ligand-responsive regulatory protein. Second, the expressed protein product has the same intrinsic hierarchy of affinities for natural and synthetic thyroid hormones as the native receptor. Third, the molecular weights of erb-A in vitro translation products are similar to the photo-affinity-labeled rat thyroid hormone receptor (Pascual, et al., 1982). The identity of erb-A as the thyroid hormone receptor could be further substantiated by demonstrating its transcriptional regulation of T$_3$-responsive genes such as the growth hormone gene.

Analysis of the hGR and hM has revealed the proteins to be composed of a series of functional domains. (See Experimental Sections I and IV, and Weinberger, et al., 1985a; also see Carlstedt-Duke, et al., 1982; Dellweg, et al., 1982; Reichman, et al., 1984; and Sherman, et al., 1978.) These include a cysteine-rich region which contains structural similarity to a repeated cysteine-rich region which contains structural similarity to a repeated cysteine-rich sequence found in Xenopus 5S gene transcription factor IIIA and other transcriptional regulatory proteins (Miller, et al., 1985; Berg, 1985) as well as carboxy-terminal sequences, which encode the steroid-binding domain (see Experimental Section II and Weinberger, et al., 1985a; also see Kumar, et al., 1986). Extension of this analogy to the thyroid hormone receptor would predict its hormone binding region to be localized near the carboxy-terminal end of the molecule (FIG. III-6). Putative DNA binding sequences would be found in the cysteine-rich region (FIG. III-6) where DNA binding properties of the hGR and hER appear to be localized (see Experimental Section II, and Kumar, et al., 1986; also S. Hollenberg and R. M. E. unpublished data).

III. G. Thyroid Hormone Receptor and Oncogenesis

Expression of the v-erb-A product in avian erythroblasts is required for maintenance of the fully transformed phenotype (see Graft et al., 1983; Frykberg, et al., 1983; Sealy, et al., 1983; and Kahn, et al., 1986). Chickens infected with viruses lacking the v-erb-A gene display a less virulent disease, while in vitro these infected erythroblasts differentiate spontaneously and grow only with complex media supplements. Cells infected with erb-A+/erb-B+ virus, however, have an increased capacity for self-renewal and display a leas differentiated phenotype. Structural alterations of the v-erb-A protein could give rise to a product exerting aberrant properties of growth control. For instance, changes at the carboxyl terminus might affect thyroid hormone binding activity, as has been shown for the beta form of the human glucocorticoid receptor; resulting in a constitutively active molecule (see Experimental Sections II and III; also see Weinberger, et al., 1985a), where changes abolish steroid binding activity. Insertional mutants in this domain also inactivate steroid binding properties (see Experimental Section II). However, deletion of the hormone binding region gives rise to a constitutively active receptor indicating that this domain plays a modulatory role in transcriptional activation (V. Giguere and R. M. E., unpublished data). These data lead us to predict that v-erb-A is unlikely to bind hormone and is rather a constitutively active form of the thyroid hormone receptor. The identification of erb-A as the thyroid hormone receptor provides the first direct evidence of a causative involvement of enhancers and their binding proteins in oncogenic transformation.

III. H. A Superfamily of Regulatory Genes

Similarity of the steroid receptors with the v-erb-A oncogene product was sufficient to allow us to propose that both have evolved from a primordial receptor gene (Weinberger, et al., 1985a). Two surprising results have emerged from the studies presented here. The first is that the occurrence of a family of erb-A proto-oncogenes implies the existence of one or more other molecules closely related to the thyroid hormone receptor. Physiological studies have not predicted the existence of a second class of thyroid hormone receptors and thus the characterization of this family may shed new light on mechanisms of developmental and homeostatic regulation. The second surprising observation from these results is the close kinship of the thyroid hormone receptors with the steroid hormone receptor family. This relationship indicates that these molecules may all be part of a superfamily of regulatory proteins that have arisen over evolutionary time to match the increasing developmental and physiological demands of more complex eukaryotes.

III. I. Detailed Description of Figures Referred to in Experimental Section III

FIG. III-1.

Restriction map and sequencing strategy (a) and nucleotide and predicted amino acid sequence (b) of human placenta c-erb-A cDNA. a, Orientations of the two subclones pheA4 and pheA12 relative to the composite restriction map. Common restriction endonuclease cleavage sites are above the linear map. Thin lines, untranslated sequences; hatched box, erb-A coding region; arrows, DNA fragments sequenced, b, Nucleotide sequence of the composite erb-A cDNA is presented in the 5' to 3' orientation. The translational open reading frame related to the viral erb-A protein [21] is shown above the nucleotide sequence. Adenosine residues (~130) are found at the 3' end of pheA12. Numbers above the translated sequence indicate amino acid residues and nucleotide numbers are on the right of the sequence.

FIG. III-1A, B-1 and B-2 Methods

Recombinant phage (~10$^6$) from each of two human placenta lambda gt10 cDNA libraries (Huynh, et al., 1985) were screened using a nick-translated (Rigby, et al., 1977) 500-bp PstI fragment isolated from pAEV-11 (Vennstrom, et al., 1980)). The hybridization mixture contained 50% formamide, 1×Denhardt's, 5×SSPE, 0.1% sodium dodecyl sulphate (SDS), 100 microgram ml$^{-1}$ denatured salmon sperm DNA and 10$^6$ c.p.m. ml$^{-1}$ of $^{32}$p-labeled PstI fragment (specific activity = 1 × 10$^8$ c.p.m. microgram$^{-1}$). Duplicate nitrocellulose filters were hybridized at 37° C. for 18 h, washed three times for 20 min each in 0.1×SSC, 0.1% SDS (1×SSC=150 Mm NaCl, 15 Mm trisodium citrate) and autoradiographed at −70° C. with an intensifying screen. Two hybridization-positive clones were isolated, subcloned into the EcoRI site of pUC8, and sequenced by the chemical cleavage method (Maxam, et al., 1977).

FIG. III-2.

Amino acid sequence comparison between the carboxy-terminal portions of the v-erb-A oncogene product, the human placenta c-erb-A polypeptide and the human glucocorticoid and oestrogen receptors. Translated amino acid sequences for both the v-erb-A protein (upper sequence) and the human placenta c-erb-A polypeptide (second sequence) were compared by aligning matching residues. A computer program for the concurrent comparison of three or more amino acid sequences (Johnson, et al., 1986) was used to align c-erb-A human glucocorticoid receptor (hGR third sequence from top; see Experimental Section I, FIG. I-2) and human oestrogen receptor (hER, bottom sequence; see Green, et al., 1986) carboxy-terminal amino acid sequences, on the basis of progressive evaluation of selected segments from each sequence. Amino acid residues matched in at least three of the polypeptides are boxed. Amino acid matches between the two erb-A polypeptides are indicated by an asterisk above the top sequence in each column. Amino acid identities between the steroid receptors are designated by crosses below the sequences. Hyphens, gaps inserted to maximize the number of matches in the comparison. Cysteine residues conserved between the four polypeptides printed white-on-black.

FIG. III-3a, b and c.

Southern analysis and chromosome mapping of human placenta DNA with c-erb-A DNA probes. a, Human term placenta DNA was digested with restriction endonucleases and products were separated on a 0.8% agarose gel. DNA's were transferred to nitrocellulose paper (Southern, 1975) and hybridized in 50% formamide, 5×SSPE, 1×Denhardt's, 0.1% SDS, 100 microgram ml$^{-1}$ salmon sperm DNA with the 450-bp SstI fragment from the pheA4 which was nick-translated to a specific activity of 5×10$^8$ c.p.m. microgram$^{-1}$. The filter was washed in 0.1×SSC, 0.1% SDS at 60° C. and exposed to X-ray film at −70° C. with an intensifying screen. Lambda HindIII DNA markers (size in kb) are aligned to the left of the autoradiogram. b, Analysis of placenta DNA using the same c-erb-A probe as in section a above, under non-stringent hybridization conditions. A parallel blot containing the same samples was hybridized as in section a, except that 35% formamide was used. The hybridized filter was washed in 2×SSC, 0.1% SDS at 55° C. and exposed to X-ray film as described above. c, Chromosome mapping of human c-erb-A genes. Human lymphocyte chromosomes were separated by laser cytofluorometry (Lebo, et al., 1984) and probed using the non-stringent hybridization conditions described in section b, but with the 1.5 kbp EcoRI insert from pheA4 as probe.

FIG. III-4a, b, c and d.

Human c-erb-A expression. a, Northern analysis of RNA's from human cell lines and human placenta. Cytoplasmic poly(A)-containing RNA (12 microgram) from HeLa, MCF-7 and IM-9 cells, or total poly(A) RNA's from HT1080 or placental were separated on a 1% agarose gel containing formaldehyde, transferred to nitrocellulose (Thomas, 1980) and probed using a nick-translated 650-bp BamHI-PstI pheA4 fragment. Cytoplasmic RNA's were isolated from the cell lines using isotonic buffer and 0.5% NP40, while the placenta RNA's were extracted from fresh tissue using guanidine thiocyanate (Chirgwin, et al., 1979). Lane 1, HeLa; lane 2, HT1080, lane 3, human placenta; lane 4, IM-9; lane 5, MCF-7. b, Synthesis of erb-A polypeptides in vitro. The $^{35}$S-methionine-labeled products synthesized using T7 polymerase-catalysed RNA transcripts were separated on a 12.5% SDS-polyacrylamide gel which was fluorographed (EN$^3$HANCE, New England Nuclear). Lane 1, control (without mRNA); lane 2, peA102 (anti-sense RNA, 4 microliters); lane 3, peA101 (sense RNA, 1 microliter); lane 4, peA101 (4 microliters RNA). Sizes of protein standards: bovine serum albumin, 66.2K; ovalbumin, 45K and carbonic anhydrase, 31K.

FIG. III-4a and b Methods.

The EcoRI insert from pheA12 which contains the entire coding region of c-erb-A was inserted into the EcoRI site of pGEM3 (Promega Biotec) in both orientations. Plasmid DNA's peA101 and peA102 were linearized with HindIII, purified on 0.8% agarose gels and used as templates for T7 polymerase-catalysed synthesis of RNA's in vitro (see Experimental Section I). After P60 chromatography, total nucleic acid material (2 micrograms) was used to program protein translation in a rabbit reticulocyte lysate system (Promega Biotec) with $^{35}$S-methionine (25 microCi, 1100 Ci mmol$^{-1}$, New England Nuclear) final volume 25 microliters.

FIG. III-5a, b, c and d.

Thyroid hormone binding to erb-A polypeptides synthesized in vitro. a, Scatchard analysis of $^{125}$I-T$_3$ binding to the erb-A polypeptides made in vitro. The erb-A polypeptides (2 microliters from the in vitro translation mixture in a total volume of 2 ml) were assayed for specific thyroid hormone binding activity using hydroxylapatite to measure the amount of bound and free labeled hormone at different concentrations of $^{125}$I-T$_3$ as described (Gruol, 1980). b, Competition of thyroid hormone analogues for $^{125}$I-T$_3$ binding to erb-A polypeptides synthesized in vitro. Samples (2 microliters) from the peA101 (sense strand)-programmed reactions were used in $^{125}$I-T$_3$ standard binding reactions (Samuels, et al., 1974) with increasing concentrations of unlabeled thyroid hormone or analogues to compete with labeled hormone. Specifically bound thyroid hormone is plotted against concentration of competitor compound. c, Competition of triiodothyronine isomers from $^{125}$I-T$_3$ binding to erb-A polypeptides synthesized in vitro. Binding reactions were performed as above adding increasing concentrations of T$_3$ isomers. Thyroid hormone bound to erb-A is plotted on the ordinate. d, Competition of thyroid hormone analogues for $^{125}$I-T$_3$ binding to 0.4M KCl HeLa cell nuclear extracts. HeLa cell nuclei were extracted with a buffer containing 0.4M KCl (Samuels, et al., 1974). The protein extract (25 micrograms) (determined by Bio-Rad protein assay) was mixed with 0.6 nM $^{125}$I-T$_3$ in standard binding reactions with increasing concentrations of thyroid hormone and analogues (Samuels, et al., 1974; Latham, et al., 1976).

FIG. III-5a, b and c Methods.

Labeled $^{125}$I-3,3′,5-triiodo-L-thyronine (New England Nuclear, 2,200 Ci mmol$^{-1}$, 0.3 nM final) was mixed with erb-A polypeptides synthesized in the in vitro translation mixture (described in FIG. III-4) in $T_3$-binding buffer (0.25M sucrose, 0.25M KCl, 20 mM Tris-HCl (pB 7.5), 1 mM $MgCl_2$, 2 mM EDTA, 5 mM dithiothreitol (DTT)) (Samuels,, et al., 1974) at 0° C. for 2 h in a final volume of 250 microliters. Specific hormone binding was determined by adding a 1,000-fold excess of unlabeled hormone and assayed by counting radioactivity eluting in the excluded volume from a Sephadex G-25 fine (Pharmacia) 0.9×4.0 cm column (Samuels, et al., 1974).

FIG. III-6.

Schematic comparison of the steroid and thyroid hormone receptors. Amino-acid sequences of the receptor molecules aligned in FIG. III-2 are represented schematically. CYS, cysteine-rich region encoding the putative DNA binding domain found in the receptor proteins (Cys-rich region residues are: c-erb-A, 102–169; hGR, 421–486; hER, 185–250) Cortisol, oestradiol and $T_3/T_4$, hormone binding regions in the carboxyl termini; 1 MM, immunogenic region of the human glucocorticoid receptor. Numbers separating boxes, percentage amino acid identities between the receptor species in the intervals between the vertical broken lines; hGR, human glucocorticoid receptor; hER human oestrogen receptor; hc-erb-A beta, human thyroid hormone receptor.

III. J. References Referred to in Experimental Section III

References

1. Berg, J., Science, 232: 485–487 (1985).
2. Carlstedt-Duke, J., Okret, S., Wrange, O., and Gustafsson, J. -A., Proc. Natl. Acad. Sci., USA, 79:4260–4264 (1982).
3. Chirgwin, J. M., Przybyla, A. F., MacDonald, R. J., and Rutter, W. F., Biochemistry, 18:5294–5299 (1979).
4. Conneely, O. M., et al., Science, 233:767–770 (1986).
5. Dayton, A. I., Proc. Natl. Acad. Sci. USA, 81:4495–4499 (1984).
6. Debuire, B., et al., Science, 224:1456–1459 (1984).
7. Dejeant A., Bougueleret, L., Grzeschik, K. -H., and Tiollais, P., Nature, 322:70–72 (1986).
8. Dellweg, H. -G., Hotz, A., Mugele, K., and Gehring, U., EMBO J., 1:285–289 (1982).
9. Eberhardt, N. L., Apriletti, J. W., and Baxter, J. D. in Biochemical Actions of Hormones, Vol. VII (ed. Litwack, G.), pp. 311–394, Academic, New York (1980).
10. Evans, R. M., Birnberg, N. C., and Rosenfeld, M. G., Proc. Natl. Acad. Sci. USA, 79:7659–7663 (1982).
11. Frykberg, L., et al., Cell, 32:227–238 (1983).
12. Graf, T., and Beug, H., Cell, 34:7–9 (1983).
13. Green, S., et al., Nature, 320:134–139 (1986).
14. Greene, G. L., et al., Science, 231:1150–1154 (1986).
15. Gruol, D. J., Analyt. Biochem. 101:387–393 (1980).
16. Huynh, T. V., Young, R. A., and Davis, R. W. in DNA Cloning, a Practical Approach, Vol. 1 (ed. Glover, D., pp. 49–78; IRL Press, Oxford (1985).
17. Jansson, M. Philipson, L., and Vennstrom, B., EMBO J., 2:561–565 (1983).
18. Jeltsch, J. M., Proc. Natl. Acad. Sci. USA, 83:5424–5428 (1986).
19. Johnson, M. S., and Doolittle, R. F., J. Molec. Evol., 23:267–278 (1986).
20. Kahn, P., et al., Cell, 45:349–356 (1986).
28. Krust, A., et al., EMBO J., 5:891–897 (1986).
21. Kumar, V., Green, S., Staub, A., and Chambon, P., EMBO J., 5:2231–2236 (1986).
22. Laemmli, U. K., Nature, 227:680–685 (1970).
23. Latham, K. R., Ring, J. C., and Baxter, J. D., J. Biol. Chem., 251:7388–7397 (1976).
24. Lebo, R., et al., Science, 225:57–59 (1984).
25. Martial, J. A., Baxter, J. D., Goodman, H. M., and Seeburg, P. H., Proc. Natl. Acad. Sci. USA, 74:1816–1820 (1977).
26. Maxam, A., and Gilbert, W., Proc. Natl. Acad., Sci., USA, 74:560–564 (1977).
27. Miller, J., Mclachlan, A. D., and Klug, A., EMBO J., 4:1609–1614 (1985).
28. Oppenheimer, J. H., Koerner, D., Schwartz, H. L., and Surks, M. I. J., Clin. Endocr. Metab., 35:330–333 (1972).
29. Pascual, A., Casanova, J., and Samuels, H. H., J. Biol. Chem., 257:9640–9647 (1982).
30. Proudfoot, N. J., and Brownlee, G. G., Nature, 263:211–214 (1976).
31. Reichman, M. E., et al., Biochemistry, 23:5376–5384 (1984).
32. Rigby, P. W. J., Dieckmann, M., Rhodes, C., and Berg, P., J. Molec. Biol., 113:237–251 (1977).
33. Samuels, H. H., and Shapiro, L. E., Proc. Natl. Acad. Sci. USA, 73:3369–3373 (1976).
34. Samuels, H. H., Stanley, F., and Casanova, J., J. Clin. Invest., 63:1229–1240 (1979).
35. Samuels, H. H., Tsai, J. S., Casanova, J., and Stanley, F. J., J. Clin. Invest., 54:853–865 (1974).
36. Samuels, H. H., Tsai, J. S., and Cintron, R., Science, 181:1253–1256 (1973).
37. Sealy, L., Privalsky, M. L., Moscovici, G., Moscovici, C., and Bishops J. M., Virology, 130:155–178 (1983).
38. Sherman, M. R., Pickering, L. A., Rollwagen, F. M., and Miller, L. K., Fedn. Proc., 37:167–173 (1978).
39. Southern, E. M., J. Molec. Biol., 98:503–517 (1975).
40. Spindler, B. J., Mellon, S. H., and Baxter, J. D., J. Biol. Chem., 257:11627–11632 (1982).
41. Spurr, N. K., et al., EMBO J., 3:159–163 (1984).
42. Tata, J. R., and Widnell, C. C., Biochem. J., 98:604–620 (1966).
43. Thomas, P., Proc. Natl. Acad. Sci., USA, 77:5201–5205 (1980).
44. Tsai, J. S., and Samuels, H. H., Biochem. Biophys. Res. Commun., 59:420–428 (1974).
45. Vennstrom, B., Fanshier, L., Moscovici, C., and Bishop, J. M., J. Virol., 36:575–585 (1980).
46. Weinberger, C., Sollenberg, S. M., Rosenfeld, M. G., and Evans, R. M., Nature, 318:670–672 (1985a).
47. Weinberger, C., Hollenberg, S. M., Rosenfeld, M. G., and Evans, R. M., Science, 228:740–742 (1985b).
48. Yaffe, B. M., and Samuels, H. H., J. Biol. Chem., 259:6284–6291 (1984).

EXPERIMENTAL SECTION IV

Cloning of Human Mineralocorticoid Receptor Complementary DNA: Structural and Functional Kinship with the Glucocorticoid Receptor IV. A. Summary Low-stringency hybridization with human glucocorticoid receptor (hGR) complementary DNA was used to isolate a new gene encoding a predicted 107-kilodalton polypeptide. Expression studies demonstrate its ability to bind aldosterone with high affinity and to activate gene transcription in response to aldosterone, thus establishing its identity as human mineralocorticoid receptor (hMR). This molecule also shows high affinity for glucocorticoids and stimulates a glucocorticoid-responsive promoter. Together the hMr and hGR provide unexpected functional diversity in which hormone-binding properties, target gene interactions, and patterns of tissue-specific expression may be used in a combinatorial fashion to achieve complex physiologic control.

IV. B. Introduction

The hypothalamic-pituitary-adrenal axis integrates a variety of neuroendocrine inputs to regulate the synthesis and secretion of the adrenal corticosteroids. These steroid hormones exert effects on growth, development, and homeostasis by their interaction with intracellular receptor proteins that directly regulate the transcription of sets of target genes (1,2). Two receptor systems have been defined for the corticosteroids; these are termed the glucocorticoid receptor (GR) and the mineralocorticoid receptor (MR). Early functional assays classified the corticosteroids as either glucocorticoid, by their effect in promoting glycogen deposition in the liver, or mineralocorticoid, by their effect in promoting sodium retention by the kidney. However, each steroid class is not restricted to interacting with only its cognate receptor, and glucocorticoids, in particular, can have substantial mineralocorticoid activity (1-3).

It is now evident that the MR has significant in vitro affinity for both glucocorticoids and mineralocorticoids (3,4). Since the circulating levels of glucocorticoids are several orders of magnitude higher than those of aldosterone, the primary mineralocorticoid, glucocorticoid activation of the MR may be functionally significant. Whereas the secretory epithelia of tissues such as kidney and intestine regulate electrolyte and water balance in response to aldosterone, it is possible that additional mechanisms confer these tissues with sensitivity to mineralocorticoids (5). No clear functional role has emerged for the MR expressed in other tissues, but physiological responses in brain may result from glucocorticoid interactions with the MR (5-7).

Despite the availability of high-affinity radioactively labeled ligands, the MR has been refractory to purification, and its biochemical properties, in comparison to GR, remain poorly understood. Application of the techniques of molecular biology to the study of the MR would facilitate its biochemical characterization and, eventually, an understanding of the genes under its transcriptional control and the roles their products play in homeostasis.

Molecular cloning of the glucocorticoid (see Experimental Section I and refs. 8,9), estrogen (10), and progesterone (11) receptors has permitted the determination of their primary amino acid structures and prediction of functional domains common to this family of regulatory proteins. Experimental dissection of glucocorticoid (see Experimental Section II and ref. 12) and estrogen (13) receptors has revealed a centrally located DNA-binding domain rich in cysteine, lysine, and arginine, and a carboxyl-terminal region where steroid hormones interact. Functional studies of GR suggest that hormone binding to the carboxyl terminus unmasks the DNA binding region to permit interactions of receptor with DNA and activation of transcription (14, 15). Comparison of the cysteine-rich DNA-binding regions of steroid and thyroid hormone receptors shows a high degree of relatedness between these molecules (16). The invariant cysteine residues have led to the hypothesis that coordination of $Zn^{2+}$ metal atoms maintains a structural configuration for DNA binding analogous to that proposed for Xenopus 5S gene transcription factor IIIA (17). The steroid-binding regions of the steroid receptor family also show substantial conservation consistent with evolution of various receptor classes from a common ancestral precursor (11, 16).

We have used the structural similarity between steroid hormone receptors to isolate a gene product closely related to the human glucocorticoid receptor (hGR). Nonstringent hybridization with an hGR probe was used to isolate a human genomic DNA fragment highly related to the hGR cysteine-rich sequence. Using this DNA as a probe, we obtained complementary DNA's (cDNA's) that code for a molecule having a strong homology with the hGR from the cysteine-rich region to the carboxyl terminus. When expressed in cells, this molecule binds aldosterone with high affinity and activates aldosterone-response transcription of the long terminal repeat (LTR) of the mouse mammary tumor virus (MMTV). The overlap of the ligand and DNA sequence specificities of this human mineralocorticoid receptor with those of hGR suggest that the distinct roles traditionally assigned to these regulatory molecules should be reconsidered.

IV. C. Isolation of hMR cDNA

For the identification of glucocorticoid receptor-related genes, human placenta DNA was digested with restriction endonucleases, fractionated by agarose gel electrophoresis, and the fractions were hybridized with hGR 1.2, an 1100-bp fragment of hGR cDNA containing sequences encoding the DNA-binding domain (see Experimental Section I; also ref. 15). Southern blot analysis revealed several distinct bands specific to low-stringency hybridization conditions (compare FIG. IV-1; A and B). The 2.5-kilobase pair (kbp) HindIII fragment (bracketed by asterisks in FIG. IV-1B) was well resolved from other hybridizing bands and was judged suitable for direct genomic cloning. HindIII-digested DNA from human placenta was preparatively size-fractionated on an agarose gel, and the 2.5-kbp region was isolated for the construction of a genomic library. This lambda gt10 library was then screened under conditions of low-stringency hybridization with hGR 1.2 as the probe. The insert from one positive genomic clone, lambda HGH, was nick-translated and used as a probe on a Southern blot under high-stringency hybridization conditions (FIG. IV-1C). The 2.5-kbp HindIII signal corresponded to that seen under nonstringent conditions, indicating that a portion of the desired genomic fragment had been isolated. Sequence analysis of the insert from lambda hGH revealed an exon of 140 base pair (bp) flanked by intron sequences (FIG. IV-1D). Overall this exon has 68 percent nucleotide identity with the homologous hGR cDNA sequence, but a region conserving 85 nucleotides out of 104 probably confers its cross-hybridization properties. This highly conserved region corresponds to a portion of the hGR DNA-binding domain (15). The lambda HGH exon codes for 46 amino acids beginning with 16 nonconverted residues and followed by the first of the highly conserved cysteine residues characteristic of steroid hormone receptors (8-11). Of the next 30 residues, 28 are identical to hGR. These analyses demonstrated the isolation of a genomic fragment containing a sequence related tor but clearly distinct from, that found in the hGR cDNA sequence (see Experimental Section I).

The insert from lambda HGH was used as a probe to screen cDNA libraries for clones corresponding to this hGR-related gene. Mineralocorticoid receptor was considered a candidate to be encoded by such a gene. Since kidney is known to be a mineralocorticoid-responsive tissue, several human kidney cDNA libraries were screened. Eleven positive clones were isolated from these lambda gt10 libraries at a frequency of three to four per $10^6$ recombinant phage. Two overlapping clones, lambda hk2 and lambda hk10, were subjected to nucleotide sequence analysis and together found to span 5823 nucleotides (FIG. IV-2A, B-1 and B-2). The exon-intron boundaries of lambda HGH were verified by sequencing these cDNA clones. The lambda hk10, encompassing nucleotides 1 to 3750, contains a large open reading frame predicting the entire primary amino acid sequence. The DNA insert from lambda hk2 extends from nucleotides 802 to 5823, but contains an internal 351-bp deletion from 2235 to 2586. Three additional clones were examined and determined to have the same structure as lambda hk10 in the deleted region. It is likely that the deletion in lambda hk2 represents either a cloning artifact or a rare messenger RNA (mRNA) splicing error (18). The sequence of the reported 3'-untranslated region downstream of nucleotide 3750 is derived from lambda hk2. The composite sequence of these two cDNA's is termed hMR (FIG. IV-2A). With the first in-frame ATG (position 223) downstream of an in-frame termination codon (position 136), hMR has a 5'-untranslated region of at least 216 nucleotides. The sequence surrounding this first ATG agrees with the consensus described by Kozak (19). This predicted initiator methionine codon begins an open reading frame encoding 984 amino acids. Following a termination codon (position 3175) is a 2.6-kb 3'-untranslated region with a typical polyadenylation signal (AATAAA) found 17 nucleotides upstream of a 70-nucleotide poly(A) (polyadenylated) tract. Long 3'-untranslated regions are a characteristic feature of steroid hormone receptor mRNA's (see Experimental Section I; also refs. 9–11).

IV. D. The DNA- and Hormone-Binding Regions

The protein encoded by hMR cDNA has the structural properties of a steroid hormone receptor closely related to hGR. Comparison of the predicted amino acid sequence of hMR with that of hGR demonstrated high degrees of homology with both the hGR DNA binding ana steroid binding domains. The hMR gene encodes a protein of 984 amino acids with a predicted molecular size of 107 kD, significantly larger than the 777 residues of hGR. This size discrepancy is primarily due to the large amino terminus, which bears no homology to hGR. Considerable heterogeneity of size and sequence for this region exists between the receptors for glucocorticoid, estrogen, and progesterone (see Experimental Section I; also refs. 9–11). Amino acid homology begins in the centrally located DNA region with 94 percent amino acid identity in 68 residues (FIG. IV-3). Separating the DNA-binding domain and the carboxyl-terminal steroid-binding domain is a region with relatively low sequence conservation found between other steroid hormone receptors. It has been speculated that the region may serve as a molecular hinge between the two domains (see Experimental Section II and ref. 13). Comparison with hGR shows this region of hMR to contain an additional 24 amino acids including a sequence of 4 glutamines followed by 8 prolines encoded by repetitive nucleotide elements. The significance of this unusual sequence in terms of origin and function is unclear, but structure-breaking prolines are consistent with a hinge region. A comparison of the carboxyl-terminal 250 amino acids of hMR with hGR shows 57 percent amino acid identity as well as a number of conservative amino acid substitutions. Some of these substitutions may preserve hydrophobic regions necessary for steroid hormone interaction.

IV. E. Expression and Hormone Binding

We have used transfection of the monkey kidney cell line CV1 and its derivative (that is, SV40 T antigen-transformed) cell line COS-1 (referred to as COS) to study glucorticoid receptor function. (See Experimental Section II.) High levels of polypeptide expression from transfected hMR were essential to facilitate steroid-binding experiments in transfected cells. Since plasmids containing the SV40 origin of replication can replicate to high copy numbers in COS cells, an expression vector for hMR coding sequences similar to pRShGR alpha, used previously in hGR studies, was constructed. The plasmid, pRShMR, contains the hMR coding sequence, under the control of the promoter from Rous sarcoma virus, and the SV40 origin of replication (FIG. IV-4A).

Ligand specificity of the hMR protein was determined by preparing cytosol extracts from COS cells transfected with pRShMR. Two days after transfection, cells were harvested, and hormone binding was measured by a dextran-treated charcoal assay. Mock-transfected control extracts had no specific binding activity for [$^3$H]aldosterone, whereas extracts from pRShMR-transfected cells found significant amounts of [$^3$H]aldosterone with high affinity. A dissociation constant ($K_D$) of 1.3 nM for the binding of [$^3$H]aldosterone was determined by a Scatchard analysis (FIG. IV-4B). This value is in good agreement with those reported for aldosterone binding to mineralocorticoid receptor (2, 20). Competition experiments were then performed to examine the ability of different unlabeled steroids to compete with 5 nM [$^3$H]aldosterone for binding when present at 1-, 10-, or 100-fold molar excess (FIG. IV-4, C and D). This provided a measure of the relative affinity of each of these steroids for hMR. The results of these experiments show that aldosterone, corticosterone, deoxycorticosterone, hydrocortisone (cortisol) all have very similar affinities for hMR. Dexamethasone, progesterone, and spironolactone demonstrated weaker binding affinity while estradiol competed very poorly for binding to hMR. Overall, this hierarchy of affinities indicated that hMR encoded the human mineralocorticoid receptor (2, 20).

IV. F. Transcriptional Activation

Steroid hormone action is characterized by hormone-dependent modulation of target gene transcription. The assay for transcriptional regulation by transfected hGR in CVI cells (see Experimental Section II) was adapted to hMR (FIG. IV-5a, b and c). The expression plasmid used for steroid-binding assays, pRShMR, was cotransfected with a reporter plasmid called GMCAT, which contains the MMTV LTR linked to the bacterial gene for chloramphenicol acetyltransferase (CAT). Thus CAT activity provides an enzymatic assay for the transcriptional activity of the MMTV promoter. The MMTV promoter contains several glucorticoid response elements (GRE's), enhancer-like DNA sequences that confer glucocorticoid responsiveness via interaction with the GR (21). It was possible that hMR, because of the near identity of its DNA-binding domain to that of hGR, might also recognize the MMTV LTR. When CV1 cells were cotransfected with pRShMR and GMCAT, we observed full CAT activity. This activity was independent of added aldosterone suggesting that, in contrast to transfected hGR, sufficient hormone was present in serum (fetal calf serums 5 percent) to fully activate hMR (FIG. IV-5B). In the presence of charcoal-treated serum (22) CAT activity became responsive to the addition of exogenous aldosterone (FIG. IV-5C), indicating that hMR cDNA encodes a functional steroid hormone receptor. While the hMR was also activated by the glucocorticoid agonist dexamethasone, the hGR did not respond to even supraphysiological concentrations (10 nM) of aldosterone.

IV. G. Tissue-Specific Expression

We examined the expression of MR mRNA homologous to hMR cDNA in rat tissues by Northern blot hybridization (23). Classical mineralocorticoid target tissues such as kidney (24) and gut (25), as well as tissues such as brain, pituitary, and heart, contained mRNA homologous to hMR (FIG. IV-6). Aldosterone-sensitive cells in kidney are primarily restricted to the distal and cortical collecting tubules (2), and therefore a modest level of expression in this tissue was not unexpected. High levels of MR (type I corticosteroid-binding sites) have been reported in rat brain, particularly in the hippocampal formation (4, 6). In comparing dissected hippocampal RNA with RNA prepared from total brain, we found a striking enrichment of message in the hippocampus. While aldosterone binding has been reported for pituitary (26), cultured aortic cells (27), and spleen (28), no such activity has been reported in muscle. Liver expresses GR, but has no detectable high-affinity aldosterone-binding activity (29), and as would be expected no hybridization to liver RNA was observed. Reprobing of the same Northern blot with an analogous portion of hGR cDNA demonstrated hybridization to mRNA species of different sizes, and indicated that the MR and GR do show differential patterns of tissue-specific expression.

IV. H. Chromosome Mapping

To determine the chromosomal location of the mineralocorticoid receptor gene, we tested hMR against a panel of rodent-human somatic cell hybrids retaining different combinations of human chromosomes (30). The DNA fragments specific for the mineralocorticoid receptor gene segregated concordantly with human chromosome 4 in 15 hybrid cell lines. Discordant segregation was observed for all other human chromosomes, including chromosome 5, site of the glucocorticoid receptor gene (see Experimental Section I and ref. 31). To confirm the assignment to chromosome 4, we tested a restricted set of microcell hybrids; each of which carry one to three human chromosomes (32), for the hMR gene by Southern analysis (FIG. IV-7). Six EcoRI fragments detected by the coding portion of lambda hk2 co-segregate with chromosome 4 in this hybrid panel. In particular, the hMR gene is present in HDM-1132B, a cell line that carries chromosome 4 as its only human chromosome.

IV. I. Implications for Adrenal Corticosteroid Physiology

Human mineralocorticoid receptor cDNA encodes a polypeptide that is highly homologous to the human glucocorticoid receptor. In the DNA-binding domain, hMR maintains approximately 94 percent amino acid identity to hGR while the steroid-binding domain localized in the carboxyl terminus has 57 percent identity. The recently reported sequence (11) of the rabbit progesterone receptor (rPR) also has a high degree of relatedness to hMR. Comparison of the amino acid identity in hGR and rPR structural domains with that of hMR (FIG. IV-8) demonstrates the remarkable similarity of these functionally distinct regulatory proteins. The homology of hMR with rPR is almost identical to the hGR-hMR comparison, with 90 percent of the amino acids shared in the DNA-binding domain and 56 percent in the steroid-binding region. In contrast, a comparison of the same regions of hMR with human estrogen receptor (10) indicates 56 percent identity in the DNA binding domain and 21 percent sequence identity in the steroid-binding carboxyl terminus. The degree of structural homology shared by hMR, hGR, and rPR, and the structural relatedness of their ligands, suggests that they may comprise a subfamily of steroid hormone receptors.

Expression of the hMR polypeptide in COS cells by transient transfection permitted the evaluation of its steroid-binding potential. The results of these analyses indicated that hMR cDNA encodes a human mineralocorticoid receptor. Scatchard analysis demonstrated that extracts from cells transfected with pRShMR bound [$^3$H]aldosterone with a $K_D$ of 1.3 nM, while reported $K_D$ values for aldosterone binding to MR range from 0.5 to 3 nM (2). This is the single most important criterion in defining this gene product as the human mineralocorticoid receptor. Steroid-binding competition studies have further supported this identification of hMR. The mineralocorticoid deoxycorticosterone and the glucocorticoids corticosterone and cortisol compete as effectively as aldosterone itself, whereas the synthetic glucocorticoid dexamethasone and progesterone have lower affinities for the hMR.

The extensive amino acid sequence identity in the presumptive steroid-binding domains of hMR, hGR, and rPR is compatible with the similar ligand-binding properties of these receptors. The mineralocorticoid, glucocorticoid, and progesterone receptors exhibit a limited ability to discriminate between the similar 21-carbon atom structures of the mineralocorticoids, glucocorticoids, and progestins. This lack of specificity is particularly relevant to the MR and GR. For example, the MR binds glucocorticoids with an affinity equal to that for aldosterone. Indeed, it may be that only in tissues such as kidney, where additional mechanisms confer selective response to aldosterone, does the MR function as a classical mineralocorticoid receptor (3, 5). The MR also binds progesterone with a high affinity, but one lower than its affinity for corticosteroids. There is some indication that progesterone may act as a partial agonist or antagonist of mineralocorticoid action (33), and it is not clear whether glucocorticoids act as full agonists in binding to the mineralocorticoid receptor. Similarly, the GR binds glucocorticoids with a $K_D$ between 20 to 40 nM and it binds aldosterone with a $K_D$ between 25 to 65 nM (2). Therefore, the important distinction between the hormone-binding properties of MR and GR may not be one of ligand specificity, but rather of a high-affinity versus a lower affinity receptor for the corticosteroids.

The function of the hMR in vivo is complicated by the serum cortisol-binding protein, transcortin. This protein sequesters cortisol and, because of its differential distribution, transcortin could influence local glucocorticoid concentration. High levels of transcortin in kidney would reduce available cortisol from plasma to favor aldosterone sensitivity, whereas low levels of transcortin in the brain would suggest that, in the central nervous system, glucocorticoids may be the predominant hMR ligand. Thus, the preferred physiologic ligand for hMR apparently varies depending on the site of receptor expression (3). This model and others (5) have been proposed to explain the responsiveness of some tissues to aldosterone despite much higher levels of competing glucocorticoids.

The degree of homology between hMR and hGR in the DNA-binding domain (only four amino acid residues differ in this conserved 68-residue region) suggests that these receptors may recognize similar regulatory elements. The activation of the MMTV LTR by the transfected hMR in response to both aldosterone and dexamethasone supports this conclusion, although the progesterone receptor has also been demonstrated to regulate this promoter (21). Furthermore, differences between hMR and hGR in the DNA-binding domain, or in other regions such as the highly divergent amino termini of these molecules, may influence target gene specificity in ways not revealed in this assay. However, we have utilized transcriptional regulation of the MMTV LTR by hMR and hGR to examine their activation by mineralocorticoids and glucocorticoids. While the hMR response was approximately equivalent with either 10 nM aldosterone or dexamethasone, hGR was activated by dexamethasone but was insensitive to aldosterone in this assay. Transcriptional activation by hMR in response to exogenous cortisol was also observed. These data indicate that in transfected cells both mineralocorticoids and glucocorticoids can activate hMR-mediated gene transcription. On the basis of this functional property, we conclude that the hMR is highly responsive to adrenal corticosteroids and therefore may function as a glucocorticoid receptor.

In addition to elucidating the pharmacologic and physiologic function of the mineralocorticoid receptor in coordinating response to corticosteroids, the isolation of hMR cDNA will facilitate investigation of the role of hMR in a number of disease states, among them hypertension and pseudohypoaldosteronism (PHA). An association of mineralocorticoids with hypertension has been recognized for several decades, and it may be that hMR-mediated sodium retention and increased blood volume are, in part, responsible for some forms of hypertension (34). PHA is an autosomal recessive disorder characterized by lack of responsiveness to normal or elevated aldosterone levels. Recent work has demonstrated diminished or complete loss of high-affinity aldosterone-binding sites in patients with this disease (35) which is likely to result from a mineralocorticoid receptor genetic defect. The chromosomal mapping of the hMR gene suggests the PHA locus should reside on chromosome 4.

Cloning and expression of functional hMR has provided unexpected insight and should stimulate new interest into the mechanisms underlying physiologic complexity, and allow the development and testing of new models for the coordinate regulation of gene networks.

IV. J. Detailed Description of Figures Referred to in Experimental Section IV FIG. IV-1a, b, c and d.

Isolation of a genomic sequence related to the hGR gene. (A) High-stringency Southern analysis of human placenta DNA digested with the indicated restriction endonucleases. hGR cDNA (hGR1.2) was used as a probe. Sizes of lambda DNA fragment markers (in kilobase pairs) prepared by HindIII digestion are indicated next to the autoradiogram. (B) Low-stringency Southern analysis. The 2.5-kbp band bracketed by asterisks in the HindIII lane was the sequence targeted for direct genomic cloning. (C) Isolation of this genomic sequence in a clone designated lambda HGH is demonstrated by its use as a probe on a similar Southern blot. The lambda HGH genomic fragment contains the hybridizing internal EcoRI fragment isolated from this cloning. (D) The intron-exon structure of the lambda HGH genomic fragment and its homology with hGR. The hGR-related exon found within lambda HGH is boxed in black with its predicated amino acid sequence. Conserved cysteine residues are indicated with white dots. Portions of intron sequence with consensus splice donor and acceptor sites underlined are shown flanking the exon. Nucleotide homology with the hGR is shown underneath. Nucleotide numbers for hGR are from FIG. I-2-1 and 2-2, discussed in Experimental Section I; also see Hollenberg, et al. (1985) (ref. 8) for publication of the study used herein as Experimental Section I. For Southern analysis, we digested DNA from human term placenta with restriction endonucleases, and products were separated on a 0.8 percent agarose gel. The DNA's were transferred to nitrocellulose paper and hybridized under either stringent or nonstringent conditions. Stringent hybridization was performed with 50 percent formamide, $5 \times SSPE$ (NaCl, NaH$_2$PO$_4$, EDTA, pH 7.4) $1 \times$ Denhardt's, 0.1 percent SDS, salmon sperm DNA at 100 microgram/ml, and probe ($10^6$ cpm/ml) at 42° C. For nonstringent hybridization, 35 percent rather than 50 percent formamide was used. Washing conditions consisted of $0.1 \times SSC$ (standard saline citrate) with 0.1 percent SDS at 60° C. for stringent analyses and $2 \times SSC$ with 0.1 percent SDS at 55° C. for nonstringent filters. Washing conditions with the 338-bp inset from lambda HGH as probe were modified to $2 \times SSC$ with 0.1 percent SDS at 68° C. For isolation of lambda HGH, human placenta DNA (300 microgram) was digested with HindIII and size-fractionated on a 1 percent low-melting agarose gel (Seaplaque, FMC). The gel was sliced in 0.5-cm strips, and the DNA was purified by phenol extraction and ethanol precipitation. DNA (2 microgram) from the fraction corresponding in size to the band bracketed by asterisks in (B) was repaired with Klenow DNA polymerase for EcoRI linker addition. After digestion with EcoRI and removal of excess linkers on a Sepharose 4B column, this DNA was ligated to EcoRI-digested lambda gt10 DNA and packaged in vitro (lambda arms and extracts from Vector Cloning Systems, San Diego, Calif.). About $4 \times 10^5$ independent recombinants were screened under conditions identical to those used for the nonstringent Southern analysis to obtain lambda hGH.

FIG. IV-2a, b-1 and b-2.

Nucleotide sequence and primary amino acid structure of human mineralocorticoid receptor. (A) Composite structure of hMR aligned with a line diagram of some restriction endonuclease cleavage sites (EcoRI sites shown at nucleotides I and 5823 and derived from linkers). The composite was assembled from two overlapping lambda gt10 clones, lambda hk10 and lambda hk2. Parentheses in the line diagram of lambda hk2 indicate a 351-bp deletion. The hatched box indicates predicted coding sequence with initiator and termination codons indicated. (B) Complete nucleotide sequence of hMR and its predicted primary amino acid sequence. Underlined are a 5' in-frame termination codon upstream of the predicted initiator methionine and four potential polyadenylation sites (AATAAA). Human kidney lambda gt10 libraries (18) were screened with the insert from lambda HGH under the same conditions described for Southern analysis under high-stringency conditions with this probe. Overlapping deletions of each cDNA were obtained (36) by the Cyclone rapid deletion subcloning method (International Eiotechnologies). Deletion clones were sequenced by the dideoxy procedure (37), and any gaps or ambiguities were resolved by the chemical cleavage method (38). DNA sequences were compiled and analyzed by the programs of Devereux, et al. (39) and Staden (40).

FIG. IV-3.

Amino acid homology of mineralocorticoid receptor with glucocorticoid receptor. The primary amino acid sequence of hMR has been aligned with that of hGR for maximum homology by introducing gaps as indicated by dots. Numbers were taken from FIG. IV-2 for hMR and from FIG. I-2 for hGR. No significant homology was found upstream of the region shown. Vertical lines indicate identical amino acid residues. Arrows show putative boundaries of the DNA-binding (DNA) and steroid-binding (Steroid) domains. The amino-terminal border of the DNA-binding domain was arbitrarily defined by the first conserved cysteine residue while the carboxyl-terminal limit was chosen on the basis of mutagenesis studies which indicated sequences necessary for DNA-binding and transcriptional activation (15). Several conserved basic residues that follow the DNA binding domain may also be important for these functions. The limits of the steroid-binding domain, while defined by the region of amino acid homology, are also consistent with mutational analysis. Single letter abbreviations for the amino acid residues are: A, Ala; C, Cys; D, Asp; E, Glu; F, Phe, G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

FIG. IV-4a, b, c and d.

Steroid-binding properties of expressed hMR. (A) Structure of pRShMR, the hMR expression plasmid (41). (B) Scatchard analysis of tritiated aldosteone binding in extracts prepared from pRShMR-transfected COS cells. Each point was assayed in triplicate with 100 micrograms of extract protein in a 200-microliter incubation at 0° C. for 2.5 hours. The nonspecific binding determined with a 500-fold excess of unlabeled aldosterone was approximately 20 percent of total counts. No specific binding was seen in mock-transfected cells. (C and D) Competition of unlabeled steroids for binding with 5 nM [$^3$H]aldosterone in transfected COS cell extracts. The results of two independent trials representative of these competition experiments are shown. Cold competitor was present in 1-, 10-, or 100-fold molar excess. The value for 100 percent binding was determined by subtracting the number of counts per minute bound in the presence of 1000-fold excess of unlabeled aldosterone from the counts bound in the absence of competitor. Abbreviations: Aldo, aldosterone, Doc, deoxycorticosterone; Dex, desamethasone; Spiro, sprionolactone; E21, 17 beta-estradiol; CS, corticosterone; HC, hydrocortisone; and Prog, progesterone. Subconfluent COS cells were transfected by the DEAE-dextran method (42) with 10 micrograms of pRShMR per dish. Cells were maintained for 2 days in DMEM (Dulbecco's modification of Eagle's minimum essential medium) with 5 percent charcoal-treated fetal calf serum, then harvested [in 40 mM tris-HCl (pH 7.8), 10 mM NaCl, 1 mM EDTA, 10 mM Na$_2$MoO$_4$, 5 mM dithiothreitol, antipain (5 microgram/ml), leupeptin (5 microgram/ml), and 500 microM phenylmethylsulfonyl fluoride. After centrifugation at 15,000×g for 10 minutes, extracts were adjusted to 100 mM NaCl and 5 percent glycerol before binding. Labeling reactions with [$^3$H]aldosterone (specific activity 78 Ci/mmol, Amersham) were incubated for 2.5 hours at 0° C. in a total volume of 200 microliters, and then for 10 minutes with 20 microliters of 50 percent dextran-coated charcoal (10:1 activated charcoal:dextran). After centrifugation at 15,000×g for 2 minutes at 4° C., tritium in supernatant was quantified by liquid scintillation spectrophotometry.

FIG. IV-5a, b and c.

Transcriptional activation of MMTV LTR by hMR and hGR expression plasmids in transfected CVI cells. (A) Structure of GMCAT. This plasmid was cotransfected with the steroid receptors as a reporter gene for hormone-dependent transcriptional activation (see Experimental Section II). (B) Differential CAT enzyme activity found after hMr or hGR transfection with normal serum. Transfected cells were maintained in DMEM with 5 percent fetal calf serum. Serum was treated with charcoal to eliminate free steroids in subsequent experiments so that the effects of exogenous steroids could be determined. (C) Differential induction of CAT activity by aldosterone or dexamethasone in cells transfected with hMR or hGR. CVI cells were cotransfected with 10 micrograms of either pRSVgal (control), pRShMRF or pRShGR alpha and 10 micrograms of the reporter GMCAT and cultured in the absence (−) or presence of 10 nM aldosterone (A) or 10 nM dexamethasone (D). AC, 3-acetylchloramphenicol; C, chloramphenicol. Two days after transfection by calcium phosphate coprecipitation (43), extracts were prepared for CAT assay (44). The assays were incubated for 6 hours with 50 micrograms of protein extract.

FIG. IV-6.

Northern analysis of mineralocorticoid receptor mRNA's in rat tissues. The 1270-bp EcoRI fragment (1770 to 3040) from lambda hk10 was used as a probe for the expression of homologous mRNA's in rat. Ten micrograms of poly(A)+ mRNA was used in all lanes. Migration of ribosomal RNA's (28S and 18S) are indicated for size markers. After hybridization under stringent conditions, the filter was washed twice for 30 minutes each time in 2×SSC with 0.1 percent SDS at 68° C.

FIG. IV-7.

Chromosomal localization of hMR gene by Southern analysis of microcell hybrids. The construction and characterization of these hybrids has been previously described (32). The human chromosome content of each is as follows: HDm-4A (chromosome 20), HDm-5 (chromosome 14 and an unspecified E group chromosome)t HDm-9 (chromosomes 20; 14, and 21), HDm-15 (chromosomes 21, 11, and 4), HDm-20 (chromosomes 7 and 14), and HDm-1132B (chromosome 4 only). Human (HeLa) and mouse (3T#) control DNA samples are also shown. Genomic DNA from microcell lines (10 micrograms) was digested with EcoRI and subjected to electrophoresis through a 1.0 percent agarose gel, transferred to a nylon membrane (Nytran, Schleicher & Schuell), and hybridized with a hMR cDNA probe under high-stringency conditions (FIG. IV-1). Radioactive probe was synthesized by the Klenow fragment of *Escherichia coli* DNA polymerase from two randomly primed (45) hMR cDNA templates (the 1000- and 800-bp EcoRI fragments of lambda hk2). The sizes of HindIII-digested lambda DNA fragments are indicated next to the autoradiogram.

FIG. IV-8.

Schematic amino acid comparisons of the hGR, hMR, and rPR structures. Primary amino acid sequences have been aligned schematically with the percentage amino acid identity indicated for each region of homology in the intervals between dotted lines. The amino acid position of each domain boundary is shown for each receptor. N and C represent the amino and carboxyl termini, respectively. Cys corresponds to the cysteine-rich region encoding the putative DNA-binding domain while Steroid (cortisol, aldosterone, or progesterone) designates the steroid-binding domain. The immunogenic region (IMM) of the hGR is also indicated. Amino acid residue numbers are taken from (see Experimental Section I) for hGR, Loosfelt, et al. (11) for rPR, and from our data for hMR.

IV. K. References Referred to in Experimental Section IV

1. Baxter, J. D., and Tyrrell, J. B., in *Endocrinology and Metabolism*, Felig, P., Baxter, J. D., Broadus, A. E., and Frohman, L. S., Eds., pp. 385–510, McGraw-Hill, New York (1981); Marver, D., in *Biochemical Actions of Hormones*, Litwack, G., Ed., Vol. 12, pp. 385–431, Academic Press, Orlando, Fla. (1985).
2. Fanestil, D. D., and Park, C. S., *Annu. Rev. Physiol.*, 43:637 (1981).
3. Funder, J. W., in *Adrenal Cortex*, Anderson, D. C., and Winter, J. S. D., Eds., pp. 86–95, Butterworths, London (1985).
4. Beaumont, K. t and Panestil, D. D., *Endocrinology*, 113:2043 (1983; Krozowski, Z. S., and Funder, J. W., *Proc. Natl. Acad. Sci. USA*, 80:6056 (1983).
5. Funder, J. W., Sheppard, K., *Annu. rev. Physiol.*, 49:397 (1987).
6. Reul, J. M. H. M., and deKloet, E. R., *Endocrinology*, 117:2505 (1985).
7. McEwen, B. S., deKloet, E. R., and Rosterne, W., *Physiol. Rev.*, 66:1121 (1986).
8. Hollenberg, S. M., et al., *Nature*, 318:635 (1985).
9. Miesfeld, R., et al., *Cell*, 46:389 91986).
10. Greens S., et al., *Nature*, 320:134 (1986); Greene, G. L., et al., *Science*, 231:1150 (1986).
11. Loosfelt, H., et al., *Proc. Natl. Acad. Sci., USA*, 83:9045 (1986).
12. Giguere, V., Hollenberg, S. M., Rosenfeld, M. G., and Evans, R. M., *Cell*, 46:645 (1986).
13. Kumar, V., Green, S., Staub, A., and Chambon, P., *EMBO J.*, 5:2231 (1986); Green, S., and Chambon, P., *Nature*, 235:75 (1987).
14. Godowski, P. J., Rusconi, S., Miesfeld, R., and Yamanoto, K. R., *Nature*, 325:365 (1987).
15. Hollenberg, S. M., Giguere, V., Segui, P., and Evans, R. M., *Cell*, 49:39 (1987).
16. Weinberger, C., Hollenberg, S. M., Rosenfeld, M. G., and Evans, R. M., *Nature*, 318:670 (1985); Krust, A., et al., *EMBO J.*, 5:891 (1986); Sap, J., et al., *Nature*, 324:635 (1986); Weinberger, C., Hollenberg, S. M., Rosenfeld, M. G., and Evans, R. M., *Nature*, 318:641 (1985).
17. Miller, J., McLachlan, A. D., and Klug, A., *EMBO J.*, 4:1609 (1985).
18. Deletions in other cDNA clones have been reported in these libraries [G. I. Bell, et al., *Nucleic Acids Res.*, 14:8427 (1986)].
19. Kozakl M., *Nature*, 308:241 (1984).
20. Armanini, D., Strasser, T., and Weber, P. C., *Am. J. Physiol.*, 248:E388 (1985).
21. Ringold, G. M.,, Yamamoto, K. R., Bishop, J. M., and Varmus, H. E., *Proc. Natl. Acad. Sci., USA*, 74:2879 (1977); Payvar, F., et al., *Cell*, 35:381 (1983); Schiedereit, C., Geisse, S., Westphal, H. M., and Beato, M., *Nature*. 304:749 (1983).
22. For the removal of endogenous steroids, washed charcoal was added to serum [2 g (dry weight) per 100 ml] and incubated at 37° C. for 40 minutes then at 55° C. for 30 minutes. Charcoal was removed by filtration through 0.45 then 0.2 microm filters.
23. No human cell lines have been reported to express high-affinity aldosterone-binding sites. Northern blot analysis of human ovary RNA revealed two hybridizing RNA species approximately sized at 6 and 4 kb. No aldosterone-binding activity has been reported in ovary.
24. Fuller, P. J., and Funder, J. W., *Kidney Int.*, 10:154 (1976); Matulich, D. T., Spindler, B. J., Schambelan, M., and Baxter, J. D., *J. Clin. Endocrinol. Metab.*, 43:1170 (1976).
25. Pressley, L., and Funder, J. W., *Endocrinology*, 97:588 (1975).
26. Lan, N. C., Matulich, D. T., Morris, J. A., and Baxter, J. D., *Endocrinology*, 109:1963 (1981).
26. Krozowski, Z., and Funder, J. W., *Endocrinology*, 109:1221 (1981).
27. Meyer, W. J., and Nichols, N. R., *J. Steroid Biochem.*, 14:1157 (1981); no type I receptors were detectable in an early study in heart [Funder, J. W., Duval, D., and Meyer, P., *Endocrinology*, 93:1300 (1973).
28. Swaneck, G. E., Highland, E., and Edelman, J. S., *Nephron*, 6:297 (1969).
29. Duval, D., and Funder, J. W., *Endocrinology*, 94:575 (1974).
30. Dracopoli, N. C., et al., *Am. J. Hum. Genet.*, 37:199 (1985); Rettig, W., et al., *J. Exp. Med.*, 162:1603 (1985).
31. Gehring, U., Segnitz, B,, Foellmer, B., and Francke, U., *Proc. Natl. Acad. Sci., USA*, 82:3751 (1985).
32. Lugo, T. G., Handelin, B. L., Killary, A. M., Housman, D. E., and Fournier, K., *Mol. Cell. Biol.*, in press.
33. Wambach, G., and Higgins, J. R., *Endocrinology*, 102:1686 (1978).
34. Vallotton, M. B., and Favre, L., in *Adrenal Cortex*, Anderson, D. C. and Winter, J. S. D., Eds., pp. 169–187, Butterworths, London (1985).
35. Armanini, D., et al., *N. Engl. J. Med.*, 313:1178 (1985).
36. Dale, R. M. K., McClure, B. A., and Houchins, J. P., *Plasmid*, 13:31 (1985).
37. Sanger, F., Nicklen, S., and Coulson, A. R., *Proc. Natl. Acad. Sci., USA*, 74:5463 (1977).

38. Maxam, A. M., and Gilbert, W., *Methods Enzymol.*, 65:499 (1980).
39. Devereux, J., Haeberli, P., and Smithies, O., *Nucleic Acids Res.*, 12:387 (1984).
40. Staden, R., *Nucleic Acids Res.*, 10:4731 (1982) ; Staden, R., *Nucleic Acids Res.*, 12:521 (1984).
41. Construction of pRShMR. The 3.75-kb insert from lambda hk10 was ligated into the EcoRI site of pGEN4 (Promega) oriented with-the mp18 polylinker adjacent to the 5' end of hMR coding sequence. Digestion of this plasmid (phk10) with HindIII generated at HindIII fragment spanning the polylinker site to the hMR site at position 3562; this fragment was isolated and the ends were repaired with the Klenow fragment of DNA polymerase I. Plasmid pRSVCAT [C. M. Gorman, G. T. Merlino, M. C. Sillingham, I. Pastan, B. H. Howard, *Proc. Natl. Acad. Sci., USA,* 79:6777 (1982)] was digested with HindIII and HpaI, and the HindIII-HpaI fragment containing pBR322 sequences, the RSV LTR, and the SV40 polyadenylation site was also repaired. Ligation of the hMR fragment to the fragment from pRSVCAT yielded a vector which, in the correct orientation, has hMR coding sequence driven by the RSV promoter. Sites bracketed in FIG. IV-4A were lost in this cloning step. To improve translational efficiency several upstream initiation and termination codons in the 5'-untranslated region were deleted by digesting the vector with AccI to remove an ~200-bp sequence from the mp18 polylinker to position 188 in the hMR 5'-UT region. Finally, an NdeI-linkered SV40 origin of replication was introduced into the NdeI site (12) to generate pRShMR.
42. Deans, R. J., Denis, K. A., Taylor, A., and Wall, R., *Proc. Natl. Acad. Sci., USA,* 81:1292 (1984).
43. Wigler, M., et al., *Cell,* 16:777 (1979).
44. Gorman, C. M., Moffat, L. F., and Howard, B. H., *Mol. Cell. Biol.,* 2:1044 (1982).
45. Feinberg, A. P., and Vogelstein, B., *Anal. Biochem.,* 137:266 (1984).

EXPERIMENTAL SECTION V

Identification of a New Class of Steroid Hormone Receptors

V. A. Introduction

The gonads and adrenal glands produce a large variety of steroids classified into five major groups which include the estrogens, progestins, androgens, glucocorticoids and mineralocorticoids. Gonadal steroids control the differentiation and growth of the reproductive system, induce and maintain sexual characteristics and modulate reproductive behavior. Similarly, adrenal steroids influence differentiation in addition to their vital roles as metabolic regulators. Despite this wide range of physiological actions, the effects of each steroid rest primarily upon the specific cognate receptors which it binds, and therefore steroid hormone action might be more precisely classified according to the receptors that mediate their biologic action. The successful cloning, sequencing and expression of the human glucocorticoid receptor (hGR) cDNA (see Experimental Section I, which was published as ref. 1), soon followed by those encoding the estrogen[2,3] (hER), progesterone[4] (hPR), and mineralocorticoid (hMR receptors) (see Experimental Section IV, which was published as ref. 5), plus homologues from various species[6-11], provide the first opportunities to study receptor structure and the molecular mechanisms by which these molecules modulate gene expression. Sequence comparison and mutational analysis of these proteins reveal structural features common to all classes of steroid hormone receptors (see Experimental Section II which was published as ref. 12; also see refs. 13 and 14). In particular, the receptors share a highly conserved cysteine rich region, now referred to as the DNA-tau domain, that contains all the information required for both DNA-binding and trans-activation functions of the glucocorticoid receptor[15,16]. The presence of a common segment between receptors provides the possibility of scanning the genome for related gene products. For example, hMR cDNA was isolated by using the hGR as a hybridization probe (see Experimental Section IV, which has been published as ref. 5). One way that molecular biology can advance our understanding of health and human disease and the physiology that governs these events is through the identification of new hormone response systems. In this study, using the highly conserved DNA-tau region of the human estrogen receptor cDNA as a hybridization probe, we have isolated two cDNA clones encoding polypeptides that comprise the structural features of the steroid hormone receptors.

V. B. cDNA Clones for Receptor hERR1

One approach to search for unrecognized hormone response systems is to systematically employ reduced stringency hybridization to screen recombinant DNA libraries for novel hormone receptors. The DNA-tau segment of the estrogen receptor was used to initiate these studies. Analysis of a lambda gt10 human testis cDNA library identified 3 positives at a frequency of one clone per $3\times10^5$ recombinant phages. Nucleotide sequence analysis revealed that two of these clones actually encode the estrogen receptor while the third one, spanning 2.0 kilobases and named lambda hT16, showed only partial sequence homology. In turn, this clone was used to screen human fetal kidney and adult heart cDNA libraries; resulting in the identification of 3 additional clones. Both clones from the kidney library, lambda hKE4 and lambda KA1, represent the same gene product as lambda hT16 while the cardiac clone, lambda hH3, is only partially related. The composite sequence of the three cDNA's sharing identical sequences, herein referred to as hERR1, is shown in FIGS. V-1a, b1 and b2. Assuming a poly(A) tail of ~150-200 nucleotides[17], this sequence (~2430 nt) must be nearly full length. The cDNA insert from lambda hKA1 contains nucleotide 179 to 2430 while lambda hKE4 represent a rare messenger RNA splicing error with deletion of exon 2 and insertion of intron sequences. The exon/intron boundaries suggested by lambda hKE4 were confirmed by cloning and partially sequencing the genomic fragments encoding this gene (data not shown). The sequence surrounding the first ATG agrees with the consensus described by Kozak[18] for a translation initiation site. An open reading frame of 521 amino acids predicting a polypeptide of Mr 57300 is flanked by a 775 nucleotide 3'-untranslated region.

V. C. cDNA Clone for Receptor hERR2

The characterization of clone lambda hH3 reveals it to encode a unique polypeptide highly related to hERR1. FIGS. V-2B1 and B2 shows the 2153 nucleotide sequence of lambda hH3 and the primary structure of the protein product designated hERR2. The translation initiation site was assigned to the methionine codon corresponding to nucleotides 100-102 because this in the first ATG triplet that appears downstream from an in-frame terminator TGA (nucleotides 31-33). An open reading frame containing 433 amino acids encodes a polypeptide of Mr 47600 and is followed by a 3'-untranslated region of 752 nucleotides.

V. D. Characterization of hERR1 and hERR2

As mentioned earlier, steroid hormone receptors are composed of distinct functional domains that can be identified by sequence analysis[14]. The predicted hERR1 and hERR2 polypeptides contain the expected domain features of steroid receptors. Amino acid comparison between hERR1 and hERR2 shows that these two proteins have divergent amino termini and that no homology can be detected with other classes of receptor within this region (data now shown). This finding is in agreement with previous comparison studies (see Experimental Section IV; also see refs. 5,8,10,14) which showed this region to be hypervariable in sequence. Alignment of the carboxy-terminal region of hERR1, hERR2, hER and hGR (FIG. V-3) shows that the highest degree of homology between these proteins is found in a cysteine-rich region of 66 amino acids, corresponding to the DNA-tau domain (See Experimental Section II; also see ref. 15) of the steroid hormone receptors, located between amino acid 175 and 240 of hERR1. There is a 91% amino acid identity in the comparison of hERR1 with hERR2, 68% with hER and 56% with hGR. The positions of the 9 cysteine residues are strictly conserved but the absence of a histidine residue at position 206 of hERR1 and position 134 of hERR2 marks a major difference with the previously described steroid hormone receptors. It was originally thought that this histidine residue might be involved with the conserved cysteine residues in the formation of a DNA-binding finger. The recent demonstration that this histidine residue is also absent in the corresponding amino acid sequence of the vitamin D receptor[19], another member of the ligand-binding transactivation factor superfamily, suggests that $Zn^{2+}$ atoms interact exclusively with cysteine residues in order to coordinate the formation of the proposed DNA-binding fingers present in those proteins. The putative steroid binding domain, positioned between amino acid 295 and 521 of hERR1, shows 63% identity when compared to hERR2. 36% to hER and 28% to hGR.

V. E. Tissue Distribution of mRNA's for hERR1 and hERR2

Steroid receptors are expressed in characteristic tissue specific patterns that directly correlate to their primary physiologic effects. Perhaps, the distribution of these putative receptors would provide a clue to their hidden identity. Accordingly, total RNA isolated from a variety of rat and human tissues was fractionated on formaldehyde-agarose gel electrophoresis and transferred to nitrocellulose filters. Using lambda hKA1 as a probe, a 2.6 Kb mRNA encoding hERR1 was detected in all rat and human tissues analyzed, with surprisingly high levels in the cerebellum and hippocampus and the lowest levels seen in the liver, lungs, seminal vesicles and spleen (FIG. V-1A). Thus, it appears that the hERR1 gene is widely and abundantly expressed, although present in much higher levels in the rat central nervous system. In contrast to the hERR1 mRNA expression pattern, the distribution of the mRNA encoding the hERR2 protein is restricted to a few specific tissues where very low levels of mRNA can be detected (FIG. V-4B). Using a probe derived from the clone lambda hH3; a 4.8 Kb mRNA was detected in kidney, heart, testis, hypothalamus, hippocampus, cerebellum and rat prostate. However, no hybridization could be detected in the human placenta or prostate. Considering the difference in exposure time and the resulting signal intensity, levels of hERR2 mRNA are approximately 10 to 100-fold lower than that of hERR1.

V. F. Homology Between hERR1 and hERR2

Prior studies indicate that the degree of homology of the ligand binding domains between the steroid hormone receptors reflects the structural relatedness of their ligands. For example the hGR, hMR and hPR, which show 56% identity in their ligand binding domains (see Experimental Section IV), bind closely related hormones. Indeed the hMR binds glucocorticoids with an affinity equal to that of aldosterone, and also binds progesterone with relatively high affinity (see Experimental Section IV). In the case of the hERR gene products, amino acid sequence homology reveals a relatively more distinct relationship with hER, 70% in the DNA-tau region and 36% in the steroid binding region (FIG. V-5). These levels of homology are lower than those observed between hGR, hMR and hPR and thus predict that the putative hERR proteins interact with a class of steroid hormones distinct from the estrogens. However, the homology between hERR1 and hERR2 suggests that they are receptors for either a single or two closely related steroid metabolites. Preliminary steroid binding studies using the products of in vitro translation of capped SP6 RNA produced from hERR1 and hERR2 coding sequences or expression of the two cDNA's in COS-1 cells (see Experimental Sections IV and II) have failed to demonstrate binding of any major classes of steroids, including estrogens and androgens.

V. G. Conclusion

The tissue distribution of hERR1 and hERR2 mRNA's expression suggests that each putative receptor will control distinct biological functions. How might the functions of these steroid hormone receptors have been overlooked, Most likely many of their activities have erroneously been attributed to other receptors with differences being classified as atypical effect. The recent identification of neuronal steroids[20,21] provides evidence for new steroid hormones with possible paracrine actions within the brain. Such systems could have easily escaped previous physiological detection. Thus, the isolation two novel steroid hormone receptor cDNA's marks the first step toward identifying a new hormone response system.

V. H. Detailed Description of Figures Referred to in Experimental Section V

FIGS. V-1a, b-1 and b-2.

Restriction map (A) and DNA sequence and predicted amino-acid sequence (B) of hERR1. A, The composite cDNA for hERR1 is represented at the top, with noncoding (thin line) and coding (stippled portion) sequences indicated. Common 6-nucleotide restriction enzyme sites are drawn above the linear map. Overlapping cDNA inserts used to determine the sequence are shown. The wavy line near the 5' end of lambda hKE4 indicates divergent sequence. B, Nucleotide sequence of the composite hERR1 cDNA with the deduced amino acids given above the long open reading frame.

FIGS. V-1a, b-1 & b-2. Methods.

The clone lambda hT16 was isolated from a human testis lambda gt10 cDNA library (Clonetech) using a nick-translated[22] 446-bp BglI-BamHI fragment isolated from pER945, a linker-scanning mutant[12] derived from the hER cDNA (V. Giguere and R. M. Evans, unpublished data). The hybridization mixture contained 35% formamide, 1×Denhardt's, 5×SSPE, 0.1% sodium dodecyl sulfate (SDS), 100 micrograms ml$^{-1}$ denaturated salmon sperm DNA and $10^6$ c.p.m. ml$^{-1}$ of $^{32}$P-labeled BglI-BamHI fragment ($>10^8$ cpm/microgram). Duplicate nitrocellulose filters were hybridized at 42° C. for 16 h, washed three times for 20 min each in 2×SSC, 0.1% SDS (1×SSC=150 Mm Nacl, 15 Mm sodium citrate) at 55° C. and autoradiographed at −70° C. with an intensifying screen. The clones lambda hKE4 and lambda hKA1 were isolated from a human kidney lambda gt10 cDNA library[23] using the nick-translated insert from lambda hT16. For this screening, the hybridization mixture was modified to 50% formamide and washing conditions to 2×SSC with 0.1% SDS at 68° C. The cDNA clones were digested with a number of restriction enzymes and the resulting fragments were subcloned in both orientations into the M13 sequencing vectors mp18 and mp19 and sequenced by the dideoxy procedure[24], and any gap or ambiguities were resolved by the chemical cleavage method[25]. DNA sequences were compiled and analyzed by the programs of Devereux, et al.[26] and Staden[27].

FIGS. V-2a, b-1 and b-2.

Restriction map (A) and DNA sequence and predicted amino-acid sequence (B) of hERR2. A, Schematic representation of hERR2 cDNA; some common restriction enzyme sites are indicated. The stippled box represents the predicted open reading frame. B, The complete nucleotide sequence of lambda hH3 is shown with the predicted amino acid sequence given above the long open reading frame. A short open reading frame in the 5' untranslated region is shown in bold type.

FIGS. V-2a, b-1 and b-2 Methods.

The clone lambda hH3 was isolated from a human heart lambda gt11 cDNA library (gift from Dr. L. A. Leinwand; Albert Einstein Col. of Med.) using a nick-translated 700-bp EcoRI-SmaI fragment representing the 5' portion of lambda hKA1. Hybridization and washing conditions and sequencing strategies were as described in FIG. V-1a, b-1 and b-2 for the screening of the human kidney library.

FIG. V-3.

Amino acid sequence comparison between the carboxy-terminal regions of hERR1, hERR2, the human oestrogen and glucocorticoid receptors. The four amino acid sequences were aligned for maximum homology by introducing gaps as indicated by hyphens. Numbers were taken from FIG. V-1a, b-1 and b-2 and V-2a, b-1 and b-2 for hERR1 and hERR2, from FIGS. I-2-1 and 2-2 for hGR and Green, et al.[2] for hER. Amino acid residues matched in at least three of the polypeptides are boxed. The asterisk above residue 206 of hERR1 indicates the position of the histidine residue present in the hER sequence but absent in both hERR1 and hERR2 sequences.

FIGS. V-4a and b.

Northern blot hybridization analysis of hERR1 (A) and hERR2 (B) mRNA's in rat and human tissues.

FIGS. V-4a and b Methods.

Total RNA was isolated from various tissues using guanidine tiocyanate[28], separated on 1% agarose-formaldehyde gel, transferred to nitrocellulose, and hybridized under stringent conditions using a nick-translated EcoRI-SmaI fragment from lambda hKA1 (a) and a nick-translated 1192-bp EcoRI-HindIII fragment from lambda hH3 (b). Twenty micrograms of total RNA was used in all lanes. Migration of ribosoomal RNA's (28S and 18S) are indicated for size markers. The nitrocellulose filters were autoradiographed at −70° C. with an intensifying screen for 24 h (a) and 6 days (b). Apparent difference in migration rate of the mRNA in (a) is an artifact from the gel.

FIG. V-5.

Schematic amino acid comparisons between hERR1 and hERR2; hER; hGR and human thyroid hormone receptor (hT$_3$R beta). Amino acid sequences have been aligned schematically according to the functional domain structure of the steroid and thyroid hormone receptors superfamily[14]. The percentage of amino acid identity of each receptor with hERR1 is indicated inside each domain. The amino acid position of each domain boundary is shown for each receptor.

V. I. References Referred to in Experimental Section V

1. Hollenberg, S. M., et al., *Nature,* 318:635–641 (1985).
2. Green, S., et al., *Nature,* 320:134–139 (1986).
3. Greene, G. L., et al., *Science,* 231:1150–1154 (1986).
4. Misrachim, M., et al., *Biochem. Biophys. Res. Comm.* 143 740–748 (1987).
5. Arriza, J. L. t et al., *Science,* 237:268–275 (1987).
6. Miesfeld, R., et al., *Cell,* 46:389–399 (1986).
7. Danielsen, M., Northrop, J. P., and Ringold, G. M., *EMBO J.,* 5:2513–2522 (1986).
8. Krust, A., et al., *EMBO J.,* 5:891–897 (1986).
9. Maxwell, B. L., et al., *Mol. Endocrinol.,* 1:25–35 (1987).
10. Loosfelt, H., et al., *Proc. Natl. Acad. Sci. USA,* 83:9045–9049 (1986).
11. Weiler, I. J., Lew, D., and Shapiro, D. J., *J. Mol. Endocrinol.,* 1:355–362 (1987).
12. Giguere, V., Hollenberg, S. M., Rosenfeld, G. M., and Evans; R. M., *Cell, 46:645–652* (1986).
13. Kumar, V., Green, S., Staub, A., and Chambon, P., *EMBO J.,* 5:2231–2236 (1986).
14. Evans, R. M., *Science,* (in press).
15. Hollenberg, S. M., Giguere, V.,. Sequi, P., and Evans, R. M., *Cell,* 49:39–46 (1987).
16. Miesfeld, R., Godowski, P. J., Maler, B. A., and Yamamoto, K. R., *Science,* 236:423–427 (1987).
17. Sawiki, S. G., Jelinek, W., and Darnell, J. E., *J. Mol. Biol.,* 113:219–235 (1977).
18. Kozak, M., *Nature,* 308:241–246 (1984).
19. McDonnell, D. P., et al., *Science,* 235:1214–1217 (1987).
20. Le Goascogne, C., et al., *Science,* 237:1212–1215 (1987).
21. Hu, Z. Y., Bourreau, E., Robell P., and Baulieu, E. E., *Proc. Natl. Acad. Sci. USA,* (in press).
22. Rigby, P. W. J., Dieckmann, M., Rhodes, C., and Berg, P. J., *J. Mol. Biol.,* 113:237–251 (1977).
23. Bell, G. I., et al., *Nucleic Acid Res.,* 14:8427–8446 (1986).
24. Sanger, F., Nicklen, S., and Coulson, A. R., *Proc. Acad. Sci. USA,* 74:5463–5467 (1977).
25. Maxam, A., and Gilbert, W., *Proc. Natl. Acad. Sci. USA,* 74:560–564 (1977).

26. Devereux, J., Haeberli, P., and Smithies, O., *Nucleic Acid Res.*, 12:387-395 (1984).
27. Staden, R., *Nucleic Acid Res.*, 10:2951-2961 (1982).
28. Chirgwin, J. M., Przybyla, A. F., McDonald, R. J., and Rutter, W. F., *Biochemistry*, 18:5294-5299 (1980).

EXPERIMENTAL SECTION VI

A c-erb-A Binding Site in the Rat Growth Hormone Gene Mediates Transaction by Thyroud Hormone

VI. A. Introduction

The substance 1,3,3-triiodothyronine ($T_3$) stimulates growth hormone gene transcription in rat pituitary tumor cells[1-4]. This stimulation is thought to be mediated by the binding of nuclear $T_3$ receptors to regulatory elements 5' to the transcriptional start site[5-8]. Understanding of the mechanism by which thyroid hormone activates gene transcription has been limited by failure to purify nuclear $T_3$ receptors because of their low abundance, and by the absence of defined $T_3$ receptor-DNA binding sites affecting $T_3$ regulation. Recently, human and avian c-erb-A gene products have been shown to bind thyroid hormone with high affinity (see Experimental Section III, which has been published as ref. 10; also see ref 9) and to have a molecular weight and nuclear association characteristic of the thyroid hormone receptor. In the present study, we describe the development of an avidin-biotin complex DNA-binding assay which can detect specific, high-affinity binding of rat pituitary cell $T_3$ receptors to the sequence 5'CAGGGACGTGACCGCA3', located 164 base pairs 5' to the transcriptional start site of the rat growth hormone gene. An oligonucleotide containing this sequence transferred $T_3$ regulation ot the herpes simplex virus thymidine kinase promoter in transfected rat pituitary GC2 cells, and specifically bound an in vitro translation product of the human placental c-erb-A gene. The data provide supporting evidence that human c-erb-A gene mediates the transcriptional effects of $T_3$ and also that GC2 cell nuclear extracts contain additional factors that modify the binding of pituitary $T_3$ receptors to the rat growth hormone gene $T_3$ response element.

VI. B. Characterization of Rat Growth Hormone DNA Sequences Necessary for $T_3$ Regulation (a) RAT GH GENE DELETION ASSAYS To identify the cis-active element in the growth hormone (GH) 5' flanking genomic sequence necessary for $T_3$ regulation we used a series of 5'-deleted fragments of the rat GE gene, fused to the bacterial chloramphenicol acetyltransferase (CAT) gene and transfected into rat pituitary GC2 cells (FIG. VI-1a). A 5' deletion to −235 to the transcriptional start (CAP) site transferred regulation to $T_3$ (4.6-fold, FIG. VI-1a). equivalent to constructions containing 1.7 kilobases (kb) or 307 base-pairs (bp) of 5'-flanking rat GH information (data not whown), in agreement with previous studies[5,6]. (Nucleotide positions are numbered relative to the CAP site, negative position numbers being 5' to it.) Deletions containing less than 235 bp of 5'-flanking GH information could not be assayed for $T_3$ induction because the levels of CAT expression in the absence of $T_3$ were not significantly above background. To overcome this problem, a rat prolactin enhancer element[11] was fused proximal to fragments of the rat GH gene containing 181 and 110 bp of 5' flanking information. The 5'-deleted fragment extending to position −181 gave 2.6-fold induction by $T_3$ and further deletion to position −107 from the CAP site abolished $T_3$ regulation (FIG. VI-1a).

(b) CAT ENZYMATIC ASSAY

To assay 3' deletions, fragments of the rat Gh gene were fused to the herpes simplex virus thymidine kinase (HSV tk) promoter. A fragment of the Gh gene extending from position −235 to position −45 from the CAP site produced 2.5- and 2.3-fold stimulations of CAT activity when fused to the tk promoter in native and inverse orientation, respectively (FIG. VI-1b). A 90-bp fragment extending from positions 235 to 145 bp from the GH CAP site transferred $T_3$ regulation even more efficiently than the 235-45 bp fragment, and suggests that a negative $T_3$ regulatory element might be located between 45 and 145 bp from the CAP site (FIG. 1a). CAT messenger RNA was analyzed by a primer extension technique 12 to determine whether or not the $T_3$-dependent stimulation of CAT activity which was observed in cells that had been transfected with plasmids containing the tk promoter resulted from an increase in appropriately initiated transcripts. The 235-45 bp GH fragment fused to the tk promoter gave an increase of about 4-fold of correctly initiated CAT mRNA in the presence of $T_3$ (FIG. VI-1c), a result consistent with the observed CAT activity measurements.

(c) AVIDIN-BIOTIN COMPLEX DNA-BINDING ASSAY (ABCD ASSAY)

To define further the sequences needed for $T_3$ regulation, it was necessary to document specific binding of nuclear $T_3$ receptors to the growth hormone $T_3$ regulatory element. Because attempts to map the $T_3$ receptor binding site by gel shift and footprinting assays were initially unsuccessful, a new assay to detect specific binding was devised, the avidin-biotin complex DNA-binding (ABCD) assay. Double-stranded oligonucleotides were prepared containing the 5' flanking region of the GH gene necessary for $T_3$ regulation, with biotin-11-dUTP at various positions, as shown in FIG. VI-2a. Initially a 77-bp oligonucleotide (G209-146), containing the genomic growth hormone sequence from positions −209 to −146, was used. $T_3$ receptors from GC2 nuclear extracts were labeled to high specific activity with $^{125}I$-$T_3$ and incubated with this biotinylated oligonucleotide. Protein-DNA complexes were precipitated from solution after the binding reaction, using streptavidin conjugated to agarose beads. It can be seen in FIG. VI-2b that probe G209-146 resulted in the precipitation of 6,900 c.p.m. of $^{125}I$-$T_3$ activity. This represents the binding of about 3.2 fmol of $T_3$ receptor and accounts for ~40% of the total $T_3$ receptor present in the binding reaction. Precipitation of $^{125}I$-$T_3$-labeled receptors was probe-dependent; <15% of total precipitated $^{125}I$-$T_3$ radioactivity was recovered in the absence of G209-146. Addition of a 100-fold molar excess of unlabeled $T_3$ reduced the precipitated $^{125}I$-$T_3$ to background levels (FIG. VI-2b), indicating that the $T_3$ binding protein that was being precipitated by the probe was present in limited amounts. The equilibrium binding constant for the $T_3$ receptor-DNA complex was estimated to be $1.4 \times 10^{-9}M$ (data now shown).

To investigate whether the precipitation of labeled $T_3$ receptors by G209-146 was dependent on specific rat GH sequences, a series of biotinylated probes were prepared that had no apparent sequence similarity to the growth hormone enhancer but which were the same length as G209-146 and contained the same number of biotin-11-dUTP residues. As shown in FIG. VI-2b, the addition of 100 fmol of each probe to GC2 nuclear extracts gave no measurable precipitation of $^{125}$I-T$_3$. This indicates that the precipitation of $^{125}$I-T$_3$ by G209-146 is dependent on the rat GH sequence contained in the probe.

(d) FOOTPRINTING ANALYSIS

Although early attempts to localize a T$_3$ receptor binding site using conventional footprinting techniques were unsuccessful, variation of buffering conditions in the ABCD binding assay suggested that a footprint might be achieved with crude nuclear extracts if salt and pH conditions for DNA binding were optimal (data not shown). End-labeled fragments of the GH enhancer were incubated with GC2 nuclear extracts and digested with DNase I. PAGE analysis of the digest under denaturing conditions (FIG. VI-3) gave two footprints, described previously[13,14]; one of these is shown, together with a 16-bp protected region in the antisense strand between nucleotides −179 and −164. This sequence, which in the sense strand corresponds to 5' CAGG-GACGTGACCGCA 3', is contained in the oligonucleotide probe shown to specifically bind T$_3$ receptors, and corresponds in position to a previously identified T$_3$-dependent DNase-I-hypersensitive site[19]. A clear footprint could not be detected in the sense strand itself, mainly because of incomplete digestion by DNase I in this G-rich region.

VI. C. Functionality of T$_3$ Oligonucleotide

To examine the function of this sequence in T$_3$ regulation of the GE gene, site-directed mutagenesis was used to delete 11 bp of the footprint from the wild-type enhancer (mutant G delta 166/177). Addition of T$_3$ to cells transfected with mutant G delta 166/177 fused to the tk promoter had no effect on the amount of CAT expression, although the wild-type enhancer stimulated CAT expression ninefold (FIG. VI-1b). Thus, removal of the putative T$_3$ receptor binding region, identified by oligonucleotide and DNAse I binding assays, abolished the ability of the GH enhancer to confer T$_3$ regulation to the tk promoter.

To demonstrate that the 16 base pairs from positions −164 to −179 constituted a functional T$_3$ regulatory element; a double-stranded oligonucleotide was prepared containing this sequence with seven and six bases flanking the 5' and 3' ends respectively. This oligonucleotide was inserted in its native orientation proximal to the tk promoter (construction G29TK, FIG. VI-1b). CAT expression was stimulated 2.9-fold by T$_3$ in cells transfected with this construction. Insertion of three tandem repeats of this sequence (construction G293TK) resulted in a five-fold stimulation by T$_3$.

The short oligonucleotide used for transfer of T$_3$ regulation to the tk promoter (G186-158) also specifically bound nuclear T$_3$ receptor binding site in G209-146, but this was discounted using an oligonucleotide containing the rat GE sequence from nucleotide positions −177 to −235 that failed to bind measurable amounts of T 3 receptors (data not shown). Non-biotinylated G209-146 and G186-158 were also used to compete for the binding of T$_3$ receptors with biotinylated G209-146; the relative affinity of T$_3$ receptors for G209-146 was two- to three-fold higher than G186-158 (data not shown). The apparent decrease in affinity for the shorter probe could result from a lack of bases to participate directly in the T$_3$ receptor binding reaction. This is unlikely, because the limits of the DNase I footprint lie within the ends of this probe. Alternatively, GC2 nuclear extracts could contain other factors that stabilize the binding of T$_3$ receptors to the longer probe.

VI. D. Summary and Conclusions

These experiments demonstrated that 29 base pairs of the GH gene, containing a 16-bp footprint extending from position −164 to position −179 5' to the CAP site, bound the T$_3$ receptor, were necessary for T$_3$ regulation of the rat GH enhancer, and could transfer T$_3$ regulation to the tk promoter. To test whether human c-erb-A also binds to this element, an in vivo translation product was labeled with $^{35}$S-methionine (see Experimental Section III). The product migrated as a doublet of relative molecular mass (M$_r$) 48,000 (48K) and 52K on SDS gel electrophoresis and bound T$_3$ with a k$_d$ of $5 \times 10^{+11}$ (data not shown). The binding of the human c-erb-A in vitro translation product to the G209-146 and G186-158 oligonucleotide probes containing the rat GH T$_3$ regulatory element is shown in FIG. VI-4. Both the long and short probes bound the in vitro translation product significantly, but probes lacking homology to the T$_3$ receptor binding site of The GH gene, such as P-EGF, did not. Based on the estimated specific activity of [$^{35}$S]methionine present in the in vitro translation mixture, the binding activity shown in FIG. VI-4 corresponds to 1-2 fmol of erb-A protein. Unlike GC2-cell nuclear extracts containing $^{125}$I-T$_3$ receptors, the c-erb-A in vitro translation product was bound to the same extent by the long and short oligonucleotides. Similar data were obtained using an in vitro translation product of human c-erb-A labeled with $^{125}$I-T$_3$ (data not shown). These results indicate that the c-erb-A gene product specifically binds to the identical T$_3$ regulatory sequence that is bound by T$_3$ receptors from GC2 nuclear extracts. They provide further evidence that the function of the c-erb-A gene product is to mediate the transcriptional effects of T$_3$.

Flug, et al. (1987) recently reported that the GH sequence between nucleotide positions −210 and −181 was essential for the full stimulatory effect of T$_3$ in transiently transfected GC cells, and also pointed out that this region possessed limited similarity to other T$_3$-regulated genes. Our experiments locate the T$_3$ receptor-DNA binding site between 164 and 177 bp from the CAP site; and also confirm the functional importance of the sequence between positions −210 and −181 in T$_3$ regulation of the GH gene. This could reflect an increased affinity of the T$_3$ receptor for fragments of the GH enhancer which contain this upstream element in vivo, as we observed in the in vitro DNA binding studies using crude nuclear extracts as a source of T$_3$ receptor. That the erb A in vitro translation product binds comparably to G209-146 and G186-158 is consistent with the possibility that crude GC2 nuclear extracts contain an additional factor(s) that binds to the sequence between positions −210 and −181 and stabilizes the binding of the T$_3$ receptor to its cognate binding site. Cooperative interactions between eukaryotic transcription factors is well-established[16-18]; in some cases this reflects the ability of one factor to alter the DNA-binding affinity of another. Such interactions could be important in the tissue-specific regulation of thyroid hormone action[5,6]. The ABCD binding assay used here should be useful in addressing these questions, and it is also potentially applicable to any DNA-binding protein that can be selectively radiolabeled, either with a labeled ligand, by chemical modification or by in vitro translation with labeled amino acids.

VI. E. Detailed Description of Figures Referred to in Experimental Section VI FIG. VI-1a, b and c.

Thyroid hormone responsiveness of various gene fusions containing rat GH 5'-flanking sequences. a, Responsiveness of 5' and 3' deletions of the rat GH gene. 5'-deleted fragments of the rat GH gene were fused to the CAT gene in a pSV2CAT-based vector[18], in which the SV40 origin of replication and promoter were removed. These constructions were transfected into GC2 cells and assayed for responsiveness to $T_3$. Because of low levels of basal expression of the nucleotide position $-107$ to $+8$ and $-181$ to $+8$ fragments, the rat prolactin enhancer (Prl)[11], which is not regulated by $T_3$, was placed proximal to these elements. The illustrated 3'-deleted fragments were fused to a tk promoter fragment, extending from position $-197$ to position $+54$ and placed proximal to the CAT gene in the same vector. b, Functional analysis of the putative $T_3$ receptor binding site. Mutant G delta 177/166 contains a deletion of 11 bases of the $T_3$ receptor binding site from 177-166 base pairs from the CAP site. Plasmids G29TK and G293TK contain the 28-bp region of the rat GE gene that binds the $T_3$ receptor in one and three copies, respectively. The effect of $T_3$ was determined by dividing the percentage conversion of chloramphenicol in the presence of $10^{-9}M$ $T_3$ by the percentage conversion in the absence of $T_3$. Triplicate plates were maintained in 10% fetal calf serum stripped of $T_3$ by ion exchange chromatography for two days before transfection with test plasmids using DEAE-dextran[11]. The cells were treated with hormone 24 h after transfection and assayed for CAT activity after 24 h of $T_3$ exposure. Error limits represent the standard error of the mean. Each construction was assayed two to five times. $A_n$ represents SV40 polyadenylation sites. c, Messenger RNA transcription initiation site analysis. The diagram indicates the 33-nucleotide primer complimentary to nucleotides 67 to 89 of the CAT coding sequence used to determine the CAP site of transcripts of plasmids containing the tk promoter. GC cells were transfected with test plasmids and hormone treated as described for the experiments presented in panels a and b. Primer extension analysis was performed on 50 micrograms total RNA. Lanes A and B represent the extension product from cells transfected with a plasmid containing the GH fragment extending from positions 235 to 45 from the CAP site fused to the tk promoter. Lanes C and D represent the extension product from cells transfected with a plasmid containing the tk promoter alone. No extension products were observed. The products shown in lanes A and C were from cells incubated in the absence of $T_3$ and those in lanes B and D were from cells treated with $T_3$ at a concentration of $10^{-9}M$. Lane E shows a HindIII digest of pBR322, used for size calibration (in nucleotides).

FIGS. VI-1a, b and c Methods.

Construction of CAT expression vectors containing 5'-flanking sequences of the rat GH gene from $-1.7$ kb to $+8$ bp of the CAP site has been described[11]. Fusions containing the rat prolactin enhancer were made by excising this fragment (corresponding to rat prolactin sequence nucleotide positions 1831-1530) from plasmid pPSS[11] and inserting it in reverse orientation proximal to the 5' deletions of the growth hormone element. Fusions containing the HSV tk promoter were made by excising fragments of the GH enhancer from the plasmid GPO (ref. 11) and inserting them into the BamHI and SalI sites of a pSV2CAT-based expression vectors proximal to the tk promoter at positions $-197$ to $+54$. Alternatively, the GH enhancer was placed proximal to the promoter at positions $-107$ to $+54$ in a pUC8-based vector[20] by insertion into the BamHI and SalI polylinker sites. Site-directed mutagenesis of the GH enhancer element was performed by inserting the fragment from 235-45 bp from the CAP site into the BamHI and SalI sites of M13 mp18. A 21-base oligonucleotide was synthesized which corresponded to antisense GH nucleotides $-188$ to $-157$, in which nucleotides $-177$ to $-166$ were deleted and replaced by an A nucleotide. This oligonucleotide was used to delete bases $-177$ to $-166$ in the GH enhancer using the procedure of Kunkel[21]. CAT activity was determined by radioassay of methylated chloramphenicol derivatives after thin layer chromatography[19]. Primer extension was by the method of Elsholtz, et al.[12]

FIGS. VI-2a and b.

Binding of $T_3$ receptors to oligonucleotide probes containing biotin-11-dUTP. a, Schematic representation of two oligonucleotide probes used to assay $T_3$ receptor binding to GH 5'-flanking sequences. Heavy lines, synthesized oligonucleotides with complementary 3' ends. Fine lines, bases incorporated by filling the 5' overhangs using the large fragment of Escherichia coli DNA polymerase. Asterisks, biotin-11-dUTP residues. Restriction sites for BamHI and BglII are also shown. G209-146 and G186-158 contain rat GH enhancer sequences with the illustrated 5' and 3' boundaries. b, Precipitation of $^{125}I$-$T_3$ labeled $T_3$ receptors from GC2 nuclear extracts by various oligonucleotide probes containing biotin-11-dUTP. P-EGF, PB1-B, PB2-B, and PB4-B are oligonucleotides of 68, 53, 55 and 58 base pairs containing 10, 11, 10 and 10 biotin-11-dUTP's respectively. These oligonucleotides contain 5'-flanking sequences of the rat prolactin gene that lack apparent homology to the rat GH sequence contained in G209-186. Precipitations were performed using 100 femtomole of each probe. Background, representing $^{125}I$ activity associated with streptavidin agarose beads in the absence of a biotinylated olignoucleotide probe, was 1,400 c.p.m. in this experiment. Results are plotted as the mean and standard error of triplicate points. The experiment is representative of six experiments examining the sequence specificity of $^{125}I$-$T_3$ binding.

FIGS. VI-2a and b Methods.

Isolated nuclei were prepared from rat GC2 cells according to the technique of Dingham, et al.[22] and salt extracted in 0.6M KCl, 10 Mm Hepes, pH 7.9, 0.5 mM dithiothreitol (DTT), 0.2 mM EGTA, 20 microM $ZnCl_2$ for 30 min on ice. The nuclear extract was desalted by gel filtration in buffer A (50 mM KCl, 20 mM $K_3PO_1$, (pH 74.) 1 mM $MgCl_2$, 1 mM beta-mercaptoetaol and 20% glycerol) and stored at $-70°$ C. Assay of specific binding of $T_3$ to GC2 nuclear receptors was performed as described by Samuels, et al.[23] except that $T_3$ binding reactions were performed in buffer A in the presence of 200 micrograms ml$^{-1}$ poly(dI-dC). To assay DNA binding nuclear extracts were first incubated with 1 microM $^{125}I$-$T_3$(2,200 Ci mmol$^{-1}$) for 20 min at 22° C. to label the $T_3$ receptors to high specific activity. Aliquots (40 microliters) of nuclear extract were then incubated with biotinylated probes in the presence of 200 microliters poly(dI-dC) for 40 min at 22° C. Protein-DNA complexes were precipitated by addition of streptavidin conjugated to agarose beads (BRL). The agarose beads were pelleted, washed three times with buffer A (1 ml) and assayed for $^{125}$I activity.

FIG. VI-3.

DNase I footprinting of the rat GH enhancer element by GC2 nuclear extracts. A 16-bp protected region in the antisense strand is shown. A second footprint extending from position −110 to position −40 from the CAP site is also evident. Lanes A-C, Digestion of labeled GH enhancer after incubation with GC2 nuclear extract, using 24, 12 and 4 microgram DNase I respectively. Lanes D-F, Digestion of labeled GH enhancer with 24, 12 and 4 microgram of DNase I in the absence of GC2 nuclear extract. Lane G and M, Markers. The displayed sequence corresponds to that of the sense strand within the footprinted region.

FIG. VI-3 Method.

The antisense strand of the growth hormone enhancer was labeled with $^{32}$P-dATP at its 5′ end using T4 polynucleotide kinase after BamHI digestion of pGPO and treatment with calf intestinal phosphatase. The enhancer fragment was released from pGPO by XhoI digestion and purified by agarose gel electrophoresis. Labeled GH enhancer fragment (1 ng, 8 fmol) was incubated with 25 microliters of GC2 nuclear extracts containing 12 fmol of specific T$_3$ receptor-binding activity. The DNA binding reaction was carried out for 30 min at 22° C. in Buffer A. DNase digestion was for 2 min at 22° C. using the above concentrations of DNase I in a final volume of 50 microliters. The reactions were stopped with 20 microliters 50 mM EDTA and 1% SDS. Samples were extracted once with phenol-chloroform, ethanol precipitated, and analyzed by electrophoresis on standard 10% sequencing gels.

FIG. VI-4.

Binding to oligonucleotides containing 64 and 29 base pairs of 5′ flanking GH sequence of rat pituitary cell T$_3$ and incubated with 100 fmol G209-146, G186-158 or P-EGF and assayed for binding as described in FIG. VI-2. Also, hc-erb-A in vitro translation product (4 microliters) labeled with $^{35}$S-methionine was assayed for binding to these oligonucleotides in the presence of 10 nM T$_3$. To prepare the hc-erb-A in vitro translation product, capped mRNA transcripts of an hc-erb-A complementary DNA were used to program translation in a rabbit reticulocyte lysate system[10]. Reticulocyte lysates programmed with antisense hc-erb-A mRNA had no measurable binding activity to either of the GH probes (data not shown). Results are plotted as mean and standard error of triplicate points. The experiments shown is representative of three experiments comparing the binding of GC2 nuclear T$_3$ receptors to the two GH probes and of four experiments examining the binding of the hc-erb-A in vitro translation product.

VI. F. References Referred to in Experimental Section VI

1. Evans, R. M., Birnberg, N. C., and Rosenfeld, M. G., *Proc. Natl. Acad. Sci. USA*, 79:7659-7663 (1982).
2. Diamond, D. J., and Goodman, H. M., *Molec. Biol.*, 181:41-62 (1985).
3. Spindler, S. R., Mellon, S. H., and Baxter, J. D., *J. Biol. Chem.*, 257:11627-11632 (1982).
4. Yaffee, B. M., and Samuels, H. H., *J. Biol. Chem.*, 259:6284-6291 (1984).
5. Larsen, P. R., Harney, J. W., and Moore, D. D., *J. Biol. Chem.*, 261:14373-14376 (1986).
6. Flug, F., et al., *J. Biol. Chem.*, 262: 6373-6382 (1987).
7. Casanova, J., Copp, R. P., Janocko, L., and Samuels, H. H., *J. Biol. Chem.*, 260:11744-11748 (1985).
8. Crew, M., and Spindler, S. R., *J. Biol. Chem.*, 261: 5018-5022 (1986).
9. Sap, J., et al., *Nature*, 324:635-640 (1986).
10. Weinberger, C., et al., *Nature*, 324:641-646 (1986).
11. Nelson, C., et al., *Nature*, 322:557-562 (1986).
12. Elsholtz, H. P., et al., *Science*, 234:1552-1557 (1986).
13. West, B. L., et al., *Molec. Cell. Biol.*, 7:1193-1197 (1987).
14. Catanzaro, D. F., West, B. L., Baxter, J. D., and Reudelhuber, T. L., *Molec. Endo.*, 1:90-96 (1987).
15. Nyborg, J. K., and Spindler, S. R., *J. Biol. Chem.*, 261:5685-5688 (1986).
16. Topol, J., Ruden, D. M., and Parker, C. S., *Cell*, 42:527-537 (1985).
17. Reenberg, D., Horikoshi, M., and Roeder, R. J., *J. Biol. Chem.*, 262:3322-3330 (1987).
18. McKnight, S., and Tjian, R., *Cell*, 46:795-805 (1986).
19. Gorman, C. M., Moffat, L. F., and Howard, B. H., *Molec. Cell. Biol.*, 2:1044-1051 (1982).
20. Linney, E., and Donerly, S., *Cell*, 35:693-699 (1983).
21. Kunkel, T., *Proc. Natl. Acad. Sci. USA*, 82:488-492 (1985).
22. Dingham, J. D., Lebovitz, R. M., and Roeder, R. G., *Nucleic Acids. Res.*, 11:1475-1489 (1983).
23. Samuels, H. H., Tsai, J. S., Casanova, J., and Stanley, F., *J. Clin. Invest.*, 54:853-865 (1974).

EXPERIMENTAL SECTION VII

Identification of a Novel Thyroid Hormone Receptor Expressed in the Mammalian Central Nervous System

VII. A. Summary

A complementary DNA clone derived from rat brain messenger RNA has been isolated on the basis of homology to the human thyroid hormone receptor gene. Expression of this complementary DNA produces a high-affinity binding protein for thyroid hormones. Sequence analysis and the mapping of this gene to a distinct human genetic locus indicate the existence of multiple human thyroid hormone receptors. Messenger RNA from this gene is expressed in a tissue-specific fashion with highest levels in the central nervous system.

VII. B. Introduction

Thyroid hormones are involved in a complex array of developmental and physiological responses in many tissues of higher vertebrates (1). Their numerous and diverse effects include the regulation of important metabolic enzymes, hormones, and receptors (2). The actions of thyroid hormones are mediated through a nuclear receptor, which modulates the expression of specific genes in target cells (3-5). These properties are similar to the interactions of steroid hormones with their receptors and are consistent with the recent observation of structural relatedness between steroid and thyroid hormone receptors (see Experimental Section III).

VII. C. Isolation of a Second Thyroid Receptor DNA

Despite the diversity of thyroid hormone action, it is generally accepted that thyroid hormone function occurs through a single high-affinity nuclear receptor. However, the recent characterization of the thyroid hormone receptor as the cellular homolog of the v-erb-A oncogene product (see Experimental Section III and ref. 7), along with the previous identification of multiple c-erb-A genes on human chromosomes 3 and 17 (see Experimental Section III and ref. 8), suggests the existence of multiple thyroid hormone receptors. To examine the possibility that the mechanisms underlying the multiple thyroid hormone responses may be derived from the expression of structurally distinct thyroid hormone receptors, we have isolated a complementary DNA (cDNA) clone that encodes the product of one of these related loci.

A putative neuronal form of the thyroid hormone receptor was isolated by screening a cDNA library prepared from rat brain messenger RNA (mRNA) with a 1500-bp fragment of the human thyroid hormone receptor cDNA. (See Experimental Section III which has been published as ref. 6.) From ~10$^6$ phage, three positive clones were isolated, and the complete nucleotide sequence of the largest of these, rbeA12, was determined (FIG. VII-1a and b). The sequence is 2079 bp long and contains a long open reading frame of 1230 bp with a potential initiator methionine at nucleotide position 325 and a terminator codon at position 1554. This open reading frame is preceded by a 5' untranslated region of at least 320 bp that contains three short open reading frames upstream of the putative initiator methionine and encodes a protein of 410 amino acid residues, with a calculated molecular mass of 45 kD.

VII. D. Comparison of the Second Thyroid Receptor with Other Known Thyroid Receptor Proteins Comparison of the deduced amino acid sequence from rbeA12 with that of the human thyroid hormone receptor (see Experimental Section III) reveals that the two proteins have distinct amino termini (FIG. VII-2). The first 41 amino acids of the neuronal protein and the first 90 amino acids of the human thyroid hormone receptor show no significant homology, whereas the carboxyl terminal 367 amino acids share 75% nucleotide and 82% amino acid identities. The rat protein is more related to the chicken thyroid hormone receptor (7) both in predicted size and homology, and shares 82% nucleotide and 89% amino acid identity. For reference, the chicken thyroid hormone receptor is designated alpha (cTR alpha) because of its homology to previously isolated erb-A genes (8), and the human thyroid hormone receptor is designated beta (hTR beta). Because the rat neuronal form is more related to the chicken receptor, it has been designated alpha (rTR alpha).

By analogy to the steroid hormone receptors, a cysteine-rich region in the thyroid hormone receptor is predicted to be the DNA-binding domain (see Experimental Sections III and II; also see ref. 10). In this region, the rTR alpha protein has 97% amino acid identity with the cTR alpha protein and 90% amino acid identity with the hTR beta protein. The proteins are also well conserved in the carboxyl terminal portion that is presumed to be the hormone-binding domain, again by analogy with the steroid receptors (see Experimental Section II; also see ref. 11). This region of rTR alpha shows 94% amino acid identity with cTR alpha and 854 amino acid identity with hTR beta.

VII. E. Identification of the New Thyroid Receptor

On the basis of the sequence data, it appears that the cDNA we have isolated encodes a protein different from the previously characterized human thyroid hormone receptor (see Experimental Section III). To demonstrate that the neuronal clone is a distinct gene products rbeA12 was used to identify human homologs by Southern blot and chromosome analyses. Human placenta DNA digested with various restriction enzymes was separated on an agarose gel, transferred to nitrocellulose; and hybridized with either rat or human TR-specific probes derived from overlapping regions of their respective genes (FIG. VII-3a, b and c). Different hybridization patterns were revealed for all of the restriction enzymes tested, which indicates that the two cDNA's represent distinct genes. The same probe from the rbeA12 was hybridized to laser-sorted chromosomes prepared from human lymphoid cells (FIG. VII-3C). Hybridization was observed only to chromosome 17, consistent with previous mapping studies that localized c-erb-A genes to human chromosome 17 (8). This distinguishes rTR alpha from hTR beta, which is found on human chromosome 3 (see Experimental Section III).

VII. F. Expression Studies

Expression studies were performed to determine whether the rTR alpha cDNA encodes a functional receptor protein. The product of the rTR alpha gene was first characterized by in vitro transcription followed by in vitro translation. For in vitro transcription, the EcoRI insert of rbeA12 was linked to the bacteriophage SP6 promoter by subcloning into the expression vector pGEM1. A second construction, rbeA12B, was created in an attempt to increase the efficiency of translation. The 5' untranslated region up to nucleotide position 97 was deleted, which removed two of the three short open reading frames in this region. Transcripts synthesized with SP6 polymerase were translated in vitro with rabbit reticulocyte lysates, and the [$^{35}$S]methionine-labeled products were analyzed on an SDS-polyacrylamide gel (FIG. VII-4A). Four proteins of approximately 52, 48, 35, and 33 kD were observed only when the sense strand was translated. The same four bands were observed for rbeA12 and rbeA12B. These translation products were then used to test thyroid hormone binding.

VII. G. Hormone Binding Studies

Thyroid hormone binding was measured with [$^{125}$I]3,5,3'-triiodo-L-thyronine ($^{125}$I-T$_3$). Only samples that contained the rTR alpha specific proteins exhibited T$_3$ binding. Hormone affinity was determined by Scatchard analysis, which gave a dissociation constant (K$_d$) of $2.9 \times 10^{-11}$M (FIG. VII-4B), similar to the K$_d$ observed for the hTR beta protein ($5 \times 10^{-11}$M) (4, 5) and an order of magnitude lower than that determined for the cTR alpha protein ($2.1 \times 10^{-10}$ to $3.3 \times 10^{-10}$M) (see Experimental Section III). The different K$_d$ values obtained may be due to differences in the assay systems used. In competition experiments, the rTR alpha proteins translated in vitro showed the same characteristic affinities for L-T$_3$ and L-thyroxine (L-T$_4$) as the hTR beta protein but revealed a different pattern for 3,5',3'-triiodothyroacetic acid (TRIAC) (FIG. VII-4C). TRIAC competed better for T$_3$ binding with the hTR beta protein, whereas it competed about as well at T$_3$ for binding to the rTR alpha protein. As with the hTR beta and cTR alpha proteins, there was no competition for T$_3$ binding to the rTR alpha protein by excess aldosterone, estrogen, progesterone, testosterone, or vitamin $D_1$. Thus, it appears that we have isolated a thyroid hormone receptor with binding properties similar to but not identical to those of the thyroid hormone receptors previously described (see Experimental Section III and ref. 7).

VII. H. Tissue Specificity Studies

The tissue specificity of metabolic responses to thyroid hormone led us to consider that this thyroid hormone receptor might be expressed in a restricted set of tissues. Therefore, the pattern of expression of the rTR alpha gene was determined by Northern blot analysis (FIG. VII-5). Total RNA isolated from various rat tissues was separated on a formaldehyde-agarose gel, transferred to nitrocellulose, and hybridized to the same fragment of rbeA12 used for the Southern blot analysis and chromosome mapping. A 2.6-kb RNA was observed in all tissues tested except liver. This message is also present in pituitary and muscle and is expressed in GC, rat-1, and PC12 cell lines. Densitometric scanning indicated that the level of expression of rTR alpha was 10- to 20-fold as high in brain as in any other tissue tested. Two additional RNA's of approximately 5.0 and 6.0 kb are present in about equal amounts in all tissues, although they are much less abundant than the 2.6-kb message. These bands may represent precursors of the 2.6-kb message or may be products of a related gene.

VII. I. Discussion and Conclusions

The isolation of a second mammalian thyroid hormone receptor is surprising because previous biochemical studies have not predicted the existence of more than a single receptor for thyroid hormones. In retrospect, much of the clinical and physiological studies can be interpreted as indicating the existence of multiple receptors. A form of functional heterogeneity has been suggested by the identification of patients with familial thyroid hormone resistance in which peripheral response to thyroid hormones is lost or diminished, while neuronal functions are maintained (12, 13). Furthermore, severe developmental effects associated with low circulating thyroid hormone levels (cretinism) have been classified into types severely affecting the nervous system and those more dramatically affecting peripheral functions (13, 14).

In addition to demonstrating the existence of structurally distinct forms of the thyroid hormone receptor, the form that we have characterized is expressed at high levels in the rat central nervous system. Preliminary studies utilizing in situ hybridization have revealed high levels of expression in the hippocampus, hypothalamus, cortex, and amygdala. RNA hybridization studies indicate exceptionally high levels in the cerebellum as well. Although it is known that thyroid hormones play a critical role in early brain development (14), this high level of expression is unexpected because biochemical studies have shown that brain has fewer thyroid hormone receptors than many other tissues (5, 16), and the adult brain is not responsive to thyroid hormone by traditional phosphate dehydrogenase activity (17).

The second interesting result from the expression studies is that this transcript is not present in liver, which is the tissue from which thyroid hormone receptors usually have been isolated. This absence suggests the existence of yet another form of the thyroid hormone receptor. This proposal would be consistent with the data of Underwood, et al. (18), which indicates the existence of pharmacologically distinguishable thyroid hormone responses between liver and heart. Furthermore, data from DNA hybridization studies indicate the existence of multiple genetic loci that hybridize with the cDNA clones for the mammalian thyroid hormone receptor and suggest that there may be as many as five different related loci (see Experimental Section III and ref. 8). It seems likely that some of these loci will encode additional functional molecules, which leads us to propose the existence of a family of thyroid hormone receptors that coordinately regulate overlapping networks of genes to control developmental and homeostatic function.

VII. J. Detailed Description of Figures Referred to in Experimental Section VII FIGS. VII-1a and b.

Restriction map and nucleotide and predicted amino acid sequence of thyroid hormone receptor cDNA from rat brain. (A) Schematic representation of thyroid hormone receptor cDNA from rat brain; some common restriction endonuclease cleavage sites are indicated. The hatched box indicates the predicted coding region. The 500-bp PvuII fragment (corresponding to nucleotide positions 607 to 1113) used for the hybridization studies is represented by the solid bar below the restriction map. (B) The complete nucleotide sequence of rbeA12 is shown with the predicted amino acid sequence given above the long open reading frame. The three short open reading frames in the 5' untranslated region are shown in bold type with termination codons underlined. Clone rbeA12 was isolated by using the entire EcoRI insert of pheA4 (sigma) as a nick-translated probe to screen $\sim 10^6$ phage from a rat brain cDNA library obtained from J. Arriza (19). Three positive clones were isolated, and the complete nucleotide sequence of the largest of these, rbeA12, was determined on both strands by the chemical cleavage method of Maxam and Gilbert (20).

FIG. VII-2.

Schematic comparison of the rat thyroid hormone receptor (rTR alpha) protein with the human thyroid hormone receptor (hTR beta) and chicken thyroid hormone receptor (cTR alpha) proteins. Numbers above the boxes indicate amino acid residues; numbers inside the boxes indicate the percent amino acid identity within the enclosed region with the rTR alpha protein. DNA designates the putative DNA-binding domain predicted by analogy with the human glucocorticoid receptor (amino acids 421 to 486 of the human glucocorticoid receptor), while $T_3/T_4$ designates the putative hormone-binding domain.

FIGS. VII-3a, b and c.

Southern blot analysis and human chromosomal localization of the rTR alpha gene. Human placenta DNA was digested with various restriction enzymes, separated on a 0.8% agarose gel, transferred to nitrocellulose, and hybridized to either a 500-bp PvuII fragment from rbeA12 (A) or a 450-bp SstI fragment from hTR beta (see Experimental Section III) that encompasses the DNA-binding region (B). Both blots were hybridized in 50% formamide, 5×SSPE (0.15M NaCl, 0.01M $NaH_2PO_4$, 0.001M EDTA), 1×Denhardt's solution, 0.1% SDS, and salmon sperm DNA (100 micrograms/ml) at 42° C., and washed in 2×SSC (standard saline citrate) and 0.1% SDS at 68° C. Sizes of lambda HindIII markers in kilobase pairs are indicated (C). Chromosome mapping of the rTR alpha gene. Human lymphocyte chromosomes were separated by laser cytofluorometry (21) and hybridized under the same conditions as above with the 500-bp PvuII fragment of rbeA12.

FIG. VII-4a, b and c.

In vitro translation and thyroid hormone binding of rTR alpha (A) rTR alpha was transcribed in vitro and translated in a rabbit reticulocyte lysate. The [$^{35}$S]methionine-labeled products were separated on a 7.5% SDS-polyacrylamide gel and visualized by fluorography. Lane 1, no added RNA; lane 2, rbeA12, which contains the entire 5' untranslated region; lane 3, rbeA12B, which contains only 97 bp of 5' untranslated sequence. Sizes of protein markers: bovine serum albumin, 66.2 kD; ovalbumin, 45 kD; carbonic anhydrase, 31 kD. (B) Scatchard analysis of $^{125}$I-T$_3$ binding to in vitro translated rTR alpha Lysates containing in vitro translated rbeA12B transcripts were assayed for specific thyroid hormone-binding activity by measuring the amount of hormone bound at different concentrations of $^{125}$I-T$_3$-K$_d$=2.9×10$^{-11}$M. (C) Competition of thyroid hormone analogs for $^{125}$I-T$_3$ binding to in vitro translated rTR alpha. Samples from rbeA12B programmed lysates were mixed with increasing concentrations of unlabeled thyroid hormone or analogs to compete with labeled hormone. Specifically bound $^{125}$I-T$_3$ is plotted versus concentration of competitor compound. The same competition pattern was observed in four separate experiments. In vitro transcription and translation and hormone binding were performed as described (22, 23). Open circles represent TRIAC; solid circles represent L-T$_3$; solid triangles represent L-T$_4$.

FIG. VII-5.

Tissue distribution of rTR alpha mRNA. Total RNA was isolated from various rat tissues with guanidine thiocyanate (24), separated on a 1% agarose-formaldehyde gel, transferred to nitrocellulose, and hybridized with a nick-translated 500-bp PvuII fragment from rbeA12. The tissue type and the amount of total RNA loaded are indicated above each lane. A cDNA of CHO-B, a Chinese hamster ovary cell mRNA expressed at equivalent levels in all tissues examined (25), was used as an internal standard. Positions of 28S and 18S ribosomal RNA are indicated.

VII. K. References Referred to in Experimental Section VII

1. Wolff, E. C. and Wolff, J. in *The Thyroid Gland*, Pitt-Rivers, R. V. and Trotter, W. R., Eds. (Butterworths, London, 1964), vol.1, pp.237-282; Schwartz, H. L., in *Molecular Basis of Thyroid Hormone Action*, Oppenheimer, J. H. and Samuels, H. H., Eds. (Academic Press, New York, 1983), pp. 413-444.
2. Eberhardt, N. L., Apriletti, J. W., Baxter, J. B., in *Biochemical Actions of Hormones*, Liewack, G., Ed. (Academic Press, New York, 1980), vol. 7, pp. 311-394.
3. Oppenheimer, J. H., Koerner, D., Schwartz, H. L., Surks, M. J. J., *J. Clin. Endocrinal Metab.*, 35:330 (1972) ; Samuels, H. H. and Tsai, J. S., *Proc. Natl. Acad. Sci. U.S.A.*, 70:3488 (1973).
4. Tata, J. R. and Widnell, C. C., *Biochem. J.*, 98:604 (1966); Martial, J. A., Baxter, J. D., Goodman, H. M., Seeburg, P. H., *Proc. Natl. Acad. Sci. U.S.A.*, 74:1816 (1977); Evans, R. M., Bimberg, N. C., Rosenfeld, M. G., ibid., 79, 7659 (1982).
5. Schwartz, H. L. and Oppenheimer, J. H., *Endocrinology*, 103:267 (1978).
6. Weinberger, C., et al., *Nature*, 324:641 (1986).
7. Sap, J. et al., ibid., p. 635.
8. Spurr, N. K., et al., *EMBO J.*, 3:159 (1984); Dayton, A. J. et al., *Proc. Natl. Acad. Sci. U.S.A.*, 81:4495 (1984); Jhanwar, S. C. Chaganti, R. S. K., Croce, C. M., *Somaric Cell Mol. Genet.*, 11:99 (1985).
9. Giguere, V., Hollenberg, S. M., Rosenfeld, M. G., Evans, R. M., *Cell*, 46:645 (1986).
10. Hollenberg, S. M., Giguere, V., Sequi, P., Evans, R. M., ibid., 49:39 (1987).
11. Kumar, V., Green, S., Staub, A., Chambon, P., *EMBO J.*, 5:2231 (1986).
12. Menezes-Ferreira, M. M., Bil, C., Wortsman, J., Weintraub, B. D., *J. Clin. Endocrinal Metab.*, 59:1081 (1984).
13. Burrow, G. N., in *Endocrinology and Metabolism*, Felig, P., Baxter, J. D., Broadhus, A. E., Frohman, L. A., Eds. (McGraw-Hill, New York, 1981), pp.351-385.
14. DeGroot, L. J. and Stanbury, J. B., *The Thyroid and It's Diseases* (Wiley, N.Y., ed. 4, 1975).
15. Bayrs, J. T., *Br. J. Anim. Behav.*, 1:144 (1953); Ford, D. H. and Cramer, E. B., in *Thyroid Hormones and Brain Development*, Grave, G., Ed. (Raven, N.Y., 1977), pp. 1-17.
16. Oppenheimer, J. H, Schwartz, H. L., Surks, M. I., *Endocrinology*, 95:897 (1974).
17. Barker, S. P. and Klitgaard, H. M., *Am. J. Physiol.*, 170:81 (1952); Lee, Y. P. and Lardy, H. A., *J. Biol. Chem.*, 240:1427 (1965).
18. Underwood, A. H. et al., *Nature*, 324:425 (1986).
19. The rat brain cDNA library was constructed by means of oligo(dT)-selected RNA from whole rat brain. Moloney murine leukemia virus (M-MuLV) reverse transcriptase (RT) was used for first strand synthesis; second strand synthesis was with the Klenow fragment of DNA polymerase I followed by N-MuLV RT-cDNAs were treated with SI nuclease, methylated, size-fractionated on Sepharose 4B, ligated to lambda gtII arms, and packaged. The library consists of 25×10$^6$ independent recombinants with inserts>500 bp.
20. Maxam, A. M. and Gilbert, W., *Proc. Natl. Acad. Sci. U.S.A.*, 74:560 (1977).
21. Lebo, R. V. et al., *Science*, 225:57 (1984).
22. Krieg, P. A. and Melton, D. A., *Nucleic Acids Res.*, 12:7057 (1984); Hollenberg, S. M. et al., *Nature*, 318:635 (1985).
23. For in vitro transcription, the entire EcoRI insert of rbeA12 was cloned into pGEM1 (Promega Biotec). A second construction deleting 227 bp of 5' untranslated sequence, rbeA12B, was made by inserting the T$_4$DNA polymerase-filled BgI-SmaI fragment of rbeA12 (nucleotide position 227 to the polylinker) into the SmaI site of pGEM3. For thyroid hormone binding, transcriptions were performed with SP6 polymerase and 5 to 10 micrograms of rbeA12B linearized with SstI. Transcripts were purified by P60 chromatography and translated in 150 to 200 microliters of rabbit reticulolyte lysate (Promega Biotec) in conditions suggested by the manufacturer. Thyroid hormone binding for both the Scatchard and competition analyses were determined in the same manner, except that unlabeled protein was used for the Scatchard analysis. [$^{125}$I]3,3',5:Triodothyronine (New England Nuclear, 2200 Ci/mmol, 0.3 nM final concentration) was mixed with rTR alpha polypeptides synthesized in vitro (5 to 8 microliters of the 200 microliters of lysate per binding reaction) in T$_3$ binding buffer at 0° C. for 2 hours in a final volume of 250 microliters. Specific hormone binding was determined by adding a 1000-fold excess of unlabeled hormone and assayed by counting radioactivity eluting in the excluded volume from a Sephadex G-25 fine (Pharmacia) 0.9-by 4.0-cm. column.

24. Chirgwin, J. M., Przbyla, A. F., MacDonald, R. J., Rutter, W. F., *Biochemistry*, 18:5294 (1974).

25. Harpold, M. M., Evans, R. M., Salditt-Goeorgieff, M., Darnell, J. E., *Cell*, 17:1025 (1979).

SPECIFICATION SUMMARY

From the foregoing description, one of ordinary skill in the art can understand that the present invention provides substantially pure DNA's comprised of sequences which encode proteins having the hormone-binding and/or transcription-activating characteristics of a glucocorticoid receptor, a mineralocorticoid receptor, or a thyroid hormone receptor. The invention also provides various plasmids containing receptor sequences which exemplify the DNA's of the invention. Exemplary plasmids of the invention have been deposited with the American Type culture Collection for patent purposes.

The invention is also comprised of receptor proteins, including modified functional forms thereof, expressed from the DNA's (or mRNA's) of the invention.

In addition to novel receptor DNA, RNA and protein compositions, the present invention involves a bioassay for determining the functionality of a receptor protein. It also involves two new methods for producing desired proteins in genetically engineered cells. The first is a method for inducing transcription of a gene whose transcription is activated by hormones complexed the receptors. The second is a method for engineering a cell and then increasing and controlling production of a protein encoded by a gene whose transcription is activated by hormones complexed with receptor proteins.

The DNA's of the invention can be used to make the hormone receptor proteins, and functional modified forms thereof, in quantities that were not previously possible. With the quantities of receptor available as a result of the present invention, detailed structural analyses of the proteins can now be made by using X-ray diffraction methods to analyze receptor crystals. In addition, adequate supplies of the receptor proteins mean that they can now be used to screen compounds for receptor-agonists or receptor-antagonist activity. Availability of the receptor proteins also means that they can be used in diagnostic assays.

Without departing from the spirit and scope of this invention, one or ordinary skill can make various changes and modifications to the invention to adapt it to various usages and conditions. As such, these changes and modifications are properly, equitable, and intended to be, within the full range of equivalence of the following claims.

What is claimed is:

1. A bioassay for evaluating whether compound(s) are functional ligands for hormone receptor protein(s), or functional engineered or modified forms thereof, said bioassay comprising:
    (a) culturing cells which contain:
        non-endogenous DNA which expresses said hormone receptor protein, or functional engineered or modified forms thereof, and
        DNA which encodes an operative hormone response element linked to a reporter gene,
        wherein said culturing is conducted in the presence of at least one compound whose ability to function as a ligand for said hormone receptor protein, or functional engineered or modified forms thereof, is sought to be determined, and
    (b) assaying for evidence of transcription of said reporter gene in said cells.

2. A bioassay according to claim 1 wherein the cells are mammalian.

3. A bioassay according to claim 2 wherein said cells are CV-1 or COS cells.

4. A bioassay according to claim 1 wherein said reporter gene is contained in a reporter plasmid, wherein said non-endogenous DNA which expresses said hormone receptor protein(s) or functional modified forms thereof is contained in an expression plasmid, wherein said reporter and expression plasmids also contain the origin of replication of SV-40.

5. A bioassay according to claim 1 wherein said reporter gene is contained in a reporter plasmid, wherein said non-endogenous DNA which expresses said hormone receptor protein(s) or functional modified forms thereof is contained in an expression plasmid, wherein said reporter and expression plasmids also contain a selectable marker.

6. A bioassay according to claim 1 wherein said hormone response element is selected from mouse tumor virus long terminal repeat (MTV LTR) or mammalian growth hormone promoter, and said reporter gene is CAT.

7. A bioassay according to claim 1 wherein said hormone receptor protein(s) or functional modified form(s) thereof is selected from steroid hormone receptors.

8. A bioassay according to claim 7 wherein said steroid hormone receptor is estrogen receptor.

9. A bioassay according to claim 7 wherein said steroid hormone receptor is thyroid hormone receptor.

10. A bioassay according to claim 7 wherein said steroid hormone receptor is mineralocorticoid receptor.

11. A bioassay according to claim 7 wherein said steroid hormone receptor is glucocorticoid receptor.

12. A bioassay according to claim 7 wherein said steroid hormone receptor is selected from hERR1 or hERR2.

13. A bioassay according to claim 1 wherein said monitoring comprises assaying for mRNA transcribed from said reporter gene.

14. A bioassay according to claim 1 wherein said bioassay comprises assaying for induction of transcription of said reporter gene in said cells.

15. A bioassay for evaluating whether compounds are antagonists for hormone receptor protein(s) or functional modified forms thereof, said bioassay comprising:
    (a) culturing test cells in culture medium containing:
        increasing concentrations of at least one compound whose ability to inhibit the transcription activation activity of hormone receptor agonists is sought to be determined, and
        a fixed concentration of at least one agonist for said hormone receptor protein(s) or functional modified forms thereof,
        wherein said test cells contain:
        non-endogenous DNA which expresses said hormone receptor protein(s) or functional modified forms thereof, and DNA encoding a hormone response element operatively linked to a reporter gene; and thereafter (b) assaying for evidence of transcription of said reporter gene in said cells as a function of the concentration of said compound in said culture medium, thereby indicating the ability of said compound to inhibit activation of transcription by hormone receptor agonists.

16. A bioassay according to claim 15 wherein the cells are mammalian.

17. A bioassay according to claim 16 wherein said cells are CV-1 or COS cells.

18. A bioassay according to claim 15 wherein said reporter gene is contained in a reporter plasmid, wherein said non-endogenous DNA which expresses said hormone receptor protein(s) or functional modified forms thereof is contained in an expression plasmid, wherein said reporter and expression plasmids also contain the origin of replication of SV-40.

19. A bioassay according to claim 15 wherein said reporter gene is contained in a reporter plasmid, and wherein said non-endogenous DNA which expresses said hormone receptor protein(s) or functional modified forms thereof is contained in an expression plasmid, wherein said reporter and expression plasmids also contain a selectable marker.

20. A bioassay according to claim 15 wherein said hormone response element is selected from mouse tumor virus long terminal repeat (MTV LTR) or mammalian growth hormone promoter, and said reporter gene is CAT.

21. A bioassay according to claim 15 wherein said hormone receptor protein(s) or functional modified form(s) thereof is selected from steroid hormone receptors.

22. A bioassay according to claim 21 wherein said steroid hormone receptor is estrogen receptor.

23. A bioassay according to claim 21 wherein said steroid hormone receptor is thyroid hormone receptor.

24. A bioassay according to claim 21 wherein said steroid hormone receptor is mineralocorticoid receptor.

25. A bioassay according to claim 21 wherein said steroid hormone receptor is glucocorticoid receptor.

26. A bioassay according to claim 21 wherein said steroid hormone receptor is selected from hERR1 or hERR2.

27. A bioassay according to claim 21 wherein said monitoring comprises assaying for mRNA transcribed from said reporter gene.

28. A bioassay according to claim 21 wherein said bioassay comprises assaying for induction of transcription of said reporter gene in said cells.

* * * * *